United States Patent [19]

Schober

[11] 4,388,927

[45] Jun. 21, 1983

[54] PROGRAMMABLE DIGITAL CARDIAC PACER

[75] Inventor: Robert C. Schober, Huntington Beach, Calif.

[73] Assignee: American Hospital Supply Corporation, Evanston, Ill.

[21] Appl. No.: 103,401

[22] Filed: Dec. 13, 1979

[51] Int. Cl.³ .............................................. A61N 1/36
[52] U.S. Cl. ............................................. 128/419 PG
[58] Field of Search .................... 128/419 PG, 419 PT

[56] References Cited

U.S. PATENT DOCUMENTS

| | | | |
|---|---|---|---|
| 3,557,796 | 1/1971 | Keller, Jr. et al. | 128/419 PG |
| 3,631,860 | 1/1972 | Lopin | 128/419 PG |
| 3,661,157 | 5/1972 | Fyson et al. | 128/419 PG |
| 3,693,626 | 9/1972 | Cole | 128/419 PG |
| 3,717,153 | 2/1973 | Bowers | 128/419 PG |
| 3,782,367 | 1/1964 | Hochberg et al. | 128/419 PT |
| 3,972,334 | 8/1976 | Wickham | 128/419 PG |
| 4,049,003 | 9/1977 | Walters et al. | 128/419 PG |
| 4,095,603 | 6/1978 | Davies | 128/419 PG |
| 4,163,451 | 8/1979 | Lesnick et al. | 128/419 PG |
| 4,222,385 | 9/1980 | Backhouse | 128/419 PG |

*Primary Examiner*—William E. Kamm
*Attorney, Agent, or Firm*—Emrich, Lee, Brown & Hill

[57] ABSTRACT

A cardiac pacer has separate digital filter circuits for sensing atrial and ventricular activity. Parameter data stored in memory is used by the digital filters for identifying the various components of cardiac activity, such as the P, R and T waves, as well as for identifying Premature Ventricular Contractions (PVC). A Ventricular Rate Time Out period is established from the last natural beat or stimulating pulse; and if a P wave or natural R wave is not sensed during that period, the system generates a stimulating pulse and, using T wave parameters in the ventricular filter, tests to verify capture. Loss of capture increases stimulating pulse width and amplitude to regain capture. If a P wave is sensed before the Rate Time Out period ends, the system establishes a predetermined P-R interval period to override the Ventricular Rate Time Out period in which the ventricular filter is set to detect a natural R wave in an effort to synchronize the ventricle with the atrium. Prior to the Ventricular Rate Time Out period of each cardiac cycle, the ventricular filter is set to detect Premature Ventricular Contractions. If a predetermined number of PVCs is detected, the system generates a train of stimulating signals at a rate higher than expected tachycardia in an effort to break the tachycardia cycle. Many of the system's functions can be enabled or disabled by action of the physician; and many of the system parameters can be externally programmed, such as ventricular rate, stimulating pulse amplitude and/or duration, atrial and ventricular filter parameters, P-R delay interval and others.

31 Claims, 95 Drawing Figures

FIG 1 FUNCTIONAL BLOCK DIAGRAM OF THE PORTION OF A SYSTEM CONTAINING THE INPUT DETECTORS.

FIG. 2. FUNCTIONAL BLOCK DIAGRAM OF THE CONTROL PORTION OF THE SYSTEM OF FIG.1.

ATRIAL RING LEAD IN HEART.

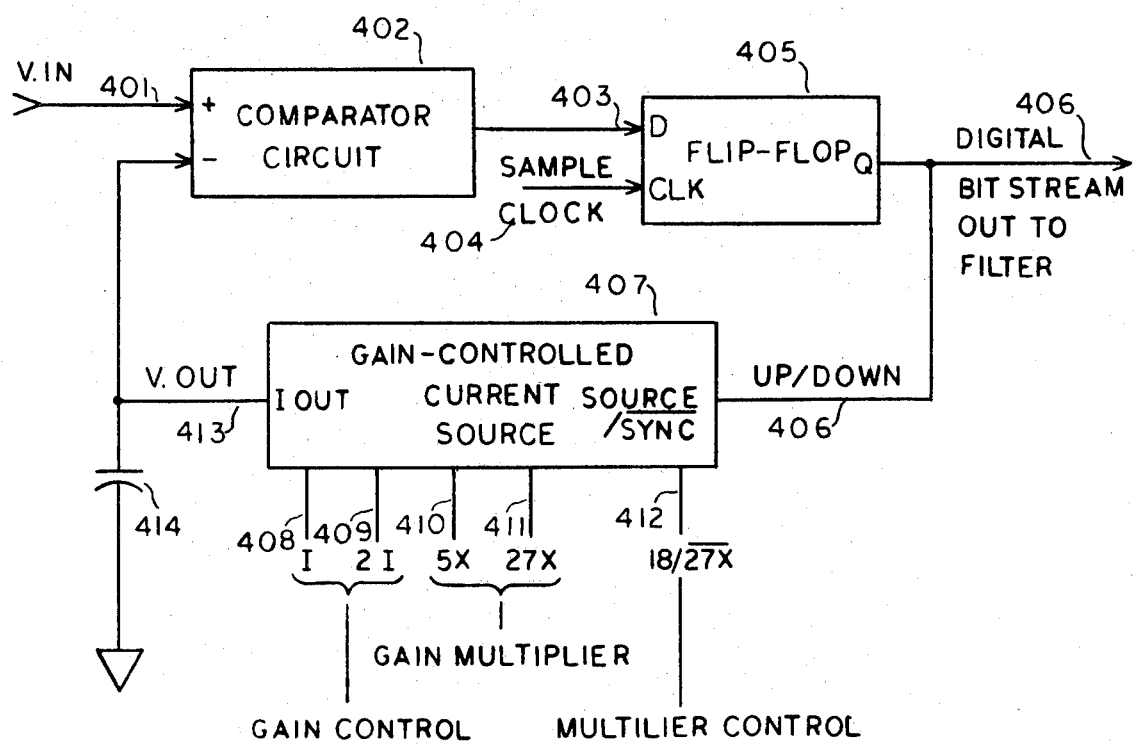
FIG. 4 – DELTA MODULATOR INPUT SIGNAL INTERFACE.
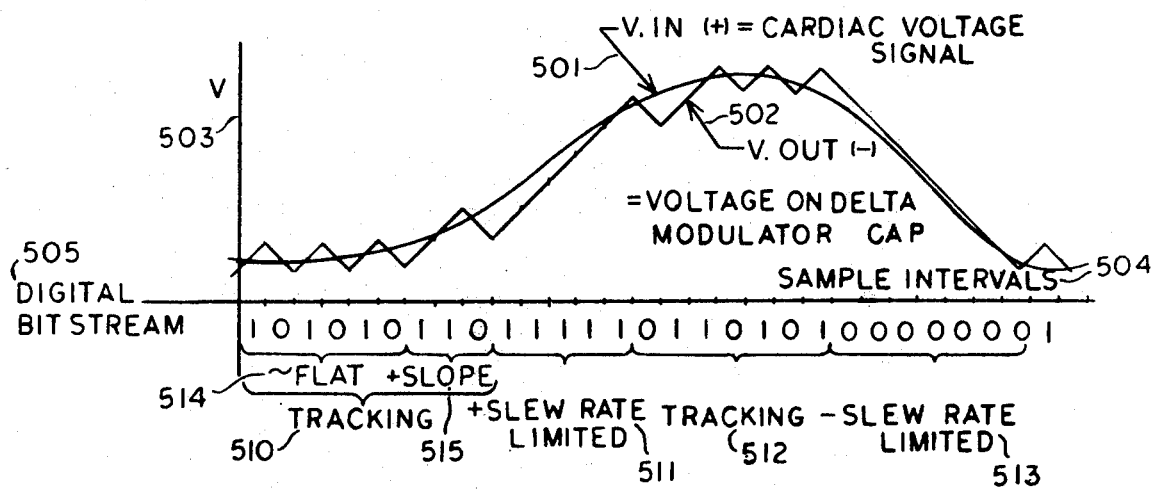
FIG. 5 – COMPARATOR INPUTS

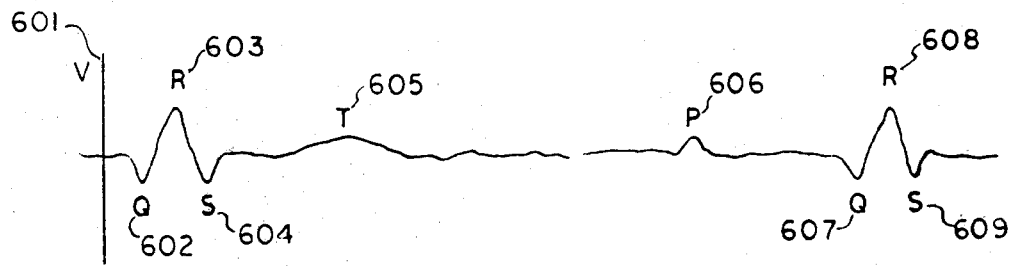
FIG.6. VENTRICULAR INPUT SIGNAL
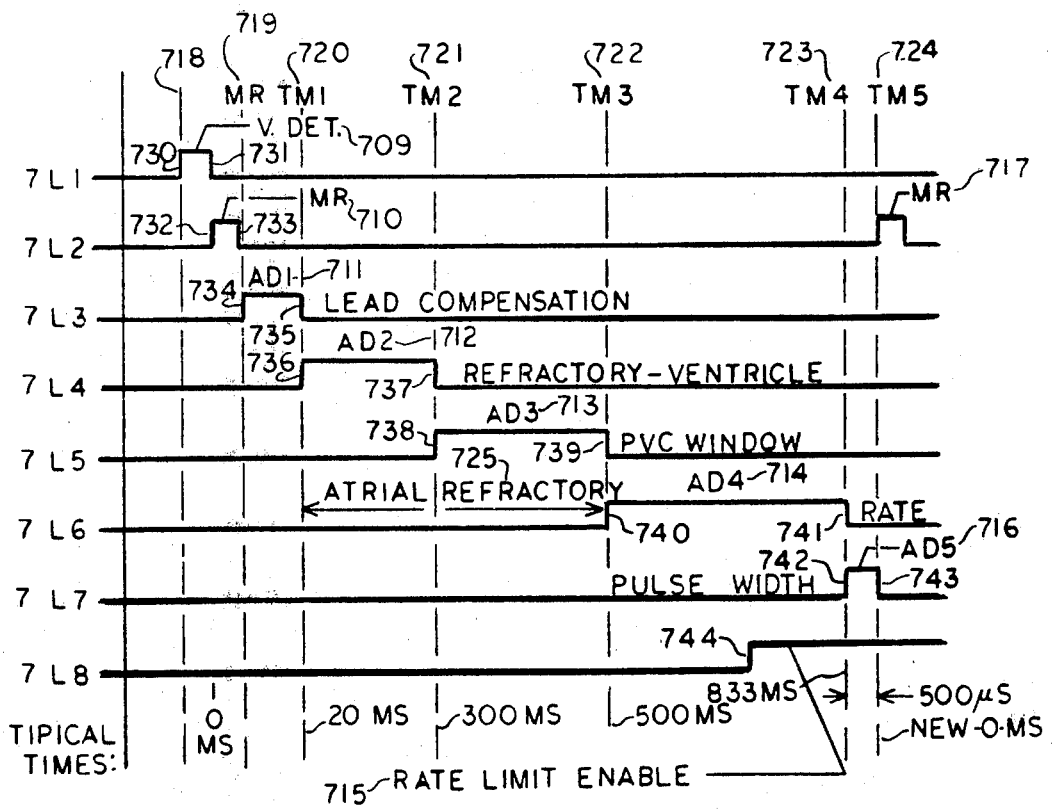
FIG.7. TIME PERIOD ADDRESS SEQUENCE STARTING WITH A NATURAL HEARTBEAT DETECTION AND ENDING WITH A STIMULATING OUTPUT.

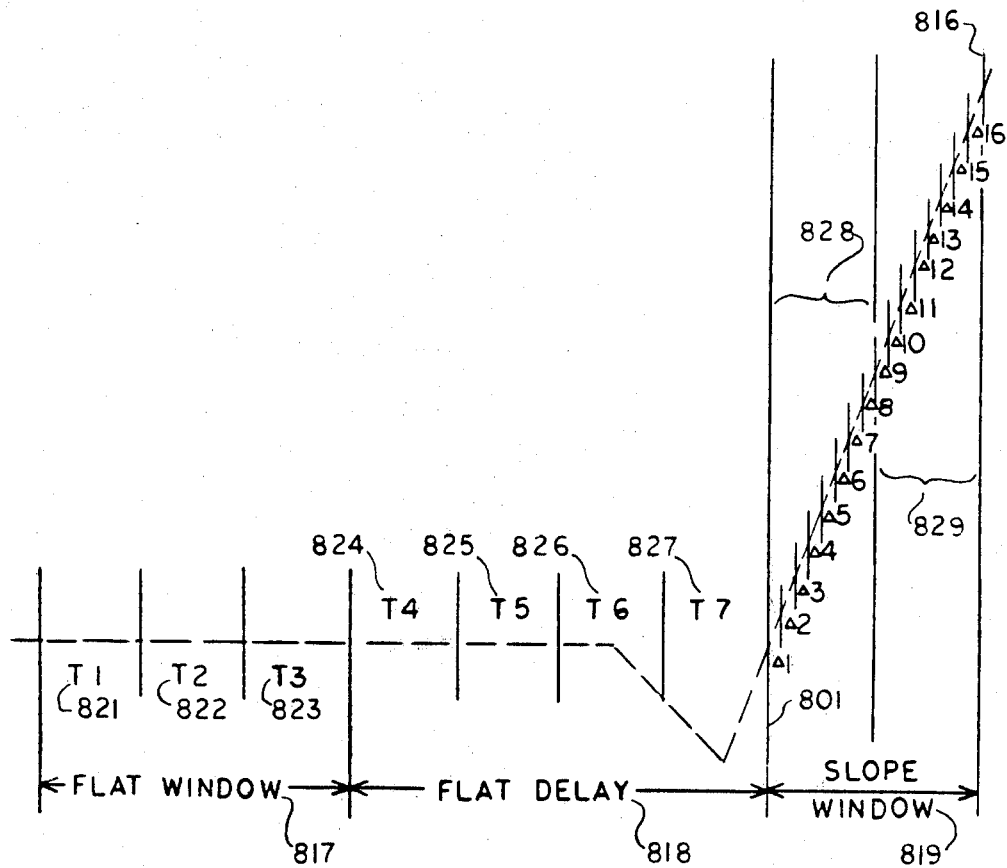
FIG. 8. DIGITAL FILTER SAMPLE AND DELAY TIME PERIOD RELATIONSHIP.

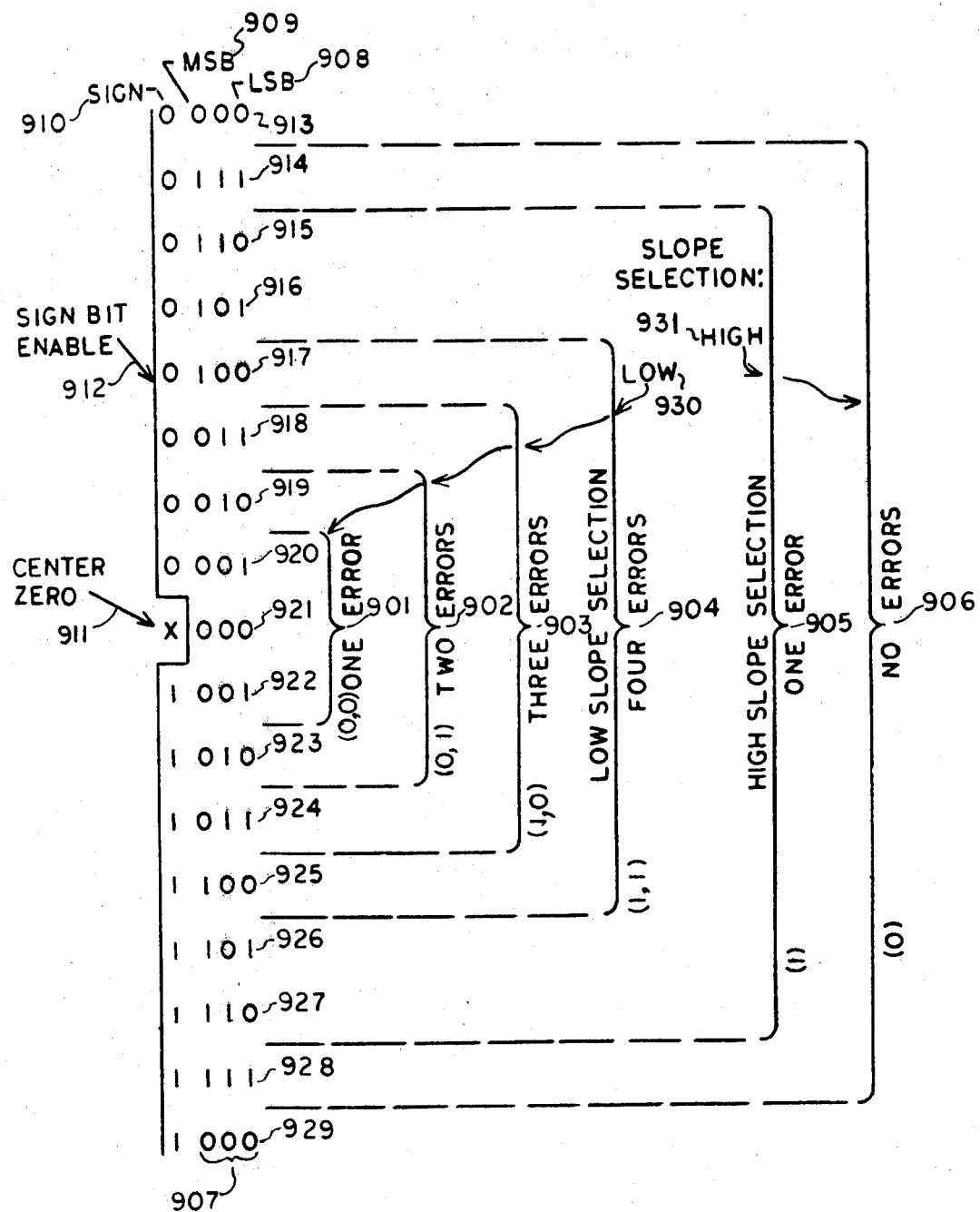
FIG. 9. CONTENTS OF UP DOWN SLOPE COUNTER

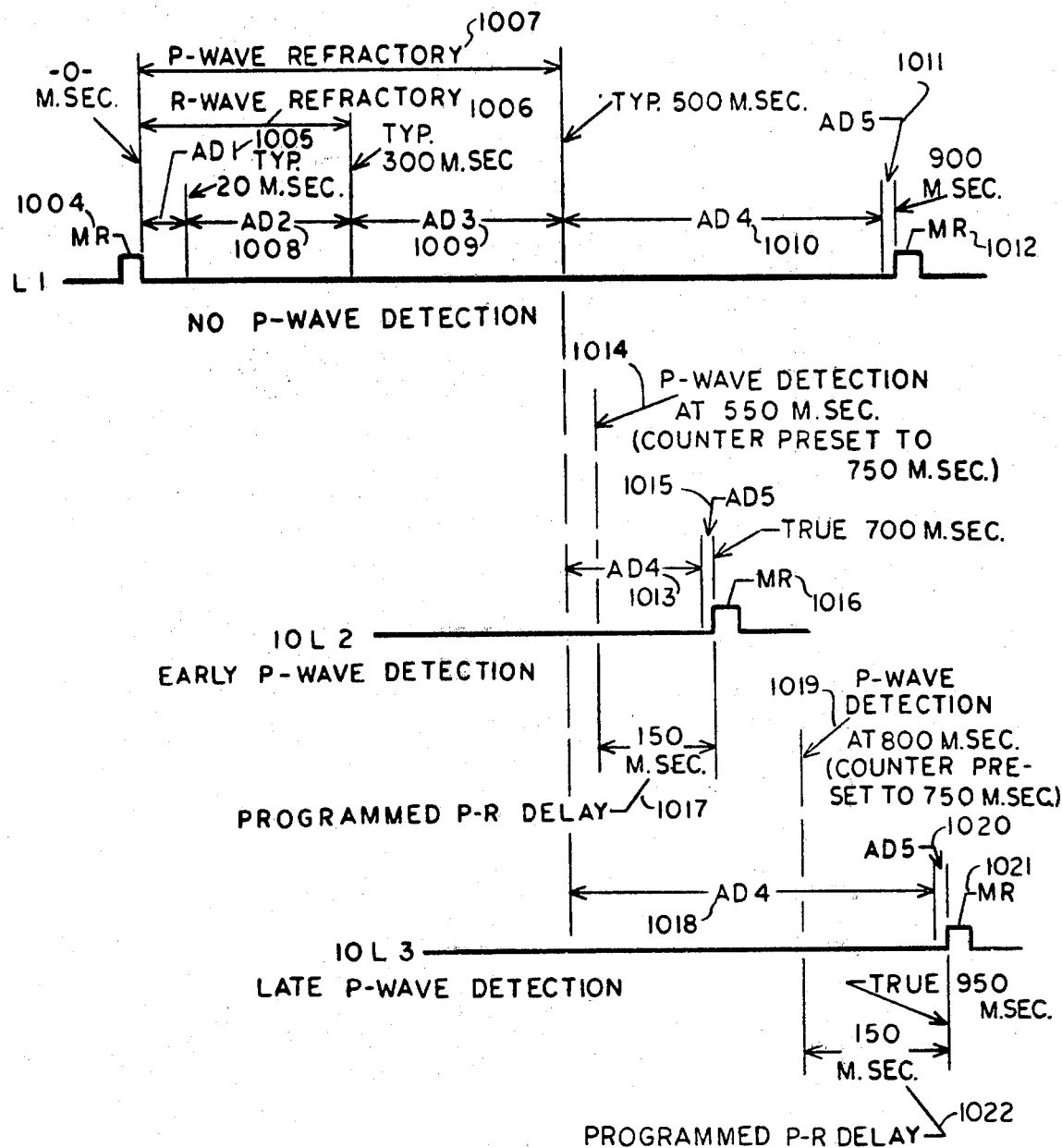
FIG.10. AD4 TIMING MODIFICATION BY EARLY AND LATE P-WAVE DETECTION.

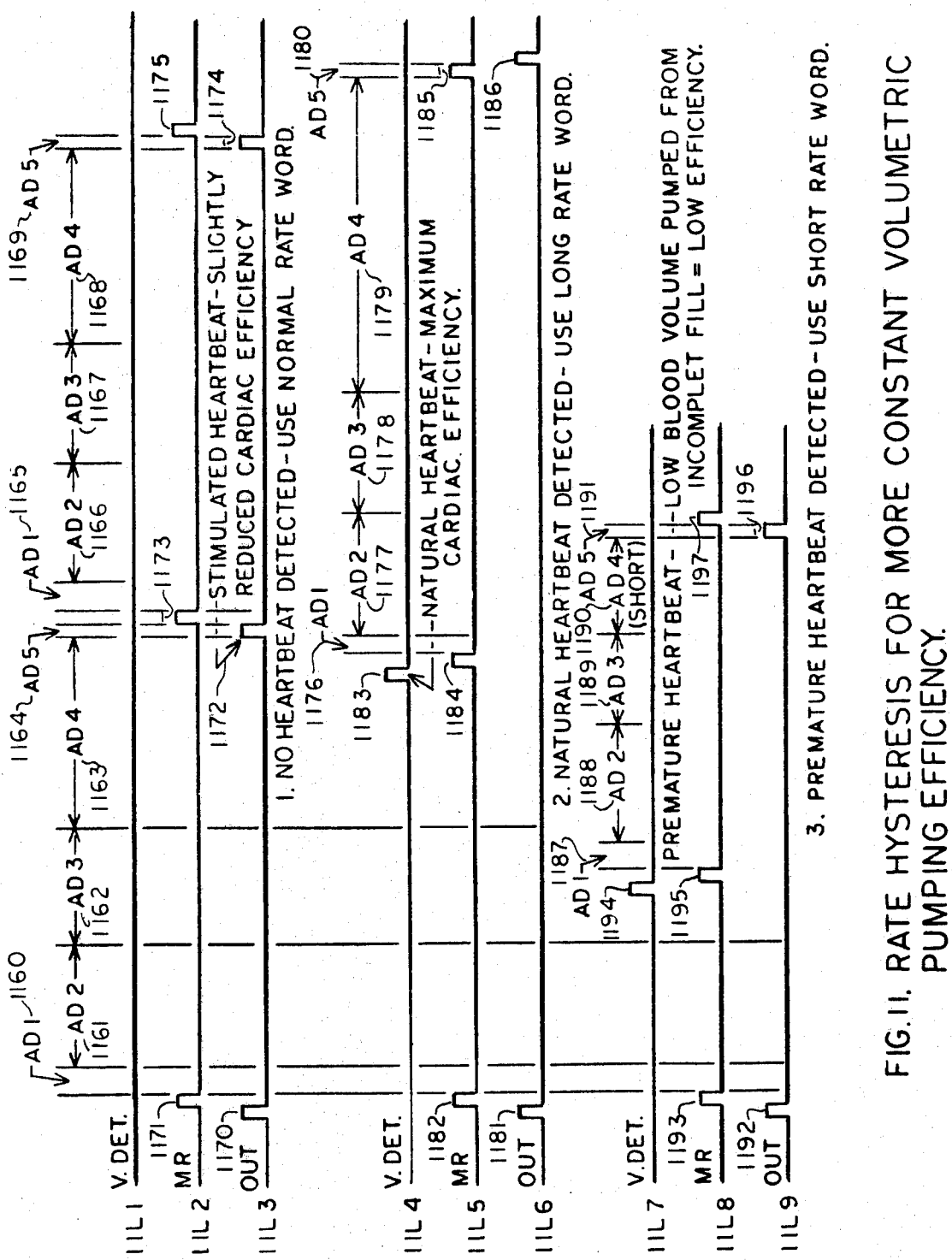
FIG. 11. RATE HYSTERESIS FOR MORE CONSTANT VOLUMETRIC PUMPING EFFICIENCY.

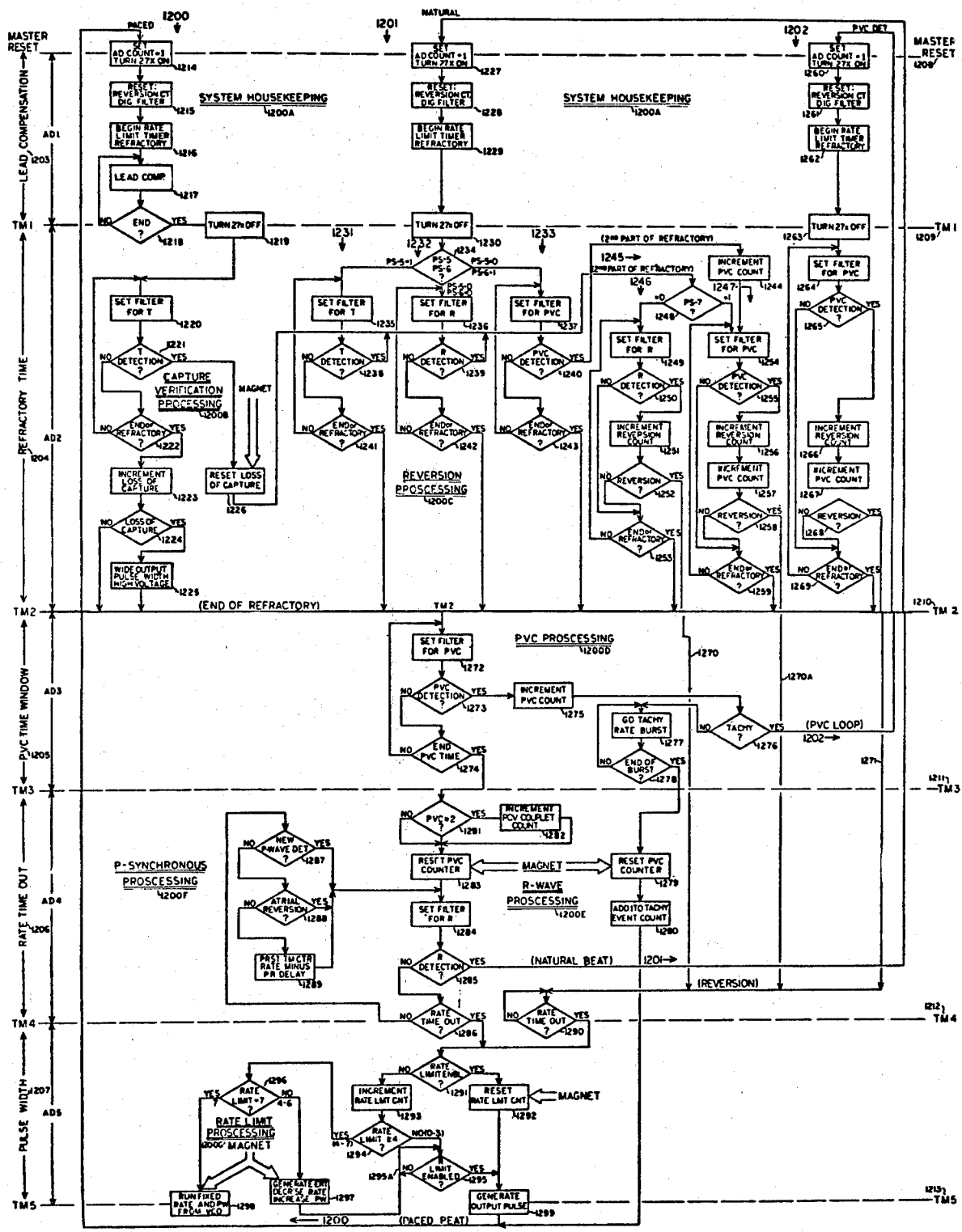
FIG 12 FLOW DIAGRAM OF PACEMAKER SYSTEM OPERATION

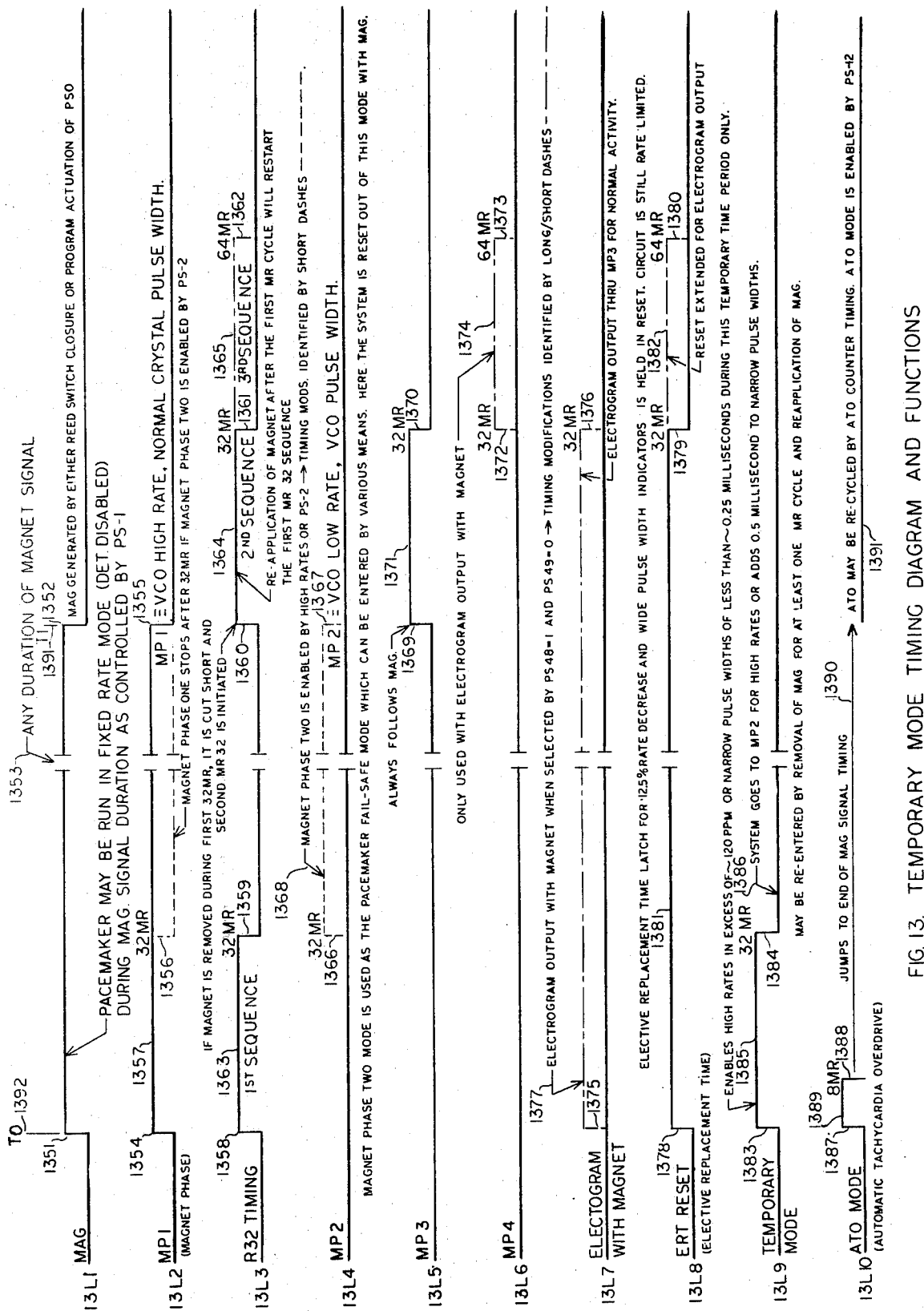

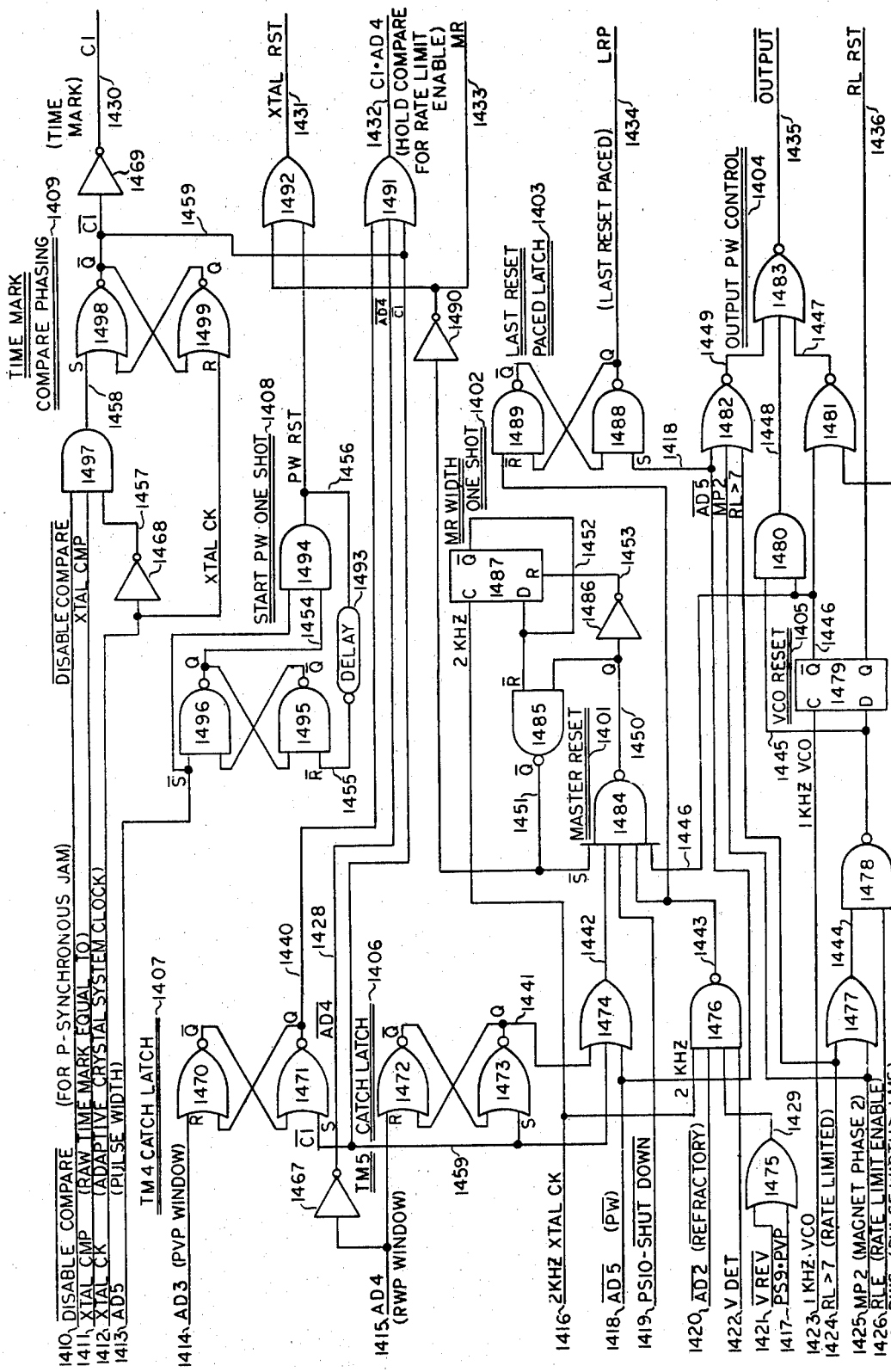
FIG. 14 STATE CONTROLLER (231) LOGIC DIAGRAM

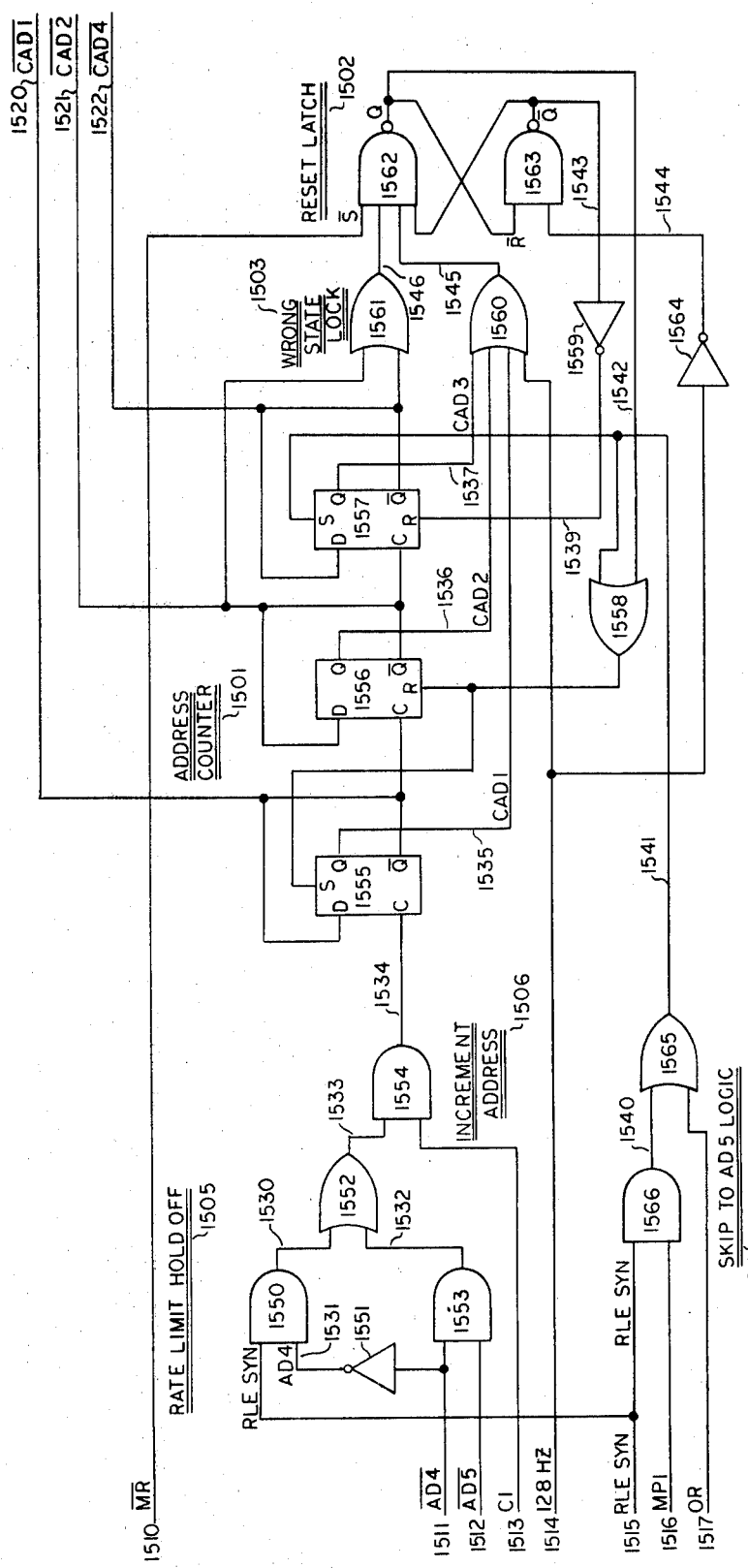
FIG. 15. TIME MARK SEQUENCE COUNTER (232) LOGIC DIAGRAM

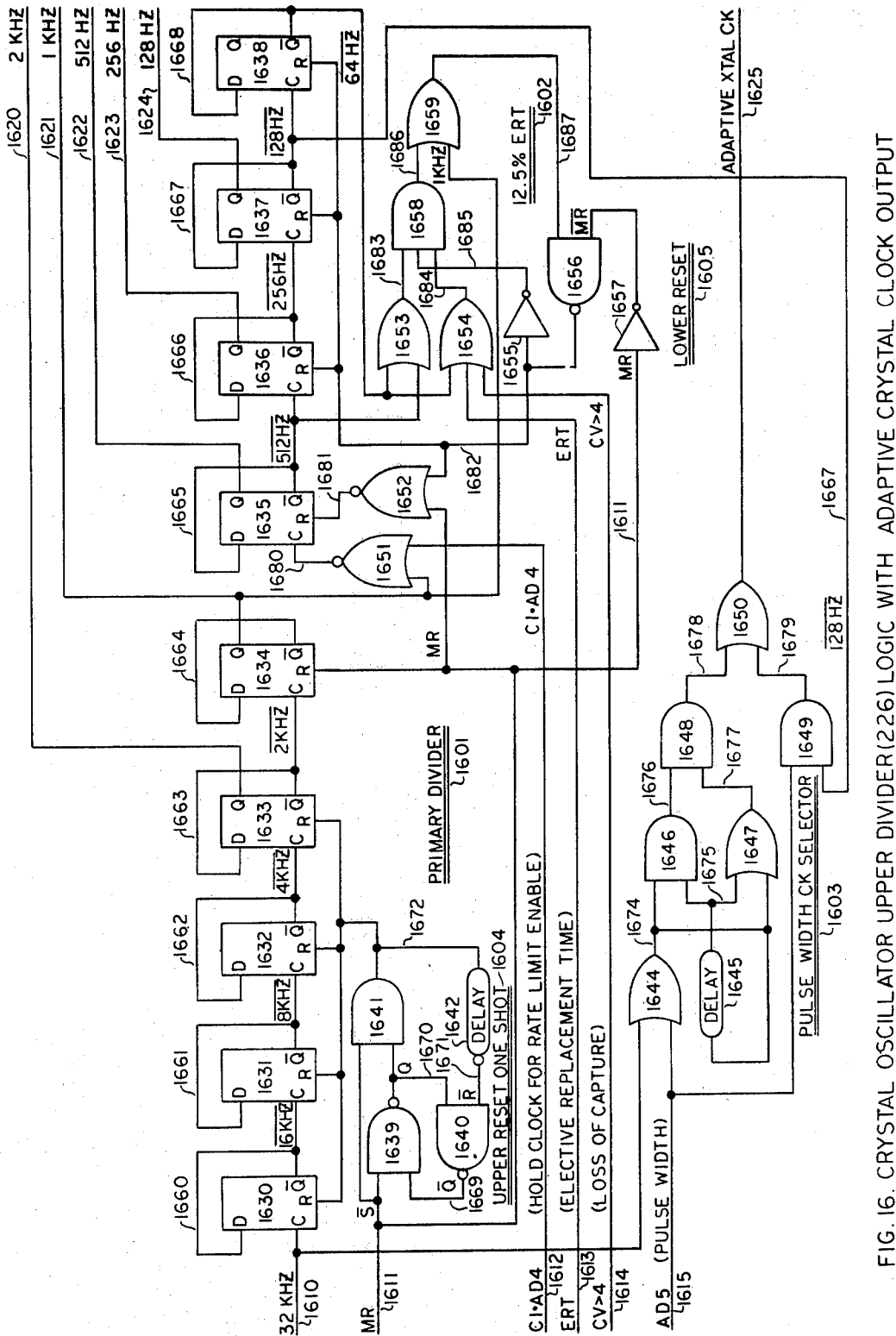
FIG. 16. CRYSTAL OSCILLATOR UPPER DIVIDER (2²⁶) LOGIC WITH ADAPTIVE CRYSTAL CLOCK OUTPUT

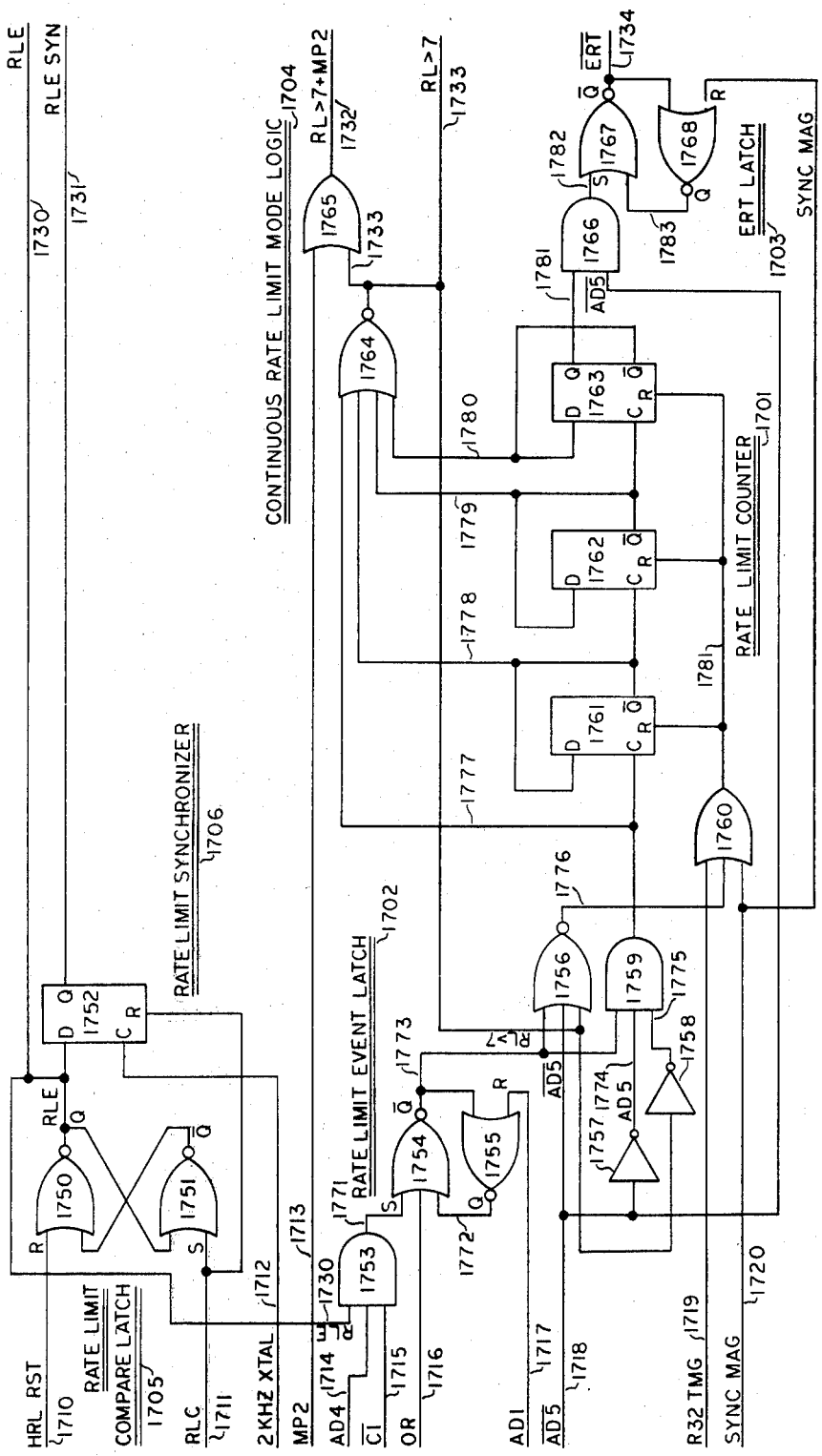
FIG. 17 RATE LIMIT CONTROLLER (236), COUNTER (237), AND SYNCHRONIZER (235) LOGIC DIAGRAM

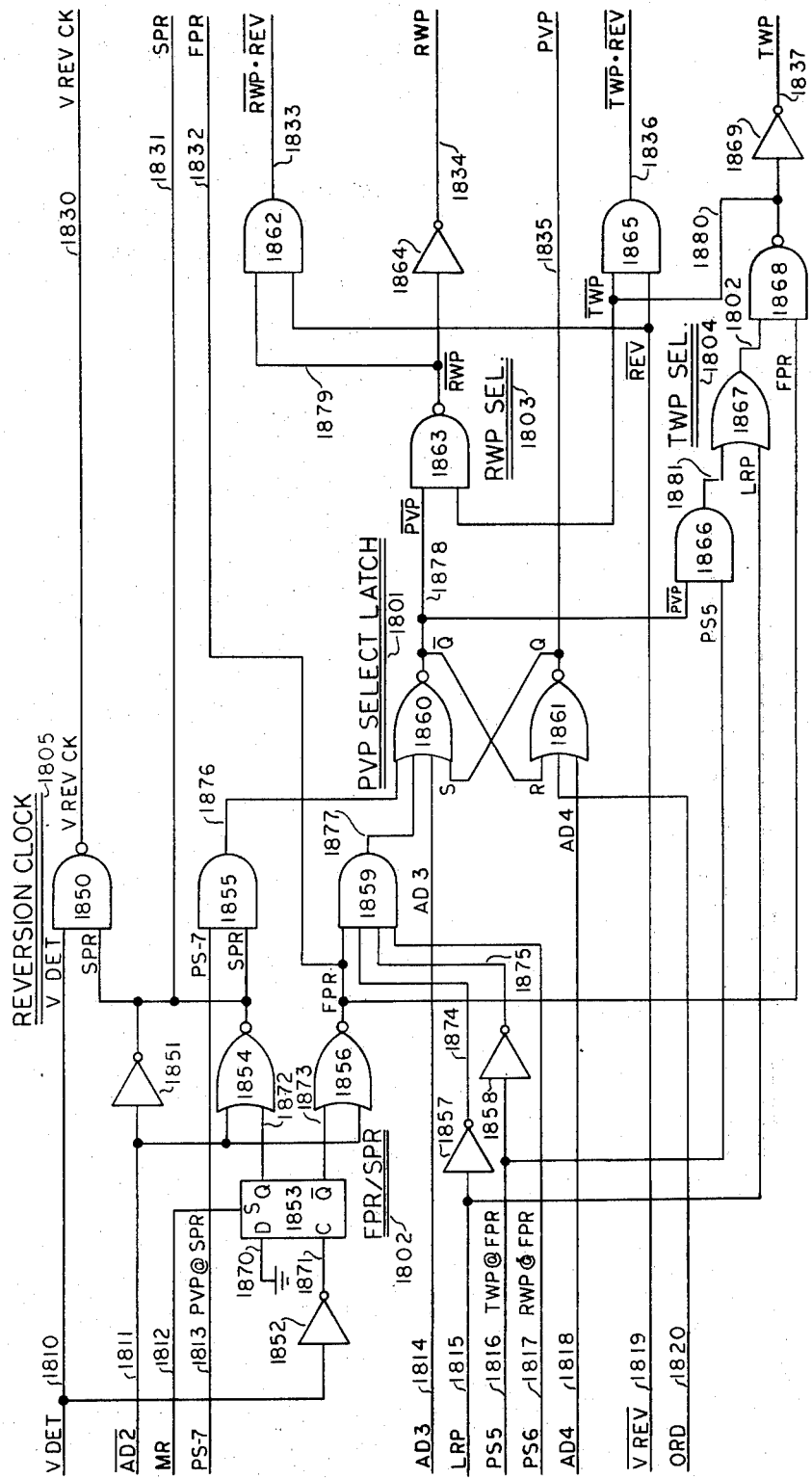
FIG. 18. VENTRICULAR DIGITAL FILTER PARAMETER CONTROLLER 233 LOGIC DIAGRAM

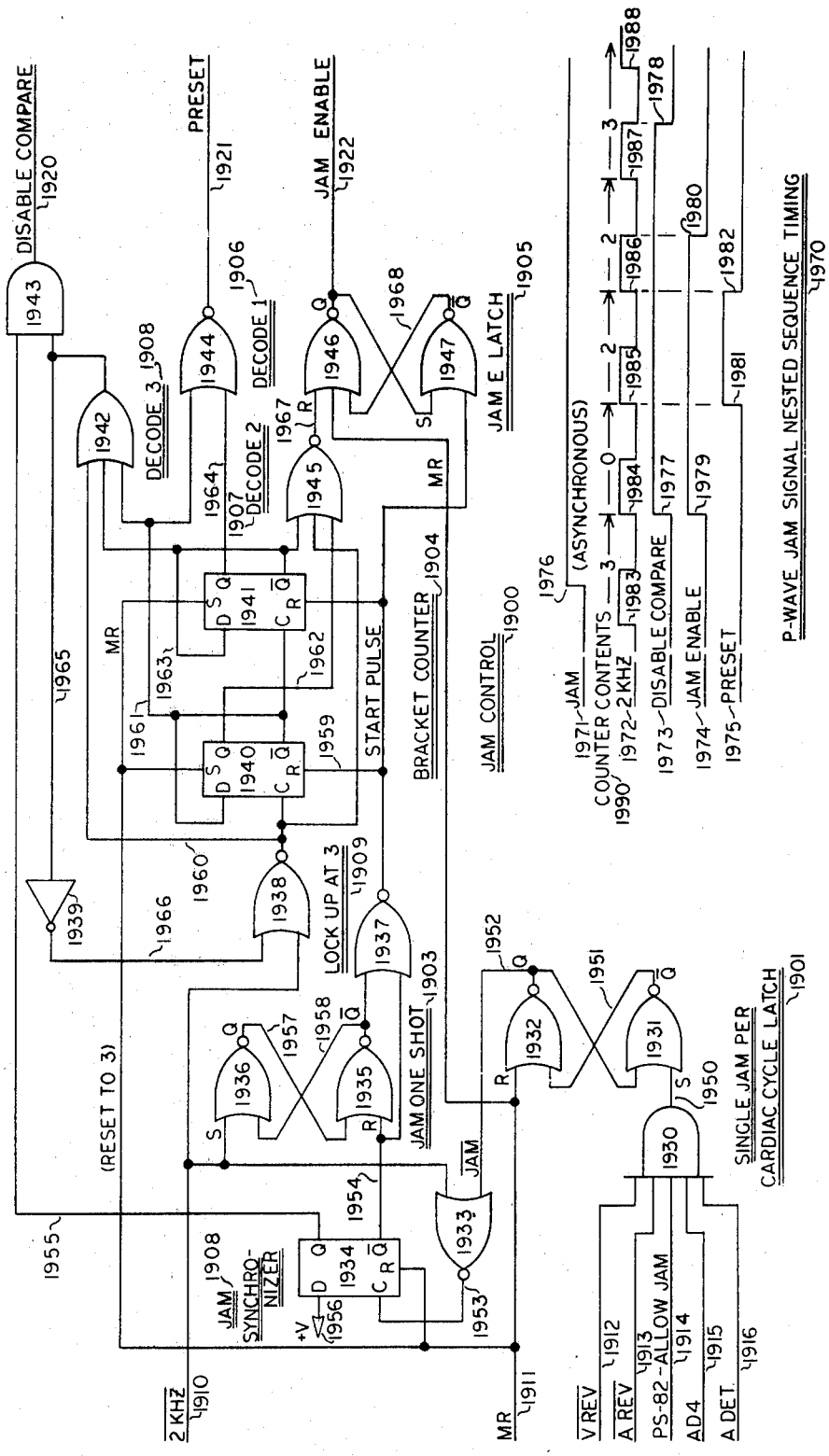
FIG.19 JAM CONTROLLER (169) LOGIC AND TIMING DIAGRAMS.

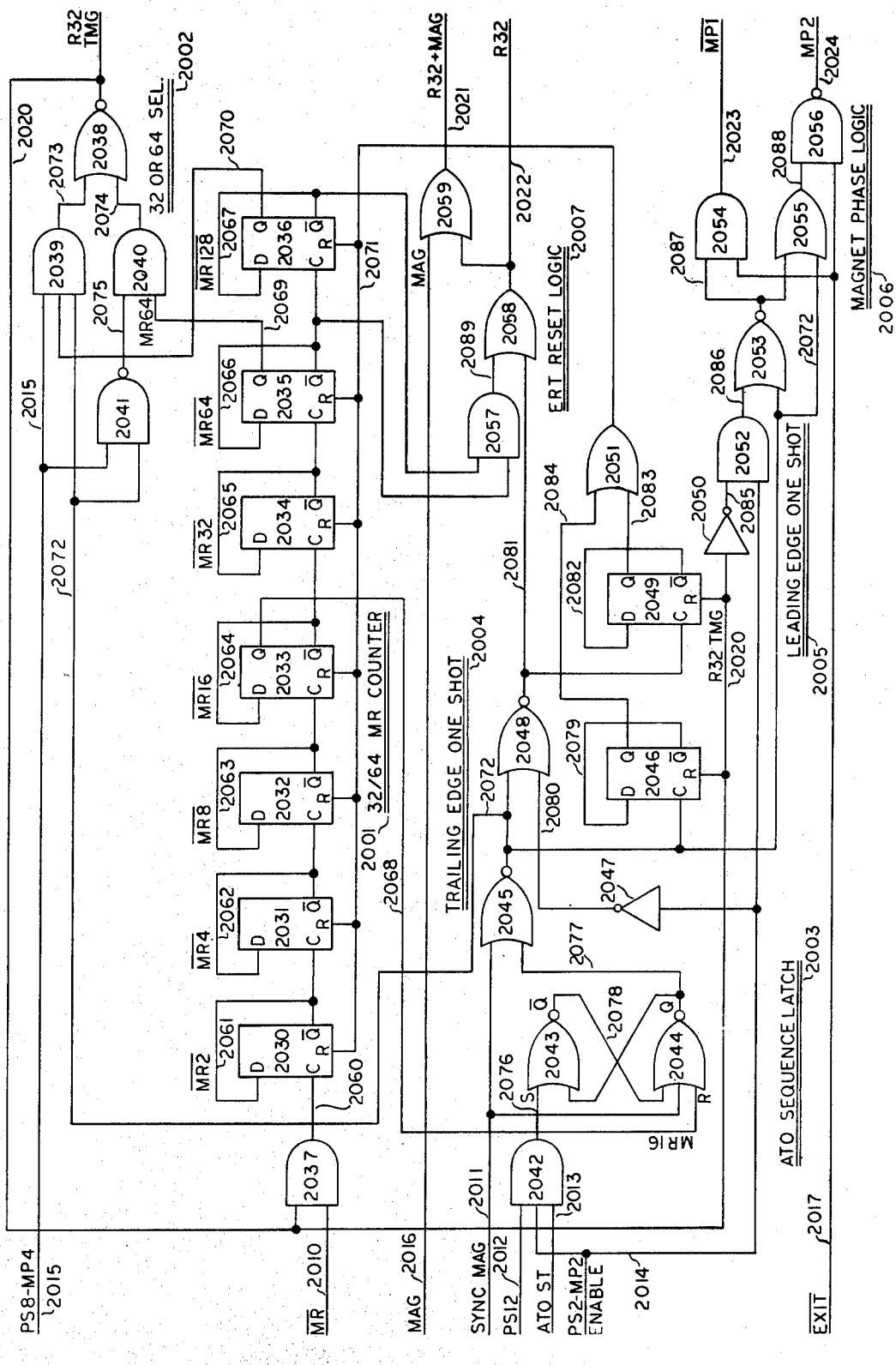
FIG. 20. TEMPORARY MODE COUNTER 239 LOGIC DIAGRAM

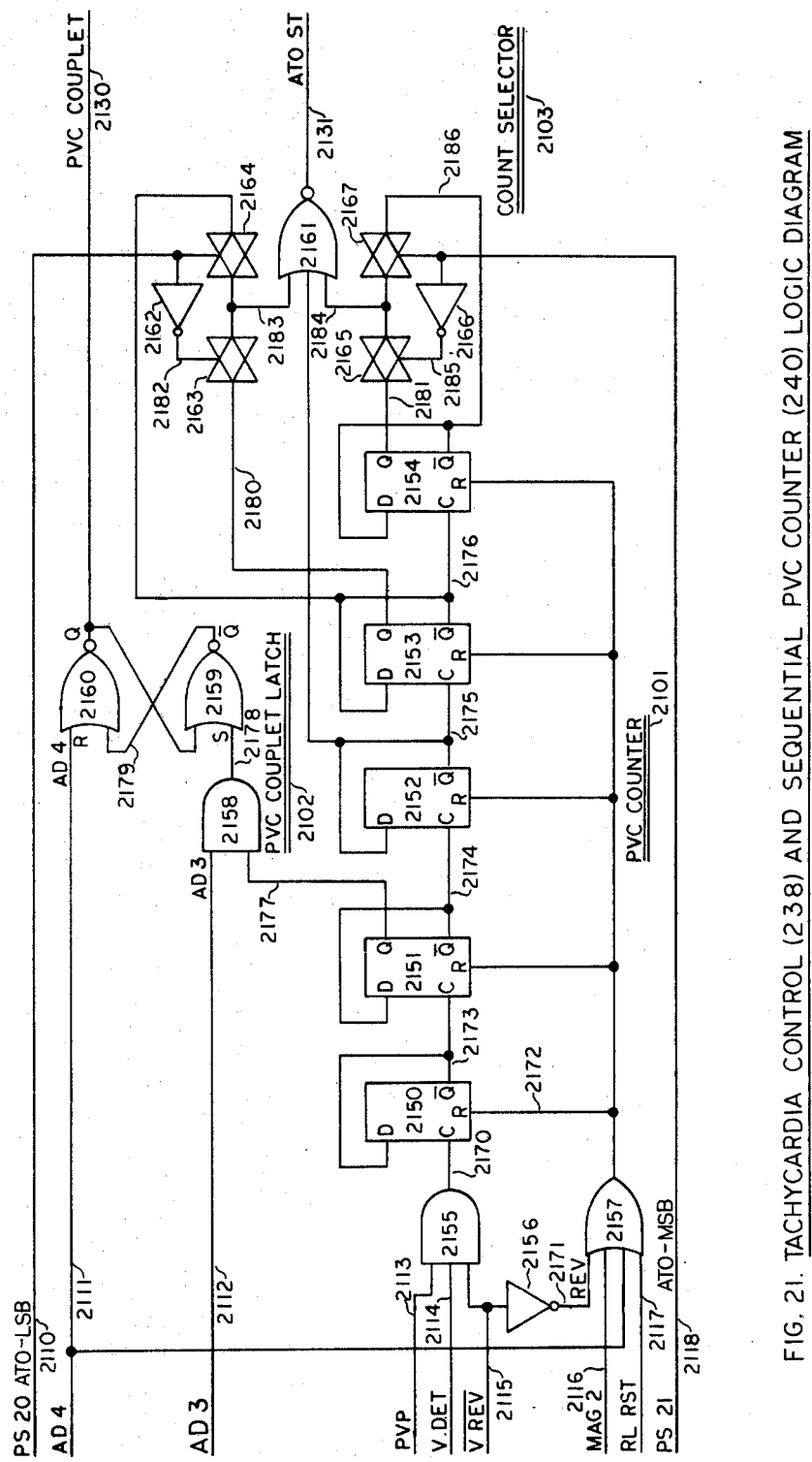
FIG. 21. TACHYCARDIA CONTROL (238) AND SEQUENTIAL PVC COUNTER (240) LOGIC DIAGRAM

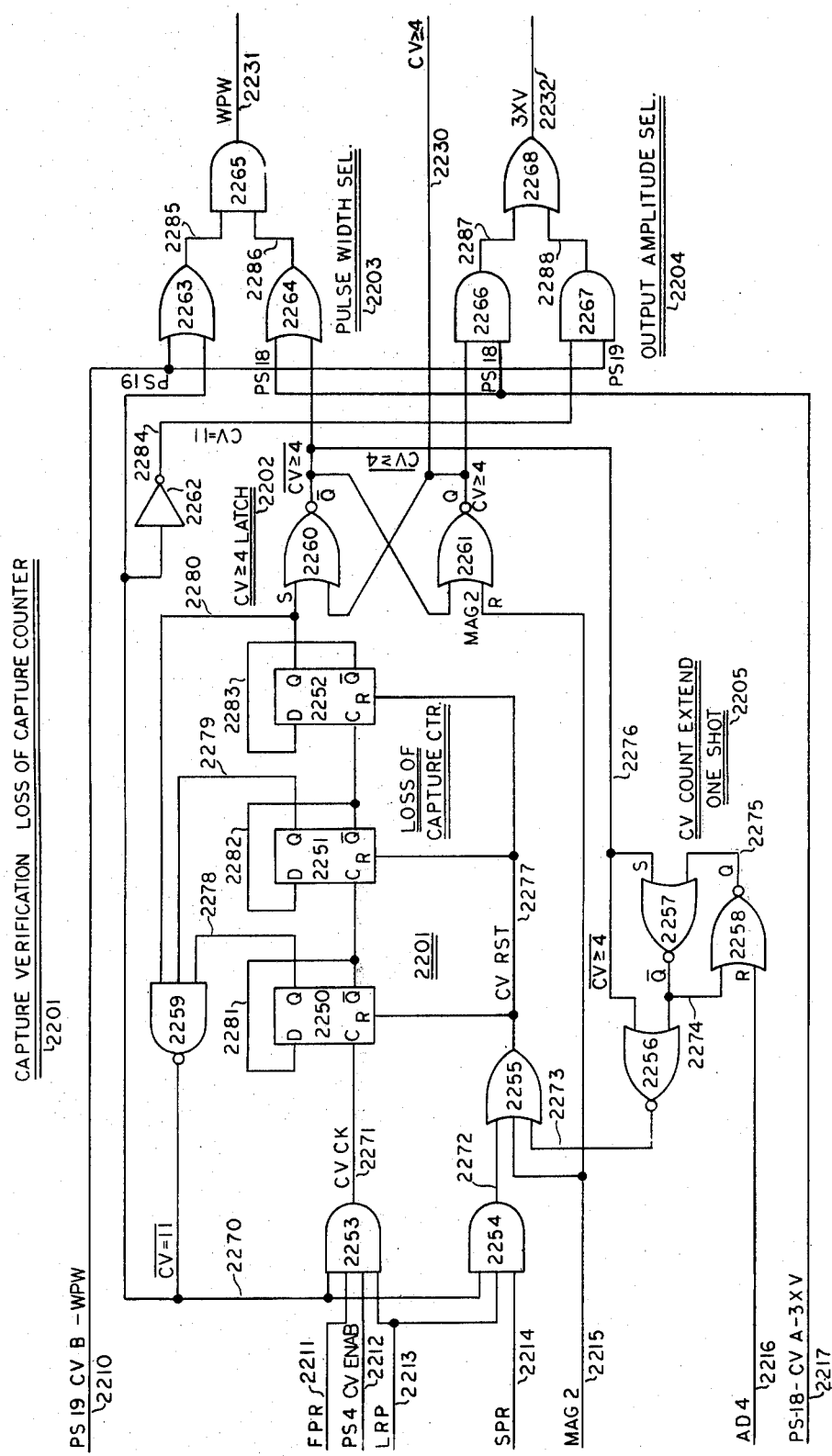
FIG. 22. CAPTURE VERIFICATION CONTROL LOGIC (228) AND LOSS OF CAPTURE COUNTER (229)

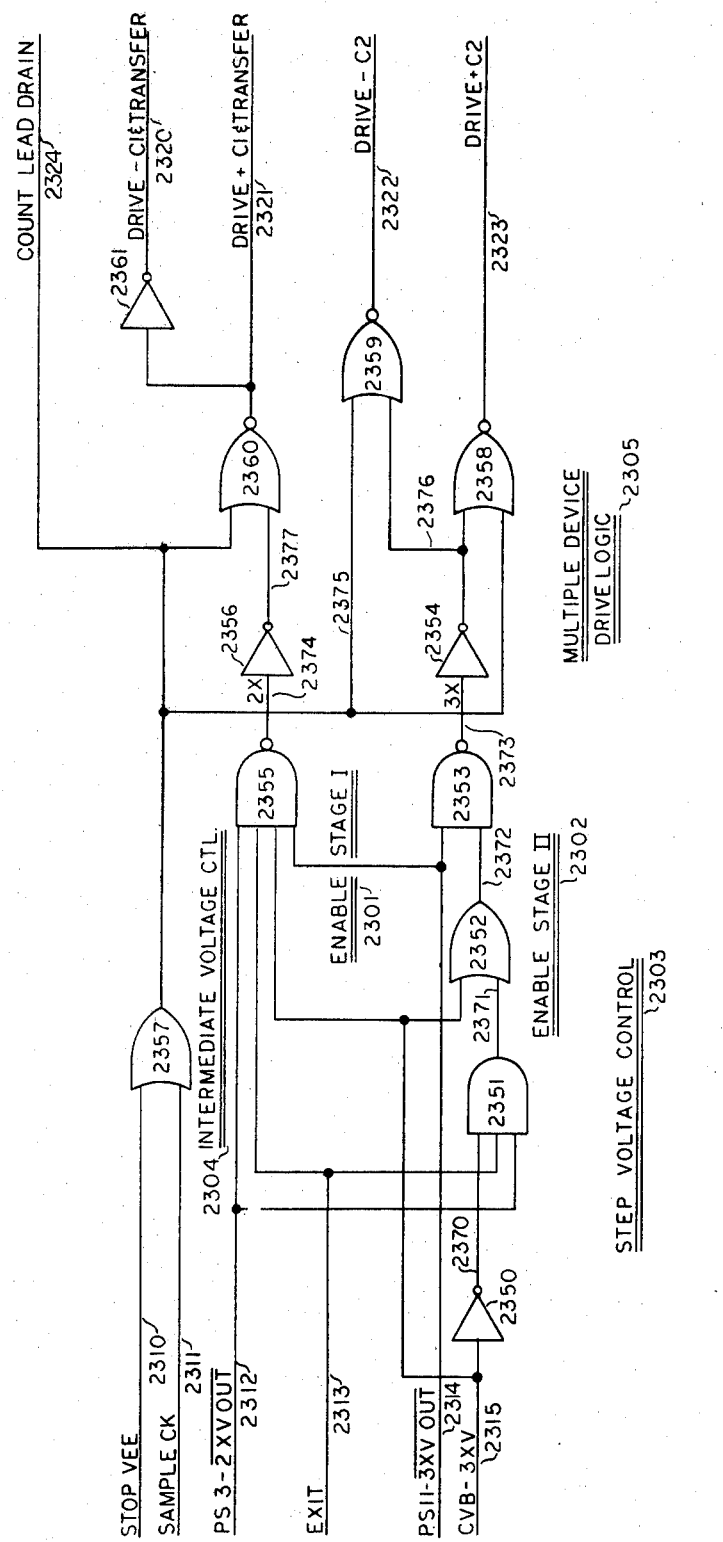
FIG. 23. OUTPUT VOLTAGE MULTIPLIER (222) CONTROL LOGIC

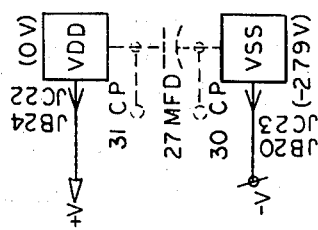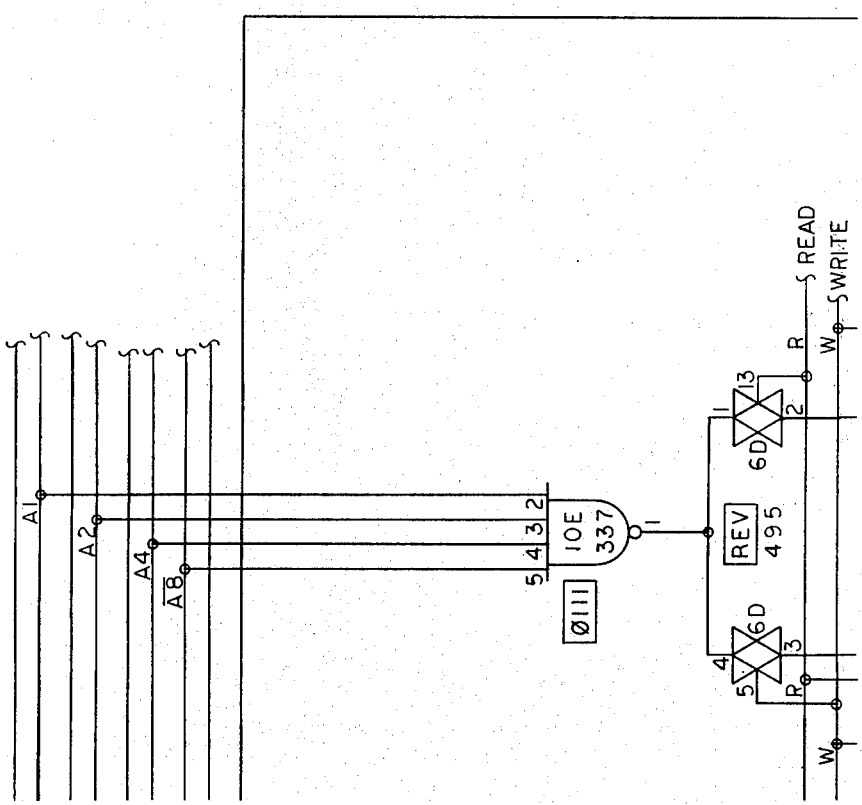
FIG. 24G

VENTRICULAR DIGITAL FILTER

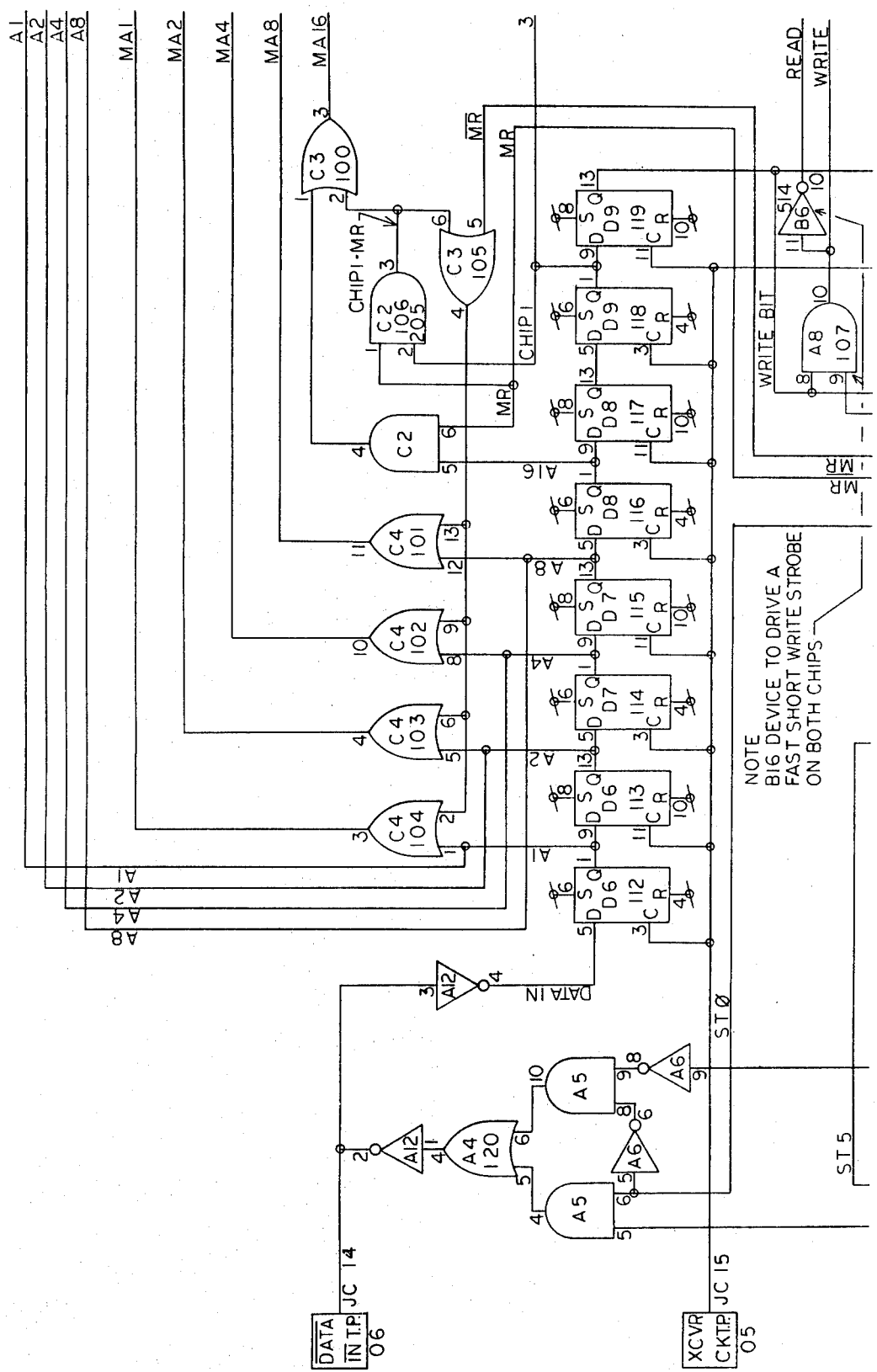
FIG.25-A

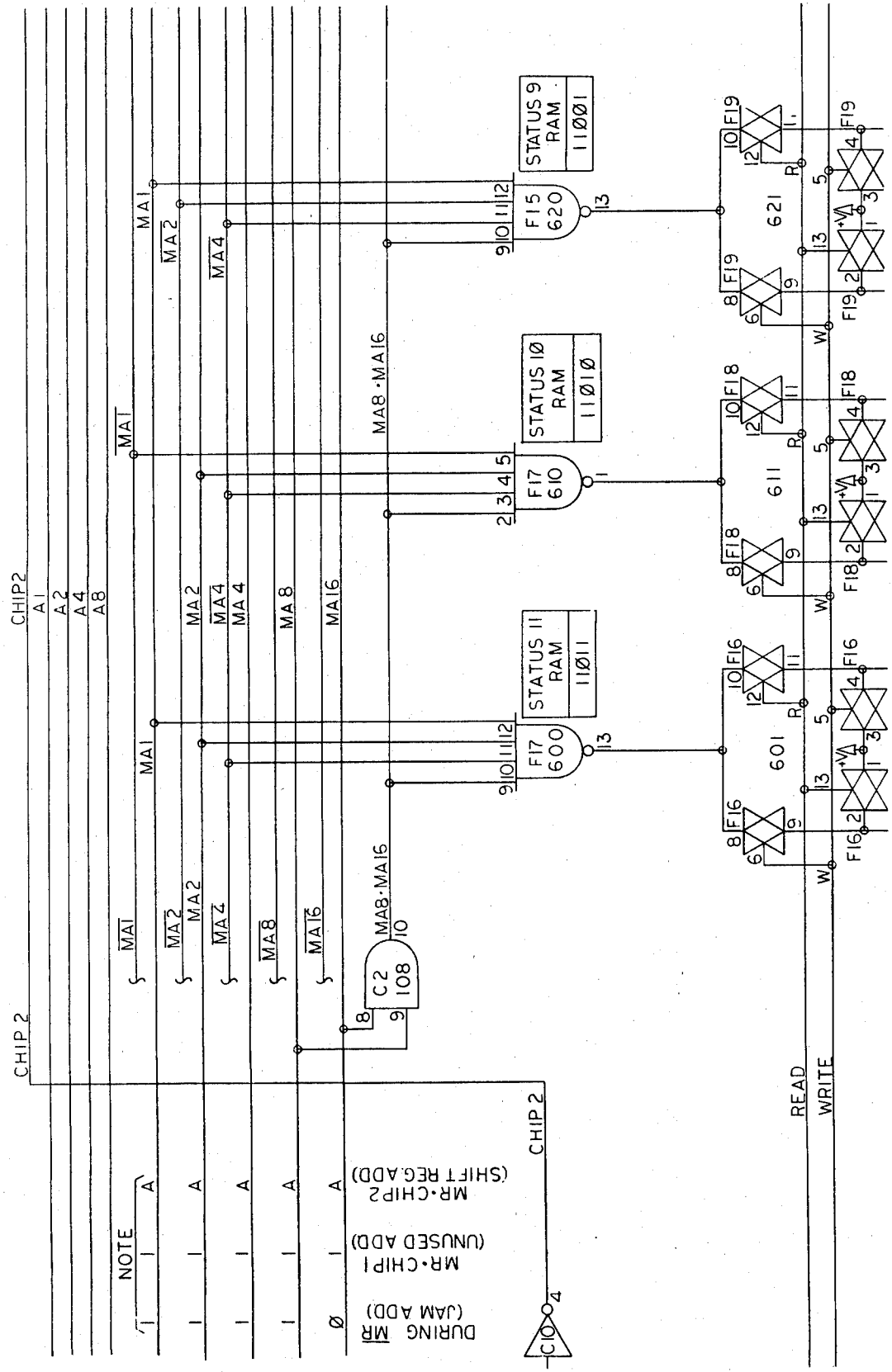
FIG.25-B

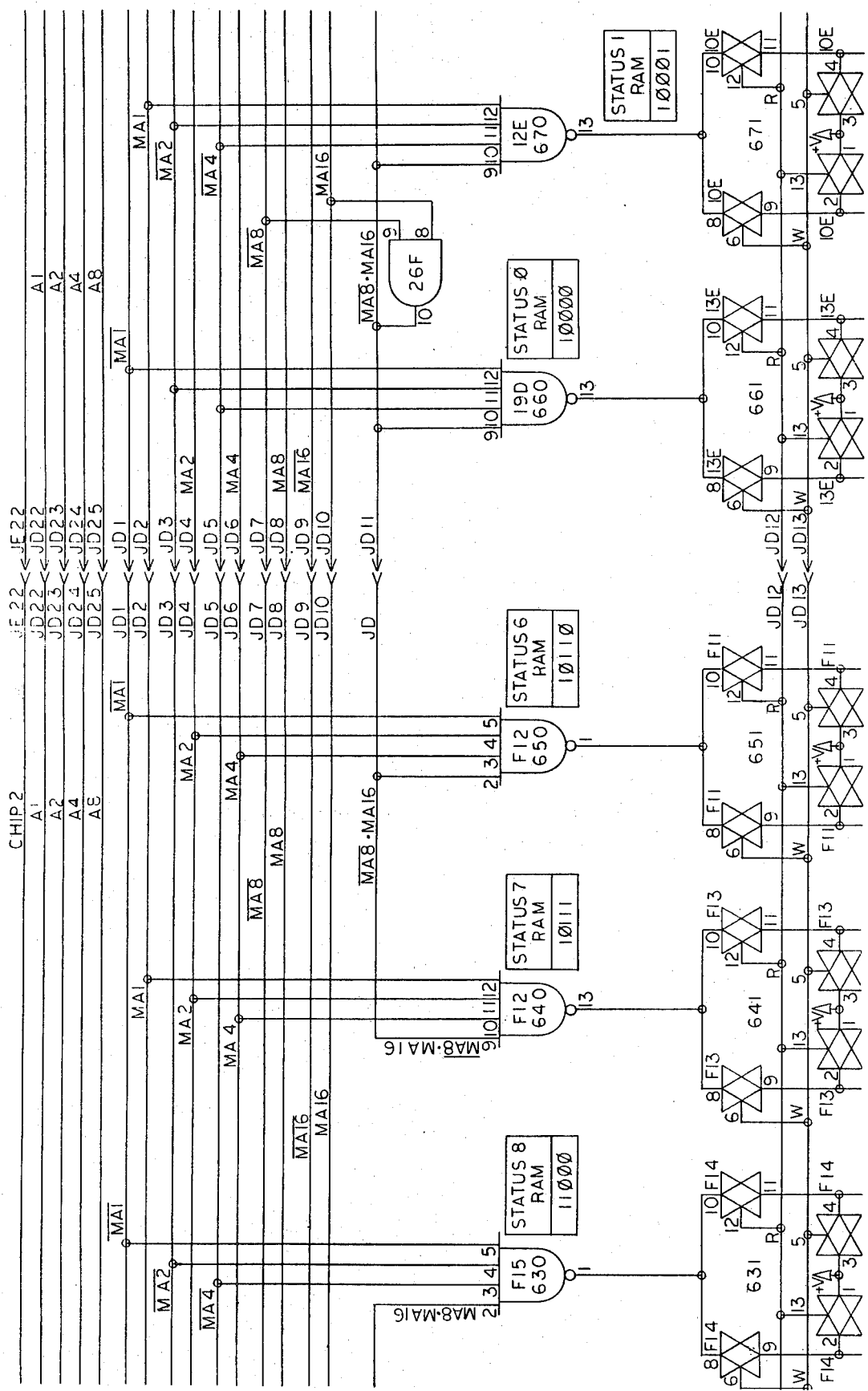
FIG.25-C

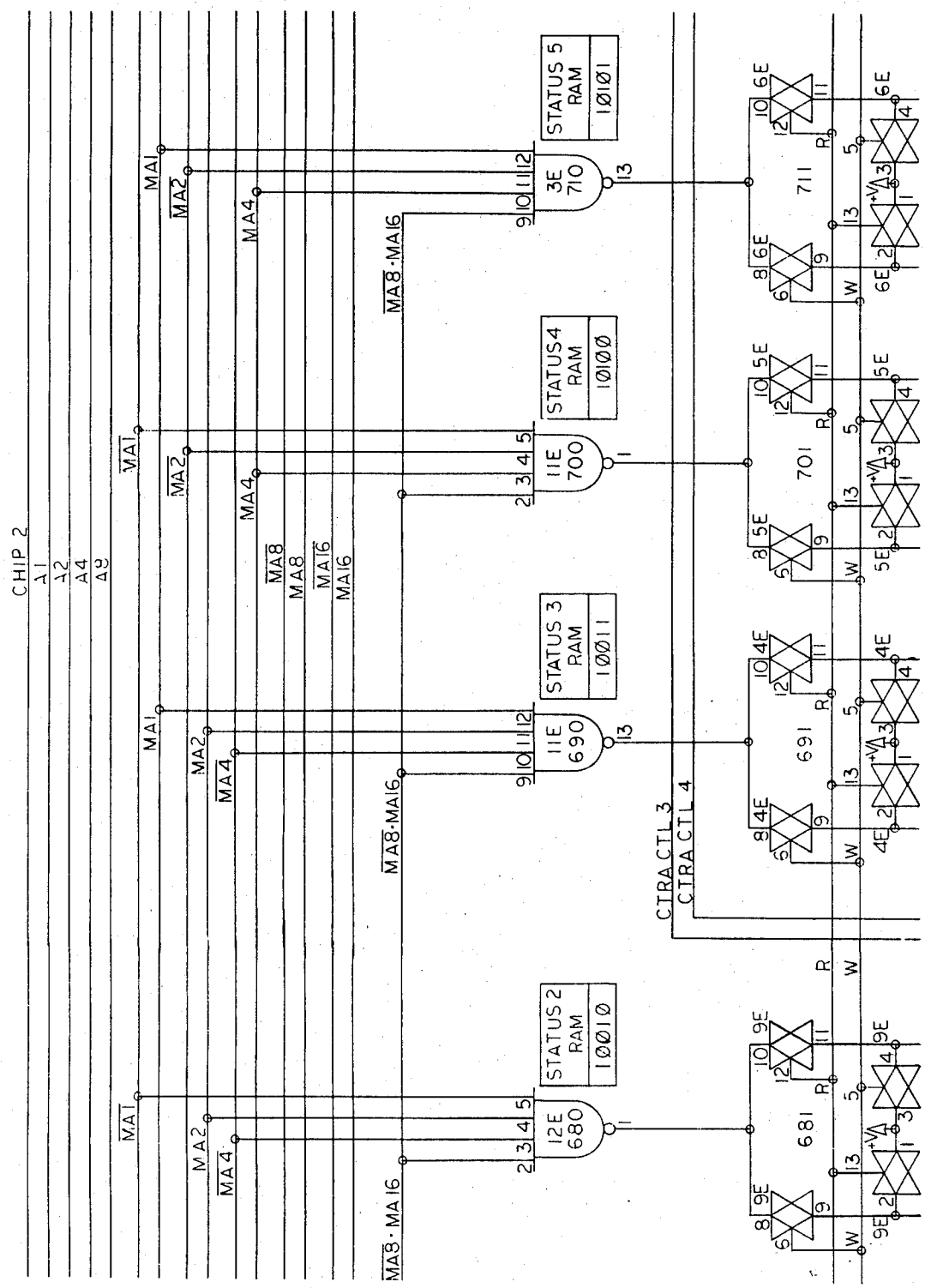
FIG.25-D

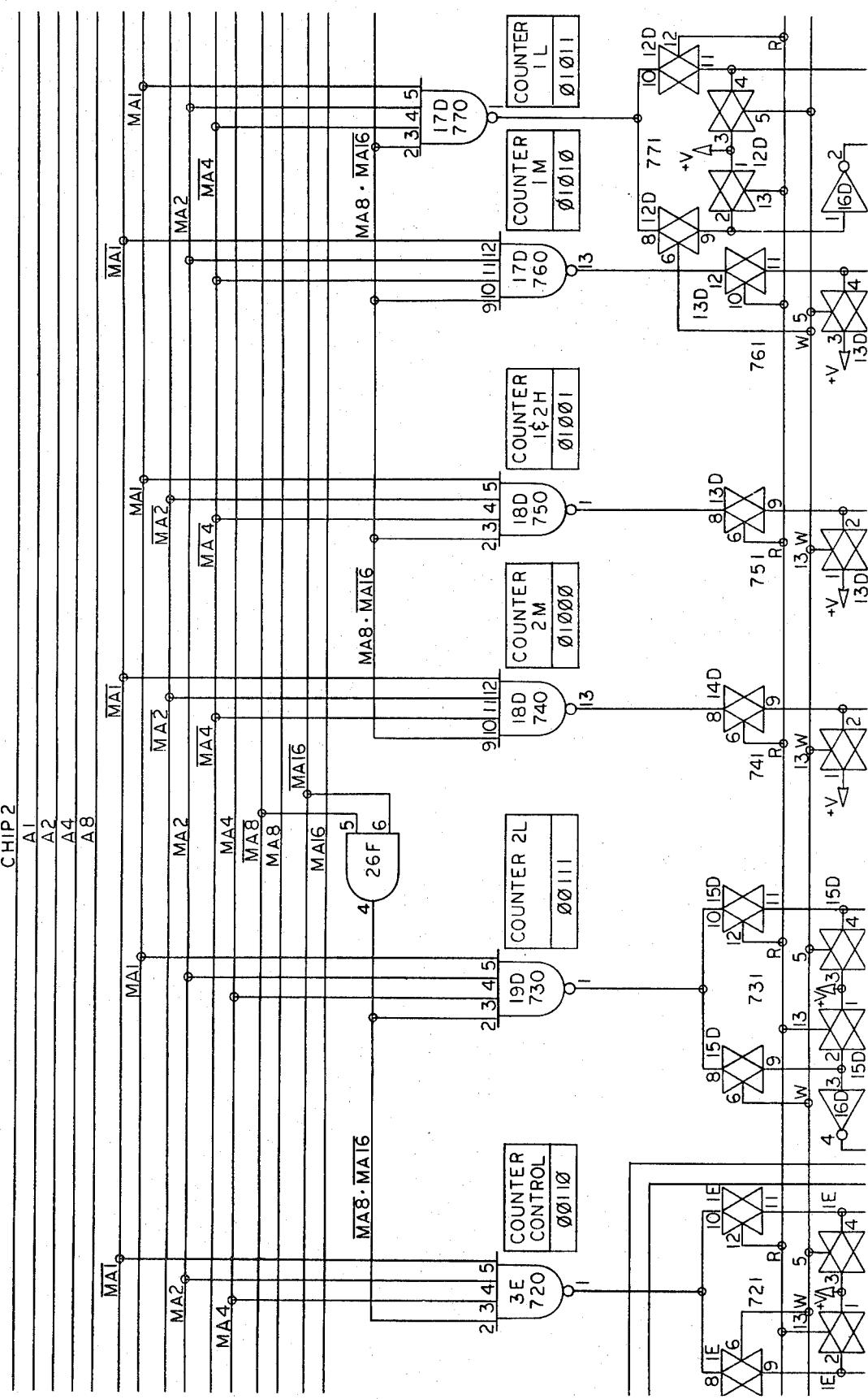

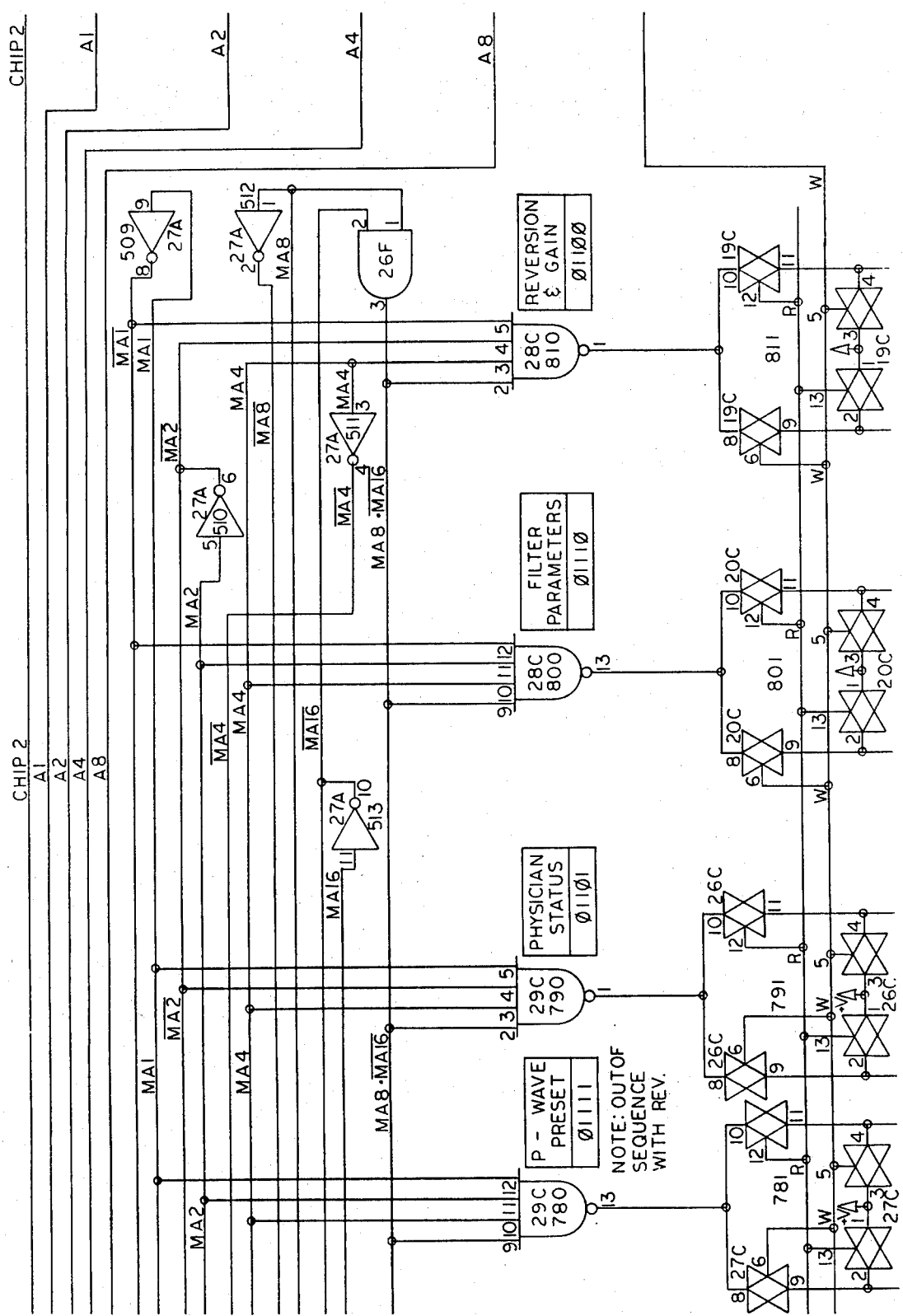
FIG.25-F

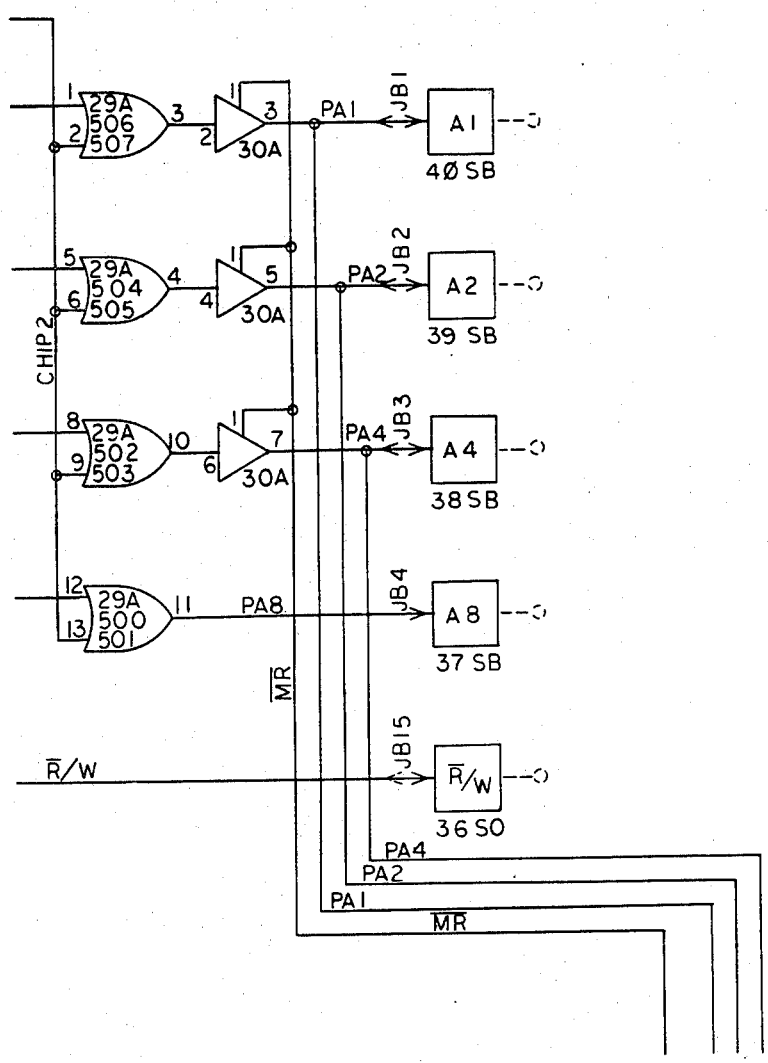
FIG. 25-G

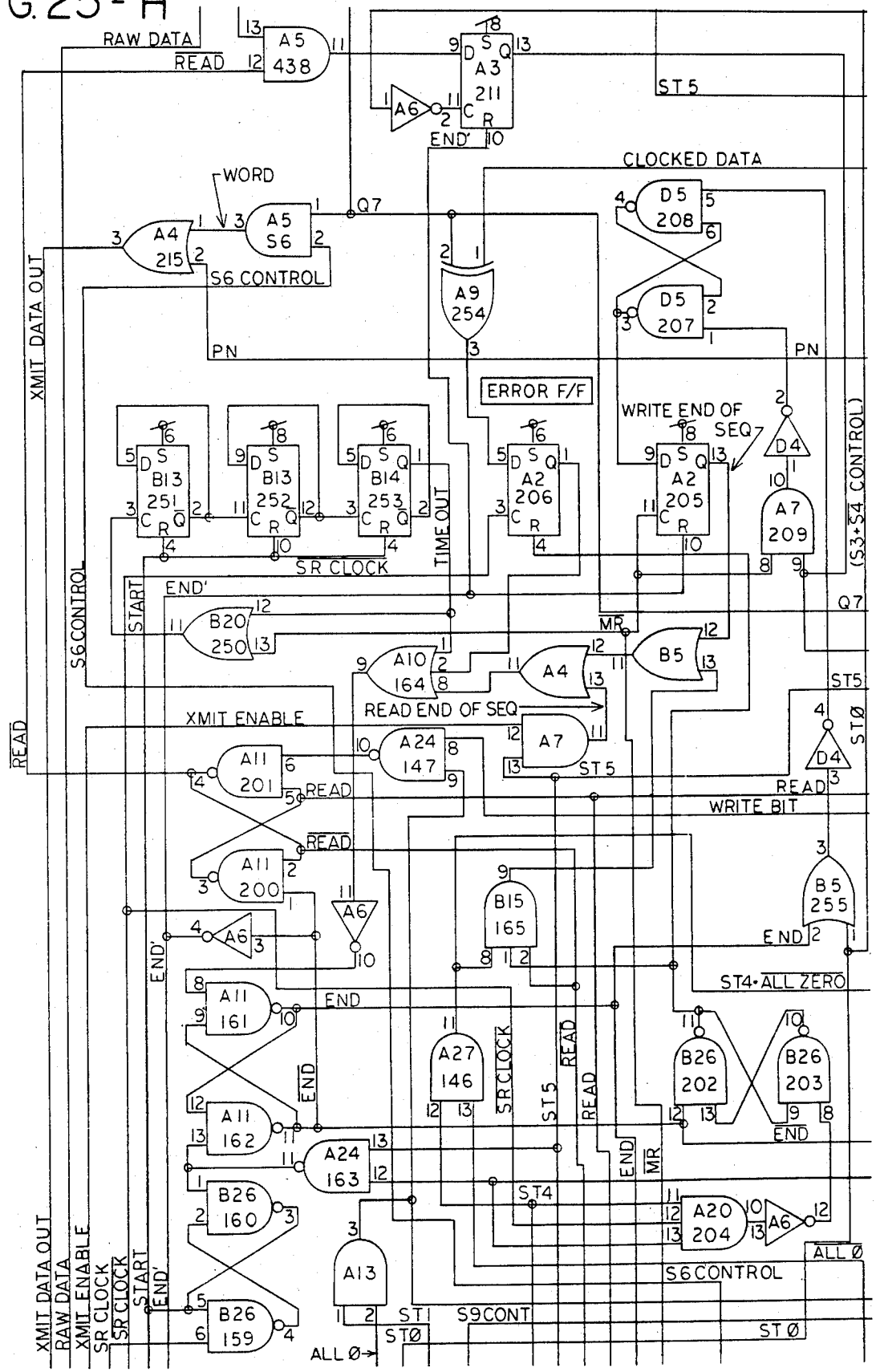
FIG. 25-H

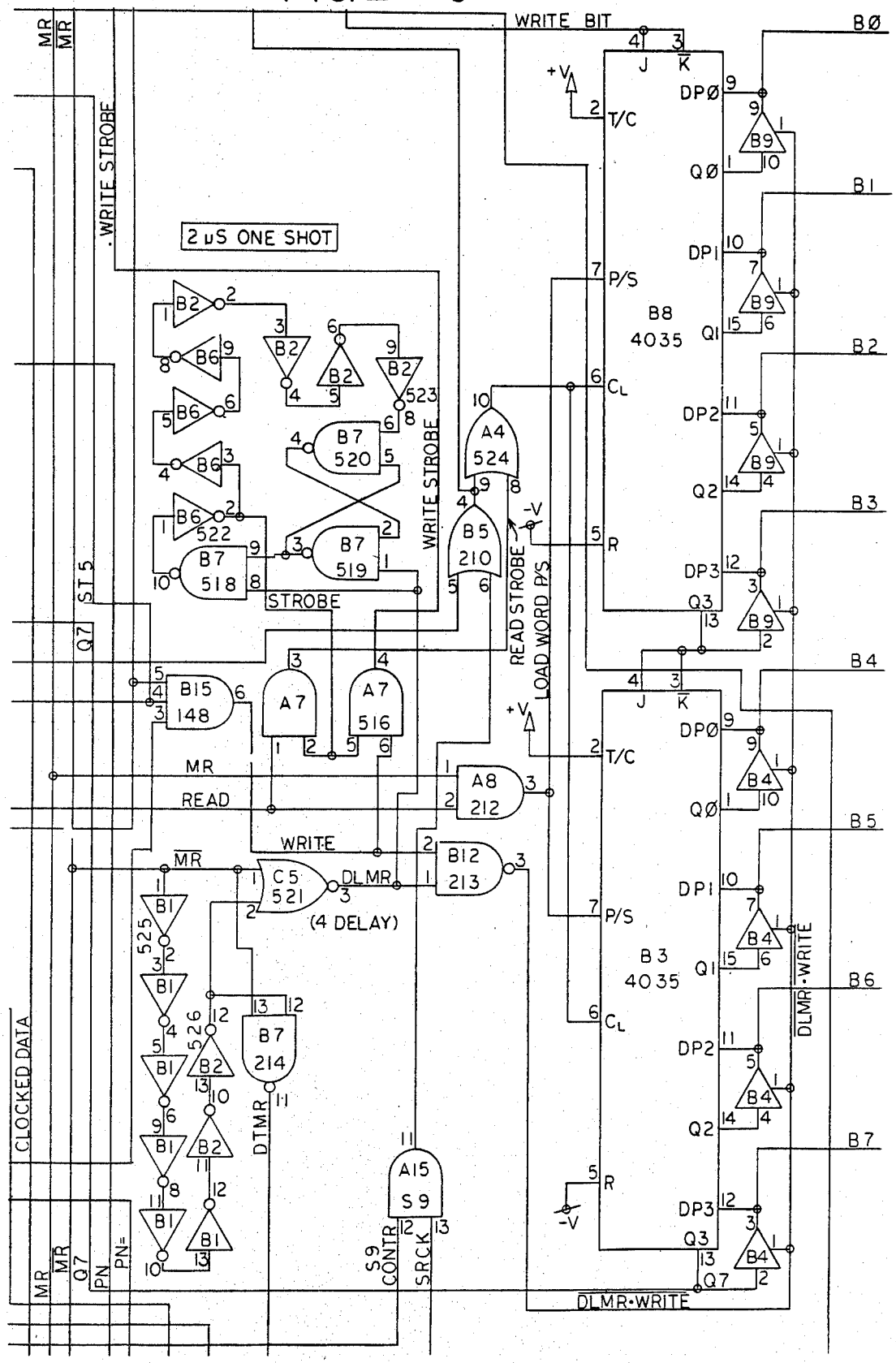
FIG. 25-J

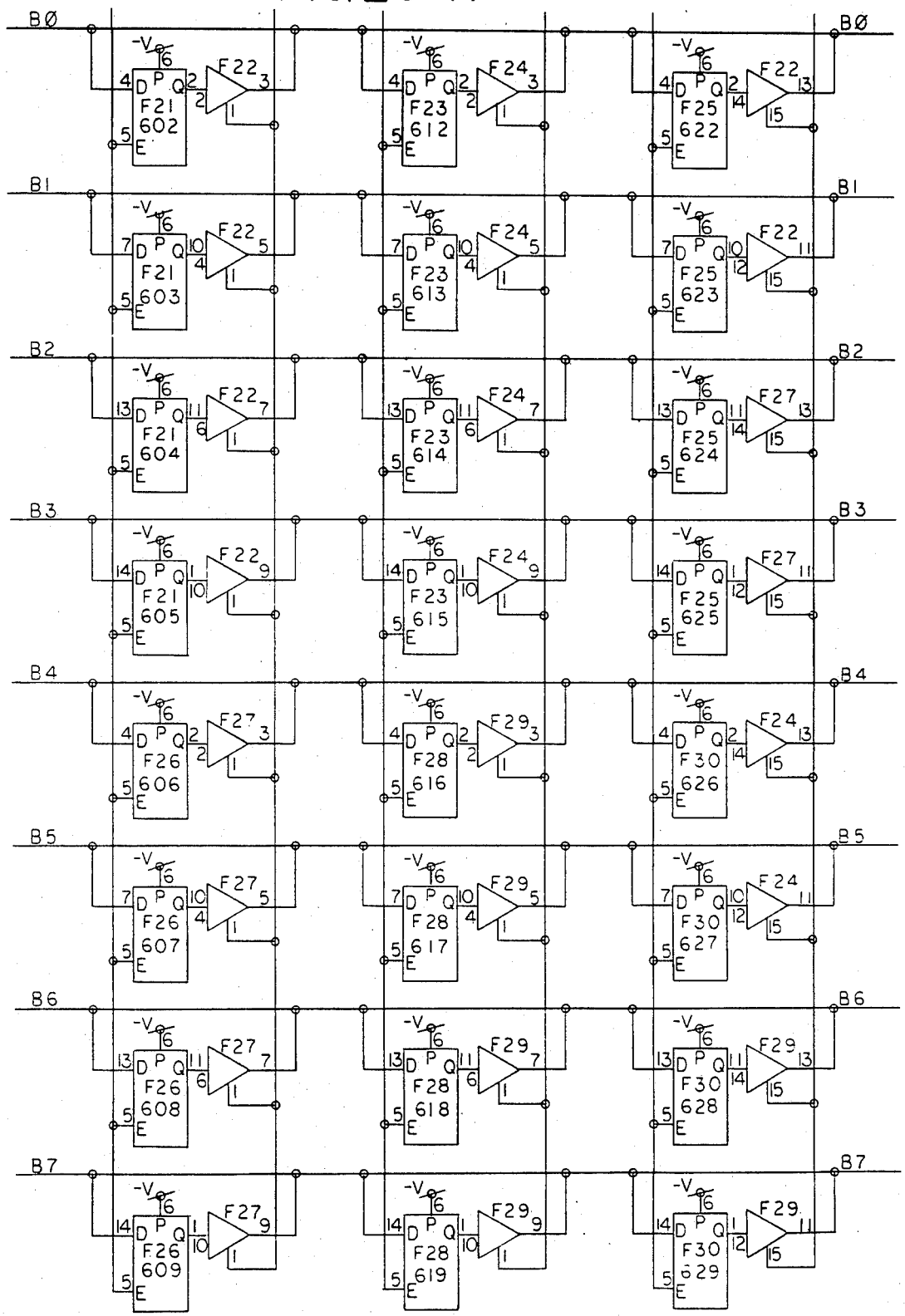
FIG. 25-K

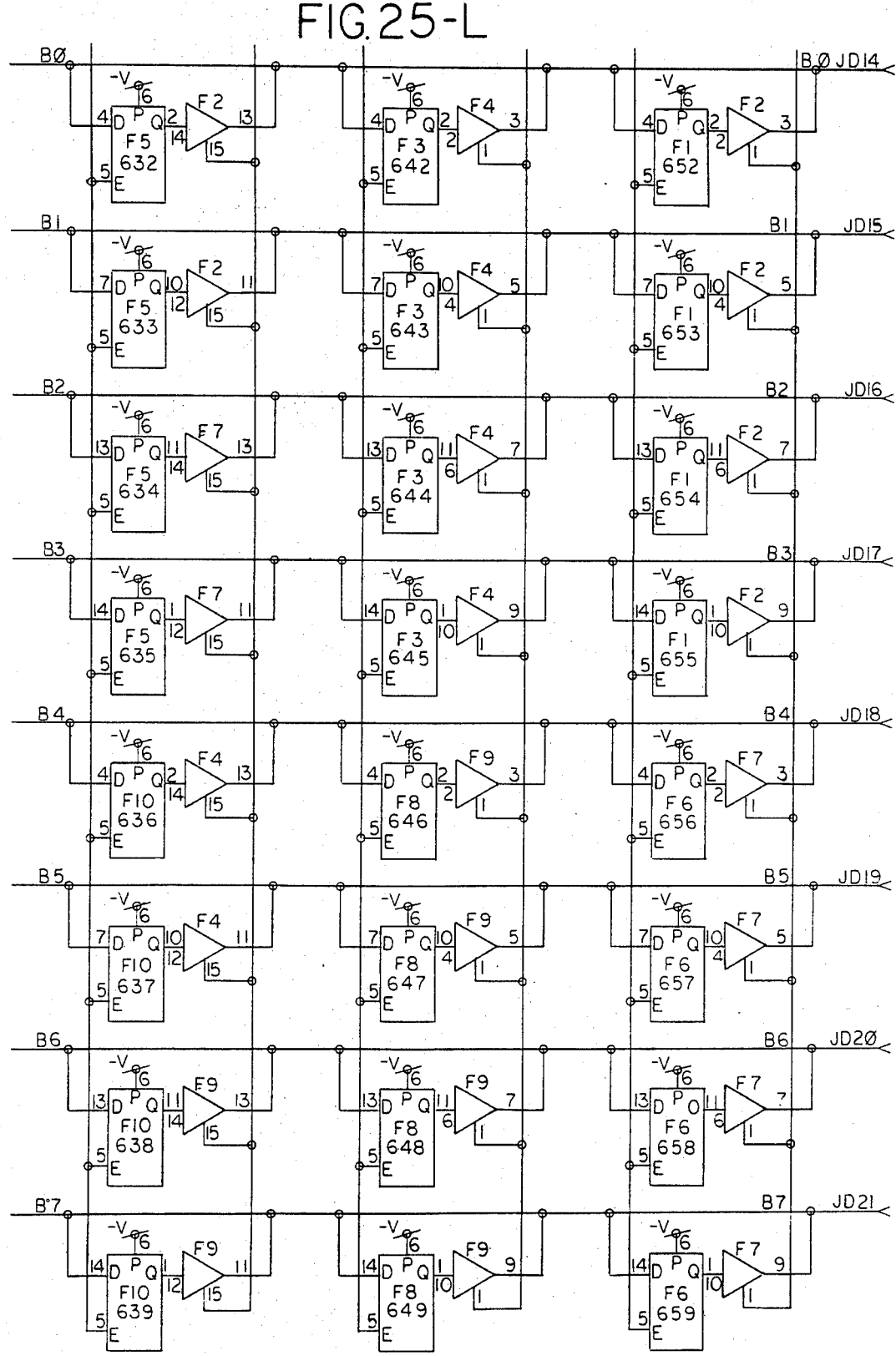
FIG. 25-L

FIG. 25-M
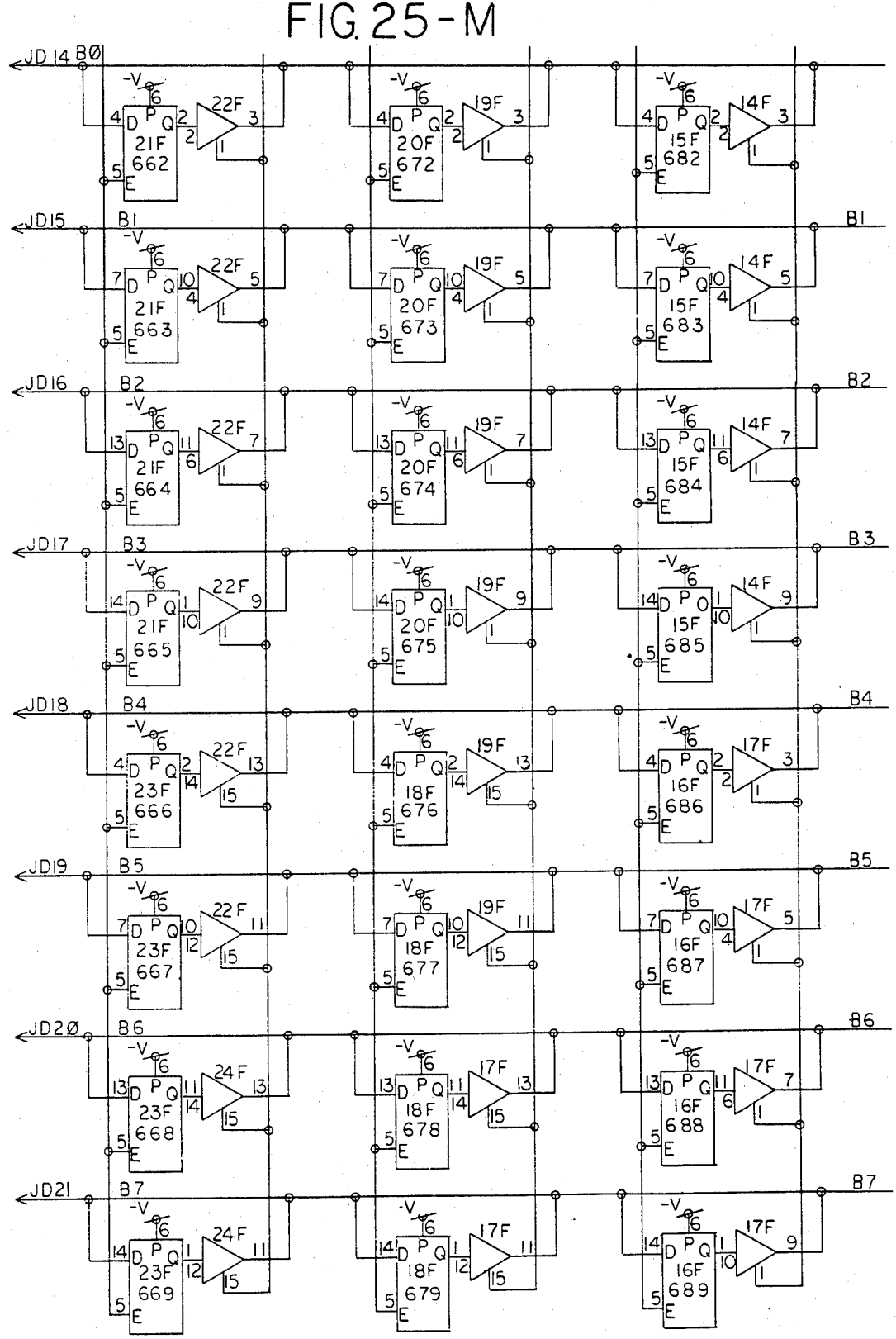

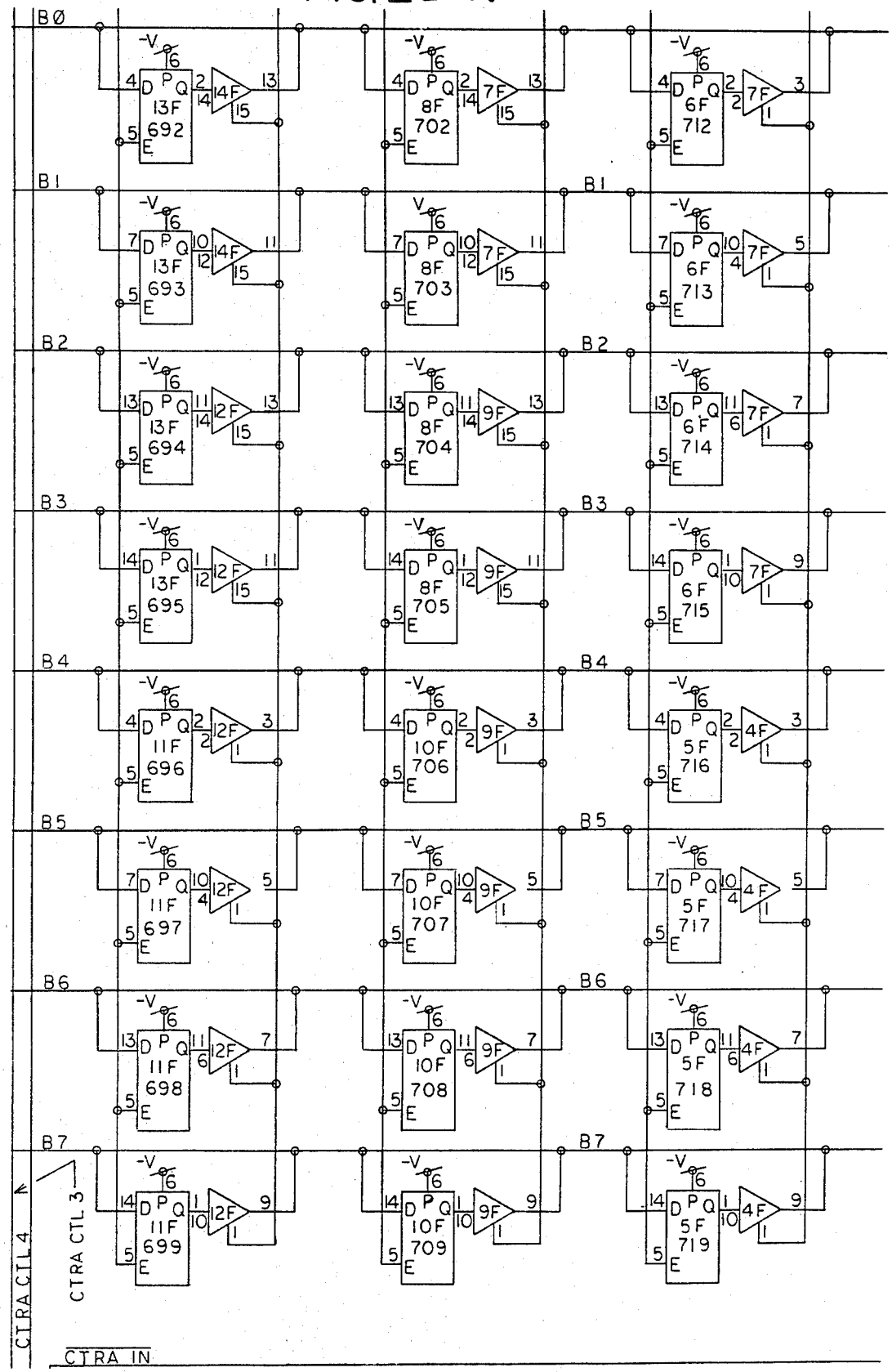
FIG. 25-N

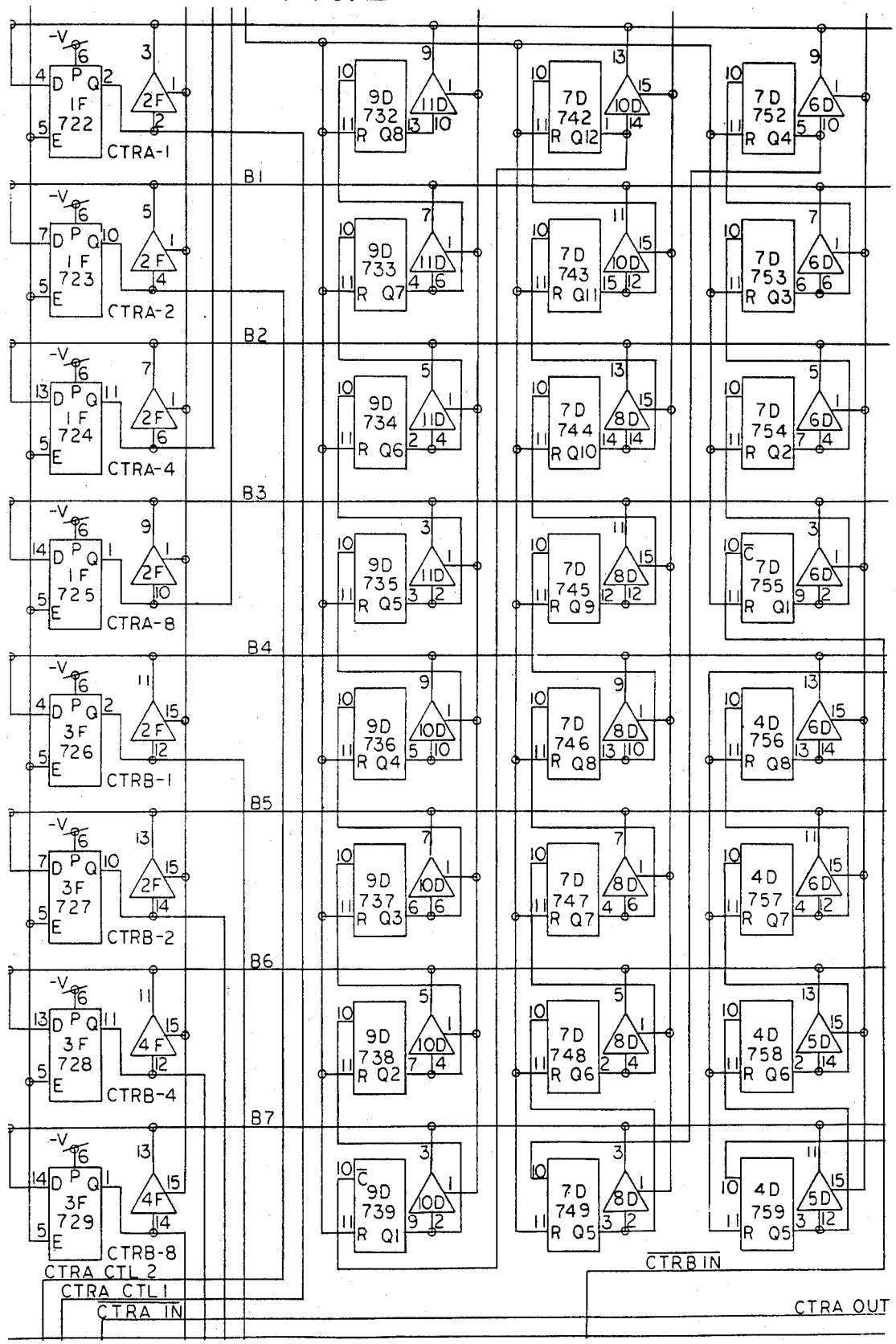
FIG. 25-P

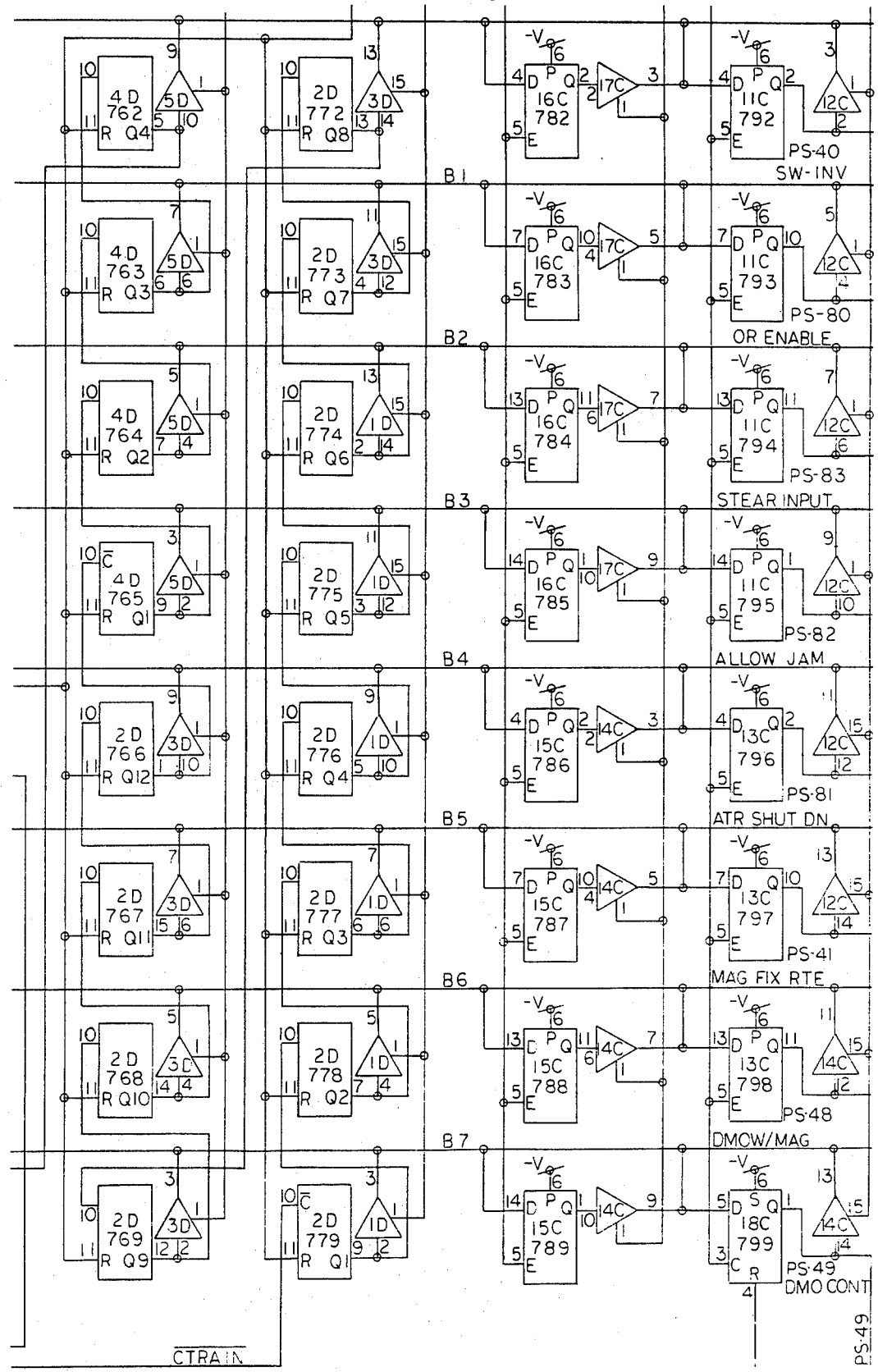
FIG. 25-Q

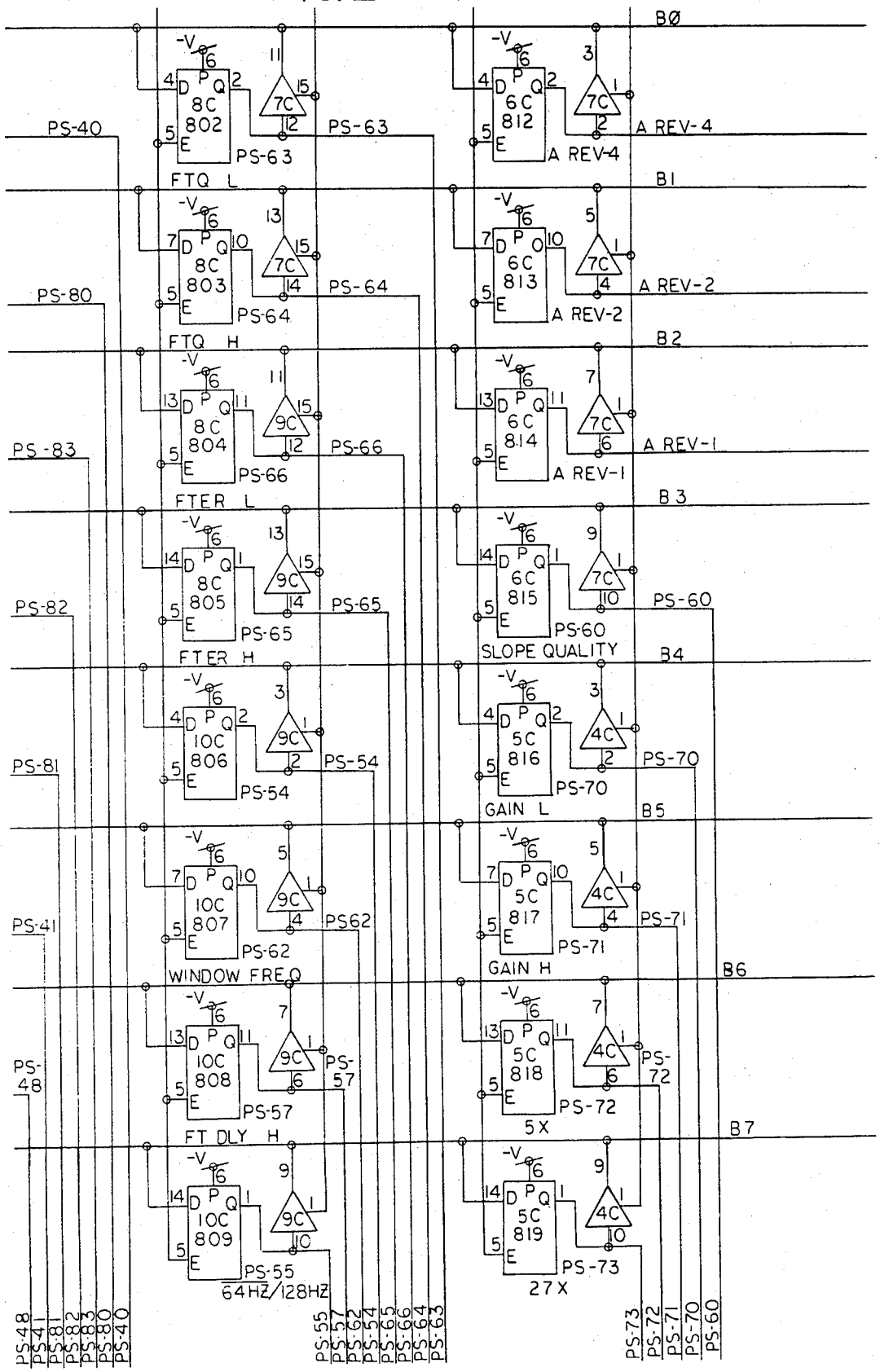
FIG.25-R

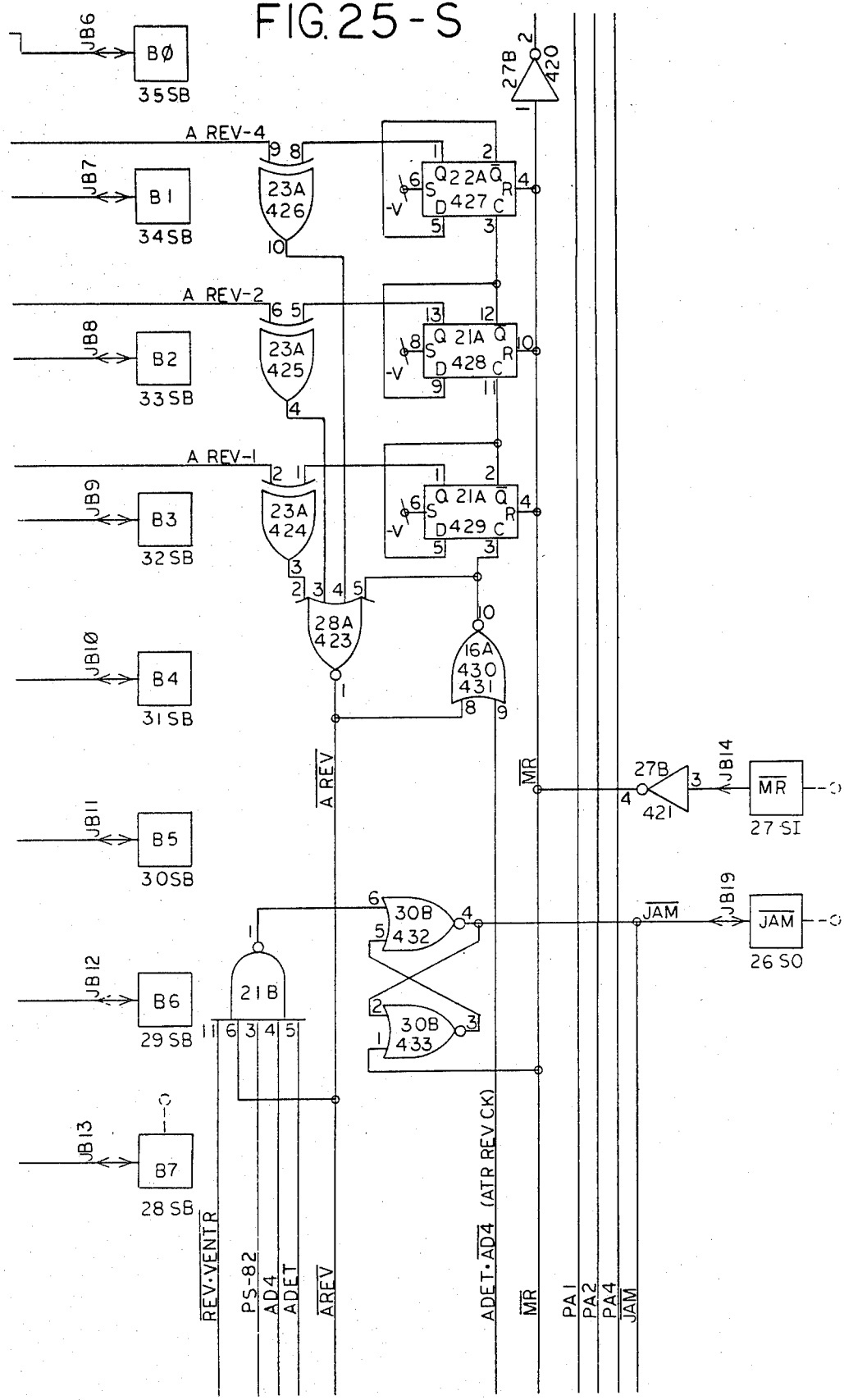
FIG. 25-S

FIG. 25-T

XMIT DATA OUT
RAW DATA
XMIT ENABLE
S R CLOCK
SR CLOCK
START
END

ALL ZERO
ST 0
ST 1

S 9 CONTROL

ST 4
ST 5
READ
READ
END
$\overline{MR}$

S 6 CONTROL

ALL ZERO
CLOCKED DATA

PN
PN =
ST4·ALL ZERO

DTMR

FIG. 25-U
SR CLOCK
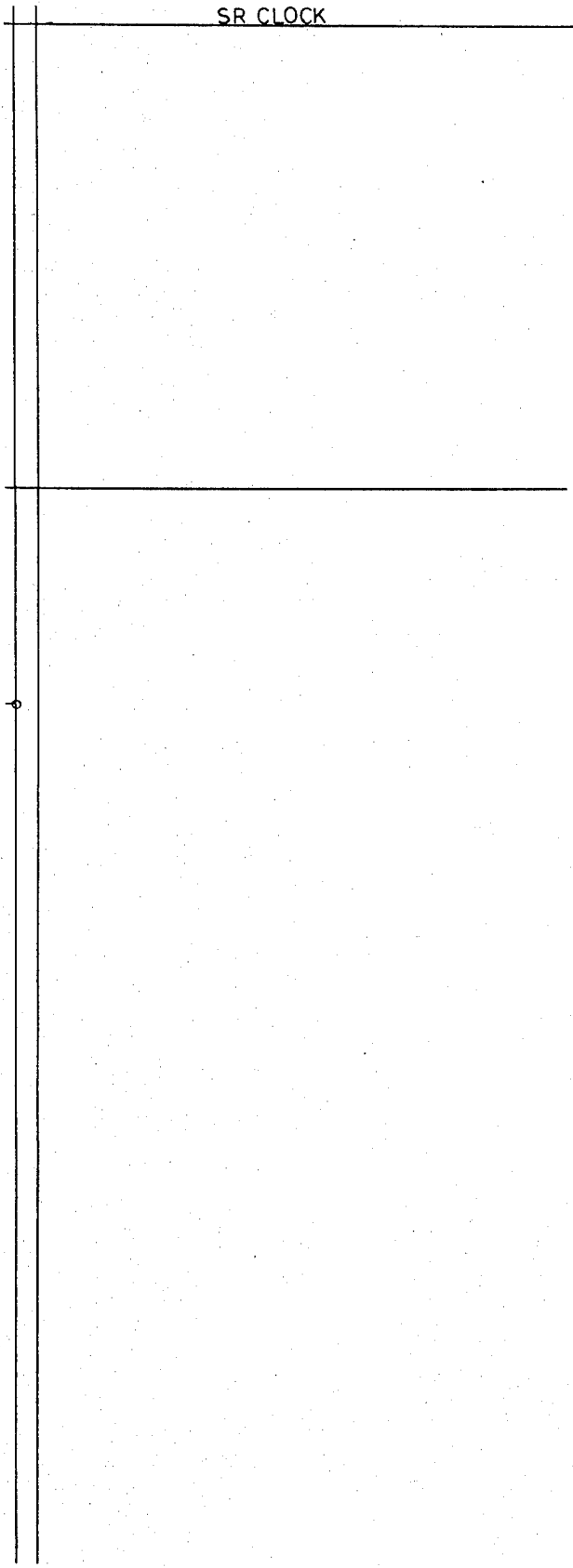

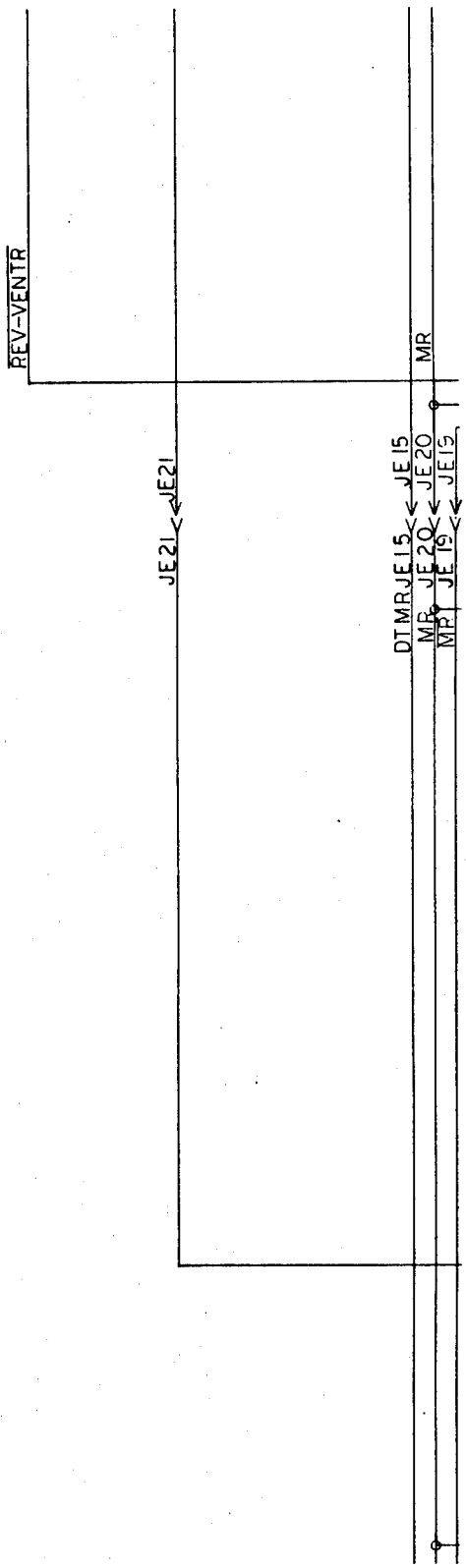
FIG. 25-V

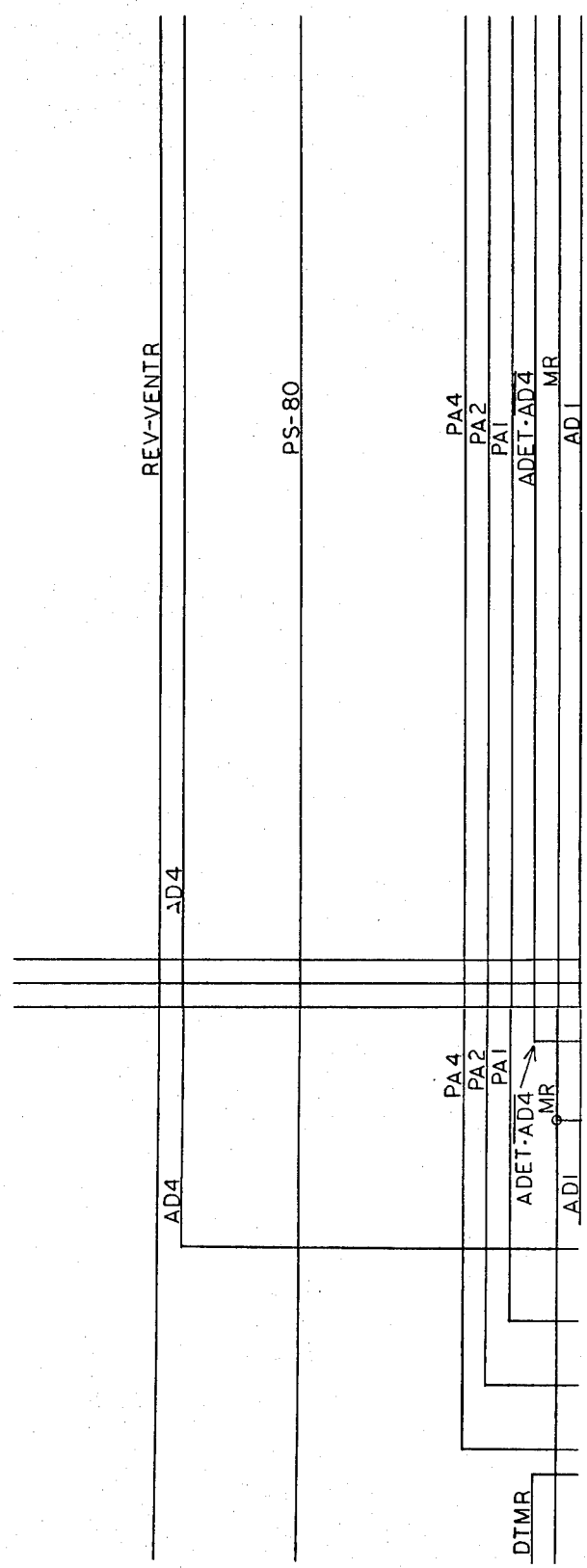
FIG.25-W

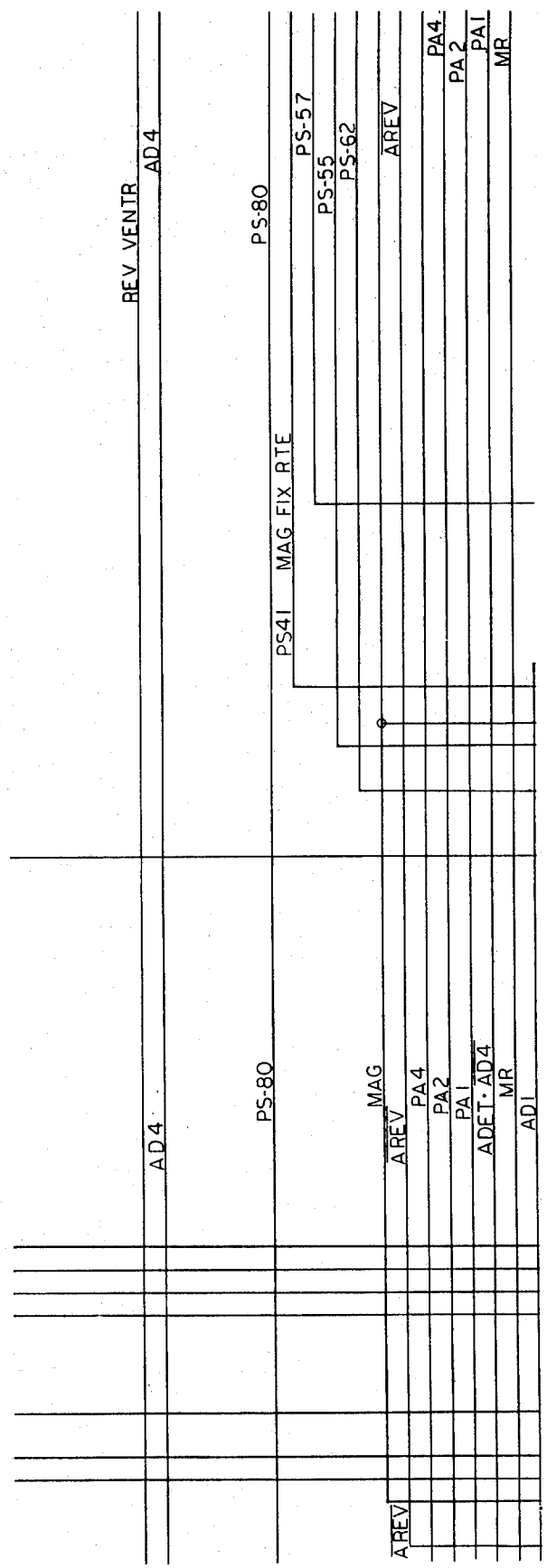
FIG. 25-X

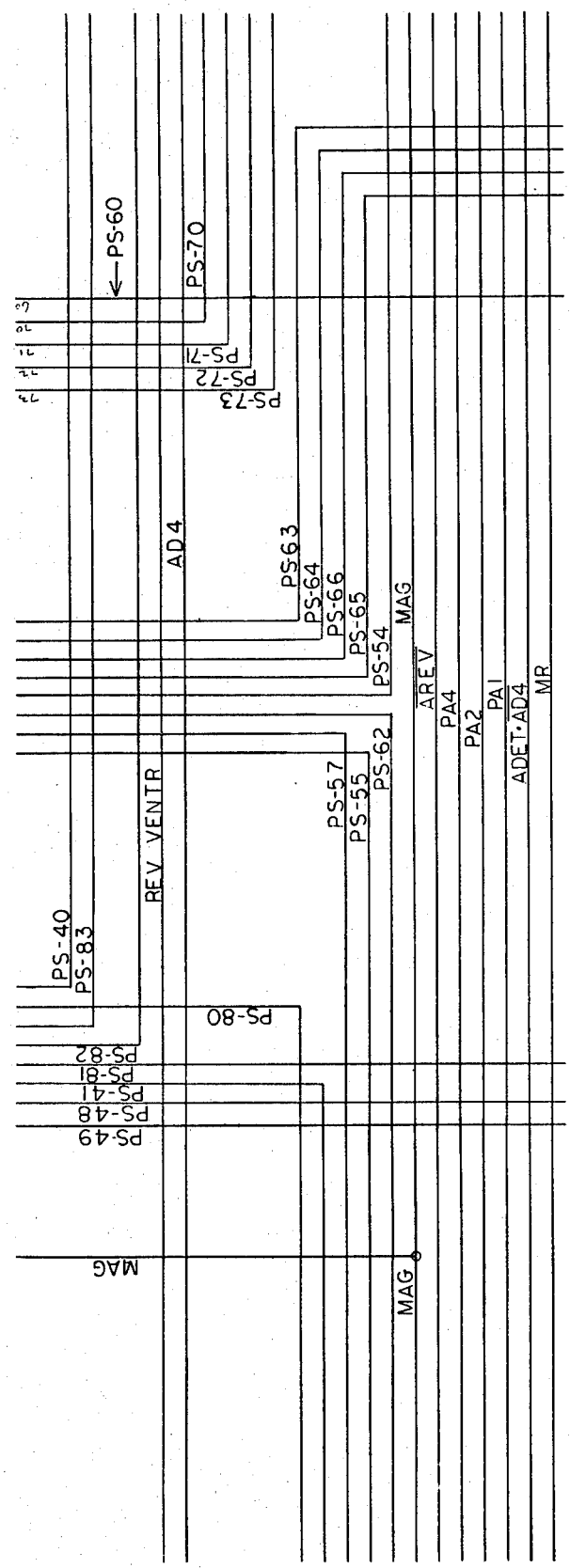
FIG.25-Y

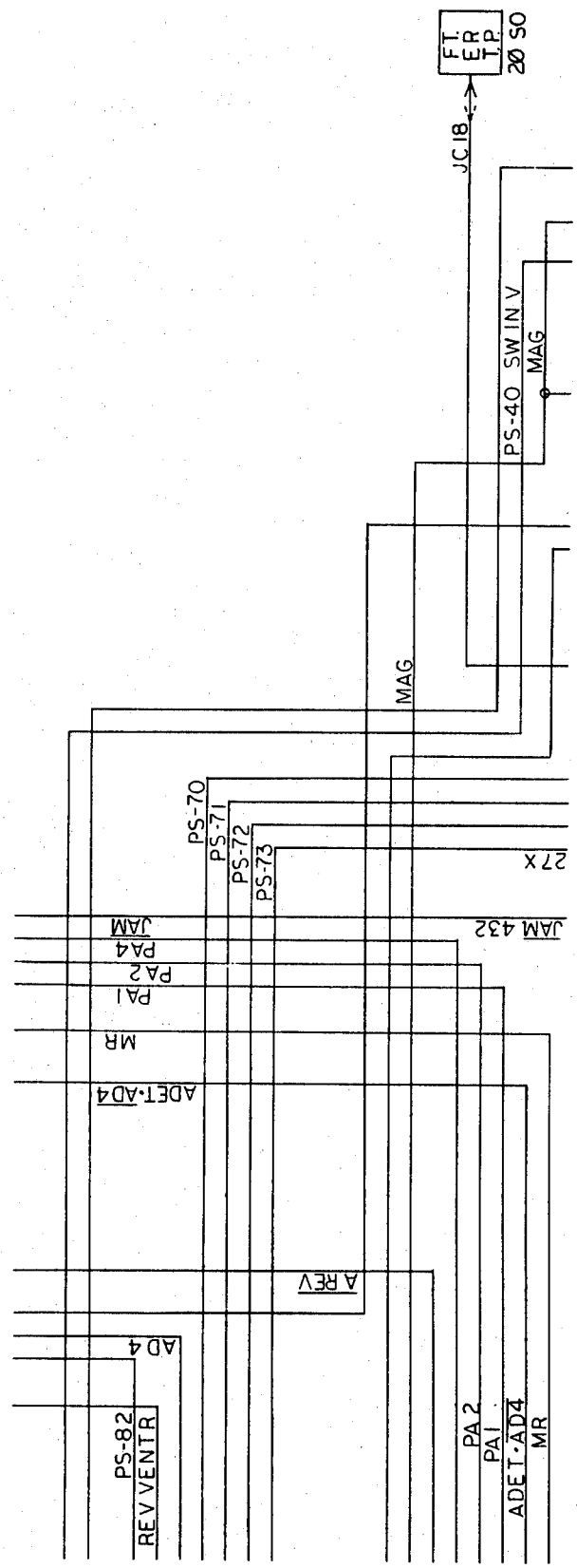

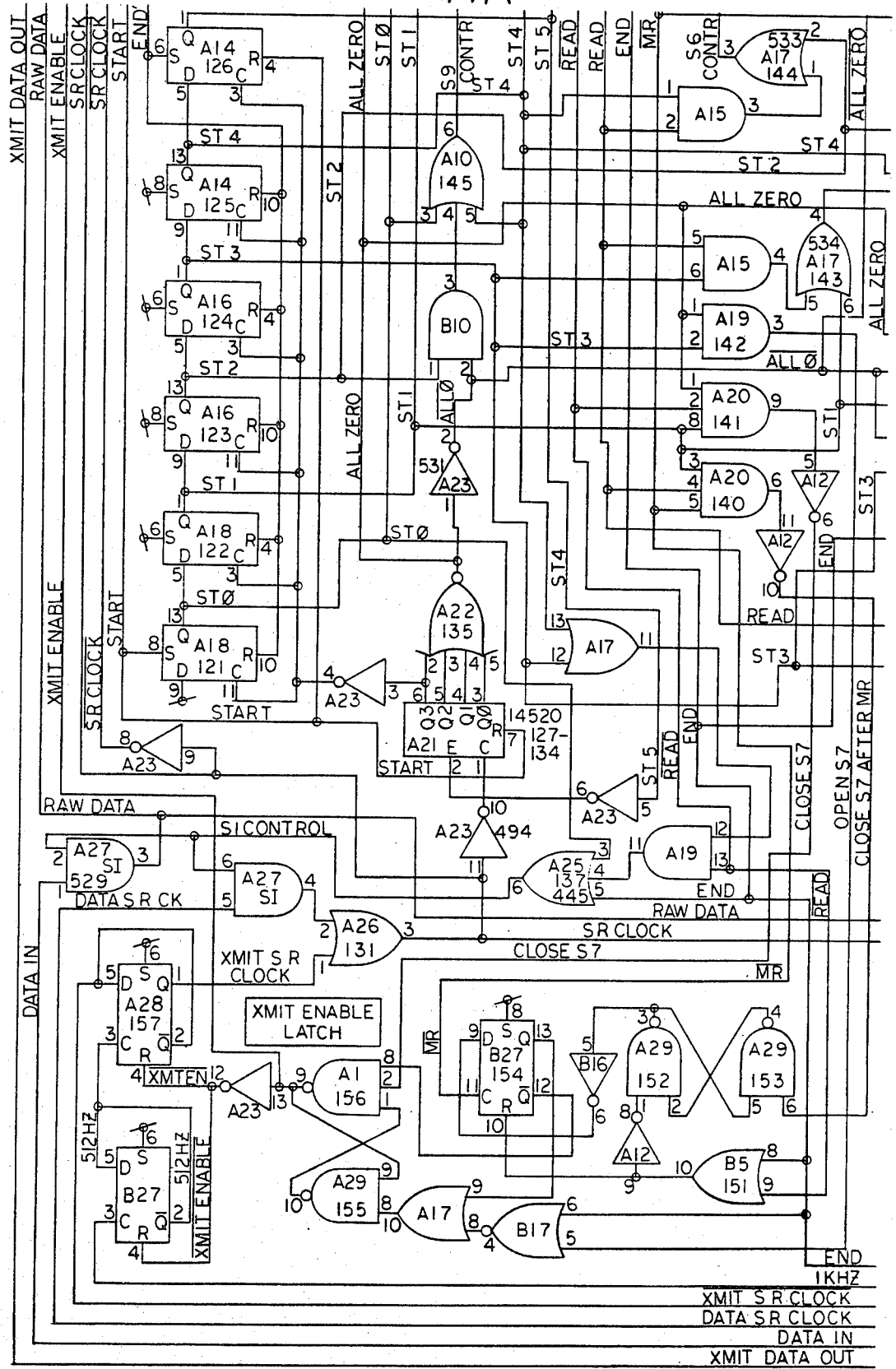
FIG. 25-AA

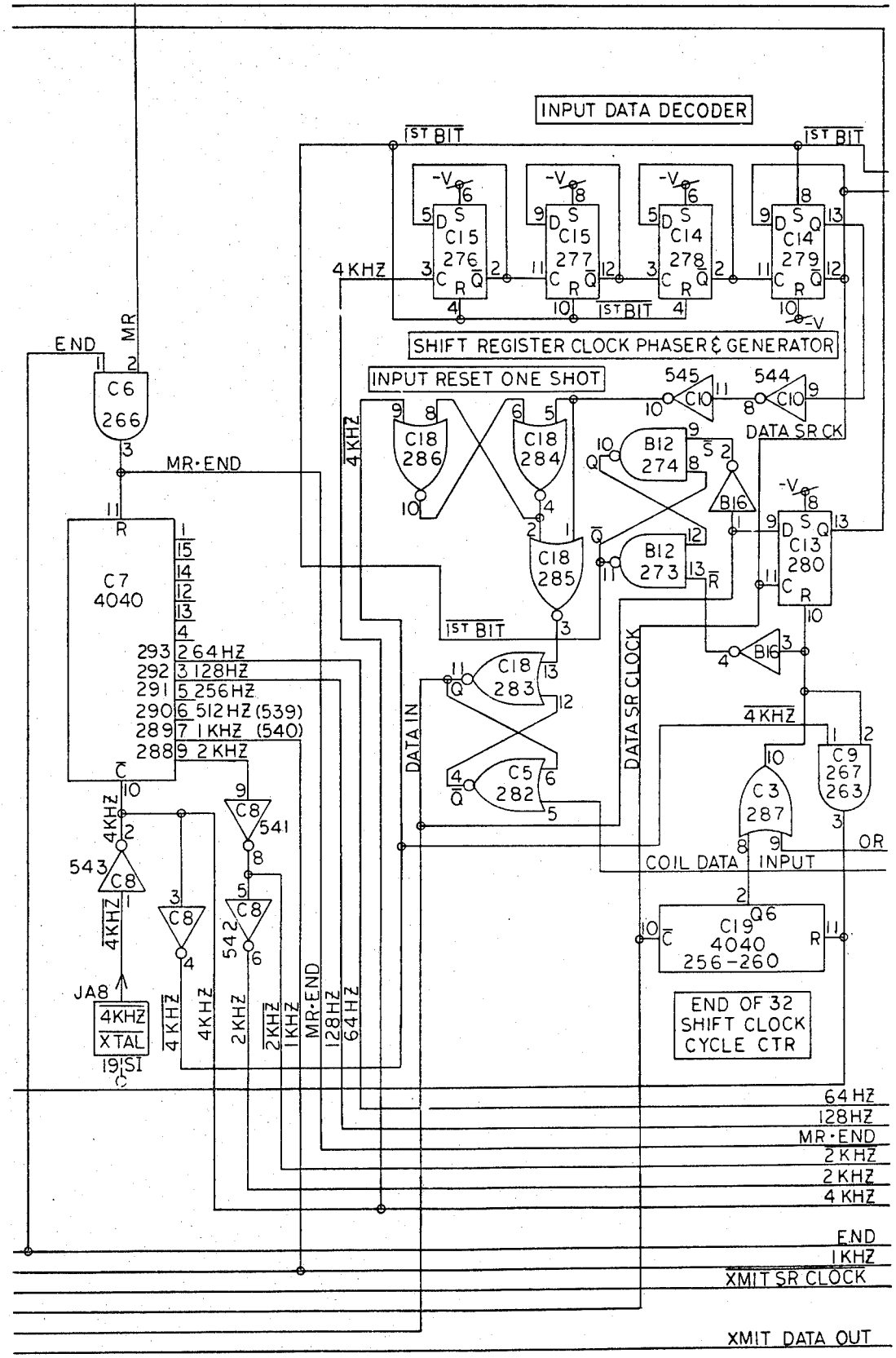
FIG. 25-CC

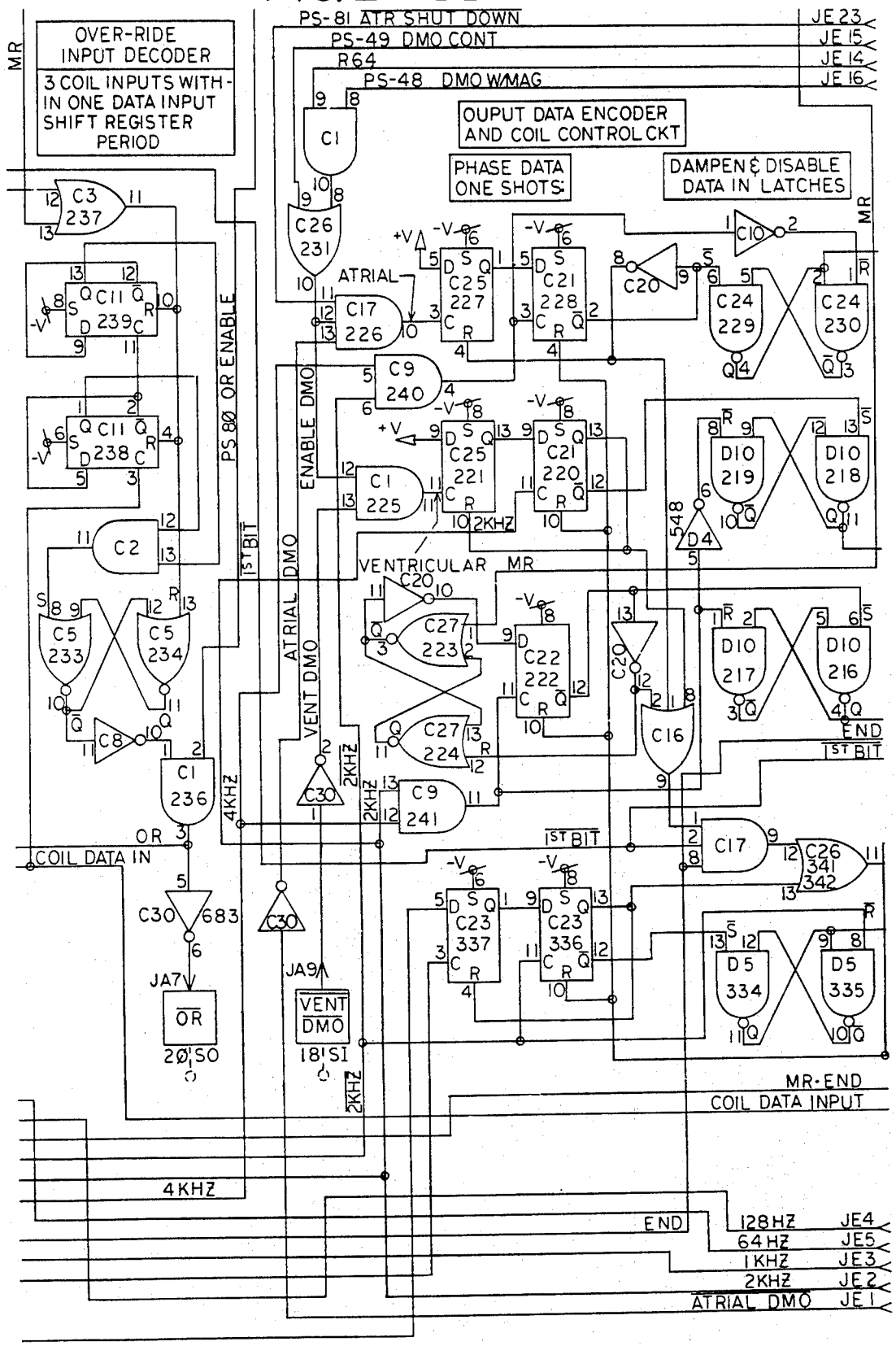
FIG. 25-DD

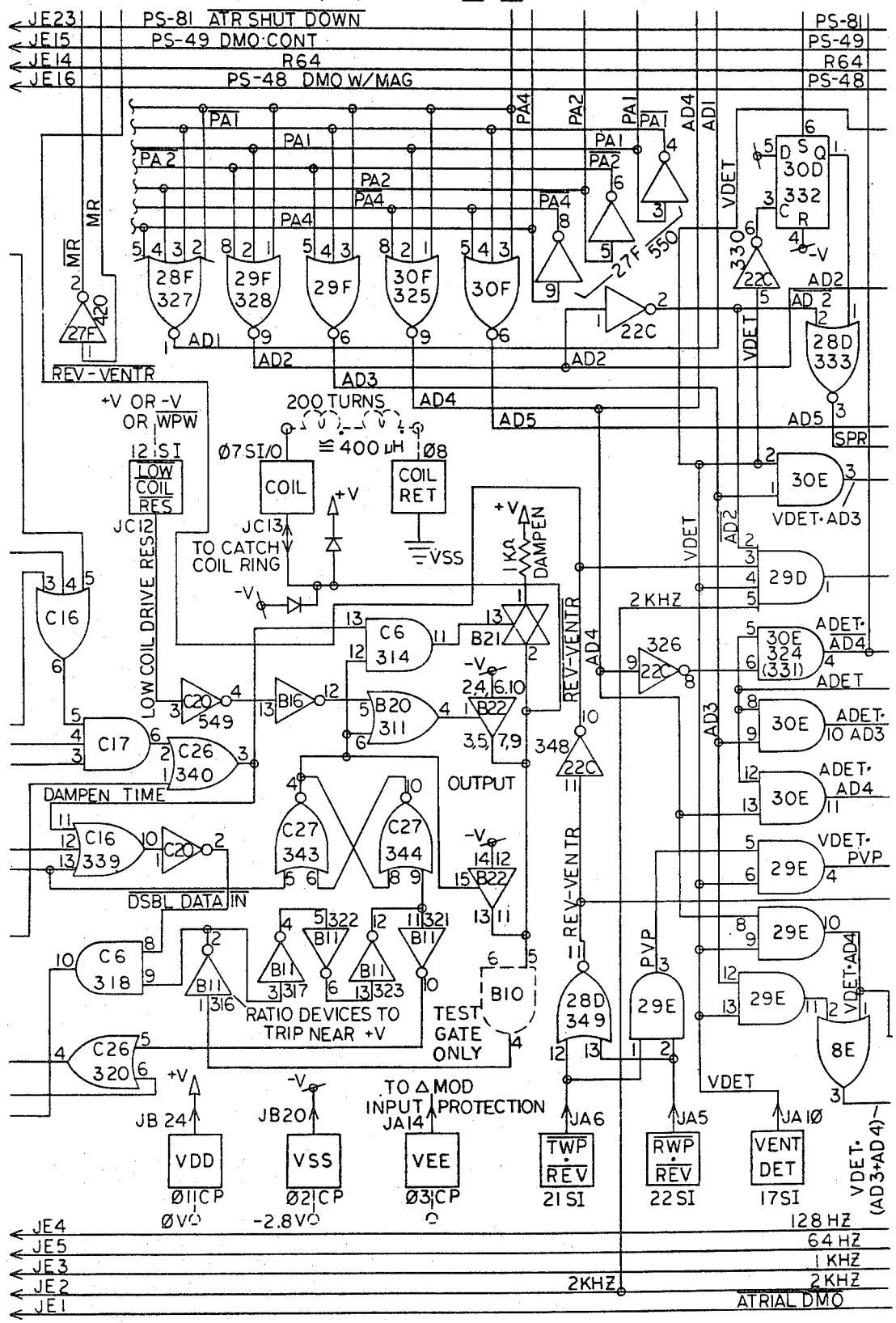
FIG. 25-EE

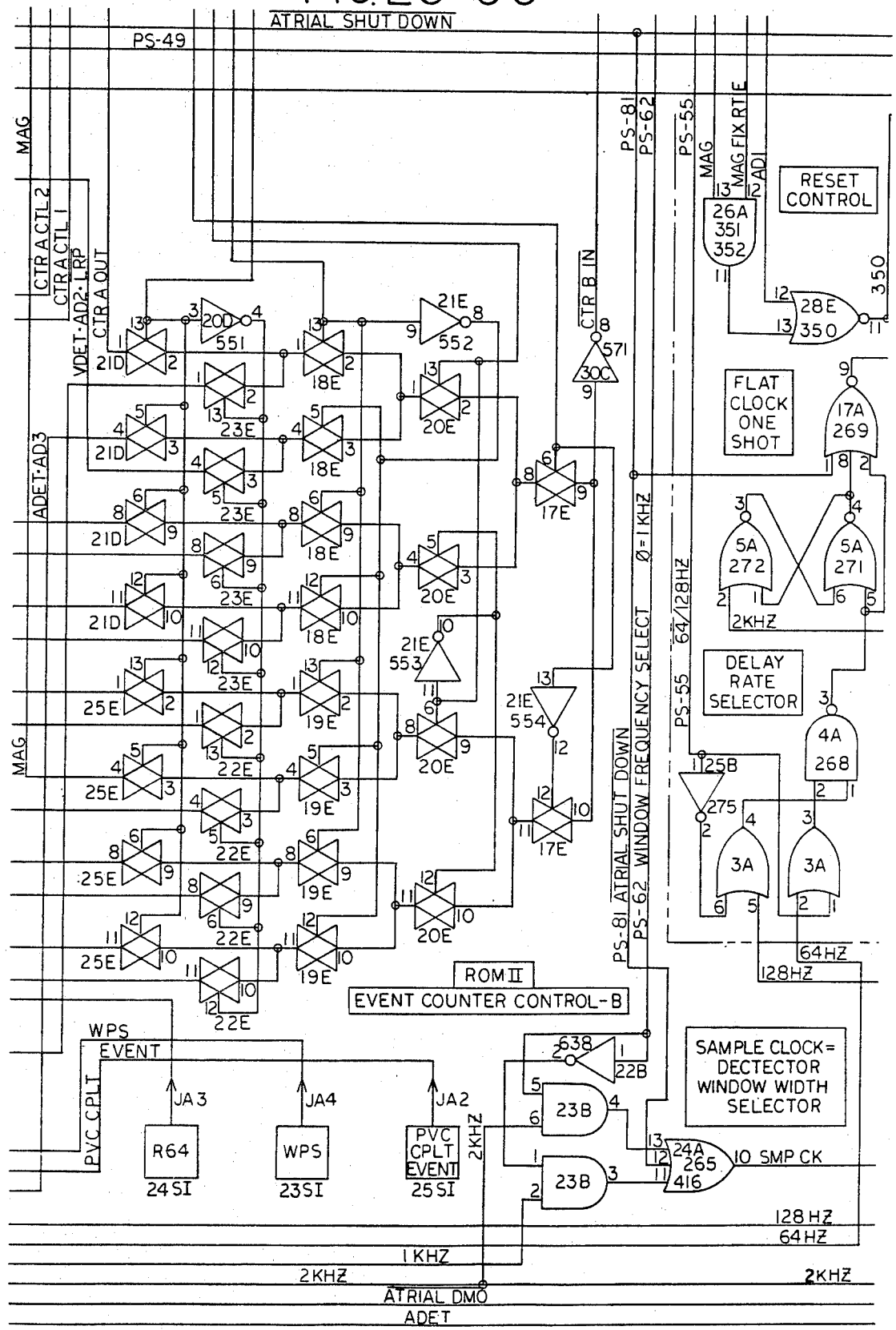
FIG. 25-GG

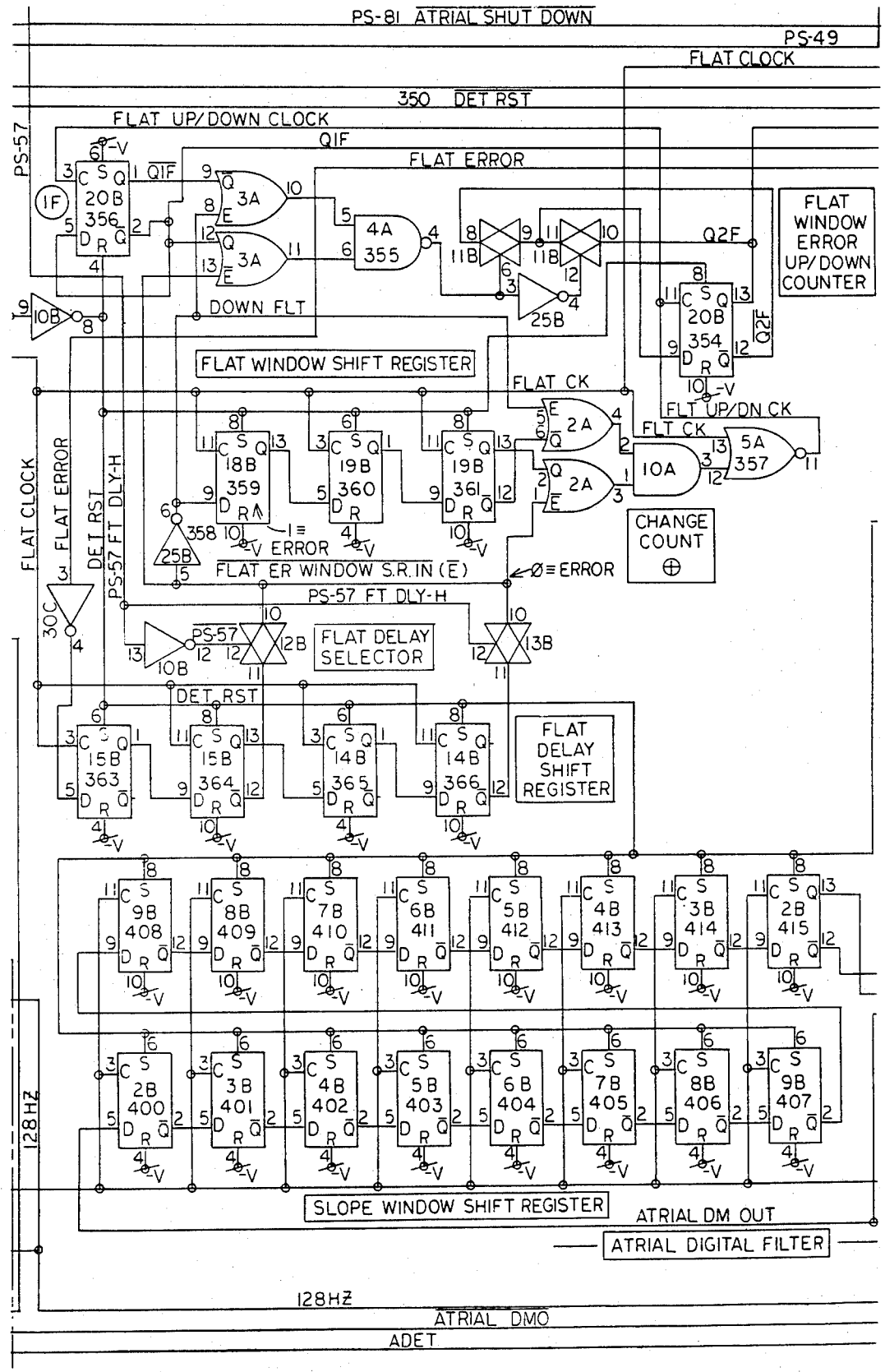
FIG. 25-HH

FIG. 25-JJ
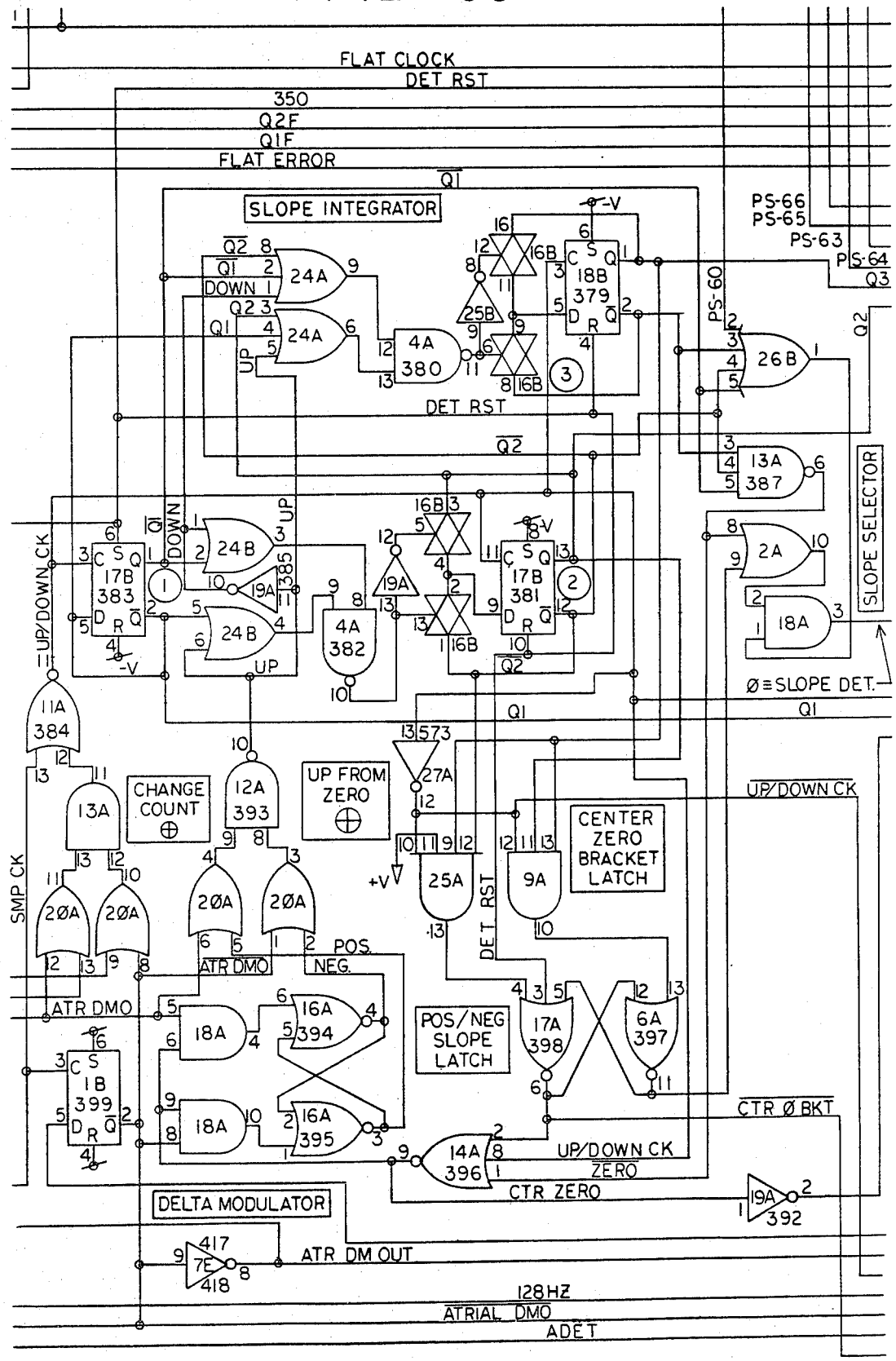

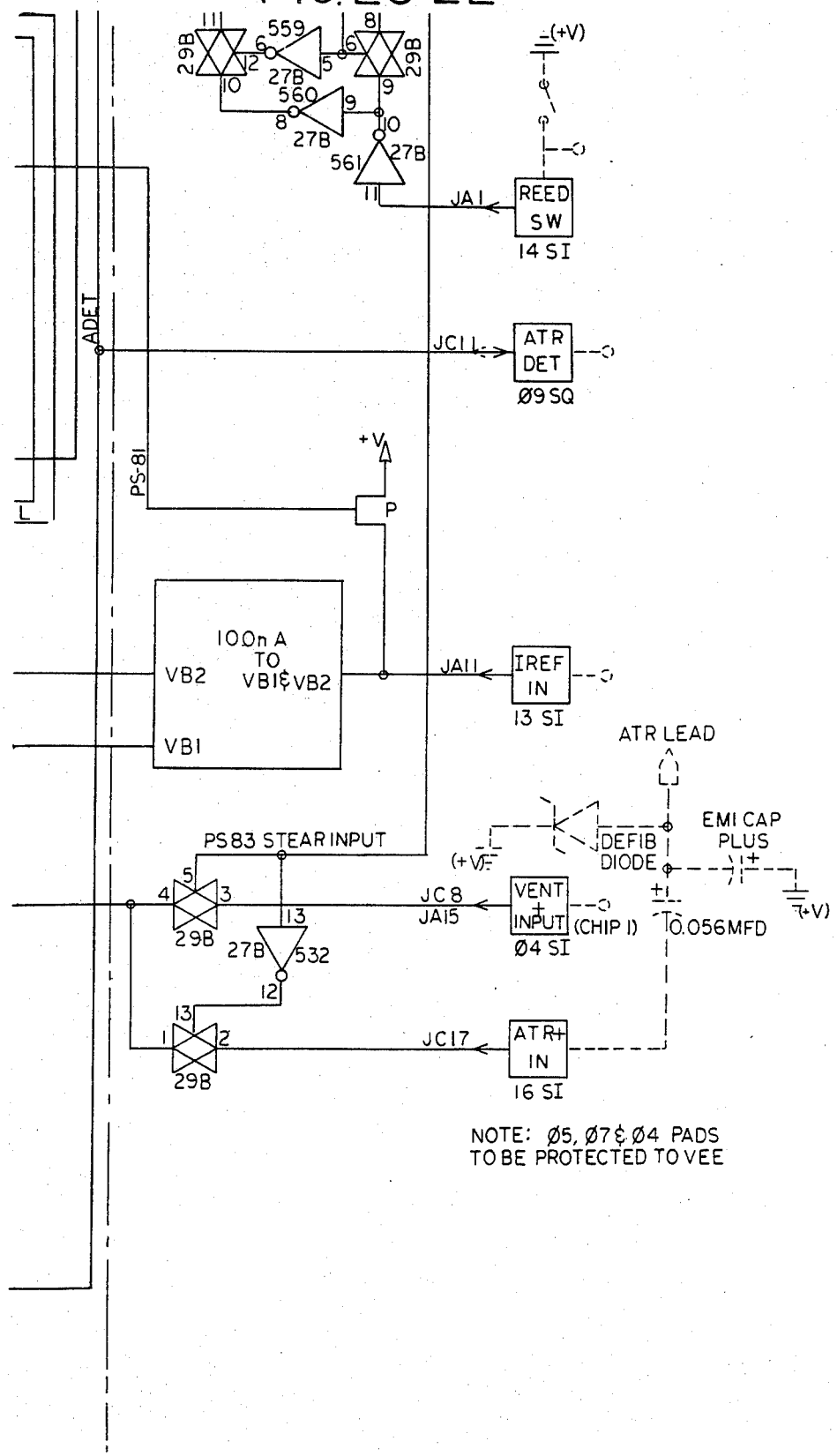

PROGRAMMABLE DIGITAL CARDIAC PACER

TABLE OF CONTENTS

ABSTRACT OF THE DISCLOSURE
BACKGROUND OF THE INVENTION
SUMMARY OF THE INVENTION
THE DRAWINGS
DETAILED DESCRIPTION
   VENTRICULAR DELTA MODULATOR
   VENTRICULAR FILTER
   TABLE I—DETECTOR'S PROGRAMMED PARAMETERS
   TIMING CIRCUITRY
   FUNCTIONS OF THE VCO
   BUS ARRANGEMENT AND MEMORY READ/WRITE
   STATE CONTROLLER
   TABLE II—STATE CONTROLLER INPUTS AND OUTPUTS
   ATRIAL FILTER; SETTING P-R DELAY; THE JAM FUNCTION
   ATRIAL INPUT STEERING
   STATUS CONTROL RAM
   TABLE III—STATUS CONTROL BITS
   SHELF LIFE STANDBY MODE
   OVERALL SYSTEM OPERATION
   FILTER PARAMETER CONTROL CIRCUITRY
   RATE LIMIT CONTROL
   VCO PULSE WIDTH GENERATION
   RATE LIMIT SYNCHRONIZER/JAM ENABLE CONTROL
   RATE LIMIT PROCESSING
   MAGNET PHASES
   TEMPORARY MODE COUNTER
   FORCED BACK-UP MODE
   AUTOMATIC TACHYCARDIA OVERDRIVE HARDWARE
   CAPTURE VERIFICATION CONTROL LOGIC
   WIDE PULSE WIDTH
   OUTPUT VOLTAGE CONTROL
   EVENT TALLY COUNTERS
   REFERENCE DATA RAM
   SOFTWARE IMPLEMENTATION OF THE SYSTEM
THE CLAIMS

BACKGROUND OF THE INVENTION

The present invention relates to cardiac pacers; and more particularly, it relates to cardiac pacers which are adapted for implantation in a patient.

The present invention is seen as providing substantial improvements in many areas of conventional cardiac pacers, both in the functioning of implanted pacers and in the circuitry and hardware used to implement a design.

One way to improve current cardiac pacers, as expressed in the literature and known to persons skilled in the art, is to establish a normal cardiac rhythm between the contraction of the upper, smaller heart chamber or atrium, and the lower or main heart chamber, called the ventricle. In a normal heart, the atrium expands and contracts, forcing blood through the tricuspid valve into the associated ventricle, thereby helping to fill the ventricle so that when the ventricle contracts (normally about 150 milliseconds after contraction of the atrium), it is filled to normal capacity, and this augments the efficiency of the heart in the sense that more blood is pumped for each cardiac cycle. This also causes the ventricular rate to follow the atrial rate as established by the sino-atrial node, thus adjusting the pacing rate to the body demands.

The most common implantable cardiac pacer in commercial use today is a demand pacer--that is, it has a single electrode which is lodged in the apex of the ventricle and senses contraction of the ventricle (an R wave). A demand pacer then establishes a predetermined time out period or escape interval during which it tries to sense a natural R wave. If no natural R wave is sensed during that period (which may be approximately 833 milliseconds), a stimulating pulse is generated and transmitted to the ventricle. If a natural heartbeat is sensed, the time out period is reset to establish a new escape interval. Thus, in a cardiac pacer of this type, no attempt is made to synchronize the contraction of the ventricle with that of the atrium.

Early attempts were made to synchronize ventricular contraction with atrial contraction (called a P wave), particularly when the prevailing practice was to use open chest surgery to implant the cardiac electrodes. The electrodes were sutured to the walls of the atrium and the ventricle respectively. Current practice, however, has tried to avoid the use of open chest surgery with its accompanying trauma and risk, and therefore the prevailing practice is to introduce a single electrode which, as indicated, is lodged in the apex of the ventricle, and to employ a second or neutral electrode on the pulse generator casing for the circuitry which is normally lodged in the abdomen or chest pocket of the patient.

The magnitude of the electrical signal accompanying atrial contraction, that is the P wave, is quite small and easily masked by ambient electrical noise or artifacts, such as those generated by muscular activity. When an electrode is sewn directly to the wall of the atrium, a P wave can be detected. However, when it became generally accepted that it is desirable to avoid open chest surgery, and therefore impossible to establish firm contact with the wall of the atrium, other electrode configurations were suggested.

One lead configuration that has been suggested is the so-called "J-lead" which uses a flat metal contact in the form of a leaf spring which opens after the electrode is inserted in the heart.

Some of these configurations were either too dangerous (i.e., possible damage to the heart by forcing the contact through the thin wall of the atrium), or too difficult to insert, or interfered with the operation of the heart to an extent that they were never widely used. Other suggested systems, which did not establish reliable contact with the wall of the atrium, made it extremely difficult to detect a P wave in the presence of the ventricular signals and normal noise.

Noise, of course, also occurs in the ventricular electrode due to muscle artifact and the many sources of RF energy a patient is likely to encounter. For this reason, implanted pacers usually incorporate circuitry which, in the presence of excess ambient noise, causes the pacer to revert to a fixed rate mode.

SUMMARY OF THE INVENTION

One of the principal objects of the present invention is to include circuitry in an implantable cardiac pacer which will overcome the above problems of reliable signal detection and identification, and enable the circuitry to detect a P wave with a ring electrode which is carried by the same catheter which holds the ventricle electrode but is located in the atrium, and not necessarily in contact with the atrial wall; and which will also reduce the probability that the pacer will revert to fixed rate pacing in the presence of high ambient electrical noise. Briefly, this is accomplished by using a first digital filter receiving the signal from the ventricle electrode, and a second digital filter receiving the signal from the atrial ring electrode.

Each of these filters includes a conversion circuit for converting the incoming signal to digital form. Briefly, the conversion circuit is a sample data circuit the output of which is a serial train of binary signals which operates on the input signal like a delta modulator, so it is referred to as a delta modulator. The output of the delta modulator is fed to a shift register. The parallel outputs of the shift register, when combined, are representative of the slope of the incoming signal over a predetermined time period or "window", the length (i.e., time duration) of which depends upon the sample rate and the number of bits in the shift register.

The P, R and T waves, Premature Atrial Contractions (PAC) and Premature Ventricular Contractions (PVC) are identified by the following characteristics: (1) a "flat" segment (i.e., slope less than a predetermined value) lasting for a preset time, followed by (2) a "flat delay" segment, and then followed by (3) an increasing signal (positive or negative) called the "high slope" segment having a slope greater than a predetermined value and, again, lasting for a preset time. These parameters (magnitude and time for the flat segment, time for the delay segment, and magnitude, slope direction, and time for the high slope segment), as well as factors which permit the physician to weight the importance of each in identifying a particular signal are programmed into the system, and capable of being changed under program control.

The parameter identification data is stored in memories called the atrial filter parameter control memory (a division of the atrial control memory) and the ventricular filter parameter control memory. The data is transmitted to the associated digital filter during the appropriate time in a cardiac cycle under control of a state controller. As will be explained, the physician has flexibility in setting these parameters and the times and conditions at which they are expected to occur. He may also set an error tolerance or acceptance in defining one or more of the parameters. Thus, the identification of the various cardiac signals can be made to be very reliable, particularly considering the continuous wave nature of commonly encountered noise (rf energy and muscle artifact) versus the impulse waveform nature of the cardiac signals.

By requiring a flat segment, followed by a flat delay segment and then a high slope segment, all the parameters of which being tailored to the signal sought to be detected, a high degree of rejection is achieved against those noises or unwanted signals which normally are encountered in a cardiac pacer.

Further, the filter parameters (which define the signal being sought) are stored in a memory and implemented in the filter under control of a state controller which, in turn, is governed by the ventricular digital filter to sense an R wave during the Ventricular Rate Time Out period, but it also permits the digital filter to sense a T wave after a stimulating pulse is generated by the pacer in an effort to verify that the heart has responded to the stimulating pulse (called "capture"). In another portion of a cardiac cycle, the filter may be set to determine Premature Ventricular Contractions (PVCs). In other words, the parameters for an R wave, a T wave, and a PVC are loaded into the ventricular filter during the time when those particular signals are expected or sought. This also enables a physician to adjust the criteria necessary to establish any of these signals so that he has control over the rejection or susceptibility of the pacer to noise or unwanted signals.

The Ventricular Rate Time Out period or escape interval is established from the last detected natural heartbeat or stimulating pulse. If a P wave or natural R wave is not sensed during that period, the system generates a stimulating pulse for pacing the heart artificially, and uses the T wave parameters in the ventricular filter to verify capture.

If a P wave is sensed before the Ventricular Rate Time Out period ends, the system establishes a predetermined P-R delay period to override the Ventricular Rate Time Out period of an effort to synchronize the ventricle within the atrium. During the P-R delay, the ventricular filter is set to detect a natural R wave which would occur in this delay period if the heart functions normally. If an R wave is detected during the P-R interval, the system resets itself without generating a stimulating pulse, but if a natural R wave is not detected during this time, a stimulating pulse is generated at the end of it to synchronize the ventricle with the atrium.

Prior to the Ventricular Rate Time Out period of each cardiac cycle, the ventricular filter is set to detect PVCs. If a predetermined number of sequential PVCs are detected, the system generates a train of stimulating signals at a rate higher than expected tachycardia, in an effort to break the tachycardia.

According to another feature of the invention, many of the major functions of the system are implemented under control of a state controller on the basis of data stored in a status control memory. This stored data can be programmed to provide great flexibility and reliability. One advantage of this feature is, for example, the function for attempting to synchronize the ventricle with the atrium (called the "JAM" function because a data word representative of a predetermined time is forced into a counter that normally stores data representative of the end of the Ventricular Rate Time Out) can be disabled. Other major functions can be locked out or disabled under program control, as will be discussed. This enables a physician to implement whatever functions he feels will fit a patient's needs with a single electronic circuit or system on which extensive use data can be obtained for reliability analysis and predictions. The physician does not have to familiarize himself with the particulars of many different types of pacers, as is now the case.

This feature of selective enabling and inhibiting of major functions or subsystems also permits a physician to change the basic operation of the pacer after implantation by external programming without operating on the patient. With the same unit implanted, the physician can make it a P-synchronous, demand or fixed rate pacer. In any of these operating modes, he has the additional flexibility to adjust or "tune" the system to the individual characteristics of the patient. For Example, if one patient has an R wave which is wider and more rounded (lower frequency content) than the normal, the physician can program the criteria for R wave detection with this knowledge. This ability is also important to accommodate the system to any changes in conditions that normally occur after implantation.

Another important advantage of the system architecture is that the pacer can be placed in a power conservation mode by the manufacturer to extend shelf life, and then the pacer can be activated by the physician upon implantation. The system uses non-volatile memory and CMOS circuitry with a crystal main oscillator and voltage-controlled back-up oscillator. In the standby mode, power is fed to the crystal clock oscillator only and all other clock signals, the detectors and the back-up oscillator are disabled until activated by a physician, or the factory at shipping time, thereby significantly reducing battery consumption while insuring start-up of the crystal oscillator.

In ordinary operation, the crystal oscillator and its associated count down circuitry determine the various timing marks in a cardiac cycle as well as the width of a stimulating pulse. The usual rate of the back-up oscillator, or VCO, is established to be slightly higher than the rate of the main oscillator. Because its rate is dependent on applied voltage, as the battery begins to deplete, the period of the back-up oscillator will eventually extend to the point where it is equal to a corresponding fixed period derived from the crystal oscillator. When this occurs, the system increases the base period derived from the crystal oscillator by 12.5% to conserve power and generates an elective replacement signal, but the system continues to detect for rate limit events—that is, a detection that the period of the crystal oscillator is still less than the period of the VCO (or in other words, the frequency is greater). If additional rate limit events are detected after the period of the crystal oscillator has been extended, it is taken as an indication of fault in the crystal or its associated count down circuitry, and the system is switched over to run at a fixed rate mode timed by the VCO only—that is, not only is the time base established by the VCO, but the width of the stimulating pulse is also derived from the VCO.

Further, if both the main (crystal) and back-up (VCO) timing systems are operating normally, the cardiac cycle period for the VCO will end during the Ventricular Rate Time Out period for the crystal oscillator. The period time out signal of the VCO is used as a Rate Limit Enable (RLE) signal for the generation of a stimulating pulse. That is, even if the main timing circuitry times out, the RLE signal will prevent the generation of a stimulating signal until the VCO period ends, thereby preventing the generation of stimulating pulses on a per beat basis at too rapid a rate for normal demand pacing operation.

When a physician tests a pacer after implantation, as by applying an external magnet, the basic timing functions are derived from the VCO, but the Ventricular Rate Time Out period is shortened in an effort to cause the generation of a stimulating pulse so that the physician can see the effect on the heart of a stimulating pulse. During this test, the width of the stimulating pulse is still determined by the main timing circuitry, thereby giving a more realistic capture verification test.

In addition to having the capability of programming many of the signal detection or noise rejection parameters in the ventricular and atrial digital filters, many other system operating parameters can be programmed. Further, some parameters may be programmed to change in response to detected conditions. For example, in the event capture is not verified after a stimulating pulse (sometimes referred to as loss of capture), the system will exhibit a response that had been programmed by the physician. The responses may include increased pulse amplitude, increased pulse duration, either one followed by the other, or neither. The rate of the system can easily be programmed by changing the Ventricular Rate Time Out period. The pulse width or pulse amplitude for stimulation may be programmed into the system, according to the needs of the patient. Other programmable parameters are the P-R delay, ventricular refractory time, and lead compensation time. When the system detects tachycardia, the number of successive PVC detections that define a tachycardia and the number of stimulating pulses that will be generated to try to interrupt tachycardia may be programmed. The system thus permits a physician to program the cardiac pacer according to what he believes is best for a given patient in a given set of circumstances. It further enables him to accomodate the system to changes in the status of the patient or to new developments in the field of cardiac pacing.

Another feature of the present invention includes positive and negative rate hysteresis (that is, changing the escape interval which is the time between a detected R wave or stimulating pulse and the end of the Ventricular Time Out period). The escape interval is shortened to a programmable period such as 550 milliseconds if a PVC condition has been previously sensed, and lengthened to a programmable number such as 900 milliseconds from a nominal pacing rate of 833 msec if an R wave has been sensed during the normal Ventricular Rate Time Out period of the previous cardiac cycle. The apparatus also includes event tally counters which are used to maintain a cumulative count of events of interest to the physician, depending on the type of problem encountered or condition of the patient. One of the more important functions that can be implemented in the event tally counters is a record of the percentage of time during which pacing (i.e., artificial stimulation) of the heart has taken place over a week's period. This and other functions capable of being performed on these counters will be further disclosed below.

Other features and advantages of the present invention will be apparent to persons skilled in the art from the following detailed description of a preferred embodiment accompanied by the attached drawings wherein identical reference numerals will refer to like parts in the various views.

THE DRAWINGS

FIG. 4 is a functional block diagram of a gain controlled delta modulator circuit which interfaces with the analog cardiac signals;

FIG. 5 is an idealized graph of an analog signal and illustrating the output of a delta modulator circuit following the analog signal;

FIG. 6 is an idealized cardiac signal;

FIG. 7 is a timing diagram relating the various timing periods of the system of FIG. 2 to the idealized cardiac signal of FIG. 6;

FIG. 8 is a closeup view of a portion of the idealized waveform of FIG. 6 illustrating the filter characteristics of the digital filters of the system of FIG. 1;

FIG. 9 is a state table illustrating the contents of the window up/down counter of FIG. 1 and the manner in which the system may be programmed to select predetermined slope characteristics of an incoming waveform;

FIG. 10 is a timing diagram illustrating synchronization of the R wave with a detected P wave;

FIG. 11 is an idealized timing diagram illustrating the positive and negative hysteresis mode of operation;

FIGS. 12 and 12A are a flow chart illustrating the operation of the system under control of the state controller;

FIG. 13 is a timing diagram for the system's interaction with the temporary mode counter as is operated by actuation of the magnetic reed switch;

FIG. 14 is a logic schematic diagram of the state controller circuitry;

FIG. 15 is a logic schematic diagram of the time mark sequence counter;

FIG. 16 is a logic schematic diagram of the crystal oscillator upper divider;

FIG. 17 is a logic schematic diagram of the rate limit controller, sequential rate limit occurrence counter, and the rate limit enable synchronizer;

FIG. 18 is a logic schematic diagram of the ventricular digital filter parameter controller;

FIG. 19 is a logic schematic diagram of the P-R delay JAM controller and its timing diagram;

FIG. 20 is a logic schematic diagram of the temporary mode counter;

FIG. 21 is a logic schematic diagram of the sequential PVC counter and the automatic tachycardia overdrive controller;

FIG. 22 is a logic schematic diagram of the sequential loss of capture counter and capture verification controller;

FIG. 23 is a logic schematic diagram of the output voltage controller;

Figure 24A:
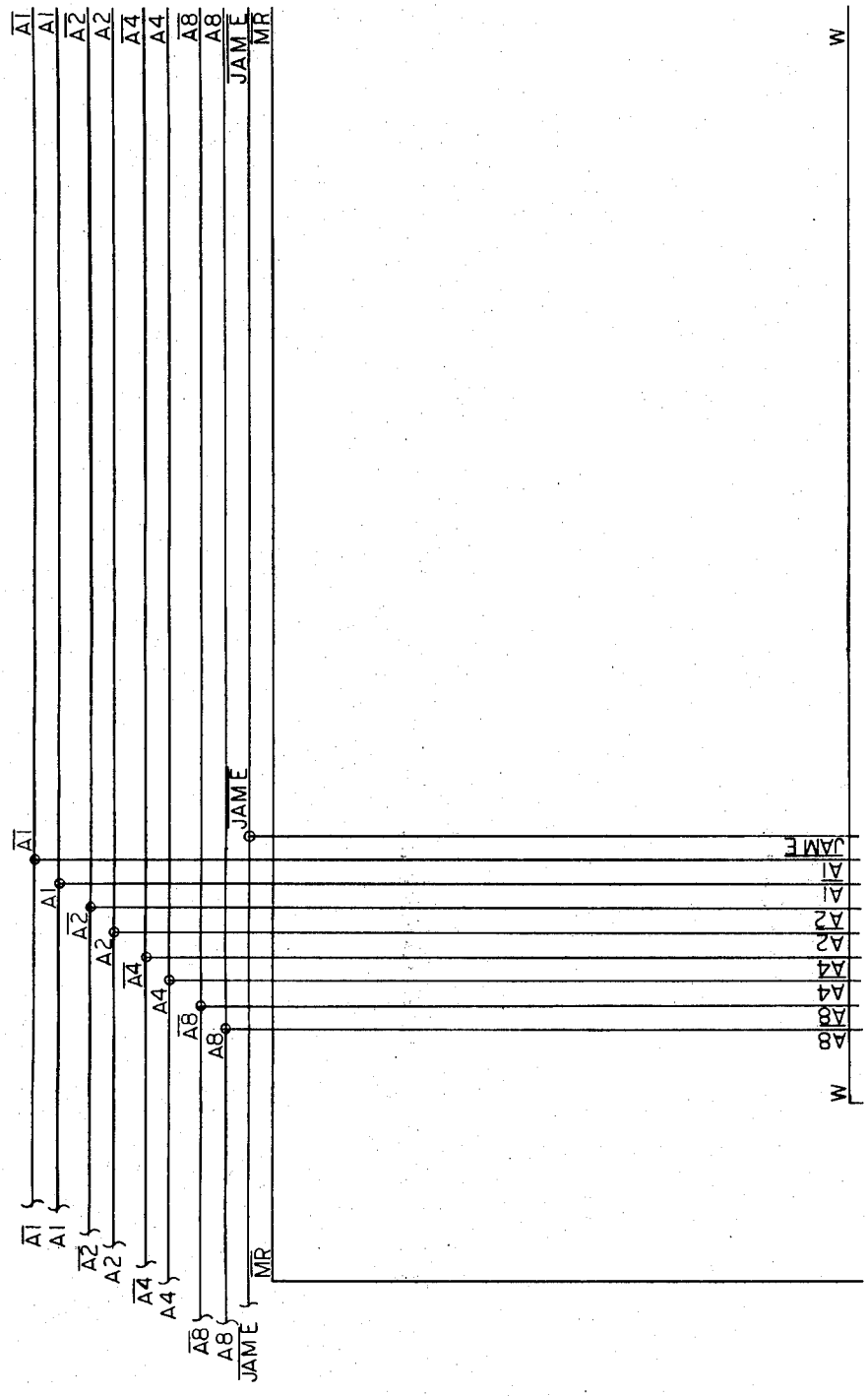
Figure 24B:
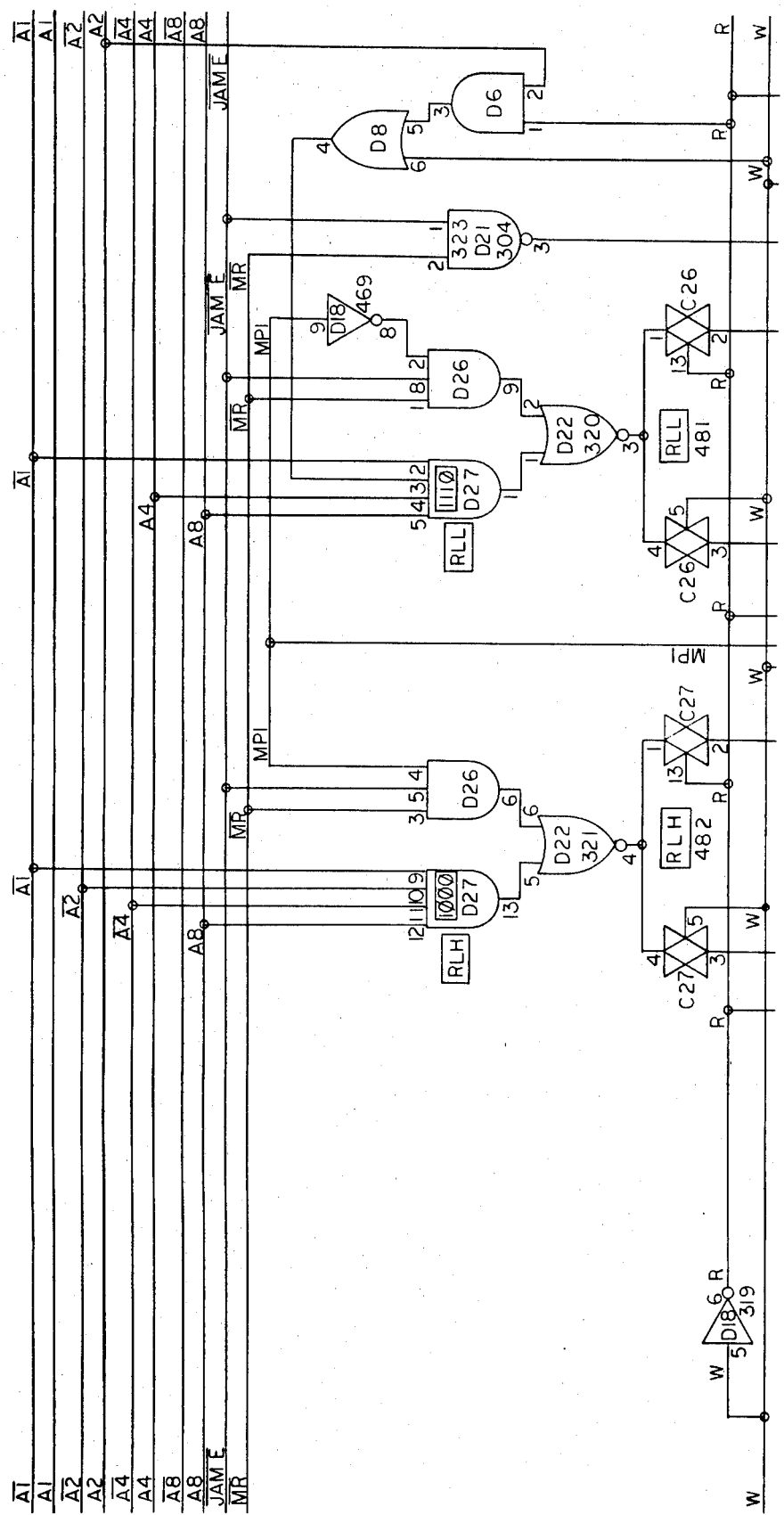
Figure 24C:
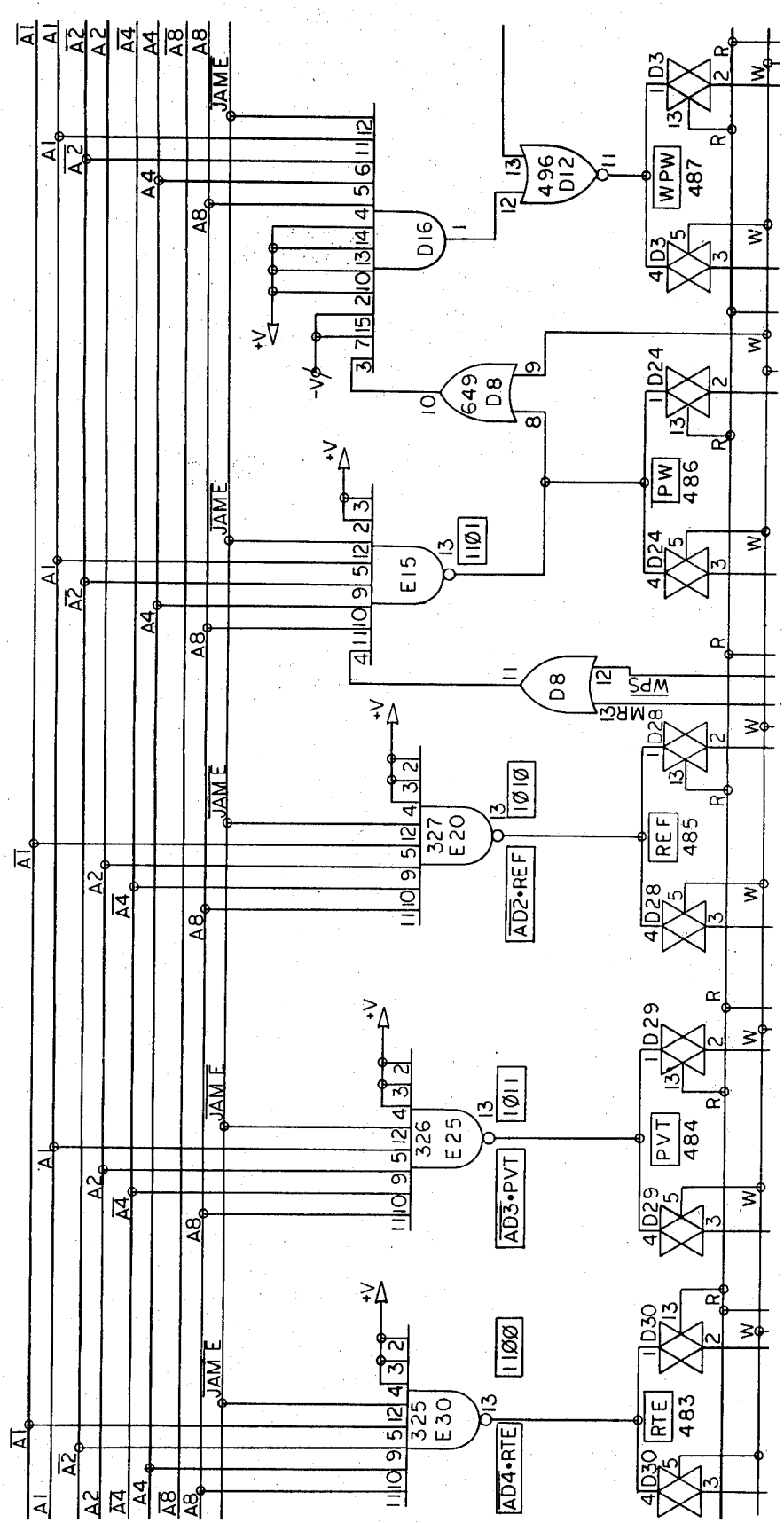
Figure 24D:
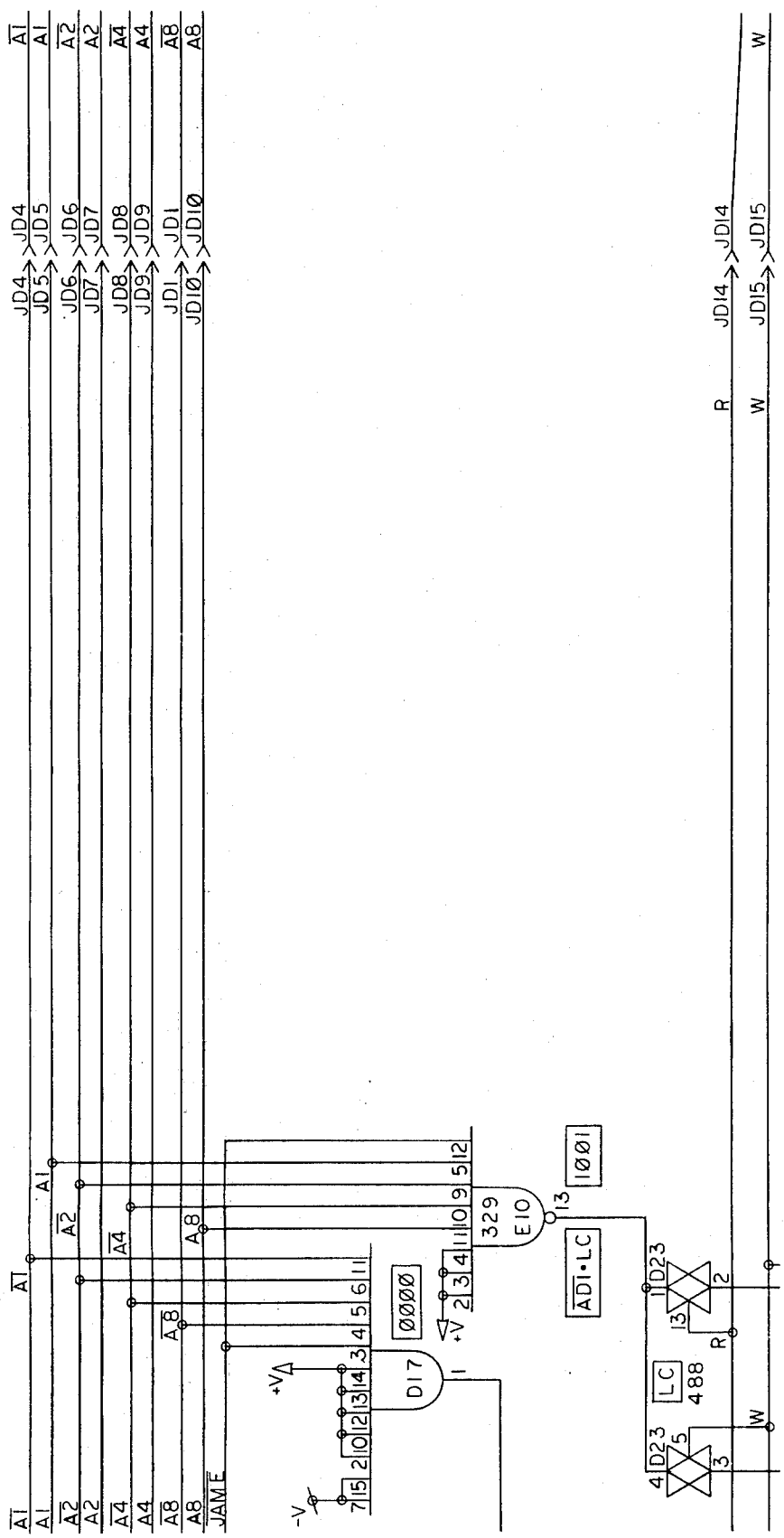
Figure 24E:
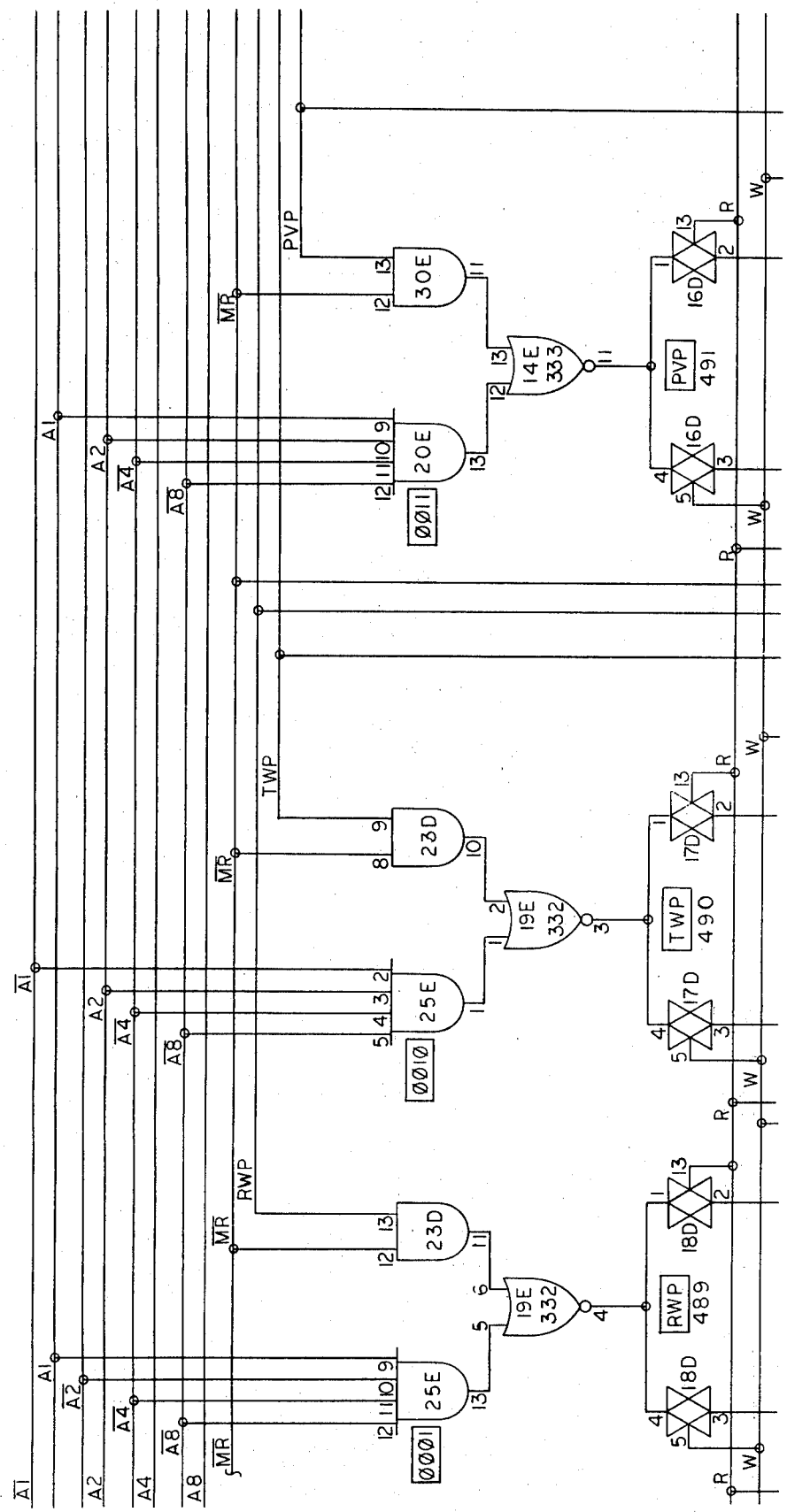
Figure 24F:
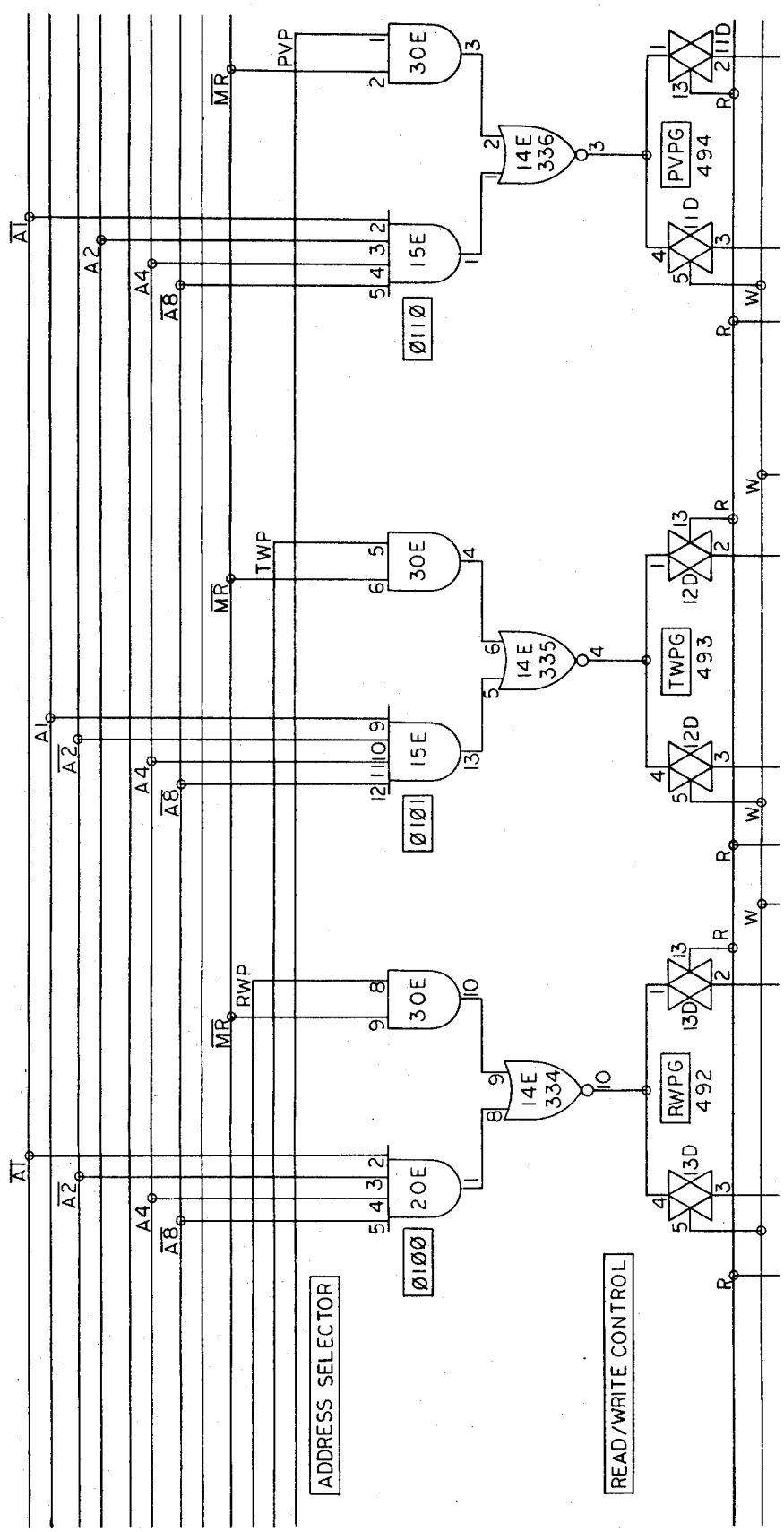
Figure 24H:
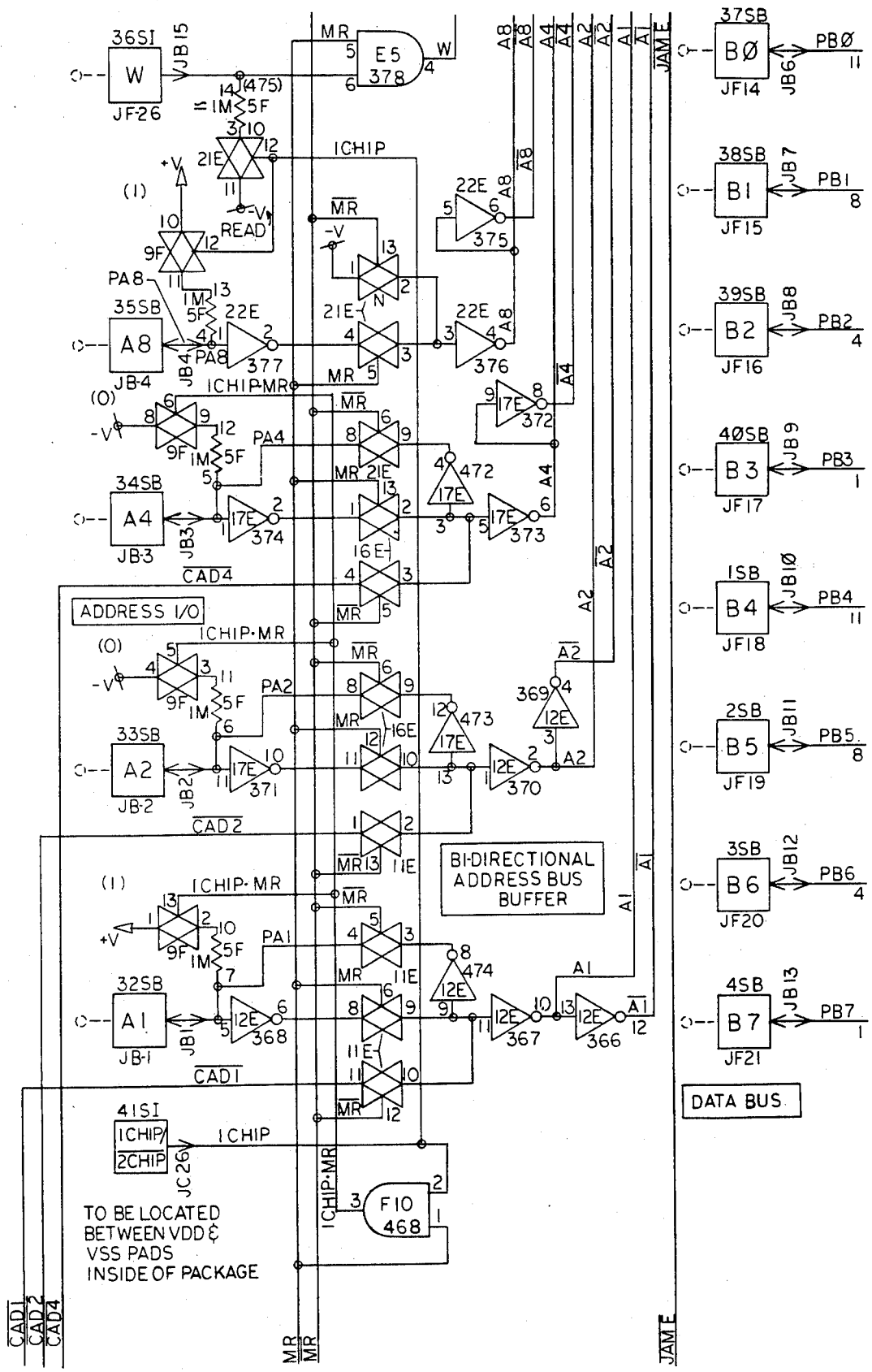
Figure 24J:
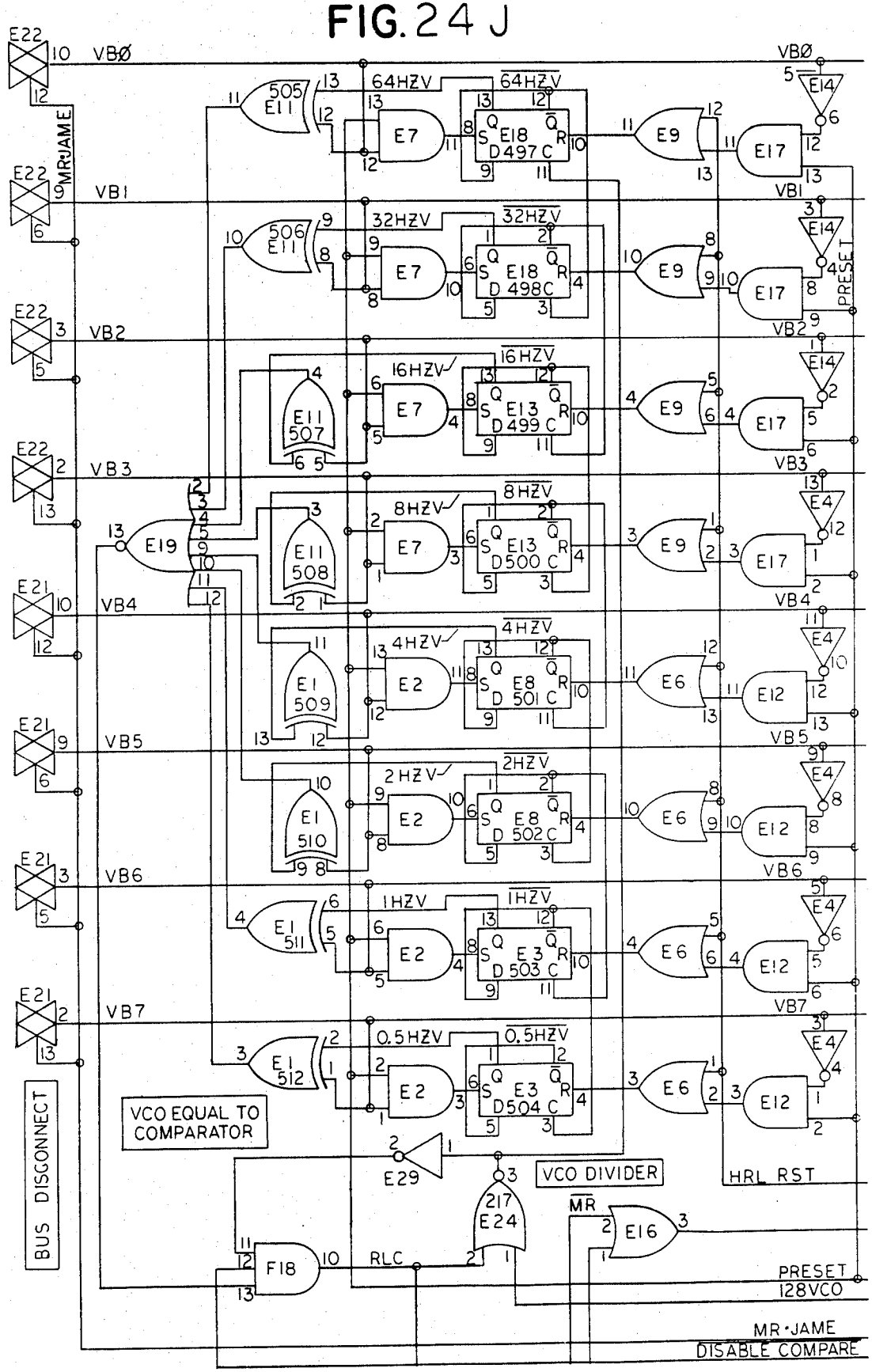
Figure 24:
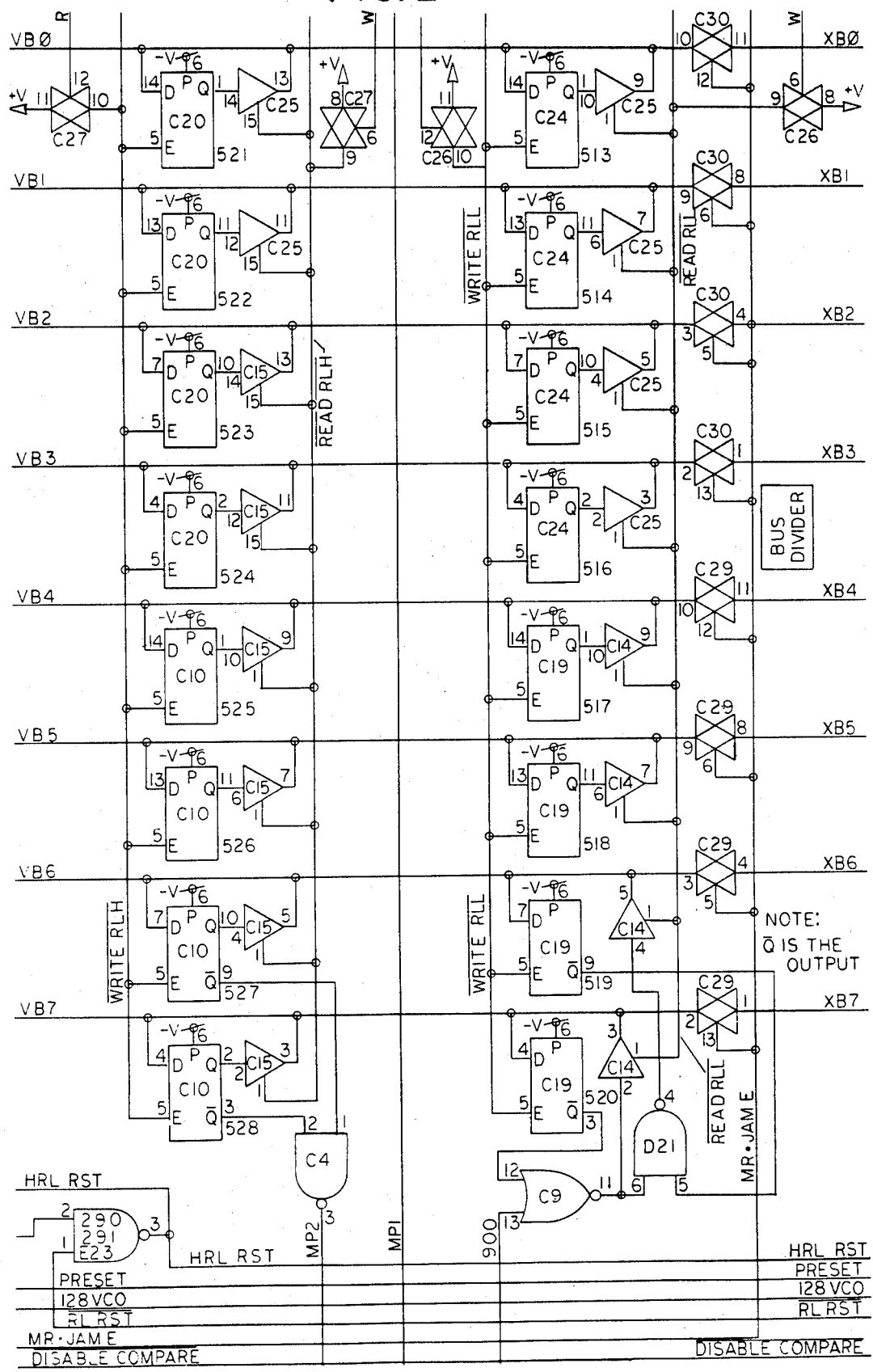
Figure 24L:
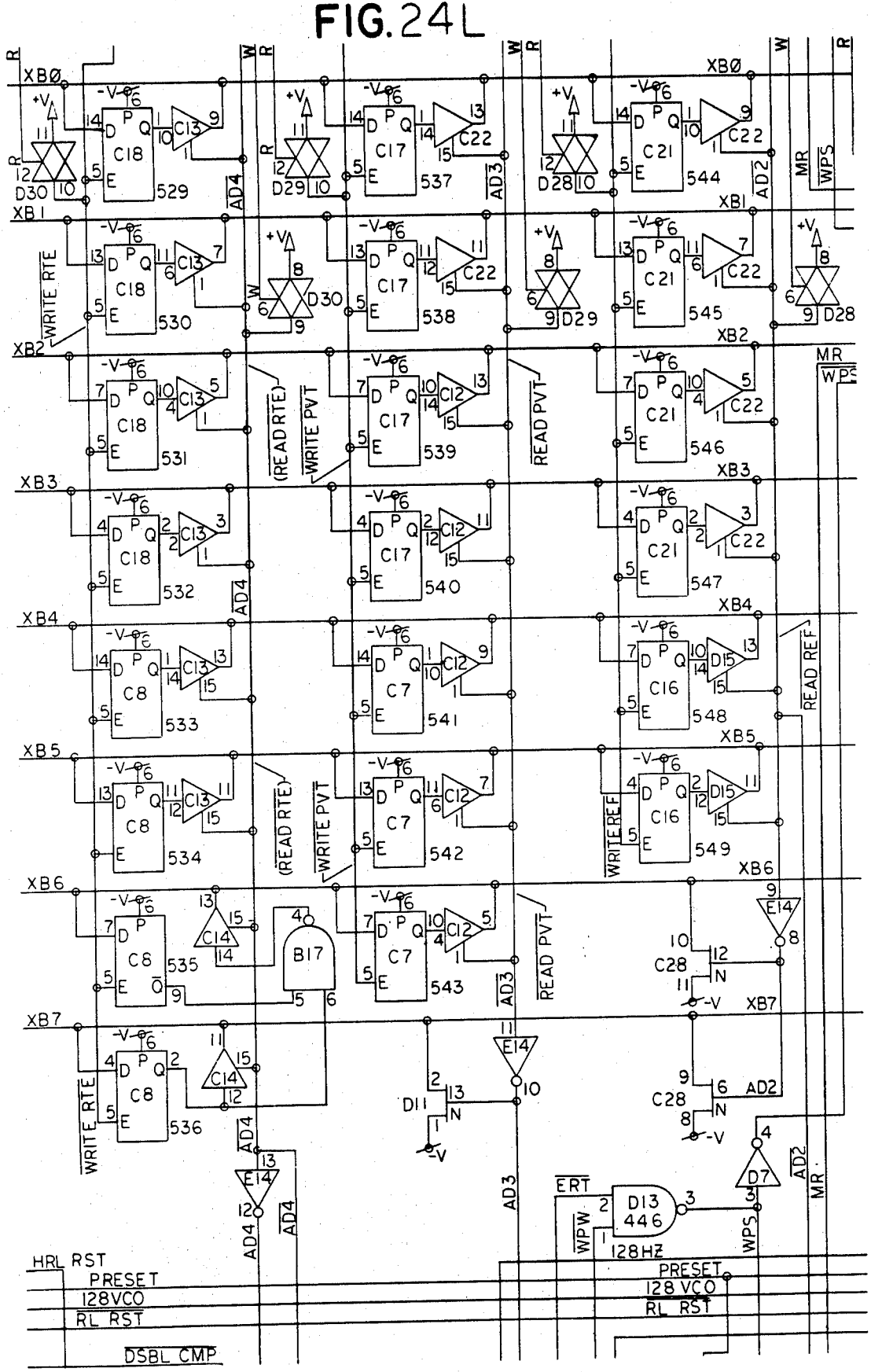
Figure 24M:
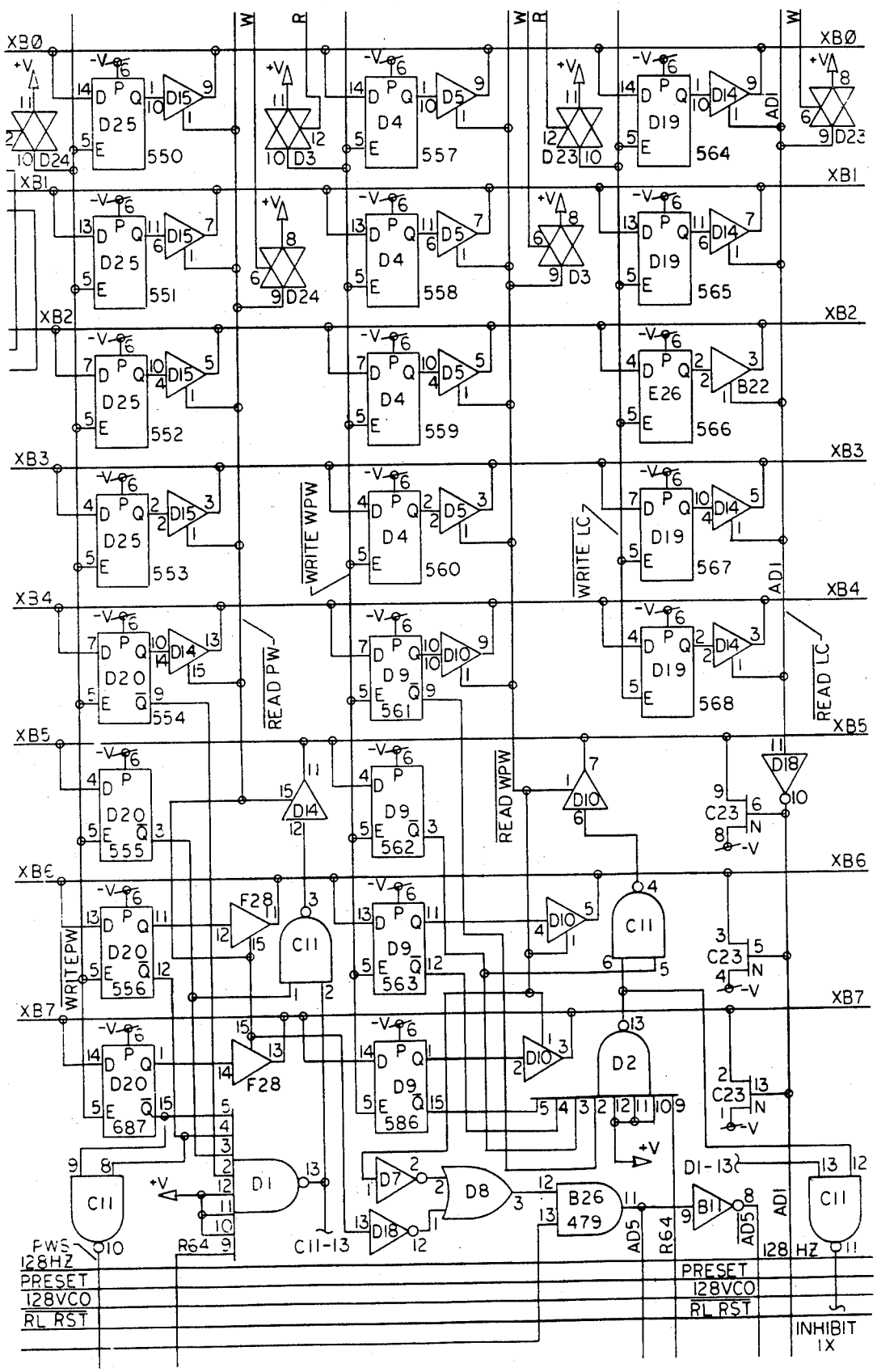
Figure 24:
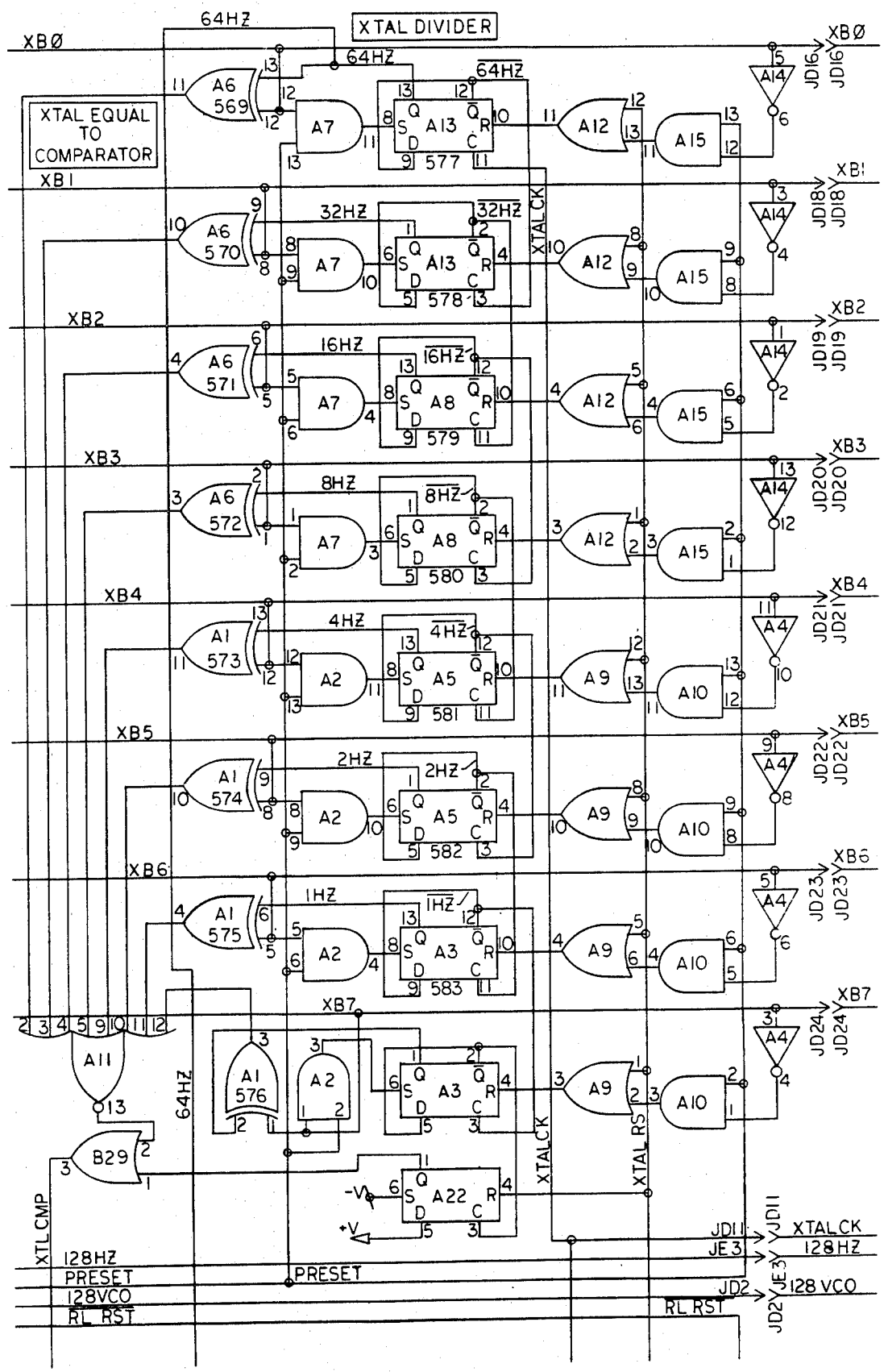
Figure 24:
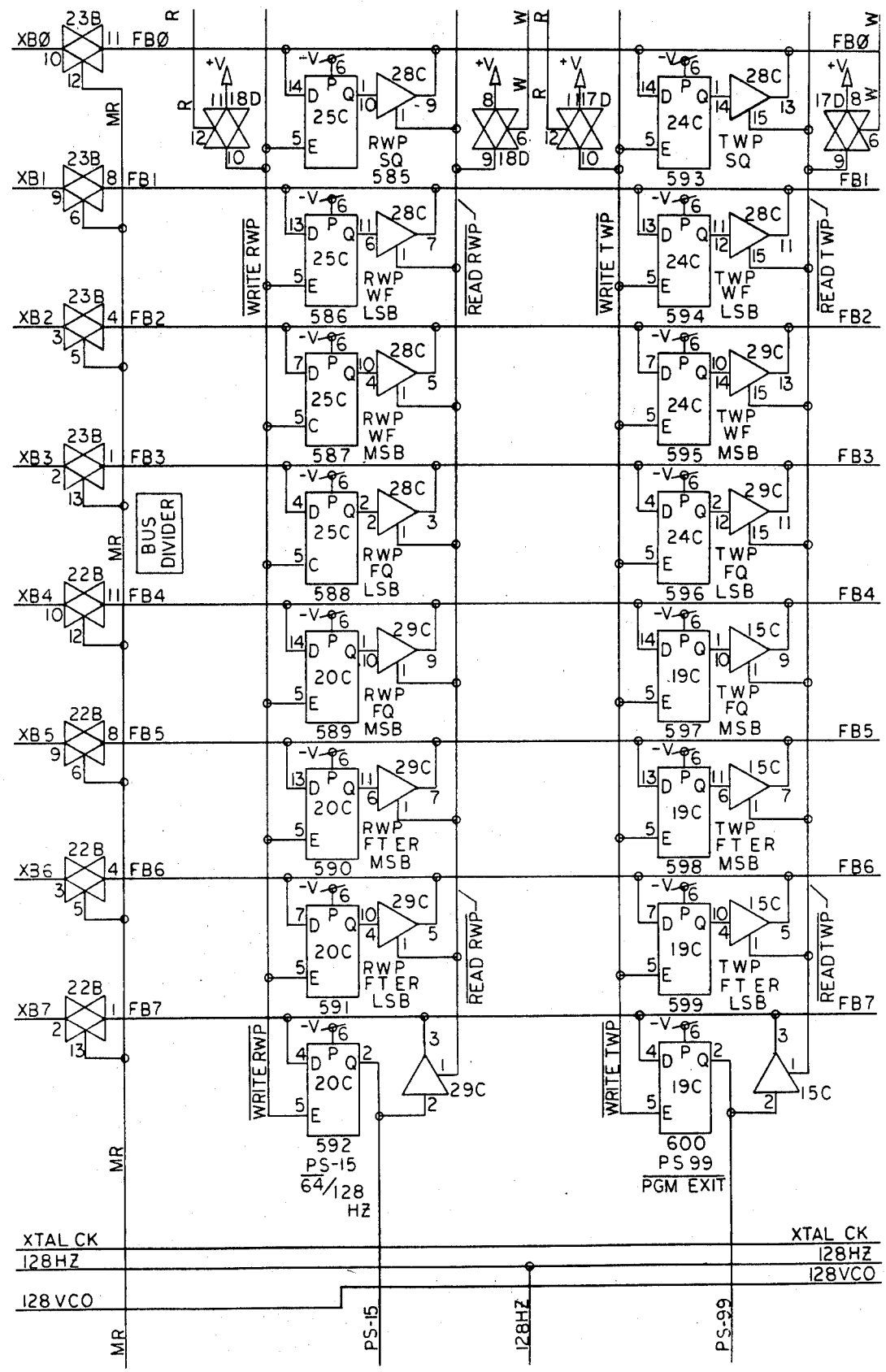
Figure 24R:
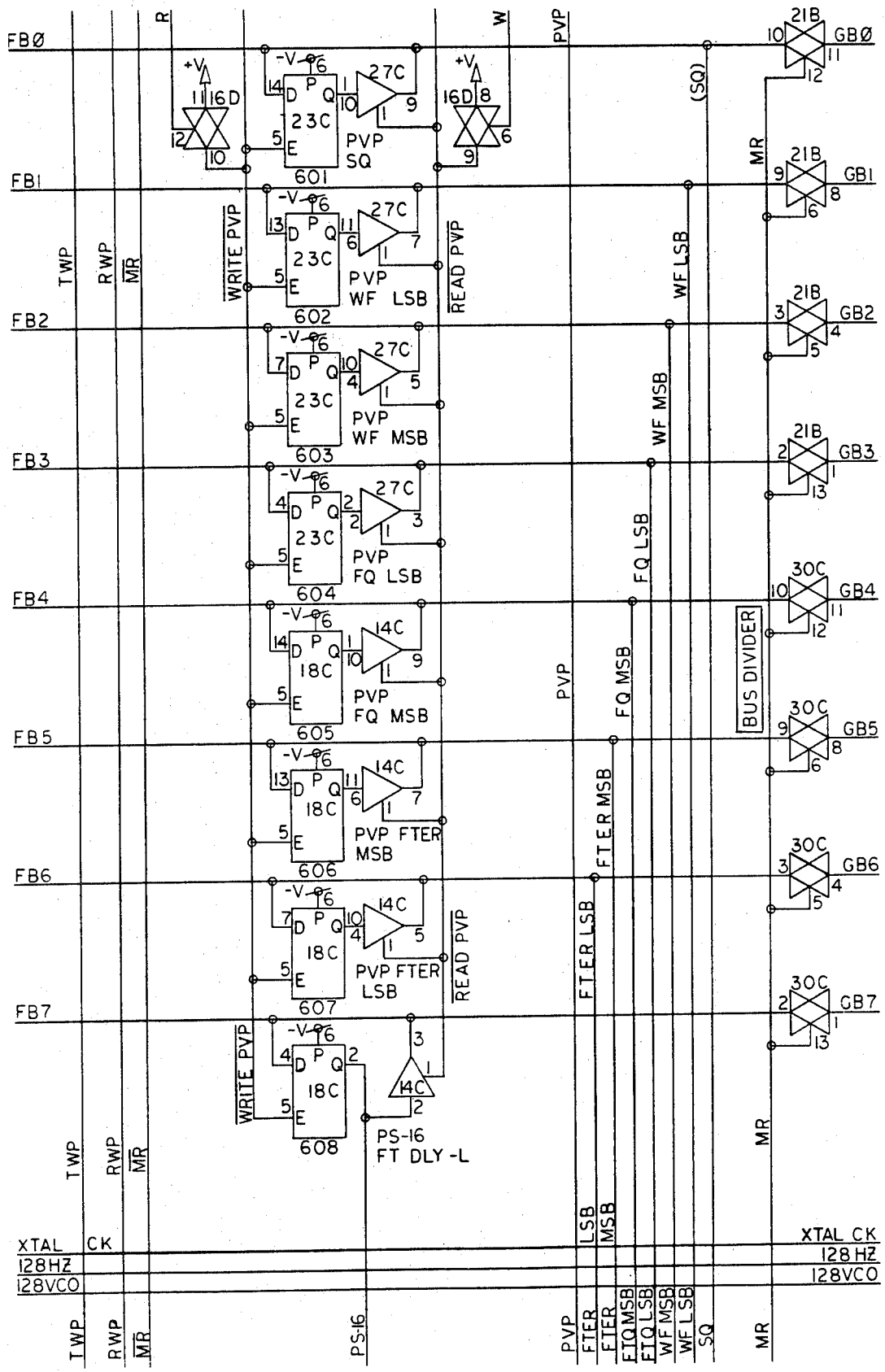
Figure 24:
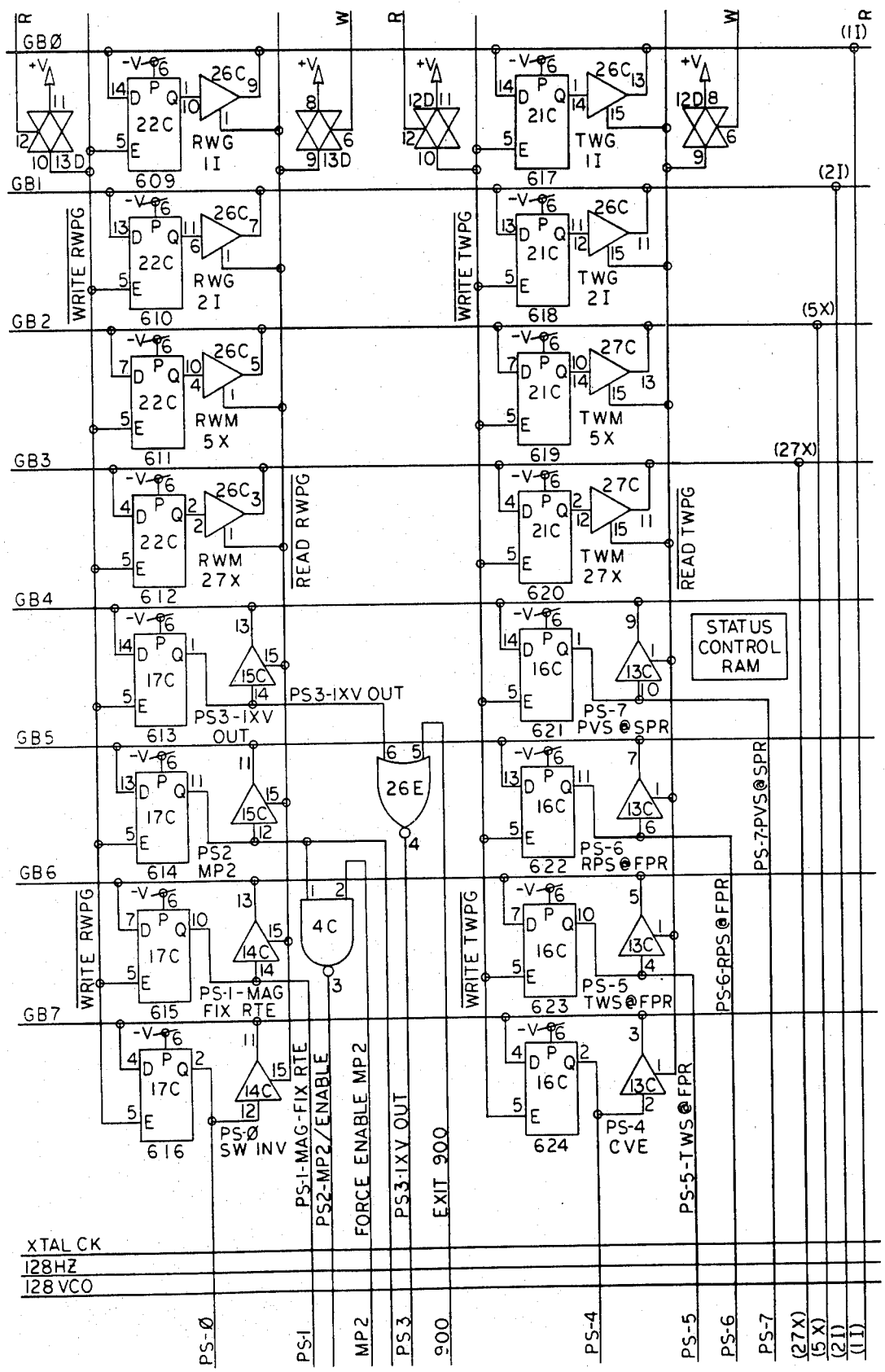
Figure 24T:
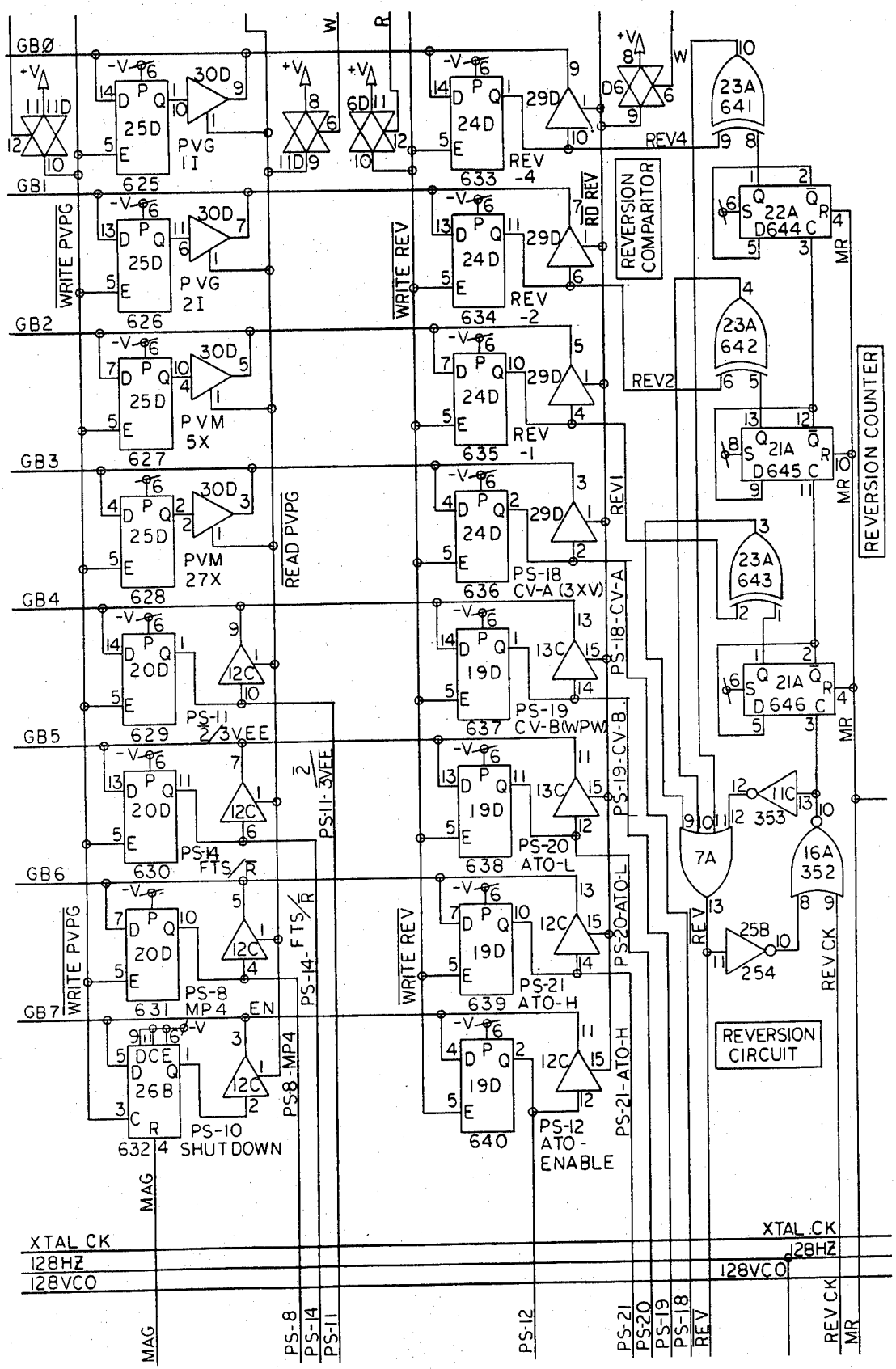
Figure 24U:
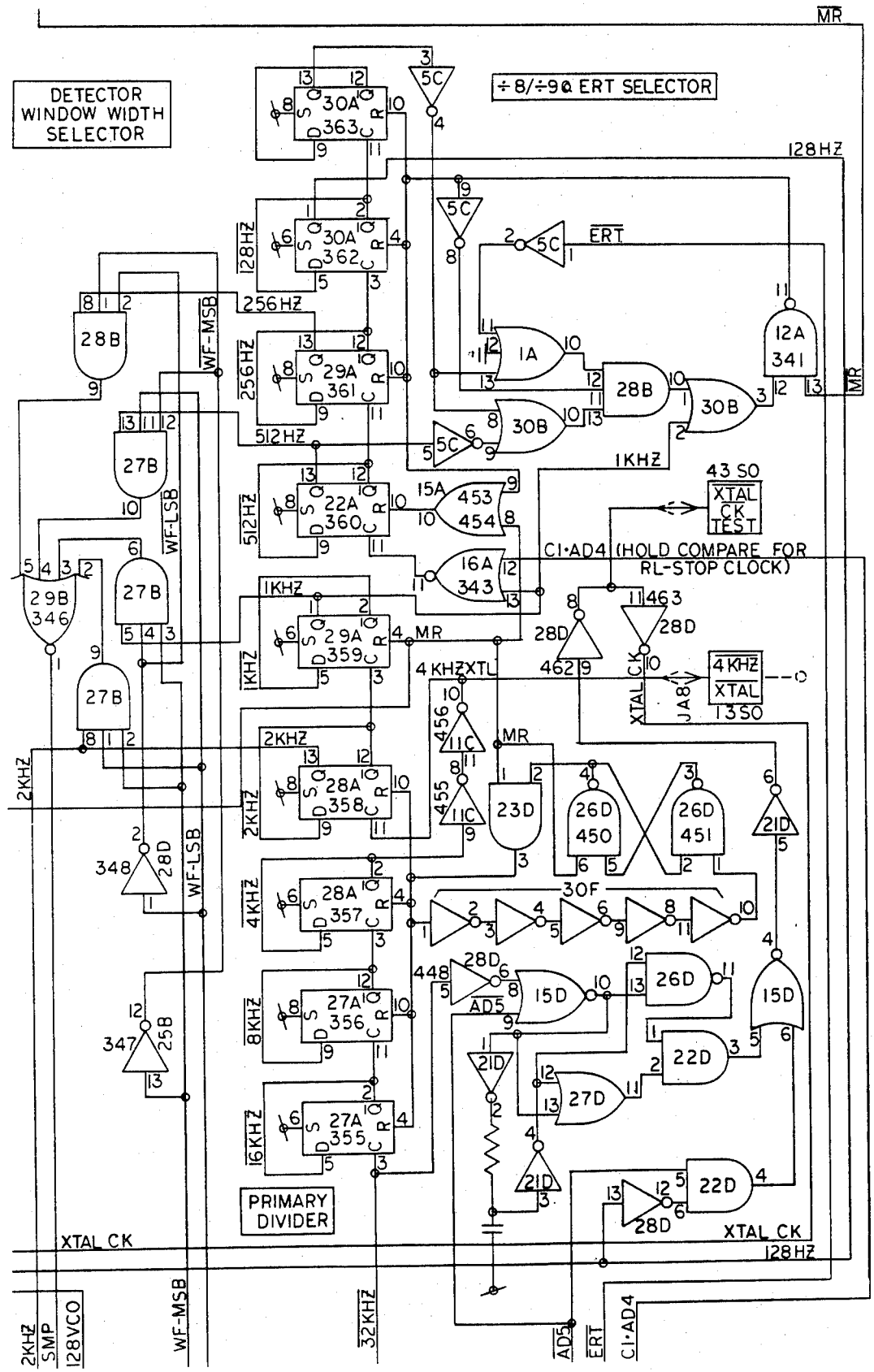
Figure 24V:
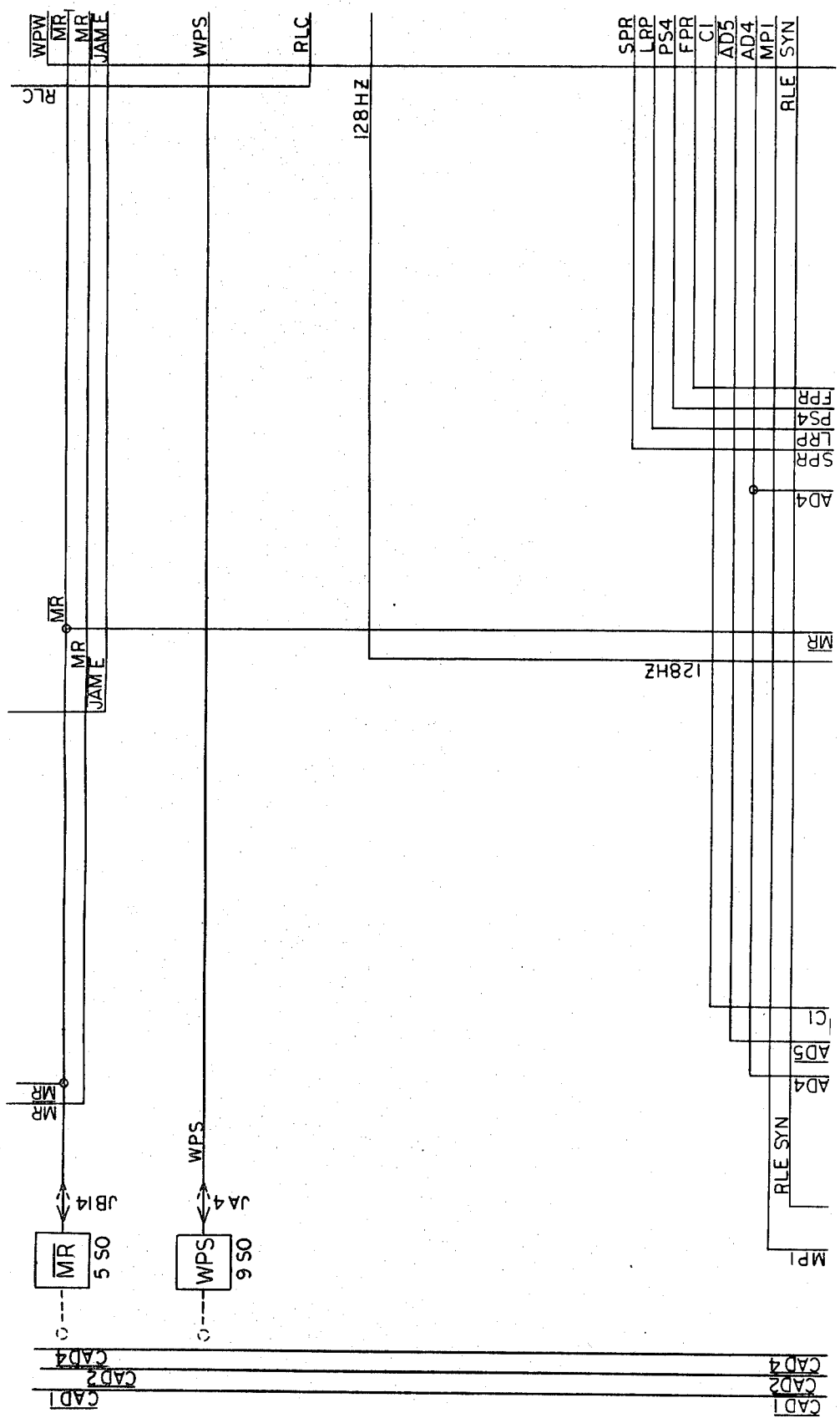
Figure 24W:
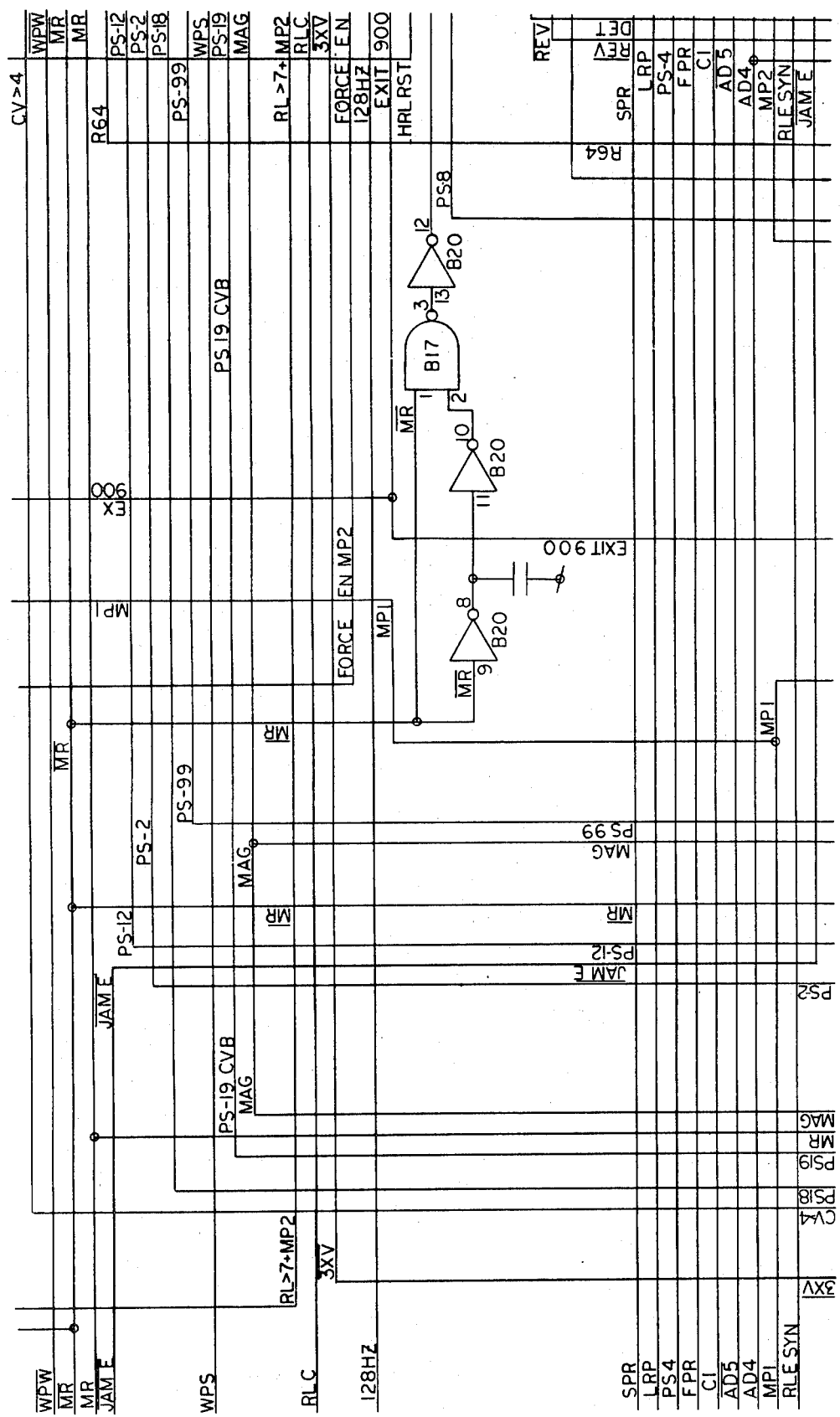
Figure 24:
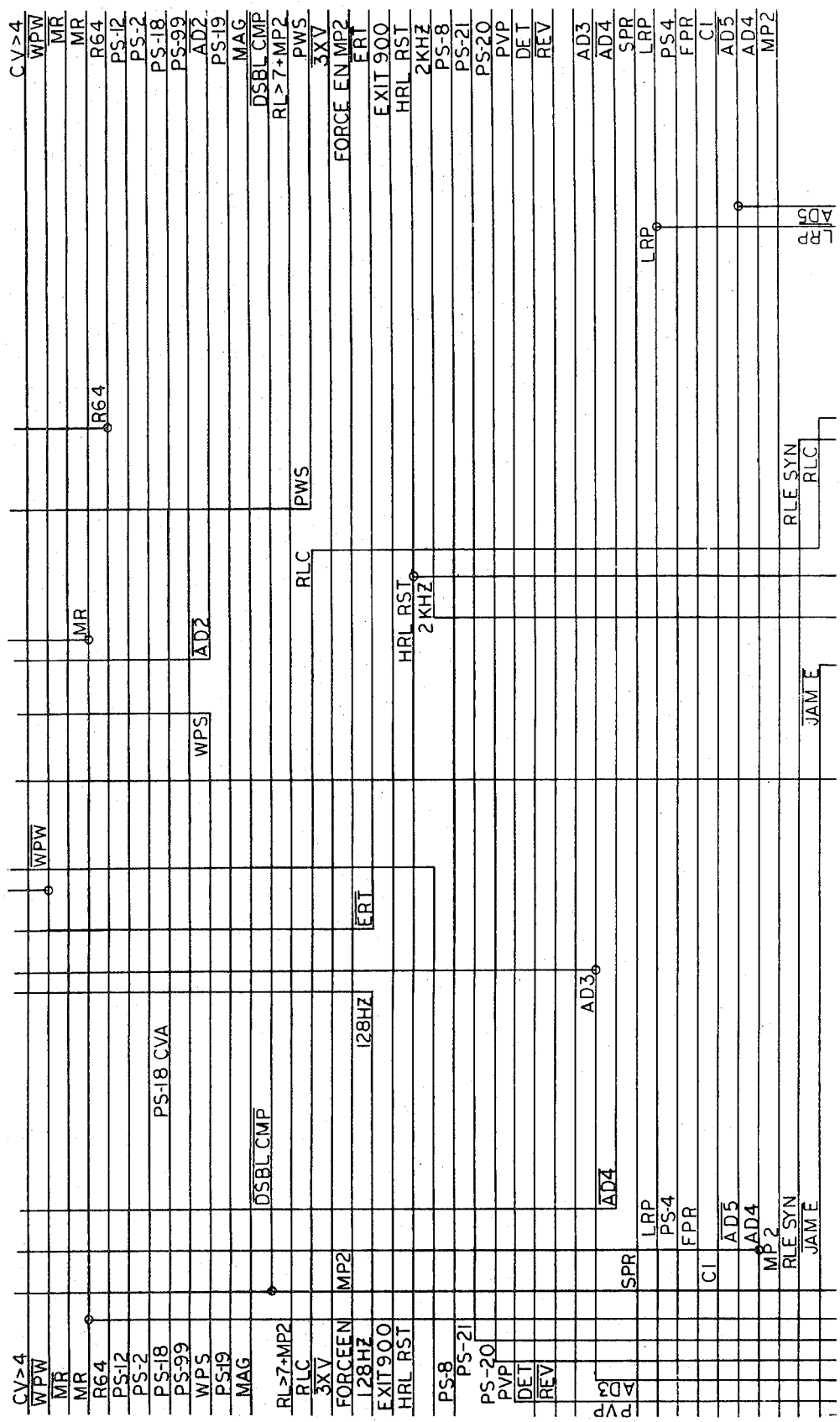
Figure 24:
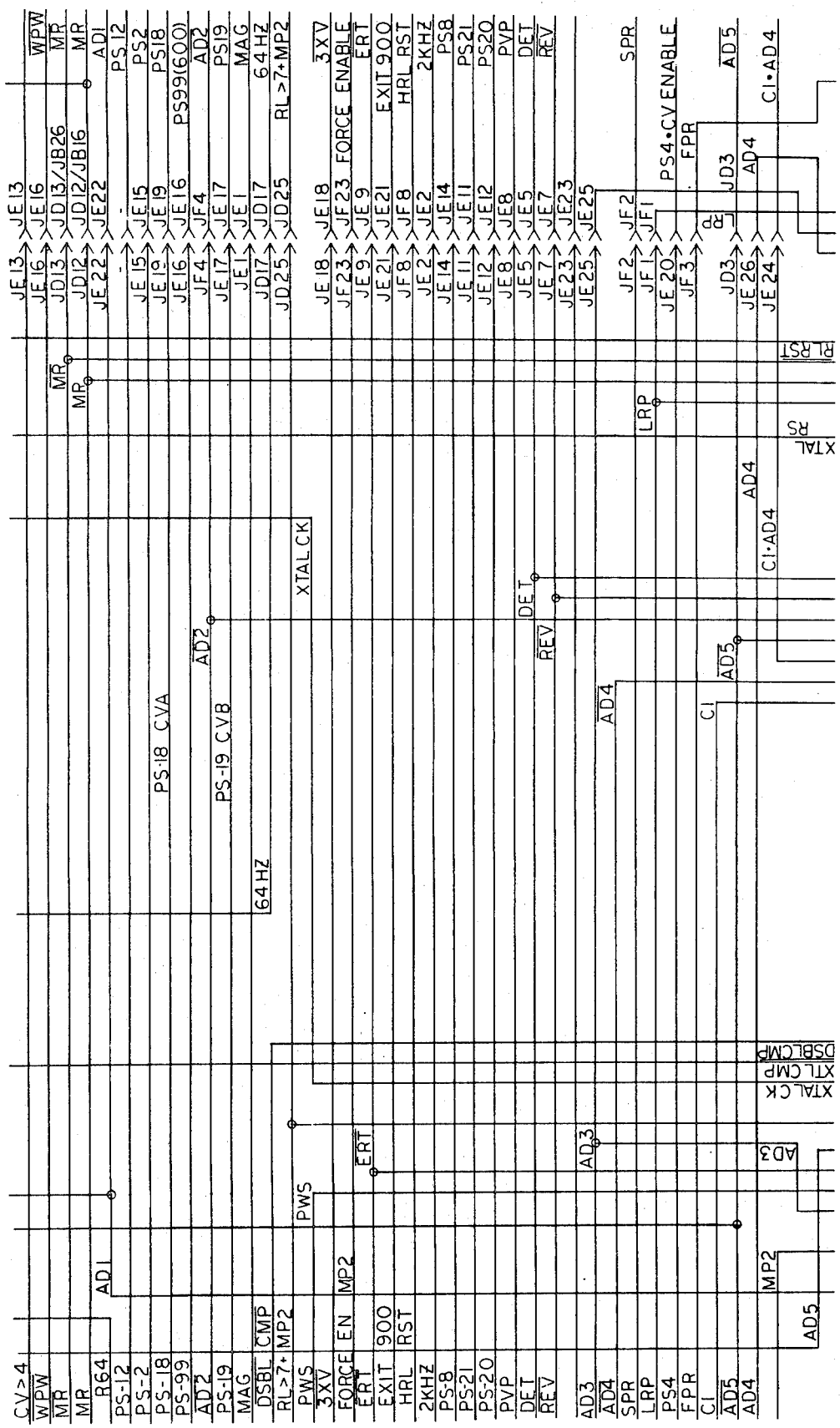
Figure 24Z:
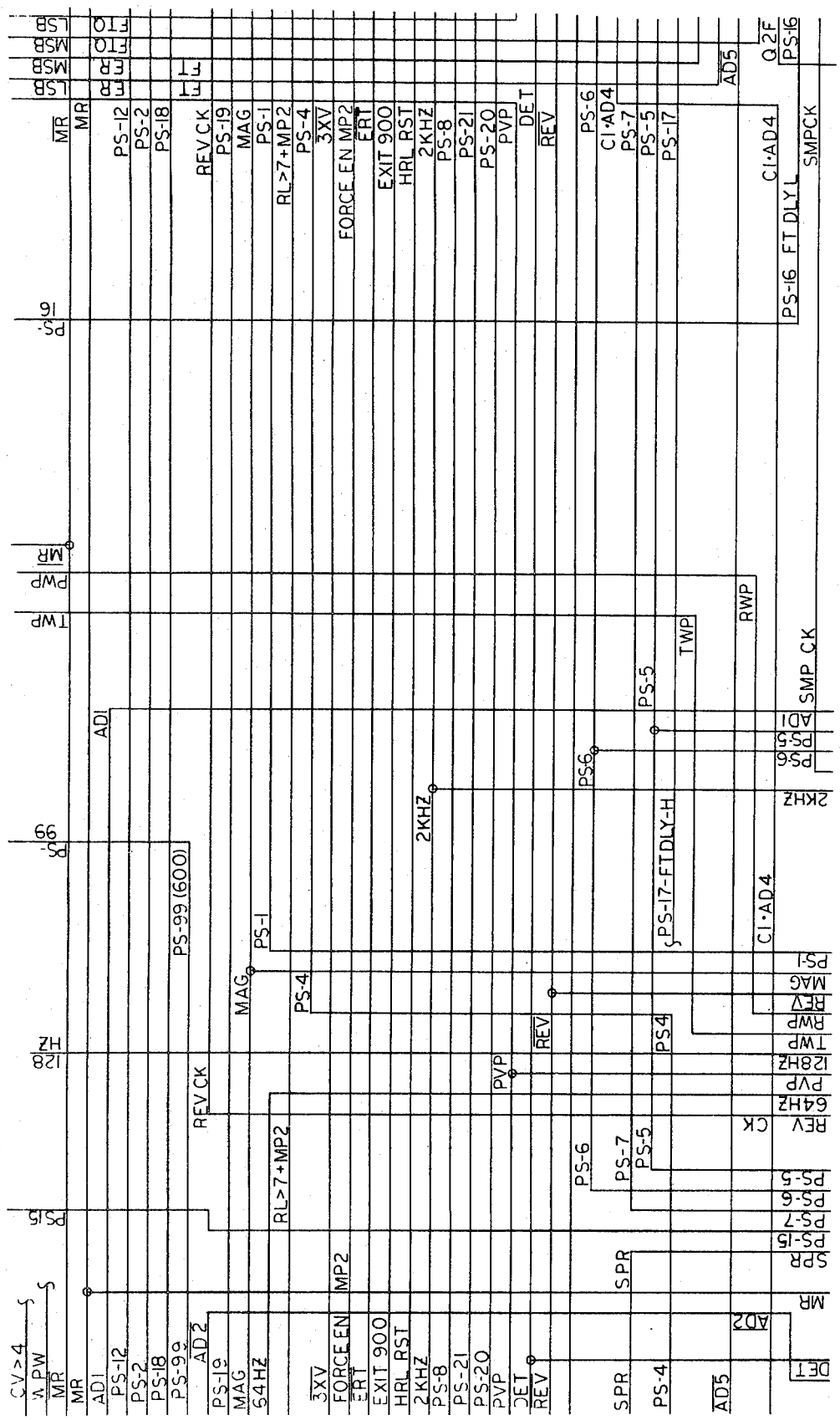
Figure 24A:
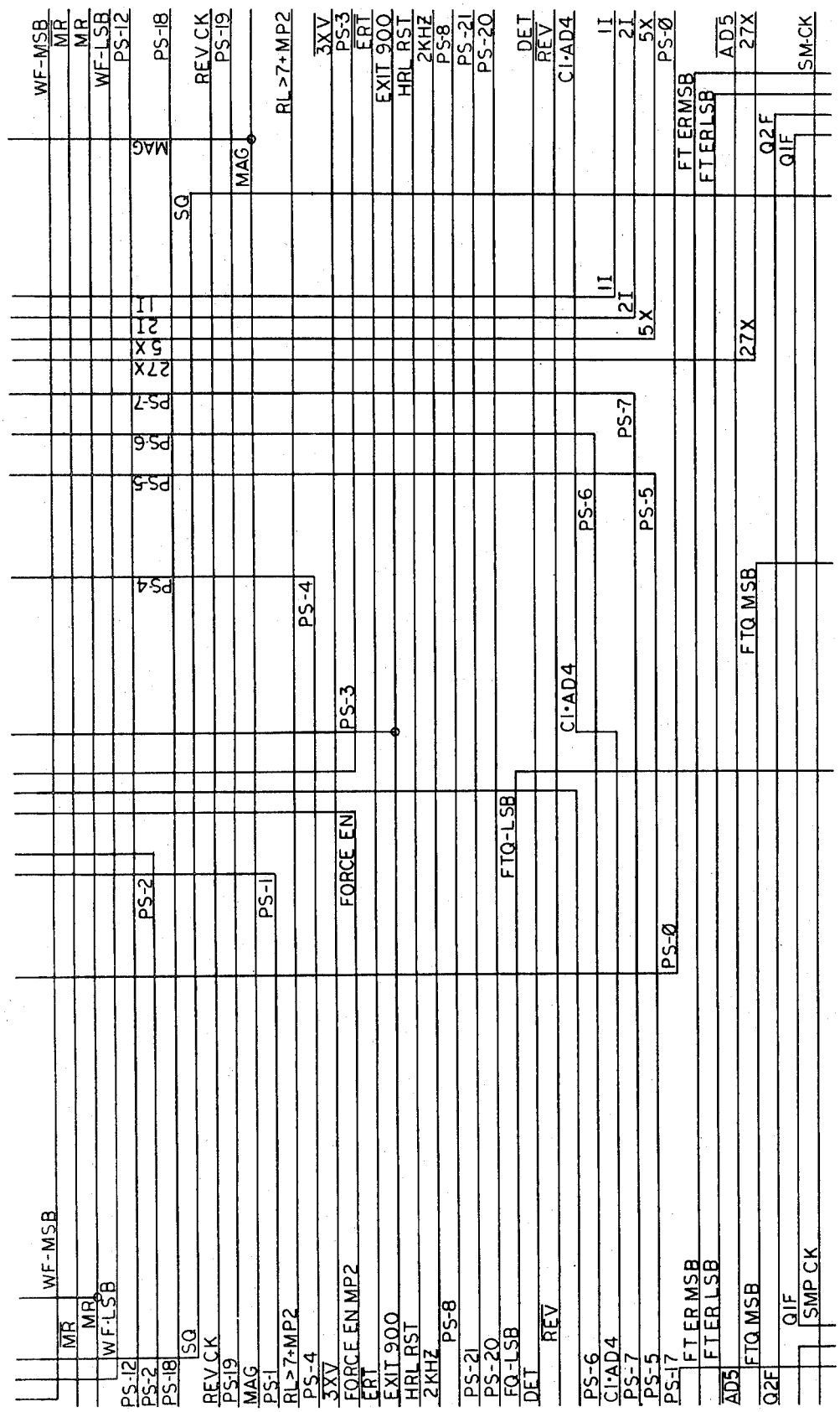
Figure 24:
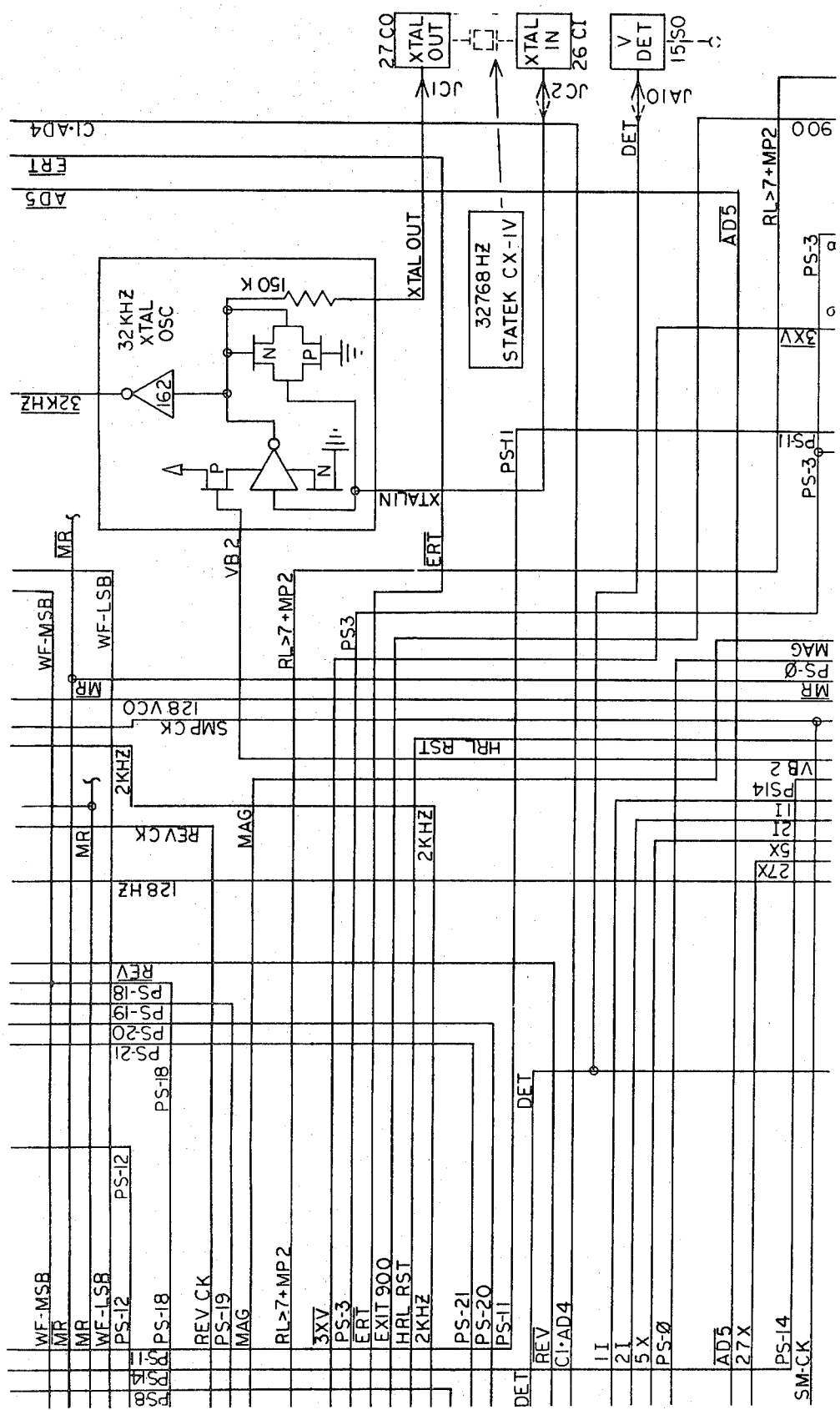
Figure 24C:
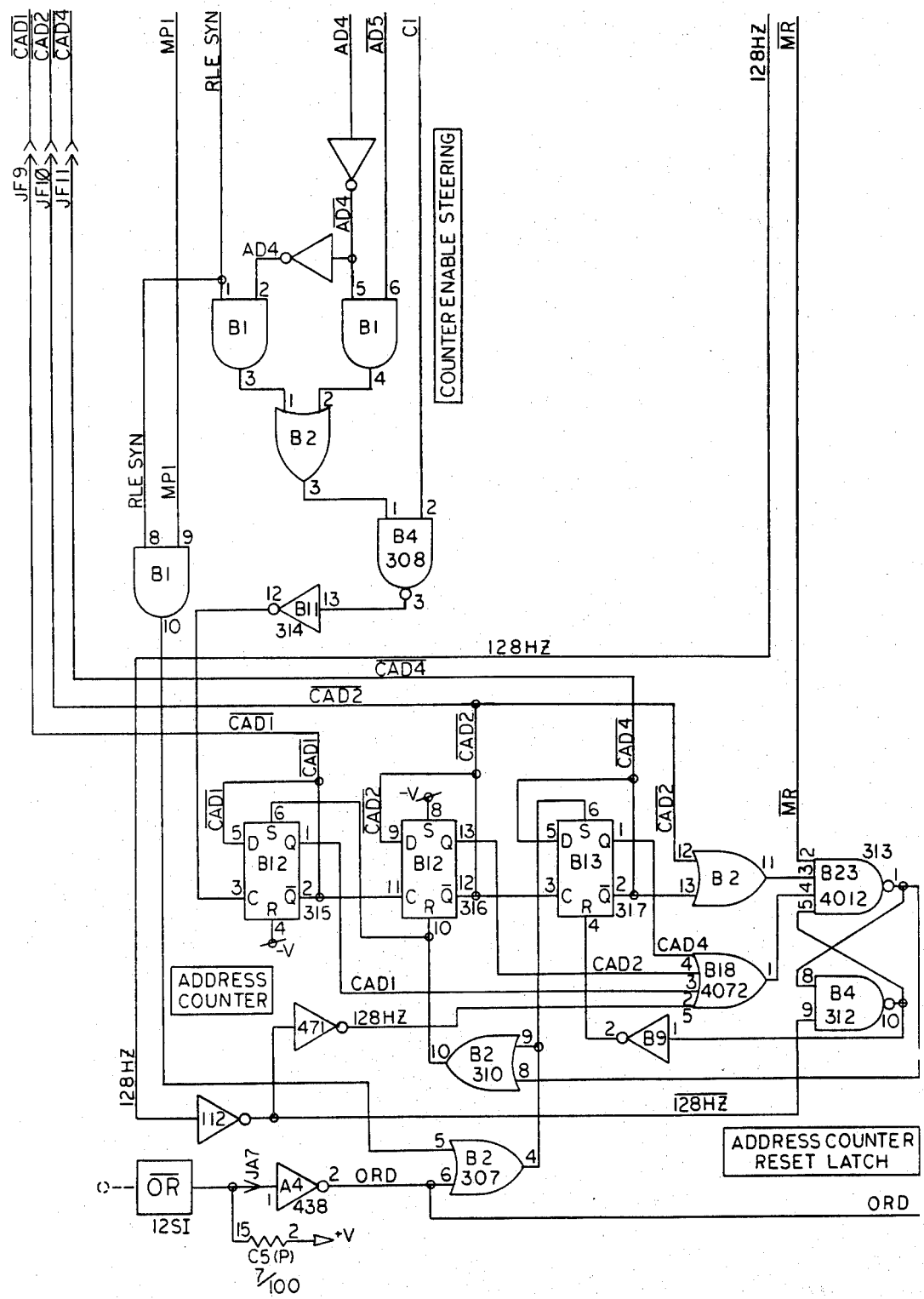
Figure 24:
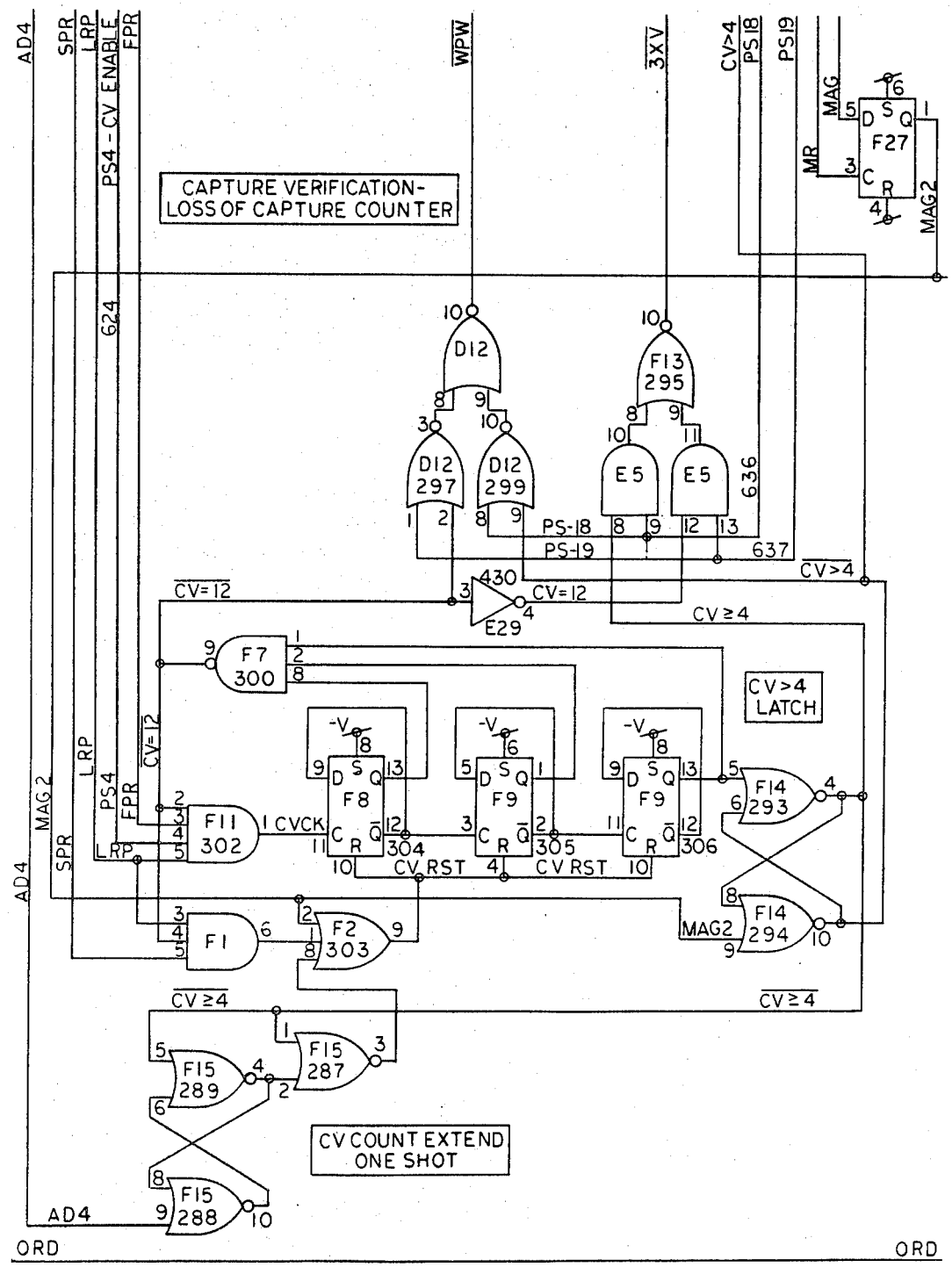
Figure 24:
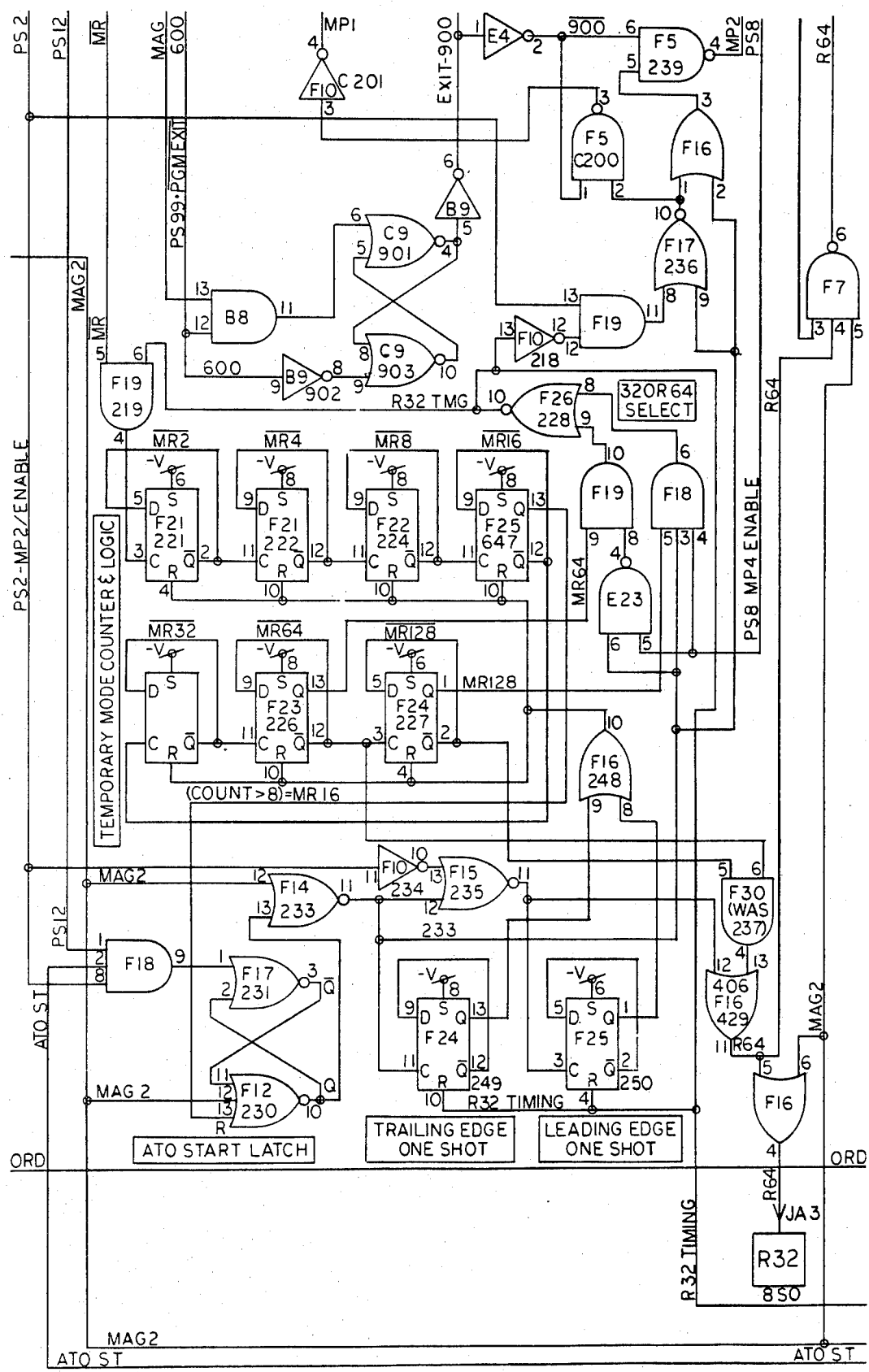
Figure 24:
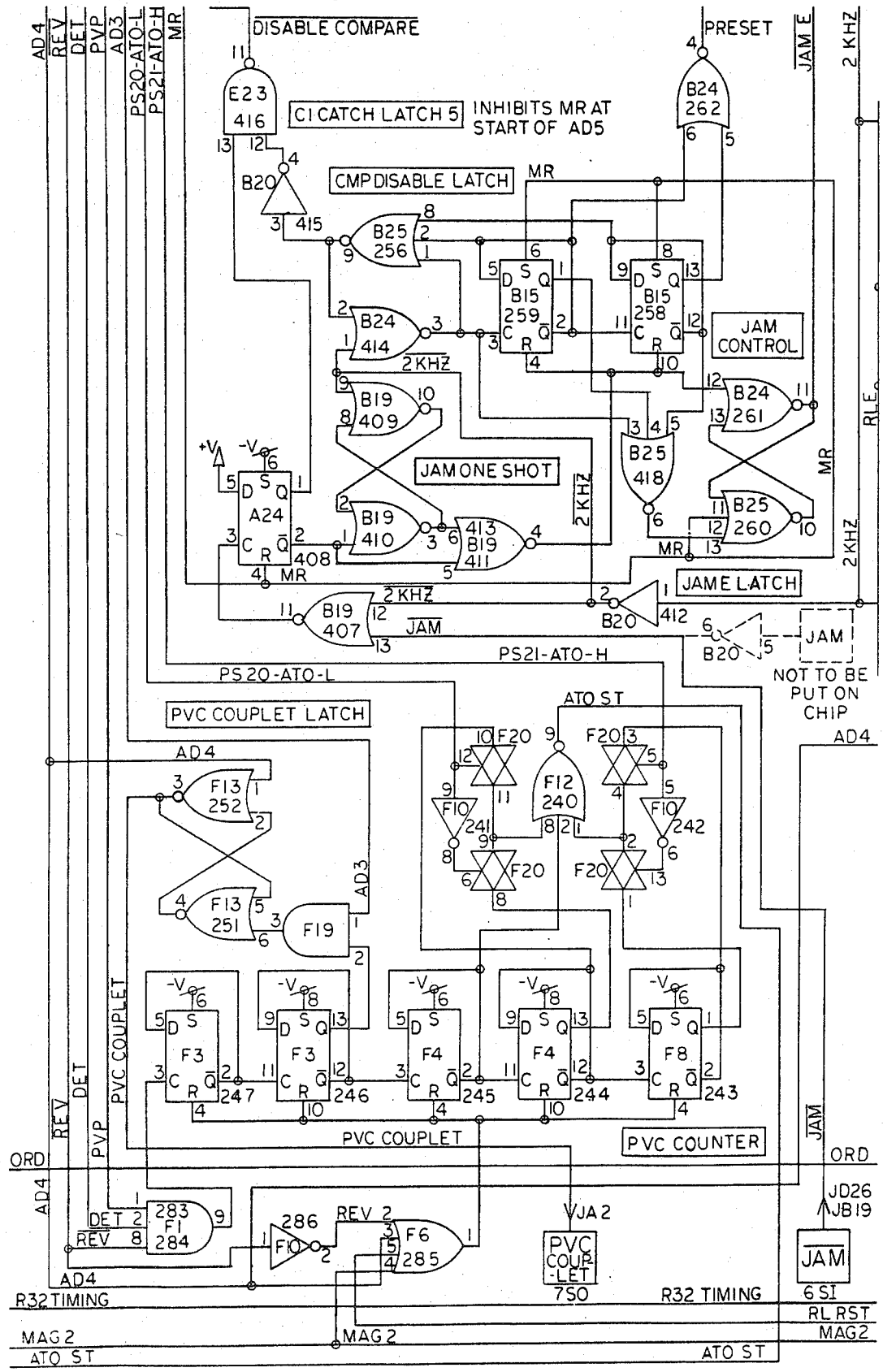
Figure 24:
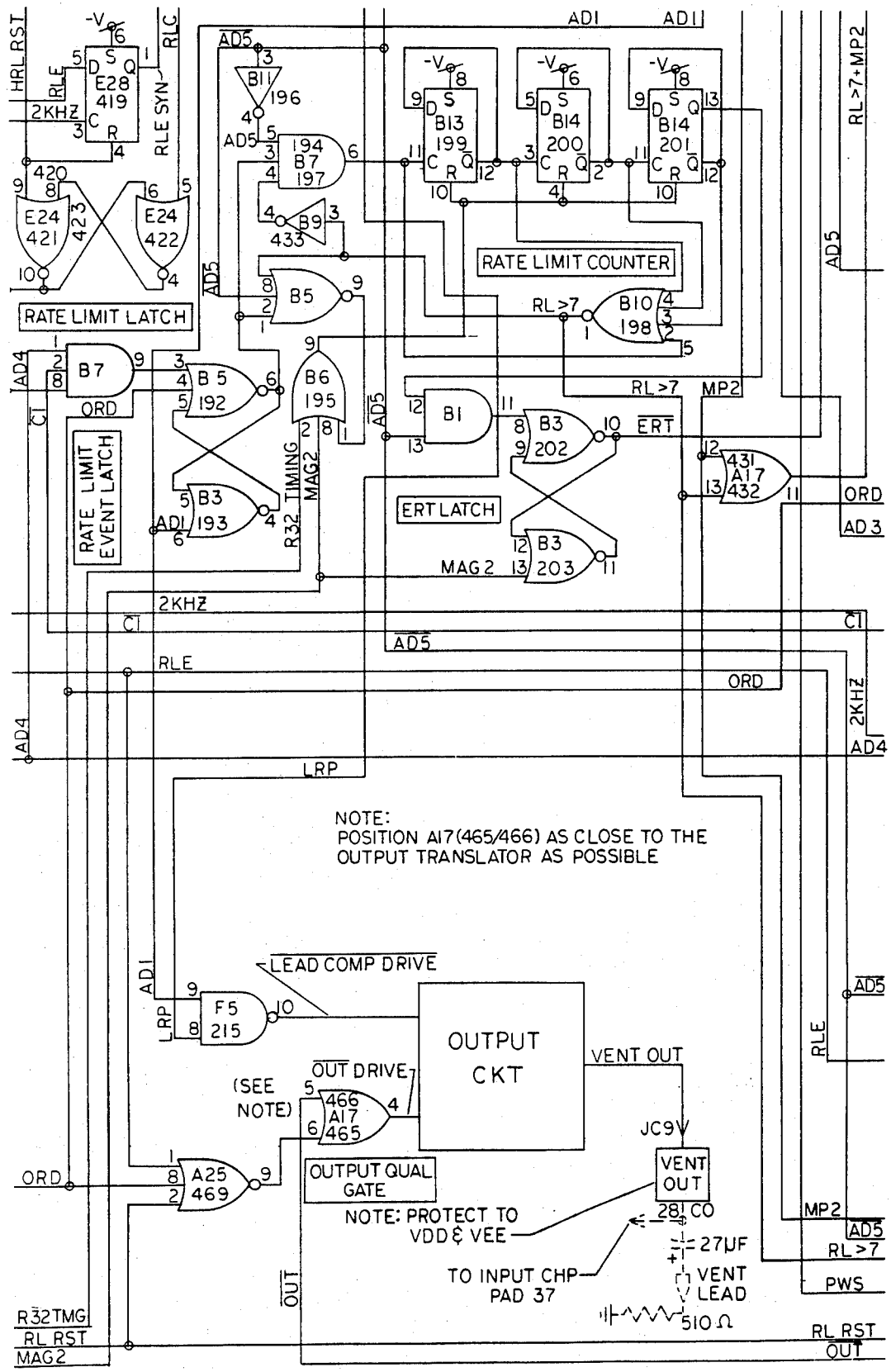
Figure 24:
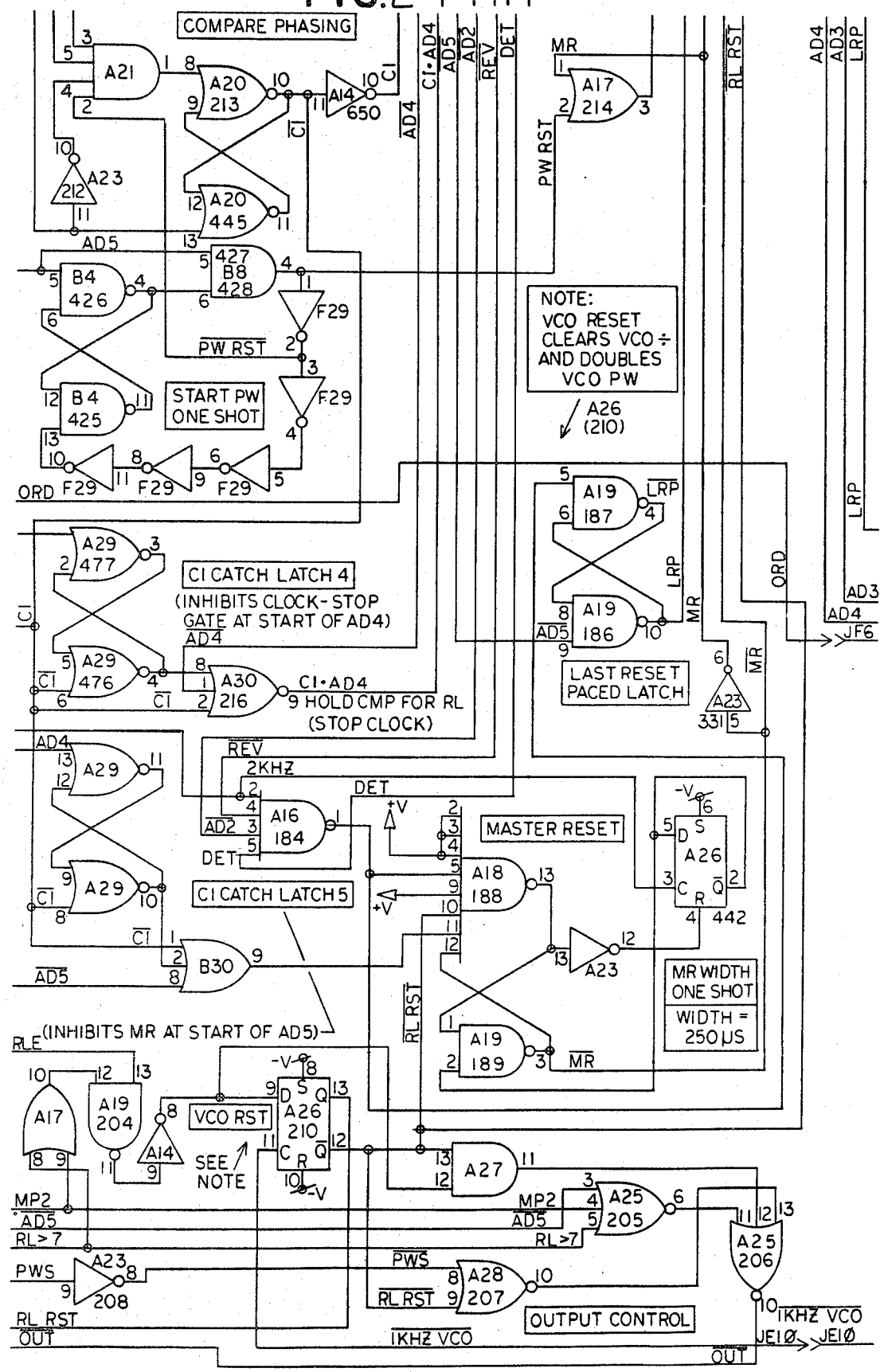
Figure 24:
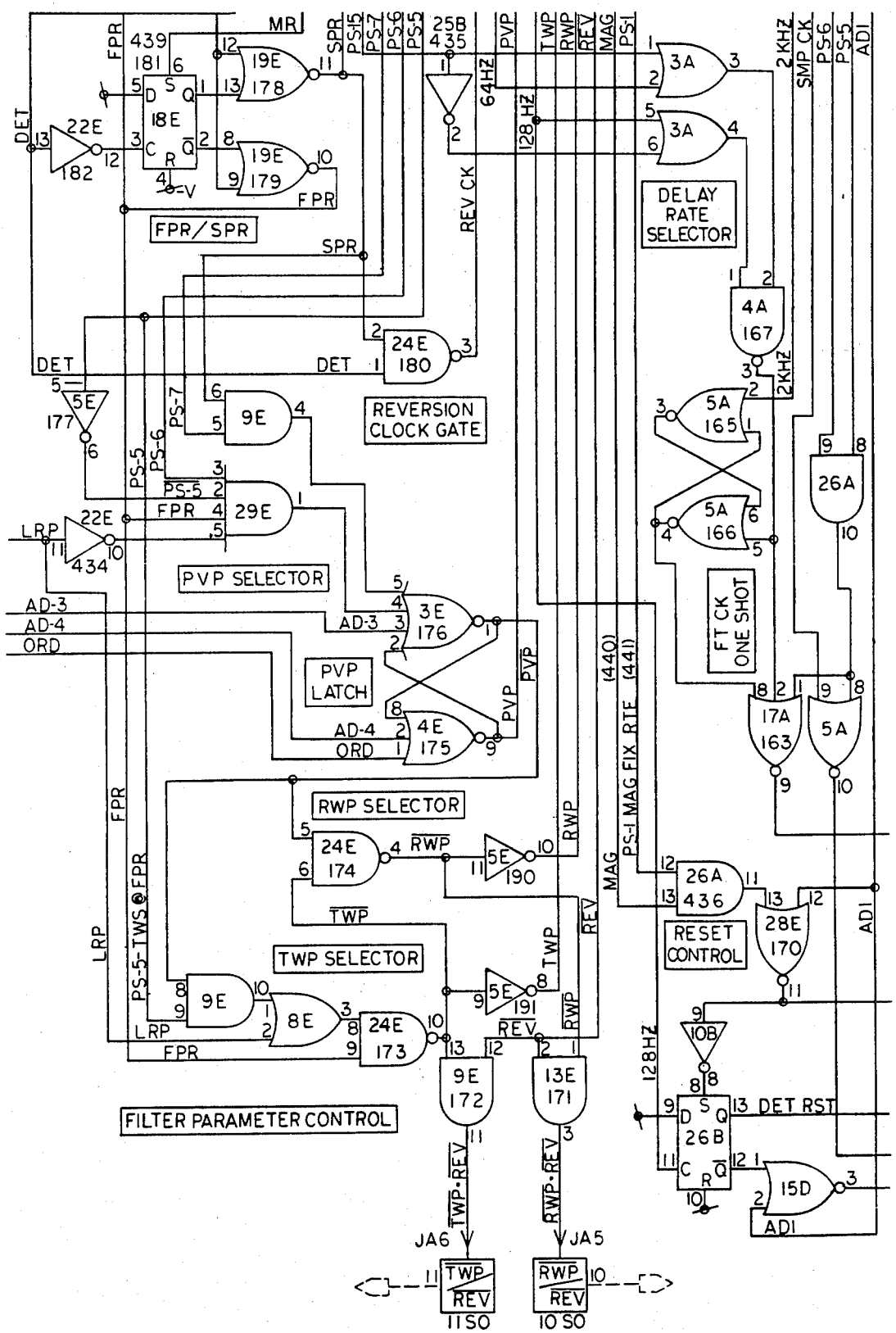
Figure 24:
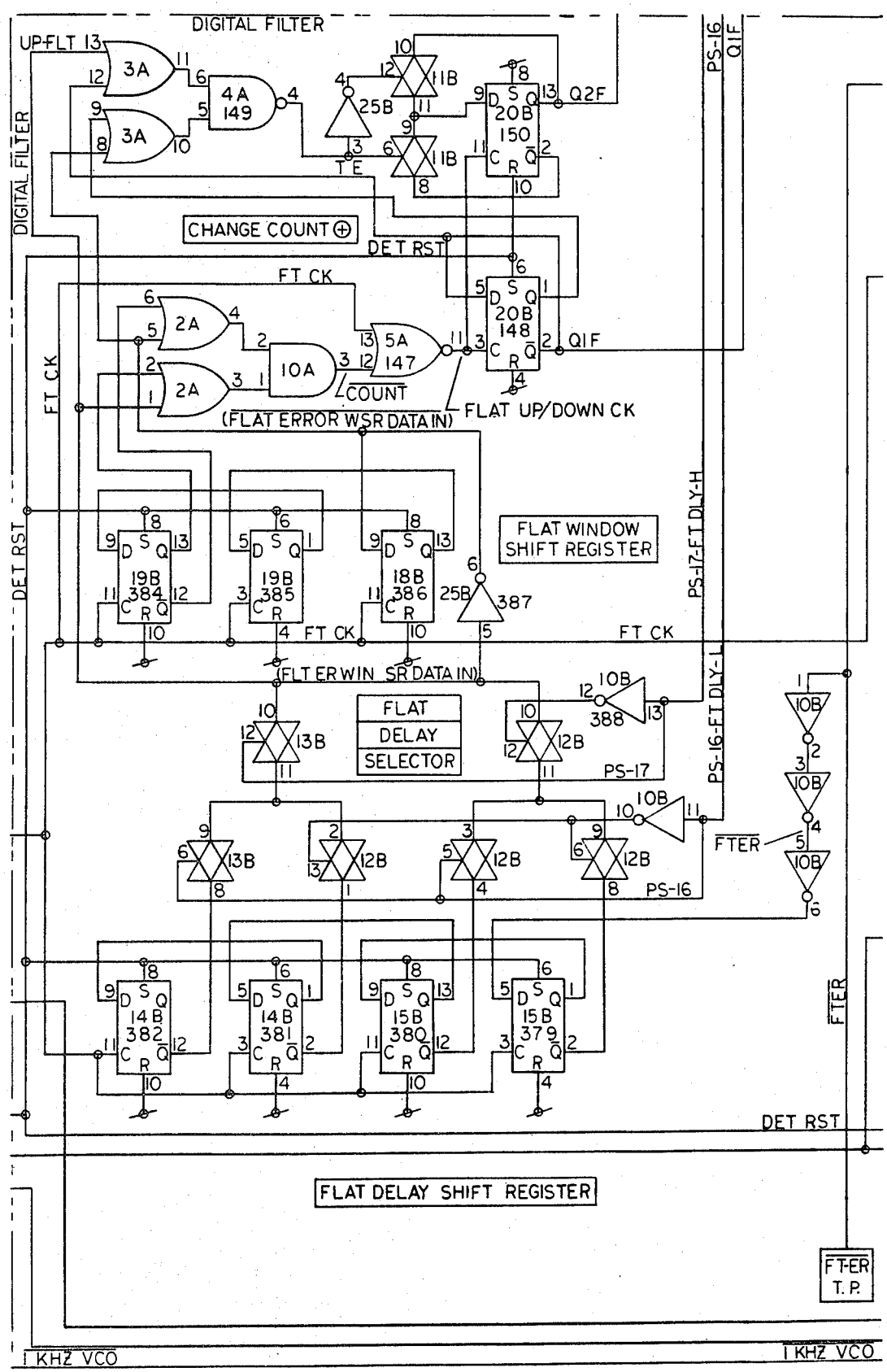
Figure 24:
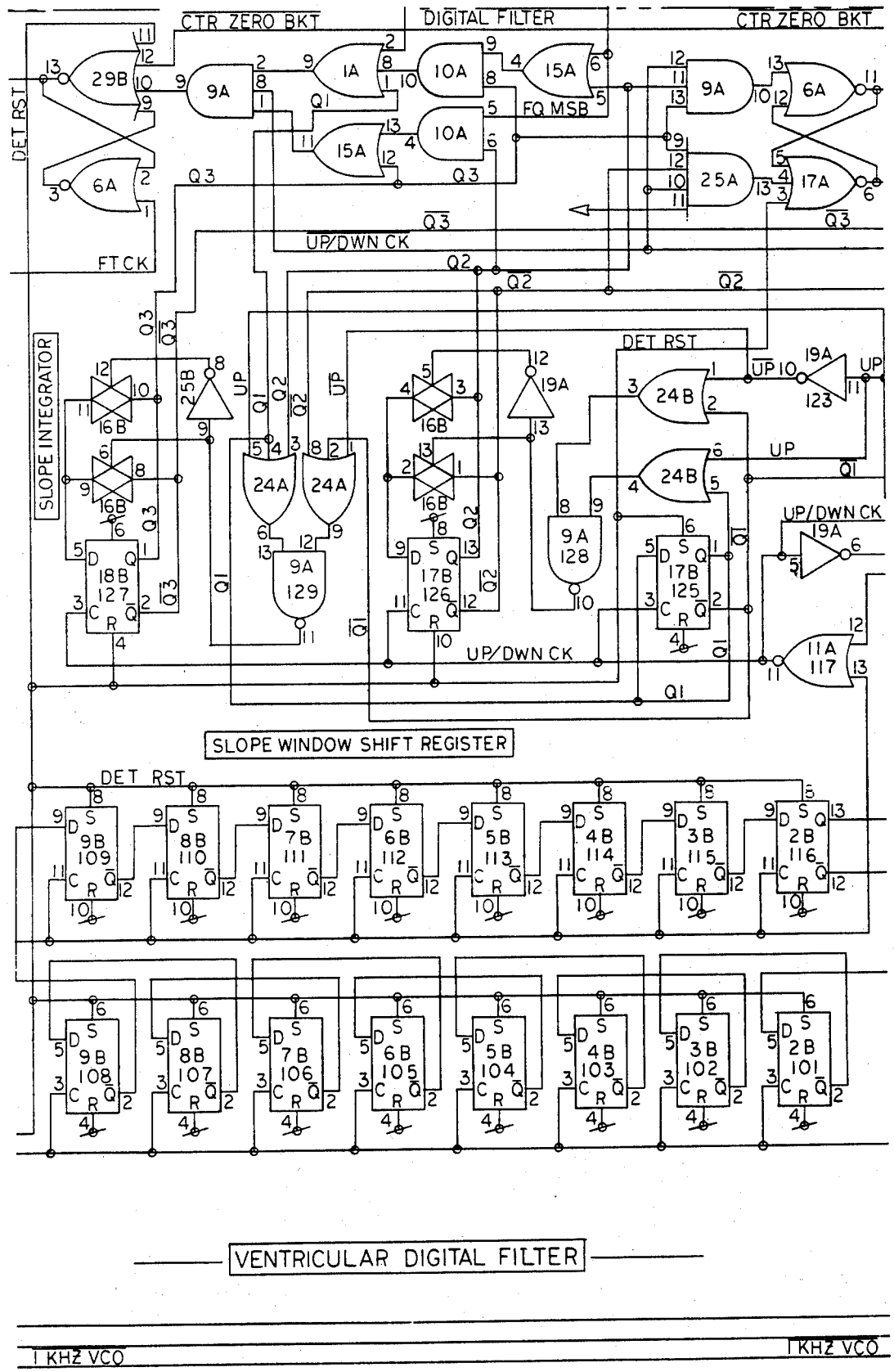
Figure 24:
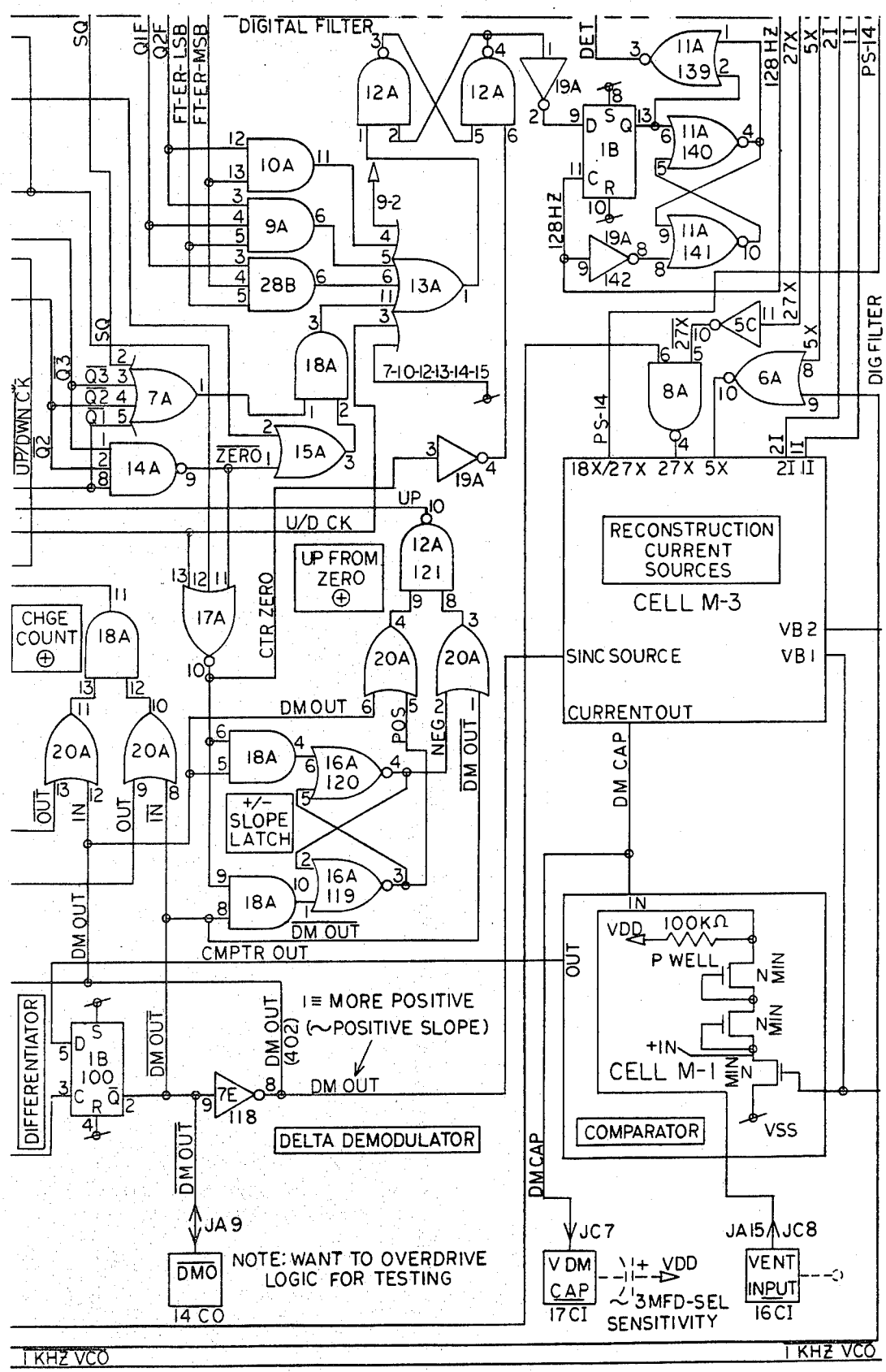
Figure 24:
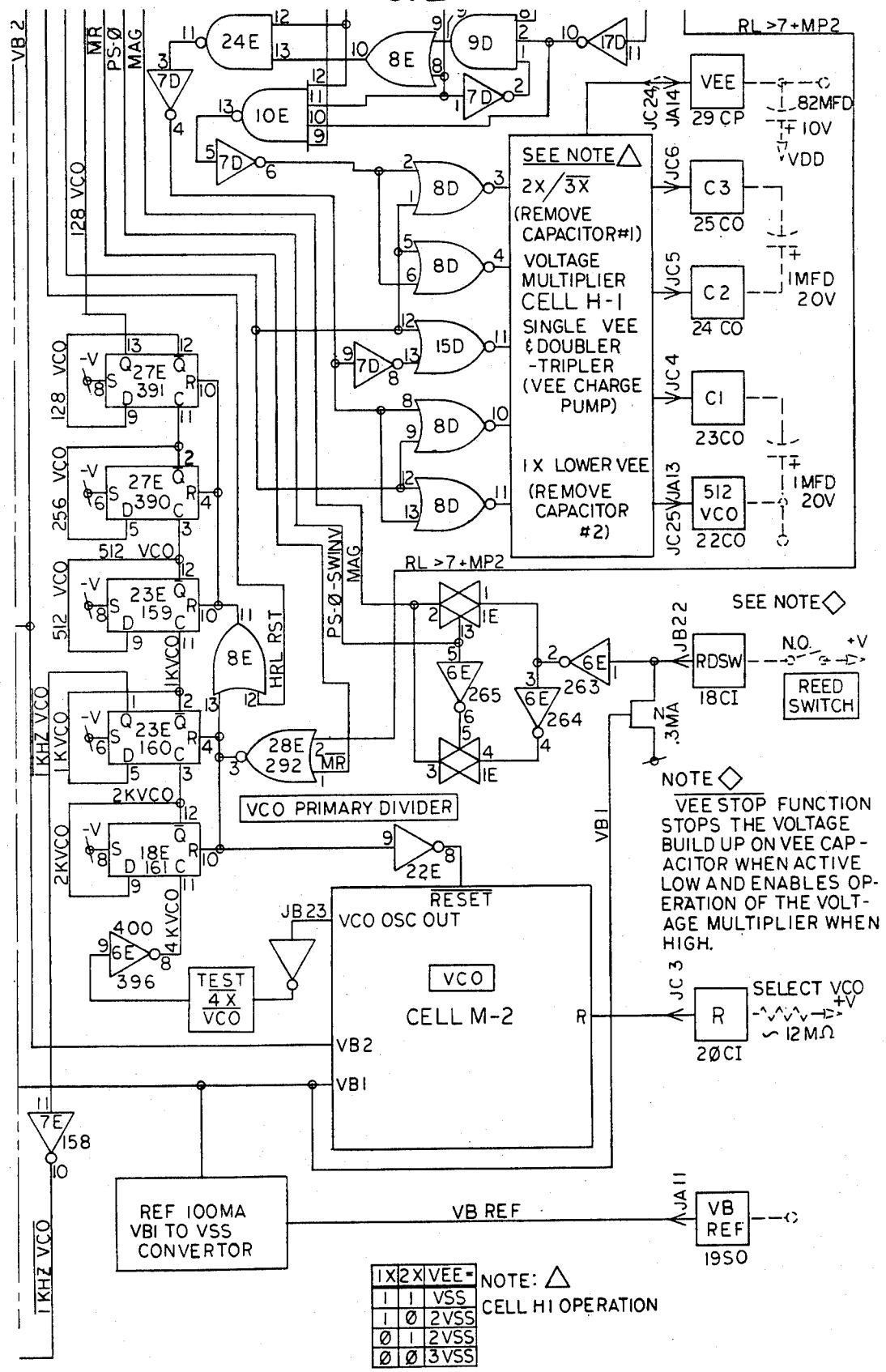
Figure 25B:
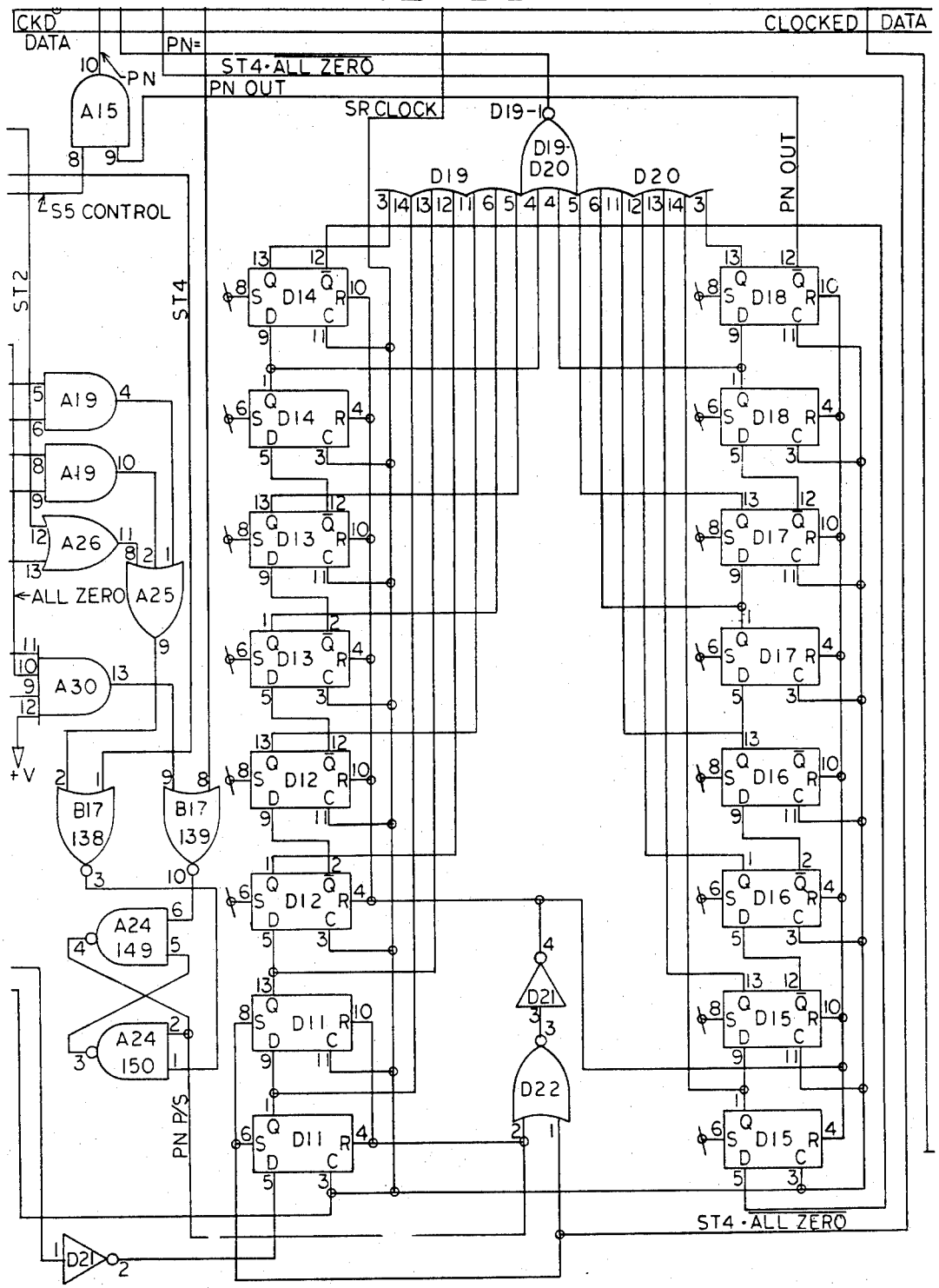
Figure 25F:
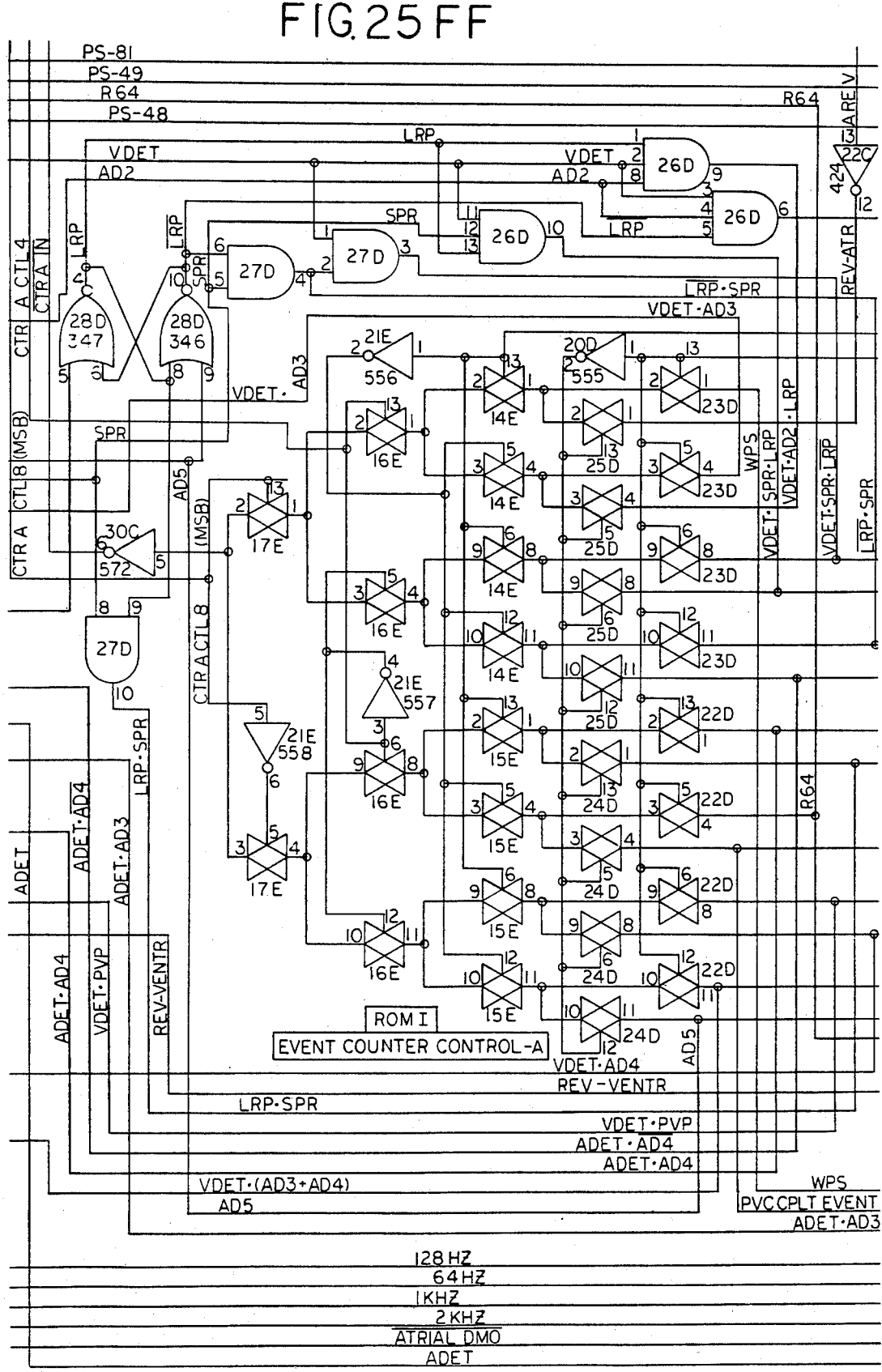
Figure 25K:
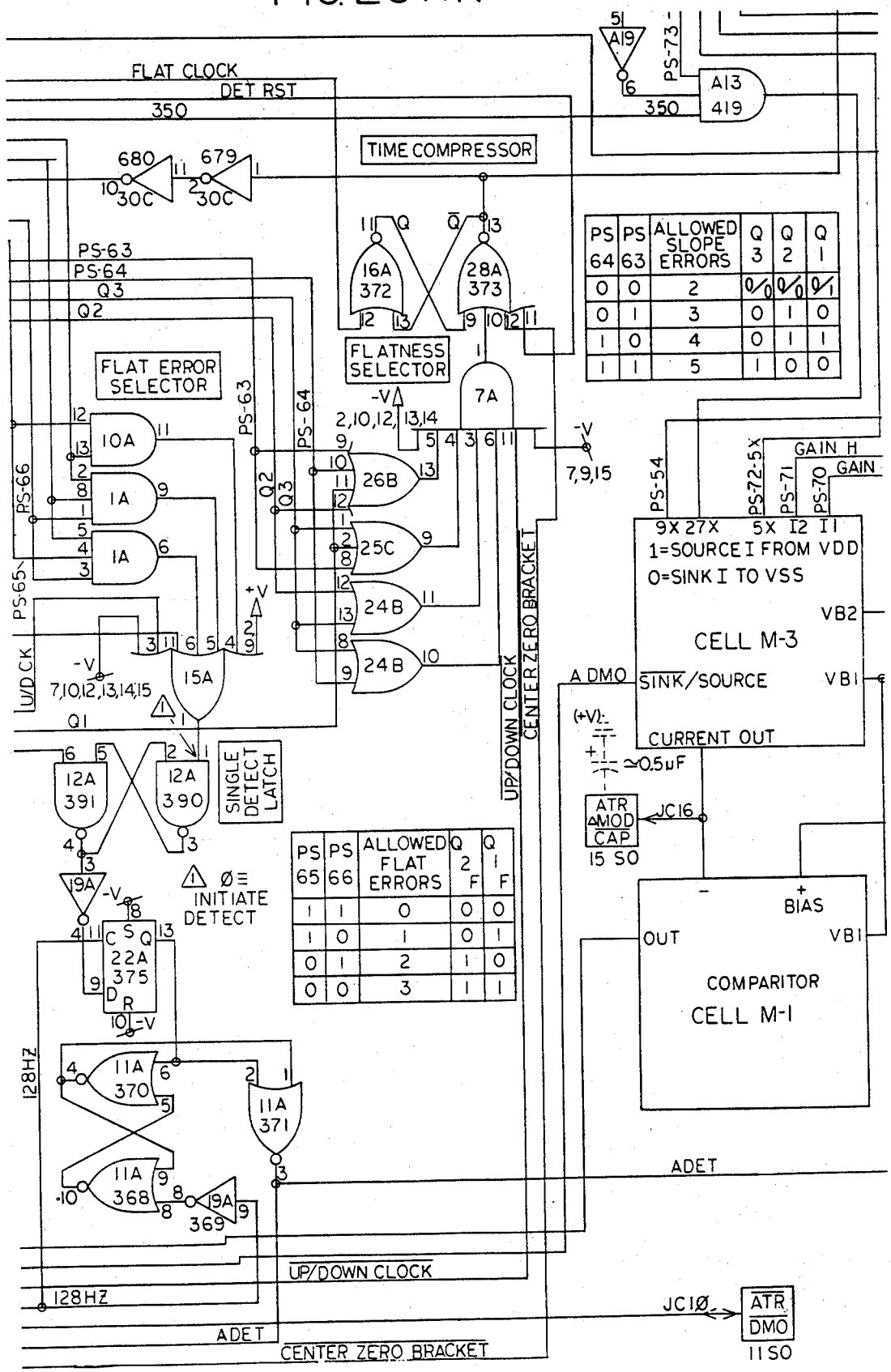

FIGS. 24A–24NN is a logic schematic diagram of the combined ventricle portion of a system incorporating the present invention;

FIGS. 25A–25LL is a logic schematic diagram of the combined atrial portion of a system, the event tally counters/selectors, the reference data RAM, and the transceiver for bidirectional communication with the external programmer—all part of a system which incorporates the present invention.

FIGS. 24A–24NN and 25A–25LL employ standard logic symbols defined in MIL-STD-806C.

DETAILED DESCRIPTION

Due to the large number of figures and reference numerals, a numeric system is adopted which has as its last two digits the particular reference numeral preceeded by the figure number in the hundred and thousands digit. For example, Reference 01 (the atrium) of FIG. 3 uses the reference numeral 301.

Figure 3:
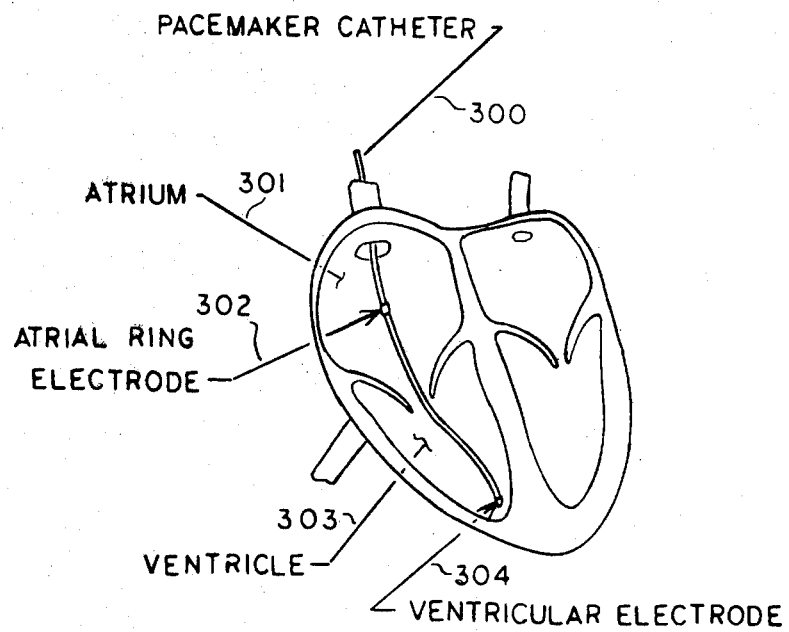
FIG. 3 is a diagrammatic view of a heart with both a ventricular sensing/stimulating and an atrial sensing electrode.

Referring first to FIG. 3, there is shown a diagrammatic illustration of a heart in which a pacing/sensing catheter 300 has been inserted. The catheter extends through the upper chamber or atrium 301, and into the lower chamber or ventricle 303, where the tip of the catheter is lodged in the apex of the ventricle. The catheter includes a ventricular electrode 304 at the tip, and an atrial electrode 302 spaced approximately seven centimeters from the ventricle electrode 304 so as to be located in the atrium. The atrial electrode 302 is shown, in the illustrated embodiment in the form of a ring electrode, but other shapes and designs including those already suggested, as mentioned above, may also be used. Further, although the atrial electrode 302 is shown within the upper chamber, it is not necessary that it touch the wall of that chamber, nor even that it be located within the atrium since it is not used for stimulating the atrium. All that is necessary is that it sense sufficient field vector from atrial de-polarization that a P wave can be detected by the atrial detection circuitry to be described. In some cases it may even be possible to detect a P wave from the signal sensed on the stimulating electrode in the ventricle.

The ventricular electrode 304 is connected by means of a ventricle lead or wire (not shown in catheter 300) to the pacemaker circuitry which is encapsulated in a moisture-proof and reaction free enclosure (not shown) in a manner known in the art, and which is normally located in the shoulder or abdomen of the patient; and the atrial ring electrode 302 is similarly connected to the circuitry by means of an atrial lead also in catheter 300. The ventricle lead is diagrammatically illustrated by the block 101 in FIG. 1; and the atrial lead is similarly represented by the block 101A. Each of the leads 101, 101A is connected to circuitry for identifying specific signals which form a part of an overall cardiac cycle or frame such as that shown in FIG. 6. This idealized signal will be discussed more below, but as is known, it comprises five major signal portions which are identified respectively as the P, Q, R, S and T waves. The P wave is associated with cellular depolarization or muscular contraction in the atrium. The Q wave is associated with initial stages of ventricle depolarization; the R-wave is associated with the peak of the depolarization of the ventricular myocardium; the S-wave is associated with the final stages of ventricular depolarization; and the T wave is associated with ventricular repolarization. The atrial repolarization is generally masked out by the QRS complex of the ventricle. Referring back to FIG. 1, the input circuitry includes an atrial filter section generally designated 100A in the lower left corner and a ventricular filter section generally designated 100 in the lower right hand corner. As will be explained, each filter is a digital filter which can be "set"—i.e., certain parameters of the filter can be changed under control of a state controller 231.

Briefly the input atrial filter 100A is associated with the atrial lead 101A and is set to identify a P wave sensed by the atrial electrode 302. Similarly, the ventricular filter section 100 is set to identify one of three waveforms, depending upon which portion of a cardiac cycle the heart has entered. This will be discussed in more detail below, but comparing FIGS. 6 and 7 (which have similar time scales), in the period identified as AD4 (the Ventricular Rate Time Out period), the ventricular filter is set to identify an R wave.

The period AD2 is the ventricular refractory period. If, during the immediately preceding cardiac cycle a natural R wave had been detected and the system generated a Master Reset pulse to reset the time base, the ventricular filter would be set in AD2 with the parameters for identifying either a T wave, an R wave, or a PVC. This gives the physician flexibility in determining how the system responds in certain cases. If, during the immediately preceding cardiac cycle, a stimulating pulse AD5 had been generated, the ventricular filter is set in AD2 to identify a T wave for verifying capture.

The period AD3 extends from the refractory period to the Ventricular Rate Time Out period, and it is a "window" in which the system tries to identify any Premature Ventricular Contractions. That is, in AD3, the parameters of the ventricular filter seek to identify PVCs.

The ventricle lead 101 is connected through a DC isolation network 102 to the input of a delta modulator circuit 104. It is the output of the delta modulator circuit 104 which is operated on by the ventricular input filter 100.

Similarly, the atrial lead 101A is connected through a conventional DC isolation network 102A to an atrial delta modulator circuit 104A, the output of which is coupled to the input of the atrial digital filter 100A.

The atrial delta modulator 104A and digital filter 100A are similar to the ventricular delta modulator 104 and digital filter 100, except that they are, of course, actuated or enabled by different signals and the ventricular digital filter 100 performs more functions during one cardiac cycle than the atrial filter. Hence, an understanding of the ventricular input signal processing circuitry will enable a person skilled in the art to readily understand the corresponding atrial digital signal processing circuitry.

VENTRICULAR DELTA MODULATOR

Referring now to FIG. 4, the output of the DC isolation circuit 102 is fed to the positive input 401 of a comparator circuit 402. The output of the comparator circuit 403 (a binary signal) is fed to the data input of a D-type flip-flop 405. The output of the flip-flop 405 is coupled to a source/sink control of a gain-controlled current source 407 along lead 406; and the output of the current source 407 is connected to a capacitor 414 and to the negative input of the comparator 402 on line 413. The capacitor 414 forms the delta modulator capacitor.

The current source 407 has five leads for programming the gain of the delta modulator. Two of these leads, designated 408 and 409 cause the output current to the capacitor 414 to increase or decrease in fixed steps. Hence, these leads change the gain of the current source but retain a linear characteristic for the delta modulator. The leads 411, 412, on the other hand, cause the gain of the current source 407 to be multiplied, and thereby cause the delta modulator to act as a logarithmic-companded analog to digital converter. The lead 412 causes a modification of the magnitude of one of the gain multipliers 411.

In operation, the comparator circuit 402 compares the magnitude of the input signal $V_{IN}$ 401 with the signal 413 on the storage capacitor 414. If the input signal 401 is greater, the comparator 402 generates the output signal 403 which is a logic "1" and the flip-flop generates a corresponding "1" output signal 406 but synchronizes it with the input clock 404 which determines the sample rate for the delta modulator. If the input signal 401 is less than the signal 413 on the storage capacitor 414, the output signal 406 is a logic "0". The output signal is thus a train of binary signals or pulses in synchronism with the clock. These signals are fed to the current source 407 which causes current to be fed to or drawn from the capacitor 414 depending on the state of the output signal 406. If the output signal is a logic 1, current is fed to the capacitor 414 to increase its charge or voltage; and if the output signal is a logic 0, charge is drawn from the capacitor to reduce its voltage by a predetermined increment. The increment is determined by sample clock 404 period and the gain of the current source 407. The signal on the capacitor 414 is thus the integrated output of the digital signal 406—i.e., its magnitude is an analog of the digital output that has been generated. Thus the digital output signal 406 is a digital derivative of the input signal 401 and therefore directly contains the slope information of the cardiac signal the delta modulator is connected to.

The relationship between the input signal 401 and the signal on the storage capacitor 414 is shown in FIG. 5 where reference numeral 501 represents an analog input signal and the waveform 502 represents the voltage on the capacitor 414. The binary output train 505 for this example is shown below the abscissa, reading left to right for the order in which they are generated. As can be seen from an observation of FIG. 5 where the input voltage has a relatively low slope, so that the current source can feed enough charge to the capacitor 414 to cause it to approximate the input signal, the output signal is a proportional series of alternating 1's and 0's, as represented by the portion designated 510 in FIG. 5. Where the input signal increases rapidly, the output signal is a series of 1's, as indicated by the portion 511; and the delta modulator is said to be positive "slew-rate limited", meaning that it is operating at the limit of its capacity to follow the rapid positive excursion of the input signal. Eventually, the signal on the capacitor 414 catches up with the input signal 512 in the illustrated example. Conversely when the input signal decreases rapidly, the output pulse train is a series of 0's for a negative "slew rate limited" portion 513 and thereafter operation proceeds as described. It will thus be observed, however, that the train of binary output signals 505 over a period of time is representative of the slope of the curve 501. The more logic 1's contained in the signal, the greater the positive slope; and conversely, the more logic 0's, the greater the negative slope. If the incoming signal were a DC level, the output signal would be alternate 1's and 0's, as indicated by the portion 514 of FIG. 5 where the slope of the input signal is low.

Returning then to FIG. 1, the delta modulator 104 has its gain adjusted by a gain control circuit 105; and its output signal is fed to a Sample Window Shift Register 106. The output signals from the delta modulator are shifted along the shift register 106. The contents of the shift register 106 represent the output of the delta modulator for a predetermined time period or "window", the length or duration of which depends upon the clock rate for the shift register.

VENTRICULAR FILTER

Before discussing the apparatus of the filter in particular, a graphical illustration of what is accomplished in the filter sections is shown in FIG. 8. In this example, the filter is set to detect an R wave, but the same principles apply equally well to the other signals being detected. For purposes of detection, the signal is divided into three segments occurring in succession. These are in order of occurrence: the Flat Window Segment designated 817, the Flat Delay Segment 818 and the High Slope Window Segment 819. Briefly, the digital filter will generate a "DETECTION" signal provided the slope of the incoming signal meets established criteria during the Flat Segment 817 and the High Slope Segment 819. The Flat Delay Segment 818 is used to define a time separation or delay between these other two segments.

Each segment or period is comprised of successive shorter periods. For the flat window 817 and flat delay 818 segments the shorter periods are "Sample Compression Groups" T1, T2 and so on, each corresponding to the time or sample data compression of the slope window signals Δ1, Δ2, etc., which become stored in a Flat Window Shift Register 114 and flat delay shift register 112. These "sample compression groups" are programmed to be either 8 or 16 milliseconds in duration (by changing the clock rate of the Flat Clock on line 131, as will be discussed). The physician also programs the Low Slope Selection Criteria 930 used for the compression groups 821-827 (i.e., he selects one of the states 901-904 of FIG. 9). The system stores an error signal in the sample compression group if the programmed Low Slope Selection Criteria 930 are exceeded during that sample compression group time period. These compression groups are shifted through the Flat Delay Window 818 into the three compression group 821-823 flat window 817 where they are tested for the number of compression group errors in the window 817. If these programmed criteria are exceeded (i.e., errors detected in each compression group time and number of compression group errors in the flat window) by more than a predetermined number (also programmed), then the criteria for that parameter are said to be violated, so that a "DETECTION" cannot be present.

The Flat Delay Segment is used to insert one to four (as programmed) "Sample Compression Groups" T4, T5, T6 and T7 (824-827) as a time delay between the Flat Window Segment 817 and the High Slope Window Segment 819. This section 818 is a programmable delay and is implemented in a Flat Delay Shift Register 112 with the selection of the programmed number of compression groups being effected in a Flat Delay Selector 113 of FIG. 1. The purpose of the flat delay section 818 is to mask or ignore the Q wave portion of the cardiac cycle due to inconsistencies between patients. The programming of the delay time enables the physician to place the Flat Delay Segment 817 safely between the Q wave and the P wave of the cardiac cycle.

The amount of time compression implemented in the Flat Window Segment 817 and Flat Delay Segment 818 are programmable to allow the physician to select the time width of the Flat Window Segment 817 and modify the delay. This is implemented in the time compressor 111 of FIG. 1, to be discussed. For the High Slope Segment 819 which is samples Δ1 to Δ16, the High Slope Selection Criteria 931 (one of the programmed states 905 or 906 of FIG. 9) are used, and a programmable higher sample rate is used for the High Slope Detection so that the high slope selection criteria become more difficult to meet.

Turning now to the apparatus of the Ventricular Filter, as indicated above, the output of the Ventricular Delta Modulator 104 is coupled to the input of the Sample Window Shift Register 106. A 2 KHz clock is fed to the sample window shift register 106 on line 119 and this clock is counted down to one of 2 KHz, 1 KHz, 0.5 KHz, or 0.25 KHz sample rates and selected according to two bits of information received on bus lines 201A comprising a portion of a Ventricular Filter Parameter Data Bus 201. This bus couples data stored in a Ventricular Filter Parameter Control RAM (Random Access Memory) designated 213 of FIG. 2 which determines the parameters of the ventricular filter. These parameters are changed for detecting T waves, R waves and PVCs, as described above, and the various control bits of each of the three parameter sets may be programmed for a given type of detection, such as an R wave, as will be clear from subsequent discussion.

The two bits of information on bus lines 201A, as indicated, set the clock (on line 119) division to generate a Sample Clock on line 127. The Sample Clock is fed to the delta modulator 104 to determine the sampling rate for the incoming cardiac signal and determine the rate at which the information is fed to the shift register 106, and it also determines the clock rate for a Slope Up/Down counter 107. The counter 107 receives, on the line designated IN (123), the output of the delta modulator 104, and on a line designated OUT (124), the output of the shift register 106. Briefly, the function of the counter 107 is to maintain a running count of the number of 1's generated by the delta modulator in the window being sampled by the shift register 106. Thus, the counter 107 is a three-bit 907 plus sign latch 910 counter, each bit corresponding to a column in 907 and the sign 910 corresponding to positive or negative relative to CENTER ZERO 911, for the table shown at the left of FIG. 9. The sign latch is set by the direction the counter increments from CENTER ZERO 911. The lines below CENTER ZERO represent negative numbers of 1's or the complement (i.e., the number of 0's contained in the sample window shift register 106). The sign bit 910 is normally used in detecting PVCs and PACs and normally ignored for other waves. This produces similar detections for either positive or negative R, T, and P waves.

The two inputs 123 and 124 to the counter 107 are fed to an internal exclusive OR gate which is clocked by the sample clock on line 127. The signal on the line IN 123 indicates what value is being clocked into the shift register 106, and the signal on the line OUT 124 indicates what value is being clocked out of the shift register 106. If there is a 0 on the IN line, and a 0 on the OUT line, or if there is a 1 on the IN line and a 1 on the OUT line, then there is not net change to the contents of the shift register 106, so the counter 107 does not count. If there is a 1 on the IN line and a 0 on the OUT line and the slope is positive, then the counter 107 counts up one, indicating an increasing positive slope. If there is a 0 on the IN line and a 1 on the OUT line, the counter 107 counts down one, indicating a decreasing slope. For negative slopes the counter 107 counts down for a 1 on the IN line and a 0 on the OUT line, indicating a decreasing negative slope; and the counter 107 counts up for a 0 on the IN line and A 1 ON the OUT line, indicating an increasing negative slope.

It is the contents of the counter 107 which define whether the incoming signal meets the programmed High Slope Selection Criteria 931 of the states designated 905 or 906 in FIG. 9 for the high slope segment 819 as well as the programmed Low Slope Selection Criteria 930 of the states 901-904 for the compression groups T1-T7 in the Flat Delay Segment 818 and the Flat Window Segment 817. Thus, the contents of counter 107 comprises a digital word that is representative of the average input signal slope over the sample window period. The time length of the window is determined by the number of bits in the shift register and the programmed sample clock period.

The contents of the counter 107 are sensed by a High Slope Selector 108 which is set via a bus line 201B of the ventricular filter parameter data bus 201 to establish either High Slope Selection Criteria 905 or 906 (depending upon the state of the bus control bit at 201B) as illustrated in FIG. 9. Two more control lines on the ventricular filter parameter bus at 201B enable a positive slope sign and a negative slope sign to independently or together qualify a high slope detection 126 for PVCs. The High Slope Selector 108 is operating at the sample clock 127 rate of the shift register 106. It generates an output signal which is a logic "1" to AND gate 109 whenever the programmed High Slope Selection Criteria are met. The other input to AND gate 109 indicates that the low slope criteria have not been violated 136.

The contents of the slope counter 107 are also fed to a Low Slope Selector 110. The selection criteria for the Low Slope Selector 110 are coupled by two lines diagrammatically illustrated at 201C of the Ventricular Filter Parameter Data Bus 201. These two bits determine which one of the four possible Low Slope Selection Criteria 930 of states 901-904 are to be employed for the Flat Window Segment 817.

If the contents of the slope counter 107 are within the criteria defined by the programmed state (901-904) of the Low Slope Selector 110, a 0 output signal is generated and fed to a Time Compressor Circuit 111. The time compressor 111 is a latch flip-flop which is set by a "1" signal from the Low Slope Selector 110 (indicating a violation of the programmed Low Slope Selection criteria), and is reset by the Flat Clock of line 131, which is derived from the 128 Hz clock 130, and hence is synchronous with it. The frequency of the Flat Clock, as defined by one bit of information on a bis line at 201D of the Ventricular Filter Parameter Data Bus 201, may be 128 or 64 Hz.

The Flat Clock determines the time duration of the compression groups T1-T7 (821-827), and it is used to shift data in determining whether the Low Slope Selection criteria are met for the Flat Segment 817 of FIG. 8. Its repetition rate is slower than the rate at which data is clocked into the slope counter 107 from which the High Slope Selector 108 determines whether the High Slope Selection criteria for the High Slope Segment 819 of FIG. 8 are met.

In other words, the sampling rate for the High Slope Segment 819 is higher than that for the segments 817 and 818. However, none of the data for Low Slope Selection is lost because the time compressor 111 is a latching circuit clocked by the low rate flat clock 131, and any time that a selection violation is sensed in the Low Slope Selector 110, a corresponding bit is transferred to the shift register 112 clocked by the Flat Clock. The Flat Delay Shift Register 112 may be a four-bit shift register, each bit corresponding to one of the time periods T4-T7 (824-827) of the Flat Delay Segment 818 at the time of detection. In other words, the Flat Delay Shift Register 112 (and associated flat detection circuitry to be described) is clocked at a much lower rate than the Sample Window Shift Register 106. Hence, the "Sample Compression Groups" T1-T7, representing time segments over which the contents of the respective registers are representative, are longer for the Flat Segment 817 and Flat Delay Segment 818 than they are for the High Slope Segment 819.

The contents of the Flat Delay Shift Register 112 are coupled to a Flat Delay Selector 113 which is programmed by two bits along lines 201E of the Ventricular Filter Parameter Data Bus 201 to determine the number of time periods or compression groups in the Flat Delay Segment 818. In the illustration of FIG. 8, FOUR sample compression groups are used.

The output of the Flat Delay Shift Register 112 is fed through the Flat Delay Selector 113 to a Flat Window Shift Register 114, which in the illustrated embodiment comprises three bits, corresponding to compression groups T1-T3 (821-823) of FIG. 8. The Flat Window Shift Register 114 corresponds to the Flat Segment 817 of FIG. 8, and the contents of this shift register are sensed by a Flat Error Up/Down Counter 115 which is similar to the previously described counter 107 except that it counts the number of ones (i.e., violations of flat criteria) in the flat window shift register 114 as a number without algebraic sign. The register 114 and the counter 115 are both clocked by the Flat Clock on line 131.

The contents of the Flat Error Counter 115 are fed to a Flat Error Selector Circuit 116 which is set by two bits on bus 201F to accept zero, one, two, or three errors for the Low Slope Selection Criterion 930—one of the states 901-904 of FIG. 9 as previously explained. If the Flat Error Selector circuit 116 is programmed to accept three errors, it is equivalent to ignoring the Flat Segment 817 because it indicates that an error would have occurred in each of the three compression groups T1-T3. In other words, the Flat Error Selector would accept up to and including three errors in the 3-bit Flat Window Shift Register.

If fewer than the programmed number of errors are found for the Flat Window Segment 817, an enabling signal called Flat Detect is transmitted along line 136 to an AND gate 109, the other input of which is a signal labeled SLOPE DETECT 126 from the High Slope Selector 108. It will be observed that at the time the Flat Error Selector Circuit 116 generates a Flat Detection signal, the contents of the flat window shift register 114 will correspond respectively to compression groups T1, T2 and T3; the contents of the flat delay shift register 112 will correspond to compression groups T4, T5, T6 and T7 (if the flat delay is so programmed to 4 compression groups), and the contents of the sample window shift register 106 will correspond to future compression groups in the high slope segment 819 of the cardiac signal.

Thus, the output signal of AND gate 109 is a signal representative of the fact that all selection criteria have been met, and this signal is fed to a Ventricular Detection Synchronizer 117 which sets a latch when a detection is present. The latch is reset only after the contents of the Up/Down Counter 107 return back through CENTER ZERO 911 (see FIG. 9). This prevents multiple ventricular detections during any one cardiac cycle complex (such as QRS). The circuit 117 also synchronizes a VENTRICULAR DETECTION with the system clock which is at a lower rate than the rate at which the Sample Window Shift Register 106 and the Ventricular Delta Modulator 104 are clocked.

The ventricular detection circuitry is initialized when a Lead Compensation (LC) address (AD1) 711 pulse is generated as a result of Master Reset (MR) and held in reset for the duration of AD1. The ADs are described in connection with FIG. 7 in the next section on timing circuitry. This detector reset loads the contents of the Sample Window Shift Register 106 with alternate 1's and 0's (representative of an initial flat slope), and it resets the contents of the slope Up/Down Counter 107 to CENTER ZERO 911 as indicated in FIG. 9. The counter 107 contains a separate latch which indicates, if the contents of the counter are all 0's, whether the counter is at either end position 913 or 929 or the CENTER ZERO position 921, referring to the chart 907 at the left side of FIG. 9. This detector reset AD1 is used to set the flat portion of the detector 100 to a full error state so that an initial delay to the first detection in AD2 (712) may be delayed out past the QRS complex previously detected (V DET 709) or created (AD5) in generating the current master reset 710 and AD1 (711) if so desired by the physician. If the first detection is delayed by a long AD1 and the flat detect 136 is enabled by the T-wave parameters, a T-wave is used for capture verification (to be discussed), otherwise a short AD1 and ignoring the flat detect 136 in the T-wave parameters will use the R-wave created by a stimulating output in the previous AD5 for capture verification.

When the flat portion of the detector is reset, AD1 in line 293 is used to set the time compressor 111 to an error state and set the Flat Delay Shift Register 112 (T4, T5, T6 and T7 in FIG. 8), the Flat Window Shift Register 114 (T1, T2 and T3) and the Flat Error Up/Down Counter 115 all to a full error state (by the set signal in line 131).

Thus, if all of the selection criteria are met, the AND gate 109 generates an output signal which is synchronized with the system clock in the Ventricular Detection Synchronizer Circuit 117, and a corresponding detection signal labeled V DET is generated on line 138.

The ventricular filter 100 is set with corresponding sets of parameters to detect R waves, T waves and PVCs during various portions of the cardiac cycle as will be subsequently described. The signal V DET on line 138 is representative of the detection of an event corresponding with the parameters which have been set in the ventricular detection filter from the Ventricular Filter Parameter Control Memory 213. The programmed parameters for the Ventricular Detector are summarized in Table I. They also apply to the atrial detector.

TABLE I

DETECTOR'S PROGRAMMED PARAMETERS

| Circuit | Reference Numerals | No. Bits | Bus Ports | Function |
| --- | --- | --- | --- | --- |
| Gain Control Circuit | 105, 105A | 5 | 202A, 199G | Sets gain of Delta Modulator 408–412. |
| Sample Window Shift Register | 106, 106A | 2 | 201A, 199A | Determines Sample Rate for Delta Modulator 104, Slope Up/Down Counter 107, and width of "window" of Shift Register 106. |
| High Slope Selector | 108, 108A | 1 | 201B, 199B | Selects criteria 905 or 906 (FIG. 9) for High Slope Segment 819. |
| Slope Sign Enable | 108, 108A | 2 | 201B, 199B | Enables positive and negative high slope signs to independently qualify the polarity of a high slope detect. |
| Low Slope Selector | 110, 110A | 2 | 201C, 199C | Selects criteria 901–904 (FIG. 9) of compression groups for Flat Delay Segment 818 and Flat Window Segment 817. |
| Time Compressor | 111, 111A | 1 | 201D, 199D | Determines rate of Flat Clock (length of "compression groups" T1–T7 of FIG. 8). |
| Flat Delay Selector | 113, 113A | 2 | 201E, 199E | Determines number of compression groups T4–T7 (824–827) in Flat Delay Segment 818. |
| Flat Error Selector | 116, 116A | 2 | 201F 199F | Determines acceptable number of violations of selected criteria for Flat Window Segment 817. |
| TOTAL | | 17 | | |

As indicated, the gain of the Delta Modulator 104 may be varied. This is accomplished in the Gain Control Circuit 105 which receives information along a Ventricular Filter Gain Control Bus 202A, as will be discussed. There are five separate bits 408–412 of information fed to the Gain Control Circuit 105. Two of these bits are additive gain control bits 408 and 409, and they set the feedback current in the delta modulator gain-controlled current source 407 of FIG. 4 so that the magnitude of the charge current to the delta modulator capacitor 414 can be set to relative values of 1, 2, 3 or 4. In addition, there are two multiplier bits 410 and 411 which control the reference for the current source 407. These can be set to relative values of 1, 5, 27, or 32. If both multiplier bits are a logical "0", the multiplier value is 1; and if both bits are a logical "1", the multiplier value is 32 (the sum of 5 and 27). Thus the charging current can be set to relative values of 1, 2, 3, 4, 5, 10, 15, 20, 27, 32, 54, etc., to form a companded or log type of output control. These four bits are dynamically controlled as the sensing circuit goes through the cardiac cycle. One additional bit 412 is used to control the high multiplier value for a lower multiplying factor of 18 in place of its normal factor of 27. This bit is not varied through the cardiac cycle. Its purpose is to give better resolution on low amplitude R-waves when set for 18X multiplication and provide the capability of the tracking high amplitude R-waves when set to 27X.

After a stimulating pulse is generated, there is a period of time AD1 (which may be of the order of 5-35 milliseconds) in which the residual charge on the stimulating electrode is compensated by shorting the lead to circuit ground. During this period the delta modulator has its high gain multiplier bit set to 18 or 27X. The delta modulator is then permitted to more rapidly adjust to the expected large step function while compensating for lead polarization voltage or follow the R-wave complex. Due to the large differance between 27X and 1X, the delta modulator is first stepped through 5X (for 8 milliseconds) on the way down to its lower AD2 value at the transition time from AD1 to AD2 in the cardiac cycle.

TIMING CIRCUITRY

The main time base is established by a crystal oscillator 227 generating a signal 251 at 32,768 Hz. This signal is fed into a Crystal Oscillator Upper Divider 226, the output of which is a clock signal which normally runs at 128 Hz and is coupled on a line 252 to a Crystal Oscillator Lower Frequency Divider 225. The lower divider 225 is a counter circuit; and its parallel outputs are coupled by means of a bus 248 to one set of inputs of a digital comparator 224. The other set of inputs to the digital comparator 224 are received from a Crystal Time Mark Data Bus 246A, which receives information from a Time Mark Memory 210. The Time Memory 210 contains a series of words which represent, in digital form, various time marks in a cardiac cycle. A typical cardiac cycle is shown in FIG. 6.

In FIG. 7 (which has approximately the same time scale as FIG. 6), there is shown a timing diagram of the portions into which a typical cardiac cycle is broken. Referring then to line 7L1, assuming that, for purposes of illustration, a natural heartbeat is detected and the pulse V DET 709 is generated by the Ventricular Detection Synchronizer 117 of FIG. 1, this pulse is transmitted on line 138 to a State Controller 231 which generates a master reset (MR) pulse as seen on line 7L2 of FIG. 7. In a manner to be described presently, a series of sequential time pulses are generated at predetermined times in a cardiac cycle which are, for the most part, programmable. These are the time marks TM1-TM5 (720-724) of FIG. 7.

The period between Master Reset 709 and TM1 720 is referred to as AD1 (711). It is during this time that digital filters are reset and compensation for residual charge on the stimulating lead is made. The time between TM1 (720) and TM2 (721) is referred to as AD2 (712); and this is the ventricular refractory time of the heart. If the heart had been electrically stimulated, capture verification by detection of T-wave takes place in this time period. That is to say, the ventricular filter 100 is set with parameters, determined by a physician, to identify a T-wave. At the physician's option, the generated R-wave could be used for capture verification by appropriate programming discussed above in connection with the ventricular filter. Technically the pacemaker's Ventricular Refractory Time Period is actually the sum of the AD1 (711) and AD2 (712) but in this embodiment AD2 (712) is referred to as Ventricular Refractory Time.

The time between TM2 (721) and TM3 (722) is referred to as AD3 (713), and during this time, the ventricular filter 100 is set to detect PVCs. If the detection criteria for a PVC are met during this period, and the system is accordingly enabled, a shortened ventricular rate time out period of 550 milliseconds may be set to try to reestablish normal sinus rhythm. This is referred to as negative hysteresis as will be described with FIG. 11 below.

The time period between TM1 (720) and TM3 (722) is the atrial refractory period 725 of the heart. The time period between TM3 (722) and TM4 (723) is referred to as AD4 (714), and it is the normal ventricular rate time out period. If a natural heartbeat is not detected by TM4 (723), then a stimulating pulse is generated during the subsequent time period AD5 (716) and a Master Reset 717 is generated immediately thereafter.

Returning now to FIG. 2, when the State Controller 231 generates a Master Reset signal, it is communicated to the crystal oscillator dividers 226 and 225 to initialize them and to a Time Mark Sequence Counter 232 (upper right hand corner of FIG. 2) to start that sequence counter. The Time Mark Sequence Counter 232 generates an address code (comprising four parallel bits) which is transmitted along a Ventricular Address Bus 249 to a Time Mark Address Decoder 206. The decoder 206 decodes the address on the bus 249 and causes the contents of the decoded address in the Time Mark Memory 210 to be placed on the Crystal Time Mark Data Bus 246. The information is then fed 246A to one input of the comparator 224. As the lower divider 225 continues to count the signals from the Crystal Oscillator, the comparator 224 will eventually detect equality on line 254 to generate one of the time mark signals TM1-TM5 (720-724) described above. These time mark data words are arranged in sequence in the Time Mark Memory 210, and each memory location, as indicated, defines in binary coded form for its associated Time Mark. Thus, the various time marks are capable of being programmed.

FUNCTIONS OF THE VCO

As seen just to the left of the Crystal Oscillator 227, a Voltage-Controlled Oscillator (VCO) 217 is used as a backup oscillator; and it has associated with it a minimal timing circuit similar to that just described, including a VCO Upper Divider 216 which feeds a VCO Lower Divider 215, the output of which is fed to a VCO Digital Comparator 214, the other inputs of which are received from a VCO Control Memory 209 which contain the same TM4 (plus an alternate) coded time mark word as the Time Mark Memory 210 for the crystal oscillator. The time mark addresses on the Ventricular Address Bus 249 are overridden by the Rate Limit Controller 236 in the VCO Control Address Decoder 205 which addresses the memory locations in the VCO Control Memory 209 and feeds the decoded time mark data along a VCO Data Bus 245 to comprise one set of inputs to the VCO Digital Comparator 214.

Whereas the crystal clock is used for generating the various timing signals in FIG. 7—namely, TM1, TM2, etc., the VCO, on the other hand, is primarily concerned with generating the Rate Limit Enable (RLE)

signal 715, so it has only one time mark which is seen as line 7L8 of FIG. 7 in relation to the multiple time marks of the crystal oscillator.

By setting the rate of the VCO to be higher than that of the Crystal Oscillator, and by using the same data in the coded time mark for comparison in both the Crystal Oscillator Comparator 224 and the VCO Comparator 214, the VCO Comparator 214 will generate an output signal (indicative of equality between both inputs) before the Crystal Oscillator Comparator 224. If the comparators 214, 224 generate their respective TM4 outputs in the proper sequence, the system operates normally. However, should the Crystal Oscillator Comparator 224 generate an output signal before the VCO Comparator 214, the VCO Comparator is used as a hold off to limit the rate of the system. In generating time mark TM4 (723), the signal RLE (Rate Limit Enable), as seen in FIG. 7, on line 7L8, is taken from the output of the VCO, not the crystal oscillator, and it is used to inhibit generation of a stimulating pulse until the signal RLE goes high, as indicated at 744. In this manner, the VCO is used to "pace" the Crystal Oscillator in the sense that the system requires an enable 744 before the stimulating pulse AD5 (716) is generated. If this sequence is wrong, the system enters into Rate Limit Processing to be described.

In addition, the VCO is used for establishing an Elective Replacement Time (ERT) indicator. That is, the rate of the VCO oscillator (actually the output clock rate 257 of the VCO Upper Divider 216) is set to be slightly higher (10 to 15 percent) than the corresponding crystal oscillator output clock rate 252 of the Crystal Oscillator Upper Divider 226 and its (VCO) repetition rate 257 is dependent on the terminal voltage of the battery as detected in the Mirror Reference Generator 218. As the battery depletes, the period of the VCO RLE 744 will increase towards the period of a corresponding crystal oscillator period TM4 (723) and when the signal RLE becomes equal to TM4 for the crystal, the system goes into a mode of operation referred to as Rate Limit Processing, described in a subsequent section with an object of establishing an Elective Replacement signal, to indicate the battery or pulse generator should be replaced. For the present, not only is the VCO used to determine battery depletion, but, as will be described, should the Crystal Oscillator fail to operate as designed, the VCO will be substituted as the main timing source in the system.

In addition, when a physician, during the course of a checkup, applies an external magnet, the VCO is used to determine the time base, not the crystal oscillator. However, the crystal oscillator determines the width of a stimulating pulse. This enables the physician to check the operability of the rate limit circuitry as well as to verify capture under realistic circumstances. Finally, as described more fully below, the rate of the VCO is used to sense moisture invasion of the pulse generator enclosure for the pacer circuitry, to determine whether moisture has breached any of the seals.

BUS ARRANGEMENT AND MEMORY READ/WRITE

It will be observed that the Ventricular Filter Parameter Data Bus 201 may be connected to a Ventricular Filter Gain Control Bus 202 by means of a set of transmission gates 244. Similarly, transmission gates 243 interconect the Crystal Data Bus 246 and the Ventricular Filter Gain Control Bus 202. Still another set of transmission gates 242 interconnect the Crystal Bus 246 with the VCO Data Bus 245; and a set of transmission gates 241 connects the VCO Data Bus with an Atrial JAM Data Bus 195.

Each individual section can serve its function during normal operation, but it is also capable of being connected into a continuous bus for writing information into or reading information from any selected memory. Each control RAM or memory is connected to the data bus by means of a set of read gates and a set of write gates, diagrammatically illustrated as R and W respectively. The read gates are used to transmit the contents of an addressed memory location onto the data bus; and the write gates are used to write from the data bus into an addressed location. For example, referring to the Time Mark Memory 210, if it were desired to change, for example, the Time Mark TM3 during a write cycle, an Address Shift Register 180 (see the center of the top row of FIG. 1), generates an address corresponding to the address of TM3 in the Time Mark Address Decoder 206 which decodes that address; and the new data would be transmitted from Data Input/Output Shift Registers 182 onto the Atrial JAM Data Bus 195, under control of a Transceiver State Controller 176. With a Master Reset (MR) signal the data bus transmission gates 241, 242, 243, and 244 connect the data bus together and the write gates (W) associated with the Time Mark RAM 210 would then be enabled, again under control of the Transceiver State Controller 176, and the new word would be written into the addressed memory location via data bus 246. This occurs during a Master Reset so the pacemaker operation is not interrupted as determined by the programmer which forms no part of the present invention. In this manner, the various operational and definitional parameters used in the system can be programmed or changed.

STATE CONTROLLER

Referring to FIG. 14, the State Controller 231 logic diagram includes Master Reset Latch 1401, Master Reset Width One Shot 1402, Last Reset Paced Latch 1403, Output Pulse Width Source Control Logic 1404, VCO Reset Width One Shot 1405, TM5 Catch Latch 1406, TM4 Catch Latch 1407, Start Pulse Width Lower Divider Reset One Shot 1408, and the crystal lower divider time mark (TM1-5) Phasing Logic 1409. The inputs and outputs to the state controller are identified in Table II.

Referring first to the Time Mark Catch Latches 1406 and 1407, the function of latch 1407 is to store the occurrence of Time Mark 4 until Rate Limit Enable has occurred in the event of the circuit operating under rate limited conditions. It also permits the rate limit enable function to occur in AD4 without interference by the incidence pulse C1 on line 1459 which also occurs at TM1, TM2, and TM3. The signal C1 is representative of an equal to comparison between the Time Mark Memory 210 and the Lower Crystal Divider 225 having occurred in the comparator 224. In other words, this occurs at TM1, TM2, TM3 and TM4 as defined by C1 within AD1, AD2, AD3, and AD4 respectively. The output of latch 1407 is coupled to a gate 1491, the output of which inhibits the crystal clock from incrementing the Time Mark Sequence Counter 232 until Rate Limit Enable 744 has occurred.

TABLE II

STATE CONTROLLER (231) INPUTS AND OUTPUTS

INPUTS TO STATE CONTROLLER

Figure 2:
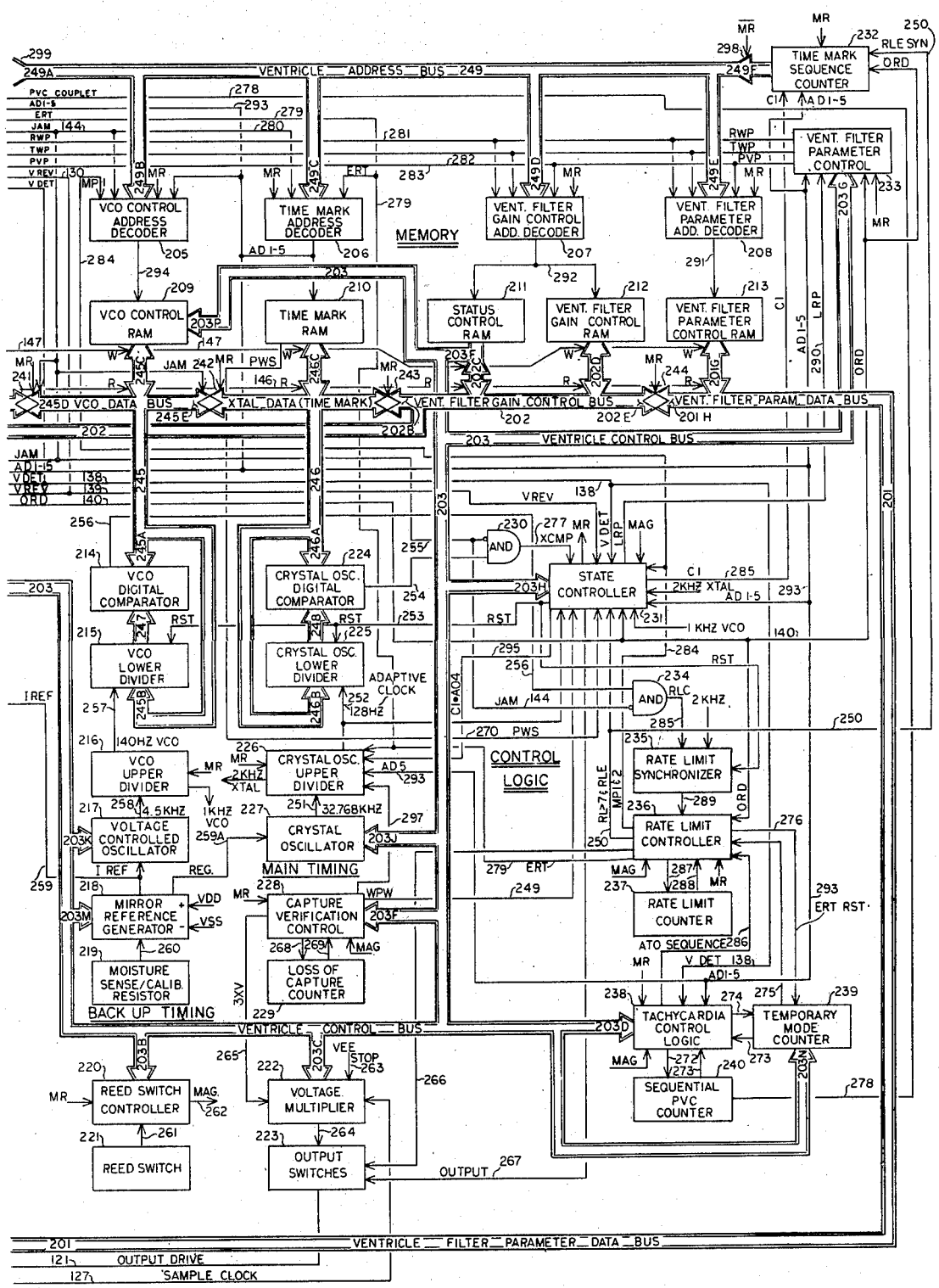
FIG. 2 is a functional block diagram of the control portion of a system incorporating the present invention.

| INPUT NAME | FIG. 14 REF. | FIG. 2 REF. | FUNCTIONAL DESCRIPTION |
|---|---|---|---|
| DISABLE COMPARE | 1410 | 255 | Inhibits the generation of a time mark (C1) during an atrial JAM sequence. |
| XTAL CMP | 1411 | 254 | Raw equal to output of the crystal oscillator digital comparator 224 indicating bus 246A equals crystal oscillator lower divider output 248. |
| XTAL CK | 1412 | 252 | Adaptive crystal derived system clock. |
| AD5 | 1413 & 1418 | 293 | Time Mark sequence address 5 = Pulse Width 716. |
| AD4 | 1415 | 293 | Time Mark sequence address 4 = R-wave time window 714. |
| AD3 | 1414 | 293 | Time Mark sequence address 3 = PVC time window 713. |
| AD2 | 1420 | 293 | Time Mark sequence address 2 = Ventricular Refractory time window 712. |
| 2 KHz XTL CK | 1416 | 2 KHz | 2048 Hz clock from Crystal Oscillator Upper Divider 226. |
| 1 KHz VCO | 1423 | 1 KHz VCO | ~1 KHz VCO derived clock from the VCO Upper Divider 216. |
| PS9 · PVP | 1417 | 203H | Allows a burst of PVCs to recycle the pacemaker refractory. |
| PS10 SHUT DOWN | 1419 | 203H | Status Control RAM Bit PS-10 used to power down pacemaker circuit. |
| V REV | 1421 | 139 | Ventricular reversion detected during current cardiac cycle. |
| V DET | 1422 | 138 | Detect output of Ventricular Detector 100. |
| RL>7 | 1424 | 250 | Circuit running in rate limit mode. |
| MP2 | 1425 | 284 | Magnet Phase 2 = force rate limited mode |
| RLE | 1426 | 250 | Rate Limit Enable 715. |
| WPS | 1427 | 270 | Wide Pulse Status indicates if the programmed Pulse Width (PW) is wider than 1 millisecond |

OUTPUTS FROM STATE CONTROLLER

| OUTPUT NAME | FIG. 14 REF. | FIG. 2 REF. | FUNCTIONAL DESCRIPTION |
|---|---|---|---|
| C1 | 1430 | 285 | Increment address (Time Mark 720–724) in Time Mark Sequence Counter 232. |
| XTL RST | 1431 | 253 | Reset Crystal Oscillator Lower Divider 225. |
| C1 · AD4 | 1432 | 295 | Hold crystal compare for Rate Limit Enable. |
| MR | 1433 | MR | Master Reset = begin new cardiac cycle. |
| LRP | 1434 | 290 | Last Reset Paced = last reset was not from a ventricular detection. |
| OUTPUT | 1435 | 267 | Output a stimulating pulse for the duration of this signal. |
| RL RST | 1436 | 253 | Reset VCO rate limit Lower Divider 214 and other functions. |

The function of latch 1406 inhibits the generation of the Master Reset pulse until the signal AD5 has terminated. The output of the latch 1406 is fed to a gate 1474 having as one input the signal AD5 on line 1418, and the output of the gate 1474 feeds the set side of the Master Reset Latch 1401 made up of gates 1484 and 1485, the output of which lasts the duration of the Master Reset Pulse. A Master Reset can occur from any one of the signals indicated as being an input to the Gate 1484. These signals may be broken down into inhibiting signals or enabling signals. The enabling signals include the coincidence of C1 and AD5 fed through the gate 1474 and representative of a time out (generating a stimulating pulse); the output of gate 1476 generates a Master Reset upon the detection of a natural heartbeat during the time periods AD4 or AD3 (non-refractory time), which may be inhibited in the event of the result of exceeding the predetermined reversion count on line 1421 if not disabled by PS9 and a tachycardial chain of PVCs (line 1417); on line 1446, when the rate timing is derived from the VCO during magnet application or when the crystal oscillator has run away. The signal which inhibits the Master Reset Latch is fed on line 1419 and is PS10 which is representative of "power down", which is a power conservation operating mode for shelf life storage which will be discussed below. Reference numeral 1402 designates a one shot circuit which defines the time duration of the Master Reset pulse.

A latch 1403 made up of Gates 1488 and 1489, called "Last Reset Paced," stores an information bit representative of whether the last reset had occurred as a result of a stimulating pulse AD5 having been generated by the circuitry, and is simply a one bit memory for this purpose, the output line being designated LRP 1434. Referring back to FIG. 2, there is a line C1 designated 285 which is fed from the State Controller 231 to the Time Mark Sequence Counter 232. It is this signal which increments the Time Mark Sequence Counter 232 for sequencing the Ventricle Address Bus 249 for generation of pulses TM1-TM5 of FIG. 7. Briefly, the Time Mark Sequence Counter 232 is a conventional digital counter 1501 shown in FIG. 15, the outputs of which indicate which portion of the cardiac cycle system is operating. An inhibit gate 1554 is used to inhibit generating the comparison signal until RLE 1516 has timed out if the system is operating in AD4, as discussed.

Referring to the Crystal Upper Divider Logic diagram in FIG. 16, it will be recalled that the system operates basically on 128 Hz. clock during time periods AD1-AD4, but during AD5, the 32 KHz crystal signal 1610 is used to generate the timing for a stimulating pulse, using the same dividers 225 and comparator 224. This is sometimes referred to as an adaptive clock 1625 because it changes frequency as a function of the portion of the cardiac cycle in which the system is operating. It is also possible to reduce the 128 Hz. frequency by 12.5% when either of the ERT 1613 or loss of capture 1614 indicators are present as discussed. The adaptive clock signal 252 is fed from the crystal upper divider 226. The state controller controls the adaptive clock along line 295. The crystal lower divider 225 is initialized twice during a cardiac cycle—once by a Master Reset, and once by means of a Start Pulse Width One Shot circuit 1408 in FIG. 14 which generates a narrow reset pulse at the beginning of AD5, which signal is fed in on line 253.

The rate limit and ERT control logic of FIG. 17 is shown as a separate functional block designated Rate Limit Controller 236 in FIG. 2. It contains the counter 1701 which counts the number of occurrences of the crossover of RLE and AD4 (indicating that the battery may be being depleted). This is discussed in more detail in connection with the flow diagram of FIG. 12.

ATRIAL FILTER; SETTING P-R DELAY; THE JAM FUNCTION

Figure 1:
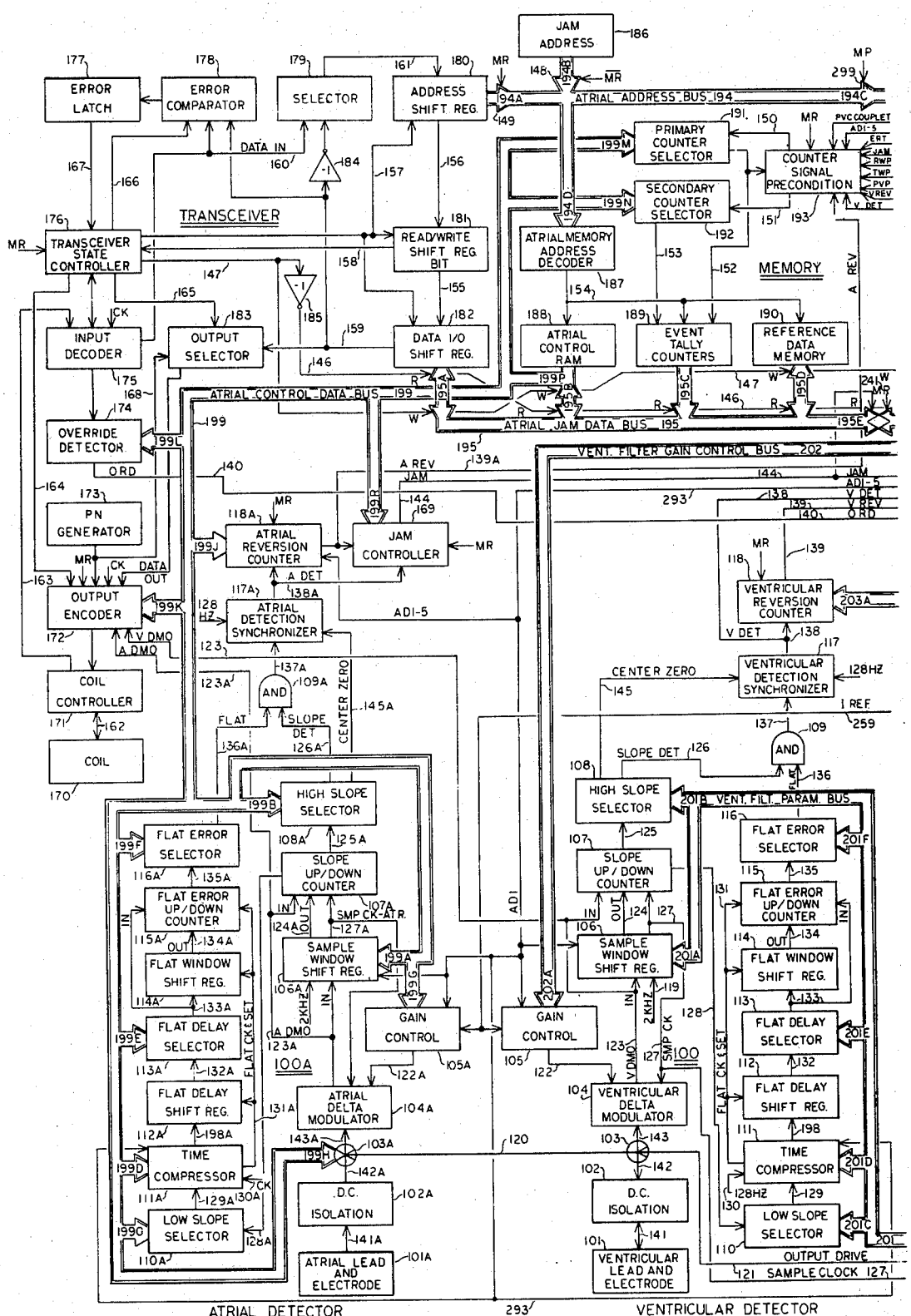
FIG. 1 is a functional block diagram of the detector portion of a system incorporating the present invention.

Referring now to the lower left hand portion of FIG. 1, and particularly the atrial filter 100A, it contains functional blocks similar to those which have already been disclosed in connection with the ventricular filter 100; and for brevity, those functional blocks in the atrial filter which have a corresponding functional block in the ventricular filter have been identified with the same reference numeral followed by an A. The atrial filter acts in a manner similar to that disclosed in connection with ventricular filter, seeking to detect a P-wave or PAC by identifying a Flat Segment, a Flat Delay Segment, and a High Slope Segment.

Coincidence of all the necessary conditions is determined in AND gate 109A, and an Atrial Detection Synchronizer 117A generates a corresponding output pulse in synchronism with the 128 Hz system clock. This output pulse is fed on a line 138A to a circuit referred to as the JAM controller 169.

The function of the JAM Controller 169 is, in the event of a P wave detection, to load a time word (the JAM word) into the Crystal Oscillator Lower Divider 225 (and VCO Lower Divider 215) which is a predetermined time to define the desired P-R delay interval relative to the Ventricular Rate Time Out Period (TM4 723 of FIG. 7). This is graphically illustrated in FIG. 10; and it will be assumed for purposes of illustration that a physician has already determined that a desirable P-R delay interval is 150 milliseconds and that the end of the Ventricular Rate Time Out Period TM4 is 900 milliseconds—that is, if a natural ventricular beat is not detected within 900 milliseconds of the previous paced or natural beat, then the system will generate a stimulating pulse. The JAM word is, therefore, a time word equal to 750 milliseconds. If the Atrial Detection Synchronizer 117A generates a detection pulse and transmits it to the JAM Controller 169 sometime in the period AD4 (it is not enabled prior to TM3 which ends the atrial refractory time), then the contents of the lower dividers 225 and 215 are set to be equal to 750 milliseconds irrespective of what the actual time is. This is accomplished along data buses 246B and 245B respectively.

Referring to FIG. 10, if the P wave is detected at 550 milliseconds in the cardiac cycle, the normal ventricular rate time out period will be shortened as indicated on line 10L2 of FIG. 10. Conversely, if the P wave is detected at 800 milliseconds into the cardiac cycle, that particular ventricular rate time out period will be extended to 950 milliseconds as indicated on line 10L3. This is done, as indicated above, to synchronize the ventricle with the atrium to establish a normal sinus rhythm in which contraction of the atrium helps to fill and time the ventricle. If a natural R wave is detected during the preset P-R delay interval, a stimulating pulse is not generated, and a Master Reset is generated to establish a new cardiac timing cycle. It will be observed that the transmission gates 242, 241 are also enabled by the JAM signal so as to connect the Crystal Data Bus 246 and the VCO Data Bus 245 with the atrial JAM Data Bus 195. Thus, the data word that is loaded into the Crystal Oscillator Lower Divider 225 is also loaded into the VCO Lower Divider 215. The word that is loaded (JAMMED) is stored as a separate word in an Atrial Control RAM 188, which is actuated by the JAM Address 186 through an Atrial Memory Address Decoder 187 for any time a P wave is detected after the ventricle refractory period and provided an MR is not being generated.

After the JAM Controller 169 disables the outputs of comparators 224 and 214 by means of Gates 230 and 234 respectively and connects the segments of the data bus as indicated, and loads the contents of the preset time memory word from the Atrial Control RAM 188 into the respective dividers 225 and 215, it then disconnects the segments of the data bus and re-enables the comparator outputs in a nested sequence 1970 as shown in the lower right hand corner of FIG. 19. It hereafter ignores any subsequent JAM signals from atrial detections 138A until a Master Reset has occurred.

Because the JAM word is loaded into the lower dividers 215 and 225 along the VCO Data Bus 245B and the Crystal Data Bus 246B (connected in common by the transmission gates 242), the word also appears momentarily on the other inputs of the comparators 214 and 224 at VCO Data Bus 245A and XTL Data Bus 246A. Thus, the comparators will generate an "equal" output during this time on lines 256 and 254; and this output signal is disabled by Gates 230 and 234 until the normal outputs from the VCO Control RAM 209 and Time Mark RAM 210 are re-established. This is what is meant by reference to a "nested sequence" above.

Atrial refractory time is defined as the time periods AD1, AD2, and AD3. During atrial refractory PAC parameters are loaded into the Atrial Digital Filter 100A and the system counts the number of atrial detections on the Atrial Reversion Counter 118A. When this count exceeds a predetermined number as indicated on the Atrial Control Data Bus 199J, a signal referred to as Atrial Reversion (A REV) 139A is generated which is used by the JAM Controller 169 to inhibit the JAM function.

ATRIAL INPUT STEERING

The overall object here is to steer the input signal, if desired, from the Ventricle Lead 101 to the Atrial Delta Modulator 104A. The reason for this is that it may be possible, in the case of a previously implanted catheter having only a single electrode implanted in the ventricle to receive enough signal identifying the P wave (even though the electrode is in the ventricle), and in that case, the signal from the ventricle lead would be routed to the atrial input filter 100A. Referring to the block diagram of FIG. 1, there is a lead 120 from the DC Isolation Circuit 102 through a tie point 103 to an analog transmission selector gate designated 103A. This may be a conventional analog switch, the other input of which is received from the DC Isolation Circuit 102A coupled to the Atrial Lead and Electrode at 101A. A signal is received on one lead of the Atrial Control Data Bus 199H, to steer either the DC insulation output from the atrial lead or the ventricle lead to atrial digital filter. It may also be desirable to implant a separate lead, not in the heart, but in muscle surrounding the pacemaker to sense a P wave in the muscle. In this case, the analog gate 103A would be used to route the output signal from the muscle lead (in place of the atrial ring lead in 101A), through the atrial DC Isolation 102A, to the Atrial Delta Modulator 104A.

STATUS CONTROL RAM

As indicated above, a main feature of the invention is that major system functions can be disabled under program control. This has two major advantages. First, from the viewpoint of manufacturing, the same large scale integrated circuit can be used to produce a "family" of cardiac pacers all of which can have the same "operational" history. The other major advantage is that once the pacemaker is implanted its operation and functional configuration can be changed substantially under program control without the need to directly access the implanted pacemaker.

The Status Control RAM is designated 211 in the block diagram of FIG. 2 and its principal function is, under program control, to selectively disable control functions. It does this by communicating along the Ventricular Control Bus 203. The memory bit locations are designated by the PS prefixes and these status bits are summarized in Table III.

TABLE III

PHYSICIAN STATUS (PS) CONTROL BIT SUMMARY

| PHYSICIAN STATUS NUMBER | SYMBOLIC NAME | BLOCK DIAGRAM REFERENCE | | FUNCTIONAL DESCRIPTION | NOMINAL STATE |
|---|---|---|---|---|---|
| | | BUS | BLOCK | | |
| PS0 | Vent - SW INV | 203B | 220 | EXCLUSIVE OR with reed switch | 0 |
| PS40 | Atr - SW INV | 203B | 220 | (inverts switch function). | 0 |
| PS1 | Vent - MAG FIX RTE | 201 A&C | 106,110 | Disables detectors with | 1 |
| PS41 | Atr - MAG FIX RTE | 199 A&C | 106A,110A | Reed Switch (MAG). | 1 |
| PS2 | MP2 Enable | 203N | 239 | Limits Rate Limit High to 32 pulses with MAG. | 0 |
| PS8 | MP4 Enable | 203N | 239 | Enables MAG Phase 4 for delta mod out w/MAG. | 1 |
| PS48 | Vent - DMO w/MAG | 199K | 172 | Vent electrogram outputs during MP1+MP2+MP3. | 1 |
| PS49 | Vent - DMO CONT | 199K | 172 | Vent continuous electrogram outputs. | 0 |
| PS88 | Atr - DMO S/MAG | 199K | 172 | Atr electrogram outputs during MP1+MP2+MP3. | 0 |
| PS89 | Atr - DMO CONT | 199K | 172 | Atr continuous electrogram outputs. | 0 |

| PS48, 88 CONT | PS49, 89 MAG | Electrogram |
|---|---|---|
| 0 | 0 | None |
| 0 | 1 | With Mag |
| 1 | 0 | Until Mag |
| 1 | 1 | Continuous |

| PS99 | EXIT | 203C | 222 | Exits to safe operating conditions (MP2 with 60 PPM min. to approx. 120 PPM max. rate, 1 or 2 ms pulse width, | 0 |
| | | 203N | 239 | | |
| | | 203P | 209 | | |

TABLE III-continued

PHYSICIAN STATUS (PS) CONTROL BIT SUMMARY

| PHYSICIAN STATUS NUMBER | SYMBOLIC NAME | BLOCK DIAGRAM REFERENCE BUS | BLOCK | FUNCTIONAL DESCRIPTION | NOMINAL STATE |
|---|---|---|---|---|---|
| | | | | and at least 2× output voltage) at the first application of mag. and stays until programmed out by programming PS99 back to zero. | |
| PS3 | IXV Out | 203C | 222 | Turns off first output voltage multiplier. | 1 |
| PS11 | 3XV Out | 203C | 222 | Turns off second output voltage multiplier. | 0 |
| | | | | PS11 PS3 Output Multiplier Stages<br>0 0 3X Both<br>0 1 2X First<br>1 1 1X None | |
| PS4 | CV Enable | 203F | 228 | Enables capture verification operation. | 0 |
| PS18 | CVA-3XV | 203F | 228 | Turns on 2nd output voltage multiplier stage. | 0 |
| PS19 | CVB-WPW | 203F | 228 | Uses wide pulse width. | 1 |
| | NOTE: Rate is decreased by 12½% as a loss of capture indicator | | | PS18 PS19<br>CVA-3XV CVB-WPW @ 4 Loss @ 11 Loss<br>0 0 WPW —<br>0 1 WPW 3XV<br>1 0 3XV WPW<br>1 1 3XV — | |
| PS12 | ATO Enable | 203D | 238 | Enab. automatic tachycardia overdrive funct. | 0 |
| PS20 | ATO-LSB | 203D | 238 | LSB of sequential PVC detections → ATO. | 0 |
| PS21 | ATO-MSB | 203D | 238 | MSB of sequential PVC detections → ATO.<br>PS21 PS20 Sequential PVC Counts<br>ATO MSB ATO LSB Before ATO Start<br>0 0 4<br>0 1 12<br>1 0 20<br>1 1 28 | 0 |
| PS80 | OR Enable | 199L | 174 | Enables Overdrive commands from external system to Overdrive system timing and deliver a stimulating pulse AD5 and reset timing with a normal paced Master Reset. | 0 |
| PS83 | Steer ATR Input | 199H | 103A | Steers atrial input from atrial lead to vent. lead. | 0 |
| PS82 | Enable JAM | 199R | 169 | Enables P-synchronous mode of pacing. | 0 |
| PS81 | ATR Shut Down | 199A<br>199C<br>199G | 106A<br>110A<br>105A | Disables clocks in atrial detector and powers it down. | 1 |
| PS 10 | Shut Down | 203M | 218 | Stops all clocking and stops all bias currents except crystal oscillator to shut down pacemaker circuit current drain to extend shelf life or disable pacemaker. Pacemaker circuit is re-enabled and operates as it was programmed prior to shut down by application of a magnet or Power-On reset. | 0 |
| PS5 | TWP @ FPR | 203G<br>201A<br>201C<br>202A | 233<br>106<br>110<br>105 | T-wave parameters @ FPR. | 1 |
| PS6 | PVP @ FPR | 203G<br>201A<br>201C<br>202A | 233<br>106<br>110<br>105 | PVP/R-wave parameters @ FPR.<br><br>In addition to selecting the filter parameters to be used during the First Part of Refractory, these two status bits also control Ventricular Detector Shut Down for fixed rate pacing mode of operation:<br><br>PS5 - TWP @ FPR  PS6 - PVP @ FPR  FPR Parameters<br>0 0 RWP<br>0 1 PVP | 0 |

TABLE III-continued
PHYSICIAN STATUS (PS) CONTROL BIT SUMMARY

| PHYSICIAN STATUS NUMBER | SYMBOLIC NAME | BLOCK DIAGRAM REFERENCE BUS | BLOCK | FUNCTIONAL DESCRIPTION | NOMINAL STATE |
|---|---|---|---|---|---|
| | | | | 1　　　　0 | TWP |
| | | | | 1　　　　1 | Fixed Rate |
| PS7 | PVP @ SPR | 203G | 233 | PVC parameters @ Second Part of Refractory Time instead of R-wave parameters. | 0 |
| | | | | PS7 - PVP @ SPR | SPR Parameters |
| | | | | 0 | RWP |
| | | | | 1 | PVP |
| PS9 | PVC RECYCLE | 203H | 231 | Enables a PVP detection to recycle the pacemaker (MR) circuit during refractory time (only when Premature Ventricular Parameters are loaded in the ventricular detector). | 0 |

One important memory bit in the Status Control RAM 211 is PSO, and it is this bit which permits program control of an externally applied Reed Switch 221. The Reed Switch is coupled to one input of an EXCLUSIVE OR gate and PSO is coupled to the other input. If PSO is a logic 0, then the Reed Switch 221 acts directly. If PSO is a logic 1 then the Reed Switch 221 is inverted in sense. The output of the EXCLUSIVE OR is a signal designated MAG or the magnet signal. This enables magnet control or simulation under program operation. It also permits the system to disable the MAG signal if the Reed Switch 221 witch fails in the closed position.

Bit PS4 enables capture verification if it is a logic 1. Hence, if it is a logic 0 then it disables the capture verification circuitry by disabling the clock signal which is fed to that circuitry. Alternatively, a status control bit could be used to inhibit the input signal to or the output signal from the circuitry whose function is being disabled, or to hold that circuitry in reset.

Another major function which can be disabled by PS12 which is entitled "ATO ENABLE". PS 12 is used to enable the automatic tachycardia operation in one logic state and to disable it in the other, disabling an output latch through which the tachycardia overdrive output signal is coupled.

Another mode of operation is fixed rate pacing. This is implemented by Status Control RAM bit PS5 and PS6. If both bits are set to a 1 the ventricular detector is disabled by removing clocks from ventricular detector logic power from the current sources, and locking the output V DET 138 in a non-active state. This would cause the pacer to revert to fixed rate pacing.

Additional PS status bits are in the Atrial Control RAM 188 and are communicated along the Atrial Control Data Bus 199 to the various subsystems. An example is PS82 which permits the JAM function to occur. It it is in a logic 0 state, the JAM function is disabled. This would inhibit the operation of any atrial detector that may have been implanted, or at a subsequent date, it would allow the use of the atrial detection circuitry. PS81 is the atrial detector enable/disable status bit which causes the atrial detector to shut down like the ventricular detector with PS5 and PS6=1 above. With PS81=1 and PS 82=0, the atrial detector can be "dry run" prior to using it in the P-synchronous mode, for evaluation of its operation over an extended period of time by recording its output in the Event Tally Counters 189 discussed in that section below.

SHELF LIFE STANDBY MODE

The pacemaker may be put into a mode of minimum consumption of power for extending the shelf life of the battery. In this mode, PS10 holds the VCO in reset through BUS 203K, the output of the Crystal Oscillator is disabled through BUS 203J, although the crystal clock is powered and circuit bias currents I REF 259 are turned off through BUS 203M. It will be appreciated that because CMOS logic circuitry is used, power need not be removed from the power buses to the circuitry since CMOS circuitry does not consume power without clocking. Further, the memory is non-volatile and information will be preserved as entered at the factory so that the system can be activated simply by the application of an external magnet. The application of a magnet (MAG signal) resets the PS10 latch, the output of which enables the operation of the crystal clock and the VCO. The PS10 latch is also reset by a Power-On reset signal derived from low battery voltage so that the pacemaker circuit will not turn itself off in the case where it is programmed to a high current state around the time of battery depletion. As summarized in Table III, this latch is set by programming PS10 of the Status Control RAM to a one.

OVERALL SYSTEM OPERATION

Referring now to the flow chart of FIGS. 12 and 12A, there are three principal paths to be taken by the system from the beginning of a cardiac cycle to the end of the refractory period which occurs at TM2. The beginning of a cycle occurs at the beginning of time period AD1 (see the left margin of FIG. 12) following a Master Reset. These paths are generally designated respectively 1200, 1201 and 1202. Path 1200 is taken if the Master Reset was generated in response to a stimulating pulse. Path 1201 is taken if a natural R wave is sensed (the signal V DET) during the Ventricular Rate Time Out period AD4. Path 1202 is taken if a PVC is detected (V DET) during the PVC detection period AD3.

The modes are determined by the status of two latches, one (1403) associated with the State Controller 231 of FIG. 2, and the other (1801) associated with the Ventricular Filter Parameter Controller 233. The first referred to as Last Reset Paced Latch 1403, of these latches is set if the system generates a stimulating output pulse signal or "paced" beat and, in this case, the controller follows the path 1200. The other latch, referred to as PVP latch (1801), stores a signal representative of a detected PVC; and in this case, path 1202 of the flow chart is followed. If both latches generate the complements of their respective signals, then path 1201 is taken indicating that a Master Reset has occurred but that it has not been generated by generating a paced beat or by detecting a PVC. It therefore has been generated by the detection of a natural R-wave heartbeat.

During the time period AD2 the system first tests for capture, in Capture Verification Processing 1200B, if a stimulating pulse had been generated. If capture is verified by detecting a waveform that satisfies the requirements for a T-wave detection parameters before the end of AD2 or if a natural R-wave had been detected in the previous cardiac cycle (path 1201), the system passes to a mode in which it tries to detect whether the patient is in a noisy environment--Reversion Processing 1200C. In this mode or phase of AD2, the noise threshold may be varied according to any one of the three parameters for which the ventricular filter 100 is capable of being set for (T waves, R waves, or PVCs), as selected by the Ventricular Filter Parameter Controller 233 which is controlled by the State Controller 231 and is programmed by the Status Control RAM 211 along Data Bus 203G. Referring to FIG. 12A, if the programmed noise threshold is exceeded, the system reverts to fixed rate pacing as controlled by the Ventricular Reversion Counter 118. In the time period AD3, the ventricular filter is loaded with PVC parameters for PVC Processing 1200D; and in the time period AD4, the ventricular filter is loaded with natural R-wave parameters for R-wave 1200E and P Synchronous 1200F Processing. When the escape interval has timed out, the system goes through Rate Limit Processing 1200G prior to producing a stimulating output pulse.

Before discussing the operation in detail it will be helpful to further understand that the term "refractory period" as used herein in reference to the ventrical refractory period can mean either the periods AD1 and AD2 or simply the period AD2, according to the context. The reason for this interchangeability is that the true ventricular refractory period of the heart includes AD1 and AD2, but the ventricular filter is held in reset during Lead Compensation (AD1), so for all practical purposes the detection and filtering circuitry is disabled during this period.

Referring now to System Housekeeping (1200A) in path 1200, after a stimulating pulse is generated, the digital filter feedback gain is multiplied by 27 in block 1214, the reversion counters and detectors are reset in block 1215, the refractory and rate limit timers are started from zero in 1216, and the residual charge on the stimulating electrode 101 is compensated in 1217. After the electrode is compensated, the 27 multiplication on the feedback is turned off in 1219, the ventricular filter 100 is loaded with T wave parameters for Capture Verification Processing (1200B) in block 1220 in an attempt to verify capture of the heart; and this is the primary function performed in this mode, as indicated in block 1221. If no detection is made by the end of the refractory period as indicated in block 1222, a loss of capture event counter (to be described) is incremented in 1223; and in this event, the system enters a programmed procedure for effecting capture. As a first step, it increases the width or amplitude (according to the procedure programmed by the physician) of the output pulse in block 1225. If loss of capture persists for the pulses of increased power the other parameter may then be increased so that both width and amplitude are increased (also in block 1225). This procedure may be reset by the physician by the application of an external magnet (see block 1226). If a T wave is detected, thereby verifying capture of the heart, the system resets the loss of capture counter in 1226 and proceeds along path 1245 for the "second part of refractory" for Reversion Processing 1200C where either R-wave parameters (Path 1246) or PVC parameters (Path 1247), as defined by the Status Control RAM 211, are loaded into the ventricular detector 100 in an attempt to detect interference noise for the remainder of refractory time to TM2 (1210). The system enters the PVC time window (1205) AD3 after TM2 where the ventricular detector is set for PVC parameters 1272 in an attempt to detect a PVC which will be described shortly.

If the Master Reset were generated in response to a natural heartbeat 1201, again depending upon the contents of Status Control Memory 211, the system may load the ventricular filter to detect either a T wave, as indicated in sub-path 1231, an R wave as indicated in sub-path 1232, or a PVC as indicated in sub-path 1233. If any of these waves are detected during the refractory period, the program shifts to a path 1245 which is referred to as the "second part of refractory". This refers to the fact that a single signal may normally be expected during refractory. This signal may be indication of a natural T wave, an R-wave from a stimulating output, or it may even be a premature ventricular contraction (a single PVC is not taken to be harmful).

The system will look for a second detection during refractory in the "second part" of the refractory period; and depending upon a status bit that has been programmed (and whether a PVC was previously detected in 1240, as indicated in block 1248, the system may be programmed to detect an R wave in sub-path 1248, or a PVC in sub-path 1247 during the second part of refractory. When either of these signals is detected, a reversion counter is incremented. If the reversion counter exceeds a preset limit, the system will proceed along either line 1270 or 1270A (FIG. 12A) to enter a Ventricular Reversion Mode, to be discussed and ultimately generate a stimulating output pulse in block 1299.

Assuming that no signal had been detected during refractory or during the second portion of refractory, the system proceeds normally into the PVC detection period, to be described shortly.

Referring now to path 1202, if a PVC is detected in time period AD3, the reversion counters 118, 118A, and detectors 100, 100A are reset in 1261, a rate limit timer and the refractory period are started from zero in block 1262; and the ventricular filter is reloaded for detecting PVCs in block 1264. If a PVC is detected in block 1265, a reversion counter is incremented in block 1266 and the PVC count is incremented in block 1267. If the reversion limit is exceeded, the system enters a ventricular reversion mode as indicated by line 1271 and ultimately generates a stimulating output pulse in block 1299. If a PVC is not detected by the end of the refractory period, the system proceeds to the normal PVC detection period, AD3.

Referring to FIG. 12A, at the end of the refractory period, the ventricular filter is set to detect PVCs in block 1272 for PVC Processing 1200. If a PVC couplet (two or more sequential PVCs) is detected in block 1281 at the end of AD3, a block 1282 may record a PVC couplet event in the Event Tally Counters 189 described below. Next, the PVC counter is reset in block 1283, and the ventricular filter is set to detect an R wave in block 1284 for time period AD4 for R-wave 1200E and P synchronous 1200F processing.

If a PVC were detected in block 1273 during time period AD3, a PVC counter is incremented in block 1275 and the system determines whether tachycardia exists in block 1276. If it does not exist, the system enters path 1202 described above. If tachycardia is detected and the system is programmed accordingly, in block 1277, a series of stimulating pulses at a predetermined high rate are generated (for example, eight consecutive pulses at 400 millisecond intervals may be used). After the end of this train of pulses, the sequential PVC Counter 240 is reset in block 1279 and in block 1280 a tachycardia may be recorded in the Event Tally Counters 189; and the system proceeds along path 1200 described above.

During the R-wave Processing 1200E, the system enables the JAM function of the Atrial Detector 100A for detection of a P-wave in 1287 and a pre-setting of the lower dividers 215 and 255 in block 1289 if the system did not detect atrial reversion at 1288.

If a natural R wave is detected during the Ventricular Rate Time Out Period AD4, as indicated in block 1285, the system proceeds along path 1201. If no natural heartbeat is detected during period AD4, the system proceeds towards rate time out in 1286.

Before discussing Rate Limit Processing 1200F, as indicated in the lower left portion of the flow chart of FIG. 12, it will be observed that once the PVC mode of operations is entered as indicated by the path 1202, the system cannot exit this mode within AD1, AD2, or AD3. In other words, time mark TM3 must be generated so the system enters time period AD4 for detecting a normal heartbeat.

It will also be observed in connection with path 1201 that a main consideration in determining whether the ventricular filter will be set to detect T waves, R waves or PVCs in time period AD2, will be the noise criterion which a physician will consider safe. In other words, the criteria for establishing an R wave will be met only by a noisier environment than necessary to identify a T wave; and a still noisier environment would be required to meet the criteria for detection of a PVC. If a patient is in a noisy environment, and the reversion requirements are met, the system will revert to fixed rate pacing.

The number of ventricular detections V DET during ventricular refractory time (AD2) is counted in the Ventricular Reversion Counter 118. The physician determines the noise threshold by programming which set of parameters T, R or PVC parameters is in the ventricular filter during AD2. If the number of counts during one refractory period exceeds a predetermined programmable number (1 to 7) then the system will automatically revert to fixed rate pacing for that cardiac cycle. A master reset pulse will re-initialize the system to its original mode and noise/reversion criteria.

The number of atrial detections A DET during atrial refractory time (AD2 plus AD3) is counted in the Atrial Reversion Counter 118A. PAC parameters are loaded into the Atrial Digital Filter during atrial refractory time in an attempt to identify Premature Atrial Contractions, and the Atrial Reversion Counter 118A is used to disable (in 1288) the P synchronous JAM in the event of atrial fibrillation or flutter.

VENTRICULAR FILTER PARAMETER CONTROL CIRCUITRY

The Filter Parameter Control Circuitry, diagrammatically illustrated in Block 232 of FIG. 2, is shown in detail in FIG. 18. Briefly, this circuitry establishes the sequence of operations described above in connection with the flow diagram of FIG. 12.

Referring then to FIG. 18, there are 3 outputs of the Filter Parameter Control circuitry designated respectively 1835, 1834, and 1837, representative respectively of Premature Ventricular Parameters (PVP), R-wave Parameters (RWP), and T-wave Parameters (TWP). If the signal on any of these lines is a Logic 1, that signal is communicated to the Ventricular Filter Parameter Address Decoder 208 and the Ventricular Filter Gain Control Address Decoder 207 to load the associated filter parameters on the Venticular Filter Parameter Data Bus 201 and the Ventricular Filter Gain Control Bus 202 respectively. This might occur, for example, in the flow chart of FIG. 12 when the system enters one of the paths designated 1231, 1232, or 1233, as described above.

The circuitry includes a PVC Latch generally designated 1801. The output of this latch generates the signal PVP which, as indicated above, enables the system to transmit or load the PVC parameters into the ventricular filter. The latch can be reset by the signal AD4 which is transmitted on a line designated 1818, or by the Override signal ORD on line 1820 which externally resets the circuitry for the generation of a pacing pulse.

The other inputs to the Filter Parameter Control circuitry are as follows: V DET (indicating a ventricular detection) on line 1810; the complement of AD2 (refractory time) on line 1811; MR (Master Reset) on line 1812; PS7 on 1813; AD3 (PVP time window) on line 1814; LRP (Last Reset Paced) on line 1815; PS5 and PS6 on lines 1816 and 1817; and the complement of ventricular reversion on line 1819.

The PVP latch 1801, in summary, can be set by the signal AD3 on line 1814, and this corresponds to the block 1272 in the flow chart.

An AND gate 1855 is responsive to input signals PS7 on line 1813, described above, and an internally generated signal SPR (Second Part of Refractory) on line 1831 for effecting the decision indicated in block 1248 of the flow chart of FIG. 12. A similar AND gate 1859 is also responsive to the following signals: PS6 on line 1817, the complement of PS5 1875 (which appears on line 1816), the complement of LRP 1874 (which appears on 1815), and another internally generated signal which appears on line 1832 which is designated FPR (representing the First Part of Refractory). The function performed by the AND gate 1859 corresponds to entering path 1233 as disclosed in connection with the flow chart of FIG. 12.

Moving now to the circuitry which causes the ventricular filter to be set with T-wave parameters 1804, as indicated by the signal TWP on line 1837, gate 1866 corresponds to entry of the path 1231 on the flow chart; and the path 1232 is entered if neither path 1231 nor 1233 are entered as described above, corresponding to a default decision. Gate 1867 and 1868, in combination, effect the mode of operation described in block 1220 and following, in the flow chart of FIG. 12. The default decision mentioned above to place the system in the operation of path 1232 is effected by the gate 1863.

Reference numeral 1853 identifies a flip-flop which is set by a Master Reset pulse on line 1812 to generate a signal FPR 1832, in combination with refractory time in gate 1856 representative of the First Part of Refractory; and the first detection thereafter is coupled in on line 1871 to clock the flip-flop 1853 to its reset state, thereby generating, in combination with gate 1854, a signal SPR 1831 representative of the Second Part of Refractory. Any additional detections during the Second Part of Refractory generate clock pulses on a line 1830 by means of a gate 1850 to increment the Reversion Counter 118. The outputs of gates 1862 and 1865 are signals coupled to the event counters, described above, to communicate to them reversion events and what parameters the system is currently operating on.

As indicated elsewhere, an external signal may be used to place the system in an Override condition if enabled by an associated PS status control bit. Such an override condition generates a pacing pulse immediately. When this signal is effected by coupling a signal designated ORD (Override) 1820 the PVP Latch 1801 is reset which causes the system to exit from any PVC mode it may have been in. This PVP signal is transmitted on output line 1835 as indicated above. As indicated, the ORD signal is also used to pre-set the Time Mark Sequence Counter 232 to AD5, as indicated in the functional block diagram of FIG. 2.

RATE LIMIT CONTROL

Referring to the logic schematic diagram of FIG. 17, the Rate Limit Controller 236 consists of the Rate Limit Event Latch and Logic 1702, the ERT Latch 1703, and the Continuous Rate Limit Mode Logic 1704. The Rate Limit Counter 237 is a 3 bit counter generally designated 1701; this is the counter which counts sequential occurrences of TM4 occurring prior to RLE indicating a rate limited condition, or "Rate Limit Event." This counter is reset every time RLE occurs prior to TM4 indicating normal operation. The resetting logic gates are designated 1756/1760, and the clocking logic gate is designated 1759.

An input gate 1753 determines whether a rate limit event occurred (the rate limit event is defined as above, namely, the occurrence of TM4 prior to RLE). This output feeds a latch 1702 made up of gates 1754 and 1755. The function of gate 1753 is accomplished by inputting AD4 on line 1714, RLE on line 1730, and comparison pulse C1 on line 1715. The comparison pulse C1 is generated by the Digital Comparator 224 when the contents of the divider 225 fed by the Crystal Oscillator equal the data word representative of TM4 which defines the end of period AD4. Normal operation (i.e., no rate limit event) is defined as AD4 on line 1714 and C1 complement on line 1715 being 1's and RLE 1730 going high to set latch 1702 resulting in a low on line 1773 which steers the incoming AD5 on line 1718 to the counter reset through Gates 1756 and 1760. If a rate limit event occurs, latch 1702, is not set by RLE going high while the other two inputs of gate 1753 are high, thereby steering the incoming AD5 through Gate 1759 (1773 is left high) to clock the counter 1701 and register a rate limit event in the counter. If, during the next sequential cardiac cycle, a rate limit event is not detected, then the counter is reset. This occurs for any cardiac cycle that a rate limit event is not detected. When the counter 1701 registers a count of 4, it sets an ERT latch 1703. This generates the ERT signal on line 1734. An ERT signal generates the WPW (wide pulse width) signal and reduces the pulsing rate by 12.5% by changing a counter in the Upper Divider 226 from a "divide by eight" circuit to a "divide by nine" circuit, a technique known in the art and is illustrated as "12.5% ERT" 1602 in FIG. 16.

The 12.5% rate change in response to ERT or loss of capture indicator is to be distinguished from the rate of the VCO which is 10-15% higher than the rate at which it operates when the battery is at a depletion level. Once the four sequential occurrences in counter 1701 have occurred as defined by the setting of ERT Latch 1703 as just discussed, and the rate of the system Adaptive Clock 1625 is decreased by 12.5%, the next cycle should reset the counter 1701. However, if it does not, and the counts continue to seven successive counts as defined, it is taken as an indication that the Crystal Oscillator has run away, and this causes the system to enter a "fail safe" mode which is essentially the same as Magnet Phase 2 (MP2), as will be discussed. The signal that causes the system to enter this mode is generated by Continuous Rate Limit Mode Logic (1704) gate 1765, inputs of which are either the signal MP2 on line 1713 or the RL>7 on line 1733 and output of the gate 1764 is on line 1733. The result is that the rate is determined by the RLL word on the VCO, and the VCO determines the pulse width (1 or 2 milliseconds depending on the PW word being programmed greater than or less than 1 millisecond).

VCO PULSE WIDTH GENERATION

Referring to the block diagram of FIG. 2, there is a line from the Time Mark RAM 210 to the State Controller 231 of the VCO circuitry. The line 270 is designated PWS (Pulse Width Status). If the programmed pulse width is less than 1 millisecond, it is sensed by the State Controller 231 along the PWS line; and it generates a signal on line 267 identified as OUTPUT. In the instance being discussed, the output pulse width when the VCO determines pulse width will be about 1 millisecond. If, on the other hand, the programmed pulse width in the Time Mark RAM 210 was 1 millisecond or greater, then the output pulse width in MP2 will be 2 milliseconds (approximately). Referring to the logic schematic FIG. 14, this occurs in a flip-flop 1479 in the State Controller 231.

If this PWS signal 1427 is in one state, the flip-flop divides the incoming 1 KHz clock signal by two on line 1423 (1 KHz VCO). There are three gates involved designated 1480, 1481 and 1482, the outputs of which are joined in a gate 1483. If the gate 1480 is enabled, the first 1 millisecond pulse width is fed to the gate 1483. If the gate 1481 is enabled, the second half of the cycle is added. The gate 1481 adds the second half cycle of the complement of the flip-flop 1479 which, as indicated previously, generates an output signal at a frequency of 512 Hz. The third gate, namely gate 1482 couples the crystal pulse width (AD5 on line 1418) to the output gate 1483. There are two other signals to the gate 1482 which disable the crystal pulse width. These are indicated on lines 1425 and 1424, and they are respectively, Magnet Phase 2 (MP2), and a signal indicating that more than seven successive rate limit events have been detected (line 1424). In other words, if either of these signals is present the crystal clock is disabled in the gate 1482. The occurrence of either of the signals on line 1425, 1424, generates a VCO derived output pulse by means of the gate 1477, in conjunction with RLE (which times this output pulse) on line 1426 which causes an enable in the gate 1478 which enables the flip-flop 1479. In the case of gate 1482, the signal AD5 not only indicates the timing of a stimulating pulse, but also the width. In the case of the gate 1480 or 1481, the signal RLE on line 1426 indicates when a stimulating pulse should be generated, and the remainder of the circuitry discussed above, defines the width of that pulse.

RATE LIMIT SYNCHRONIZER/JAM ENABLE CONTROL

Turning now to the Rate Limit Synchronizer, it is identified in the functional block diagram of FIG. 2 as 235 and along the top 1706 of FIG. 17. The output of the VCO Digital Comparator 214 is fed on a line 256 to a Gate 234, the other input of which is received from the JAM Controller 169 via 144. The function of Gate 234 is to disable the Rate Limit Synchronizer 235 during a JAM function implementation. A similar Gate 230 is associated with the State Controller 231. The reason for this is that the JAM function forces a predetermined word into both sides of the digital comparators 214 and 224 (from the bus through the bus preset lower dividers 215 and 225 respectively) and an equality would otherwise result. The output of the gate 234 is the signal RLC 295 (Rate Limit Compare). Correspondingly the output of the gate is crystal compare—namely XTAL CMP 277.

The function of the rate limit synchronizer is to synchronize the VCO derived rate limit enable signal's transition to its high or enabling state with the Crystal Oscillator derived timing to enable the generation of crystal oscillator based stimulating pulses.

Turning now to the detailed logic circuit of FIG. 17, the output of the gate 234 of FIG. 2 is indicated on line 1711—namely, the signal RLC which is derived from the VCO oscillator. The signal is used to set a latch 1705, the output of which generates a signal RLE (Rate Limit Enable) 1730 which is not yet synchronous with the Crystal Oscillator. The Master Reset signal generates a Rate Limit Reset signal on line 1710 to reset the latch 1705. When the non-synchronous Rate Limit Enable signal goes high, the D input of an edge-triggered D type flip-flop 1752 goes high, thereby enabling a 2 KHz crystal clock signal on line 1712 to clock the flip-flop 1752, thereby synchronizing the output signal on line 1731 to the incoming clock signal on line 1712. The signal on line 1731 (which may be called RLE SYN or Synchronous Rate Limit Enable) synchronizes the functions performed in the Rate Limit Circuit with the crystal clock signal. It is fed in line 250 to the Time Mark Sequence Counter 232 for forcing AD5 when operating in the Magnet Phase One mode to be described below.

RATE LIMIT PROCESSING

Returning now to the flow chart of FIG. 12A and relating the VCO pulse width circuitry to the rate limit control discussed above, if the time mark TM4 generated by the Crystal Oscillator occurs sooner than the signal RLE which is generated by the time mark word RLL in the VCO Control RAM 209 for the VCO Digital Comparator 214, a Rate Limit Event (or simply R/L Event) is detected by comparing in blocks 1286, 1291, and counted in block 1293. If RLE occurs first in block 1291, a Rate Limit Event count is reset in block 1292 and a stimulating pulse is generated in 1299, followed by a Master Reset.

Assuming that AD4 occurred before RLE, then R/L events are counted in block 1293 and tested in block 1294. For the first three such events (occurring in sequence), the Rate Limit Event counter is incremented in 1293 and the system waits until the RLE signal is generated in 1295 and then generates an output pulse in 1299. The delay is shown diagrammatically by the loop 1295A.

If four or more R/L Events have been detected in decision block 1294, then the system proceeds to decision block 1296. If four or more but less than seven sequential R/L Events are detected, it is taken as an indication that the battery has depleted and should be replaced. In this case, the rate is decreased and the pulse width is increased, as indicated in block 1297, and an ERT signal is generated. If, on the other hand, seven or more events are detected in block 1296, it is taken as an indication that the Crystal Oscillator circuit has increased dramatically in frequency. Then the system reverts to a fixed pacing in block 1298 and the cardiac cycle time base as well as the pulse width are determined by the VCO. The system cannot exit from this mode except by application of an external magnet. If four or more R/L Events are counted, the system generates a signal referred to as ERT (Elective Replacement Time) in block 1297 to indicate that at the election of a physician, the pacer should be replaced. The ERT signal switches the system to an alternate pulse width word (WPW) in the Time Mark RAM 210 for a predetermined (programmable) wider stimulating pulse width and the system decreases the adaptive crystal clock rate by twelve and one-half percent in block 1297. This is accomplished by substituting a divide-by-nine circuit in place of a divide-by-eight circuit in the crystal oscillator upper divider 226 (by means of a signal transmitted along the ERT line 279).

This action ($-12.5\%$ rate) should eliminate the asynchronous inequalities between the time periods of the VCO and the crystal oscillator. If additional coincidences are detected, it is taken as an indication that the frequency of the crystal oscillator has increased dramatically, and the system switches over to use the back-up oscillator, namely the VCO 217, as a primary time base reference. If the programmed pulse width is greater than 1 millisecond (PWS), a double width VCO output pulse is derived. It is from the time mark word Rate Limit Low (RLL) that the signal Rate Limit Enable (RLE) 744 of FIG. 7 is generated. However, during a check by a physician when he applies an external magnet, the Rate Limit High (RLH) word generates the Rate Limit Enable (RLE) signal for generation of stimulation pulse rate for which the VCO is used as the time base. If the timing were derived from the RLL time mark for generating a stimulating pulse, the system would not have increased the rate to the level desired by a physician to stimulate the heart during testing. In other words, the physician wants to pace at a higher than normal rate (for example, at 100 beats per minute) so that he can test whether the system is actually capturing the heart without competing with it as in fixed rate modes of pacing. When the magnet is applied, the Rate Limit High (RLH) word is used to define the higher fixed rate. In summary, when the magnet is applied, the Crystal Oscillator is not used to generate the time base so that time mark TM4 has no meaning. Secondly, the time mark word RLL associated with the VCO is not used, and a shorter time period identified by RLH is substituted, and this is used to determine the time of occurrence of the stimulating pulse.

Even though the VCO defines the basic cardiac cycle timing with RLH when the external magnet is applied, the width of the stimulating pulse is still determined by the Crystal Oscillator. This maintains the same pulse characteristics of a normal stimulating pulse as though the Crystal Oscillator were operating. In summary, all of the physical parameters that define an actual stimulating pulse are maintained, and it is therefore a more true test.

Since the time mark RLH is merely an address in VCO Control RAM 209 and used during magnet application, any other rate can be substituted into this location. This permits of a rate that may be slightly higher than tachycardia for any given patient. This would be useful in trying to break up tachycardia. The system is designed so that it will not go more than thirty-two outputs using the Rate Limit High word for programmed RLH rates over 120. This prevents a failure mode in which the reed switch actuated by the magnet would stick. To continue at the higher rate could possibly result in harm to the patient. This count of thirty-two is determined by (284) magnet phase 1 (see the signal MP1 to be described in connection with Magnet Phases and FIG. 13) which feeds into the VCO control address decoder 205 above the VCO Control RAM 209. At the end of the thirty-two outputs, magnet phase 2 is entered. This function of limiting the number of output pulses to a successive count of thirty-two is used when employing a high rate for tachycardia (in other words, the normal RLH word has been substituted by a "tachycardia" rate word). The limit of 32 outputs on RLH may also be enabled for RLH rates below 120 PPM by programming PS2. In summary, in normal operation, as long as the magnet is on the system is set to operate at the 100 beat per minute rate represented by the normal RLH word. If a "tachycardia" word is substituted in RLH, then the function of limiting outputs to thirty-two is implemented.

MAGNET PHASES

Referring now to FIG. 13 which is a timing diagram of the temporary modes implemented by the application of an external magnet, an overall brief description will first be given of the definitions of the magnet phases, the manner in which the different phases are exited and entered, and how they affect the system's operation. The specific circuitry for effecting these functions and operations will then be described. Turning then to FIG. 13, the signal on line 13L1 represents the application of an external magnet at a time T0 (1392) followed by the removal of the magnet at time T1 (1393). It is assumed that the magnet is continuously applied for that time and that the Reed Switch which is shown in functional block 221 in FIG. 1 is actuated (closed) by the application of the magnet.

The state of the Reed Switch 221 is sensed by a Reed Switch Controller 220 which also senses the status of Physician Status Bit PS0 on Bus 203B and performs an EXCLUSIVE OR logic function and generates a signal designated MAG (262) which is synchronized with the Master Reset Signal. It is this EXCLUSIVE OR logic function which inverts the sense of the Reed Switch. This is helpful in the event the Reed Switch becomes stuck in the open or closed position since the physician can program its inversion to avoid possible danger or entering undesired modes. The sense of the Reed Switch can be logically inverted relative to the Atrial Detector independently of the Ventricular Detector. PS40 controls the inversion for the Atrial Detector, and PS0 controls this inversion function for the Ventricle Detector. The signal MAG is representative of the state of the magnet (whether the reed switch function is logically inverted or not), and it is synchronized with Master Reset to derive a signal referred to as synchronous (or SYNC) MAG which is an input to the Temporary Mode Counter 239 to be described presently in connection with FIG. 12.

Returning then to FIG. 13, when the magnet is applied, the system enters Magnet Phase 1 (MP1) 1354, as indicated on line 13L2. Briefly, Magnet Phase 1 is defined by the following parameters: Rate Limit High RLH is used to define the rate of generation of pacing pulses (it will be recalled that RLH can be programmed); secondly, the VCO or backup oscillator is used to provide the basic cardiac cycle time base; and third, the primary or Crystal Oscillator is used to define the width of the stimulating pulse. The system operation during magnet phase 1 and 2 are also defined by the status of PS1. That is to say, if PS1 had been programmed to a 1, the system operates in a fixed rate mode for the duration of MAG. If, on the other hand, the PS1 had been programmed to a 0, the system continues to operate in a demand mode during the magnet application (MAG).

If PS2 is a logic 0, then as indicated by solid line on line 13L2 of FIG. 13, Magnet Phase 1 (1357) continues indefinitely until the external magnet is removed (1352). Normally, during the operation of Magnet Phase 1, the Rate Limit High (RLH) word is set such that the pacing rate is at approximately 100 beats per minute. This enables the physician to determine whether the stimulating pulse as defined by the primary (crystal) oscillator in its normal operating condition is capturing the heart. It also permits the physician to obtain a quantative measurement of the status of the battery since the rate is determined by the backup oscillator which, it will be recalled, has a period which is a function of the battery terminal voltage.

If at the time of the application of the external magnet, PS2 had been programmed to a 1, or if during MP1 the rate had been programmed to a rate higher than 120 beats per minute (in which case PS2 is internally set to a 1), then a circuit referred to as the Temporary Mode Counter 239 limits the operation in the current status mode to a predetermined number (such as 32) complete pacing cycles. This is determined by counting 32 Master Reset (MR) pulses in the Temporary Mode Counter 239. Magnet Phase 2 (MP2) is considered an inherently safe mode because it derives both pulse width and rate from the backup oscillator. For this reason, Magnet Phase 2 can be entered in other ways. An example of Magnet Phase 2 as an inherently safe mode, it will be recalled, was described in connection with the flow diagram of FIG. 12, and particularly in the decision block 1296 in which it was described that if seven consecutive Rate Limit Events were detected, then block 1298 was implemented. In this block, which is MP2, the system operated in a fixed rate with the rate and pulse width determined by the Voltage Controlled Oscillator.

If the rate had been programmed using RLH, to a rate higher than 120 beats per minute as indicated above, then the Temporary Mode Counter limits the system to 32 cycles of operation 1359 as diagramatically illustrated on line 13L3; and thereafter the system enters Magnet Phase 2 as just described. If nothing else happens, the system stays in MP2 as programmed until the magnet is removed as indicated at T1.

Because battery drain may have been excessive during an earlier magnet phase (for example, the rate may have been programmed to a high rate for testing purposes or for breaking a tachycardial chain), it is desirable to implement a battery voltage recovery mode; and this is defined as Magnet Phase 3, as indicated on line 13L5. Briefly, Magnet Phase 3 (1371) is entered when the magnet is removed at time T1; and it uses the Temporary Mode Counter 239 to hold a reset 1381 (13L8) on the Rate Limit Counter 237 (that is, the counter which counts rate limit events, as defined above). The Rate Limit Enable (RLE) signal described above always acts on an individual cycle basis as a rate limit below which period a stimulating pulse cannot be generated, but because the battery voltage may have been depleted, rate limit events as counted in block 1293 of the flow diagram of FIG. 12 are ignored during this battery recovery mode.

It may also be desirable to generate an electrogram, as will be described below and this is implemented by programming PS48 to a 1 and PS49 to a 0. During this phase, the outputs 123,123A of the Delta Modulators 104 and 104A are coupled to an Output Enocder circuit 172 (FIG. 1) which transmits the signal through a Coil Controller 171 to a Coil diagramatically illustrated at 170 from which an external electromagnetic signal may be detected. The physician has the option to disable either the atrial filter electrogram (if he wishes to provide an electrogram only of the ventricle signal) or the ventricle filter electrogram (if he wishes to record the electrogram of the atrium only).

Continuing on with the magnet phases, when the external magnet is removed at T1, the Temporary Mode Counter 239 is used to continue the operation of the electrogram output 1377 for an additional 32 Master Resets as to 1376 indicated in line 13L7. This enables the physician to record an electrogram for the succeeding 32 cardiac cycles in a normal mode of operation—that is, as the pacer system operates normally.

It will be observed, however, that during the generation of an electrogram, battery current drain is increased, and for that reason, the Temporary Mode Counter is used for another 32 Master Resets 1374 (13L6) MP4 to disable the counter which accumulates detections of Rate Limit Events, 237 as described above; and this is diagrammatically illustrated 1382 in line 13L8. In summary, during the generation of an electrogram, following the removal of the magnet, 32 additional cardiac cycles during MP3 are transmitted externally as an electrogram; and a recovery period MP4 is thereafter implemented to permit the battery terminal voltage to recover.

Turning now to line 13L9, the physician, in an attempt to define the limits of capture verification, may have programmed the pulse width to be very narrow. If he has done so and programmed the pulse width to less than 0.25 msec, the system, upon the application of the external magnet as indicated in line 13L9, enables the apparatus to operate at this programmed setting but upon the termination of the first 32 such cycles (as determined by the Temporary Mode Counter again), the system adds 0.5 msec to the pulse width at the end of the temporary mode. This mode can be terminated at any time by removal of the magnet and it may be re-initiated, after removal of the magnet for at least one Master Reset Cycle, by subsequently re-applying the magnet.

This temporary mode 1385 on line 13L9 also defines a mode of system operation useful for "manually" breaking up tachycardia during the application of a magnet by a physician, and aid, or the patient. If an effective high pacing rate for a patient is determined it may be programmed into RLH of the VCO Control RAM 209, where it is used to define a high or overdriving rate. Application of the magnet will output this rate (RLH) for a miximum of 32 beats as limited by the temporary mode in line 13L9.

Turning now to line 13L10, if the physician had programmed PS12 so that the system would be enabled to enter the Automatic Tachycardia Overdrive mode (ATO), then the Temporary Mode Counter 239 generates an output signal 1389 which lasts for a count of eight Master Reset Pulses. During this time 1389 the pacemaker outputs a high rate burst of 8 pulses which may be equally distributed over one or two cardiac cycles or just overdrive at a higher rate.

TEMPORARY MODE COUNTER

The Temporary Mode Counter 239, as described above counts 32 Master Resets. Referring to FIG. 20, the Temporary Mode Counter includes a seven bit counter generally designated 2001. It is reset by the incoming signal SYNC MAG on line 2011, and it is clocked by Master Resets on line 2010. The signal SYNC MAG is the signal MAG 262 generated by the Reed Switch Controller 220 of FIG. 2 which is synchronized with a Master Reset signal. One shots 2004 and 2005 store initlizing signals indicative of which magnet phase it is desired to have the system operate in. Flip-flop 2049 is set by the leading edge of MAG and immediately reset by the counter running signal R32 TMG (2020) to allow the first 32 MR pulses commencing with the application of a magnet (see line 13L3 of FIG. 13). The signal MP1 is generated on line 2023. At the count of 32 MR's, the R32 timing signal is disabled on line 2020 and this signal is fed through gates 2050 and 2052 to generate the signal MP2 and terminate signal MP1. Flip-flop 2046 is actuated on the trailing edge of SYNC MAG and is used to implement Magnet Phase 3 (see line 13L5 of FIG. 13. This phase is used, it will be recalled, to reset the Rate Limit Counter 237, and it essentially is a signal MP3 occurring when the signal SYNC MAG is in its complementary or off state.

It should be observed that line 2021 carries a signal to enable the output of the delta modulators to be coupled to the Output Encoder 172 for the transmission of an external electrogram. There is a latch generally designated 2003 which is responsive to a count of eight in the counter 2001 for generating the eight high rate pulses used in the Automatic Tachycardia Override Mode discussed in the connection with line 13L10 of FIG. 13.

FORCED BACK-UP MODE

There are situations in which it is desirable to force system operation into a predetermined mode with the forehand knowledge that that mode is intrinsically safe. By intrinsically safe, it is meant that the energy contained in the stimulating pulse is at least normal or above and that the rate of the pacing cycle is in a range which is known to be safe for a majority of patients, including particularly patients known to have cardiac disease.

One of the features of this aspect of the invention is that it can be implemented during the time an external programmer is being used to program the implanted pacer circuitry. During this time, the physician may notice something in the patient that would cause him to want to terminate programming, or he may find it necessary to seek additional information to complete his programming, or he may feel he has made a mistake and wants time to evaluate what has been done without placing the patient in a potentially dangerous condition.

To engage this mode, in any such case, the physician simply applies an external magnet which, as described above, generates a signal defined as MAG, which is a signal representative of the fact that the Reed Switch has been actuated by the application of an external magnet.

To implement this mode of operation, one of the status control bits in the Status Control RAM 211, namely PS 99 will have been programmed to a "1". If the MAG signal is generated, it is used to set a latch which generates a signal designated as EXIT.

The EXIT signal forces the system to operate in this back-up mode by effecting the following functions: (1) it forces the system to operate in Maget Phase 2, as described above; (2) it disables Magnet Phase 1 which might have been programmed to cause the system to operate at a higher cardiac cycle rate; (3) it defines a minimum cardiac rate as 60 beats per minute on the Rate Limit Low (RLL) word which also has a maximum of 120 PPM; and (4) it doubles the battery voltage in the case where it has been programmed to one times the battery voltage for the stimulating pulse.

AUTOMATIC TACHYCARDIA OVERDRIVE HARDWARE

Referring to FIG. 21, and to a gate designated 2155, which has three inputs, one of which is on a line 2114 indicating that a ventricular detection has occurred and the gate is enabled on line 2113 any time that the PVC parameters (the signal being designated PVP for Premature Ventricular Parameters) are loaded into the ventricular filter. In other words, the pulses coming out of the gate 2155 are representative of PVC detection; and they are fed to a 5-bit counter generally designated 2101. This relates to the PVC Processing 1200D and loop generally designated 1202 in the flow diagram of FIG. 12. The counter 2101 is enabled only during the time period when Premature Ventricular Parameters (PVP) are loaded in the ventricular detector. If the circuit passes through AD3 into AD4 it is taken as the end of any sequence of premature ventricular contractions to reset the PVC Counter 1283 in the flow chart of FIG. 12; and this is implemented by resetting with the signal AD4 on the line 2111. This signal is coupled through the gate 2157. Two or more counts registered in the counter 2101 sets a latch generally designated 2102 to generate a signal representative of the occurrence of a PVC Couplet (defined as two or more sequential PVCs), and this signal is generated on line 2130. The latch is reset, it will be observed by the signal AD4 on line 2111. The PVC Count signal is fed via line 2130 through an Event Counter Signal Conditioner 193, through a Counter Selector 191 or 192, to the Event Tally Counters 189.

Still referring to the drawing of FIG. 21, selection circuitry generally designated 2103 is used to select a predetermined number of counts, responsive to the contents of the counter 2101 for generating a signal which identifies a condition of tachycardia, and this signal is generated on line 2131 to commence the mode ATO (the signal being designated ATO ST for "ATO start"). ATO, it will be recalled, stands for Automatic Tachycardia Overdrive. Referring now to the Table III—Physician Status Control Bits, the control PS 20 (2110) and PS 21 (2118) are used to set the enabling count in the count selection circuitry 2103. This enables a physician to define a tachycardia condition as 4, 12, 20, or 28 successively occurring PVCs in PVP time period. The output of the count selection circuitry 2103 is fed along the line 2131=2013 in FIG. 20 and is used to enable the latch 2003 in the Temporary Mode Counter 239 described above with the the magnet phases. In connection with ATO, the first eight counts of counter 2001 may used to generate MP1 (Magnet Phase I) which runs on the programmed time period RLH for determining cardiac cycle time. This is enabled automatically—irrespective of whether an actual magnet is being applied, if enabled by PS12, which is fed into the circuitry on line 2012 to the latch 2003.

In summary, if PS12 is a logic 1, then the ATO Mode is enabled. The function of this circuitry can be disabled if desired; and because CMOS circuitry is used, the major subsections of the system may be disabled selectively without increasing power consumption by removing power from the circuits. After the ATO mode has been implemented, a signal on lead 2117 (Rate Limit Reset signal) disables gate 2157 to prevent resetting the counter 2101. This has the effect that the counter cannot be used to count PVC events for a period of time, the period of time being defined by a count of 32 from the Temporary Mode Counter 239 so that a second ATO function cannot be implemented during this period. This hold-off time period is equal to the second 1364 plus third sequence 1365, if used, on line 13L3 of the temporary mode timing diagram of FIG. 13.

CAPTURE VERIFICATION CONTROL LOGIC

The overall function of the capture verification circuitry, as described above, is to identify a T-wave after a paced output. This can be referenced to the path 1200 in the flow diagram of FIG. 12, and specifically, to the Capture Verification Processing 1200B within the First Part of Refractory prior to path 1245. The block 1220 indicates that the ventricular filter is set to detect T-waves.

Referring to FIG. 22, the circuitry is enabled by PS4 (see Table III). This signal PS4 is fed on line 2212 to a gate 2253. Every time a stimulating output is generated (AD5) a signal LRP (Last Reset Paced) appears on line 2213 to allow the signal being representative of the First Portion of Refractory 2211 to clock the three bit loss of capture counter 2201 once. The counter 2201 is incremented each time a First Part of Refractory (FPR) occurs after a stimulating output when the capture verification circuitry is enabled. The counter is reset if a T-wave is detected during this FPR period, which detection defines the beginning of the Second Part of Refractory.

To review this circuitry, first the circuitry is enabled on line 2212, next, on line 2213 there is a signal LRP (Last Reset Paced) indicating that a stimulating pulse has been generated by the system. Next, a signal on line 2211 represents that the First Part of Refractory (the signal being designated FPR) has been entered. This signal (2211=1832 in FIG. 18) is generated in the Ventricular Filter Parameter Controller 233. The signal line is not shown on the block diagram of FIG. 2 for brevity.

If the counter 2201 reaches a count of 4, a latch 2202 is set. This is the CV≧4 latch (the output signal of which is representative of the fact that capture has not been verified for four successive cardiac cycles of paced beats). This is the first stage of loss of capture.

Referring to Table III, a physician has control by means of PS18 and PS19 over the selection of one of two modes of recourse in the event of failure to verify capture. These are designated CVA-3XV (voltage magnitude increase), and CVB-WPW (pulse width increase or use of WPW word for pulse width). The resulting operation is indicated in Table III under PS18 and PS19 depending upon the status of the two bits. The circuitry which implements the function of counting to 11 is generally designated 2205 in FIG. 22, and this causes a reset of the counter 2201 after the first count of four, permitting it to count an additional 7 for a total of 11. To read Table III, for example, if the status bits PS18 and PS19 are 0, 0, then at a count of 4, the pulse width of the stimulating signal is increased, and at a count of 11, nothing else happens. If the status bits are 0 and 1 respectively, then the pulse width is increased at a count of 4 and the voltage is increased (battery voltage tripled if previously set to double or doubled if previously set to single) at a count of 11. The status bits PS18 and PS19 are coupled in respectively on the lines 2217 and 2210; and the count of 11 line is designated 2270. These signals are coupled into two selection circuits generally designated 2203 and 2204, the outputs for which are the signals WPW 2231 to increase pulse width and the signal 3XV 2232 to increase the output amplitude.

WIDE PULSE WIDTH

Wide Pulse Width is a word that is programmed and stored in the Time Mark RAM 210. This word is used by the system in place of the normal pulse width word whenever it is desired to generate a pulse width wider than the normal programmed pulse width. This may occur when an ERT signal is generated, or it may also be used in the event of loss of capture. It provides a safety margin which may be programmed into the system.

OUTPUT VOLTAGE CONTROL

The present system provides circuitry for both increasing and decreasing the output voltage from a nominal voltage. It may be desirable to decrease the output voltage in cases where the patient may experience muscle twitch under a normal stimulating current, and it may be desirable to increase output voltage where a patient has developed higher pacing thresholds such as from increased scar tissue surrounding the stimulating electrode, commonly referred to as "exit block".

To accomplish this, either the Status Control RAM 211 communicates along a Ventricular Control Bus 203C with a Voltage Multiplier circuit 222, or the Capture Verification Control circuit 228 communicates directly with the Voltage Multiplier circuit 222 along line 265. The Voltage Multiplier circuit 222 controls the state of its multiplier capacitor switches to selectively switch in or out one or more stages of voltage multiplication and apply the multiplied voltage to the pacemaker Stimulating Output Switch 223 along line 264. Briefly, this Voltage Multiplier circuit contains two small capacitors. During one-half cycle, the battery is used to charge the small capacitors in parallel so that they are charged to the full terminal voltage of the battery. During the next half cycle, the battery is connected in series with none, one, or both of the small capacitors to a large holding capacitor. Thus, there is the possibility, under program control, of either having the battery voltage alone determine the output voltage (1×V), the battery voltage plus one capacitor (2×V), or the battery voltage plus the voltage across both capacitors in series (3×V). Finer voltage control may be accomplished by stopping the voltage multiplier clock on line 263 upon reaching the desired voltage. The number of clocks required to reach this desired output voltage is an indication of output current or the load impedance. The Voltage Multiplier Control Logic is shown in FIG. 23.

EVENT TALLY COUNTERS

Referring to FIG. 1, the system includes two twenty-bit Event Tally Counters diagrammatically illustrated at 189. Each of these counters provides a counting capacity of over one million events. They may be connected in series (for example, if it is desired to count pacing pulses) thereby yielding a capacity of one trillion for counting over a time period far in excess of a human lifetime. Using only a single counter, while a capacity to count to one million, it may count continuous pacing for approximately ten days.

When the Event Tally Counters are not being used in series, one counter may accumulate sensed beats and the other counter may accumulate paced (stimulated) outputs. In this mode, the event counter system locks up both counters when either one of the counters reaches an overflow condition, so that a ratio is determined between paced events and sensed events according to the contents of the two counters. By locking up both of the counters when one of the counters reaches a maximum, the physician need not be concerned with whether one or both of the counters has gone through a cycle thereby giving a false indication.

Either of these counters may be designated, under program control, to be used to count one of sixteen different event occurrences as indicated by the Primary Event Counter Selector 191 and Secondary Event Counter Selector 192 (FIG. 1). As mentioned, the system may be programmed, for example, to count pacing pulse outputs (stimulating outputs) on one counter and sensed Master Resets (that is, signals generated in response to the detection of a natural heartbeat) on the other counter. This will determine the percentage of required stimulating pulses over the period of a week, and this information might be used to extrapolate the life of the pacer or to make adjustments in the various thresholds, according to the discretion and judgment of a physician. Some other events that one might want to detect and count are: Loss of Capture occurrences, P wave detections, P wave detections during P wave refractory, noise detections during ventricle refractory, pacemaker reversions for ventricle or atrium, Premature Atrial Contractions (PACs), Premature Ventricular Contractions (PVCs), or PVC couplets.

These counters may be used to ∓dry run" various circuit functions so they may be adjusted to the patient's individual needs, for example: P-synchronous function, capture verification, or automatic tachycardia overdrive. The counters may also be used for diagnostic purposes such as recording the occurrences of atrial or ventricular reversion.

REFERENCE DATA RAM

A Reference Data RAM 190 may be used as a status data holding RAM with a limited number of bits of memory available to the user. Preferably, it will contain the pacer model number and any revision letter, serial number, the week the pacer was implanted or the week of manufacture and the implanting (or tending) physicians names and phone number. A large portion of the RAM's capacity will be undesignated and available to the physician to store data, such as initial chronic parameters (for example, rate, intrinsic rate, pacing threshold, R wave amplitude and slope, T wave amplitude and slope, previous percentage pacing over one week, presence of muscle twitch at high amplitude, previous percent of PVCs and couplets, circuit current drain, initial magnet rate, etc.). From this initial data, progressive trends may be observed.

SOFTWARE IMPLEMENTATION OF THE SYSTEM

The pacemaker system may be operated in a mode where both Delta Modulator Signals 123, 123A are transmitted out of the body and picked up by an external computer. The external computer processes these signals on a software equivalent of the pacemaker system with some additional software for optimizing a function in response to the patient. A few examples would be filter paramater tuning, tachycardia operations, determination of the strength duration curve of the output pulse, or pacemaker circuit diagnostics. In addition to pacemaker programming, the output of the computer to the pacemaker during this interaction with the patient would be the Overide (ORD) 140 signal which causes the pacemaker to output a stimulating pulse immediately after it is detected and follow it by a Master Reset. This computer model of the pacemaker could easily be extended to an alternate embodiment of this system where the pacemaker circuit is an implantable microcomputer and this system model is a program in it. In this microcomputer configuration the circuit could be used for other biological control units such as a brain pacer by simply using different software in the system to time it differently and detect different signals.

I claim:

1. Implantable cardiac pacing apparatus comprising:
   electrode means adapted to couple a stimulating signal to the heart and for sensing a cardiac signal;
   sensing means for sensing signals on said electrode means;
   selection circuit means responsive to the signals sensed by said sensing means for detecting a predetermined component of a natural cardiac cycle;
   first timing circuit means having a first timing source operating at a first rate for generating timing signals representative of time periods in a cardiac cycle including a rate time out period during which said predetermined component is expected to occur; and
   second timing circuit means synchronized with said first timing circuit means and having a second timing source independent of said first timing source and operating at a second, faster rate for generating a rate limit enable signal defining a predetermined mimimum period relative to the commencement of a cardiac cycle and ending during a normal cardiac rate time out period; and
   generator means for generating a stimulating signal on said electrode means if said selection circuit means fails to detect said predetermined component during said rate time out period and being inhibited from generating said stimulating signal until said rate limit signal is generated by said second timing circuit means.

2. The apparatus of claim 1 wherein said first timing source comprises a crystal oscillator and wherein said generator means generates a stimulating pulse having its width defined by said crystal oscillator.

3. The apparatus of claim 2 wherein said apparatus includes a battery and wherein said second timing source includes a voltage-controlled oscillator energized by said battery and generating said rate limit enable signal at a period dependent upon the terminal voltage of said battery.

4. The apparatus of claim 3 wherein said rate limit enable signal occurs before the end of said rate time out period if said crystal oscillator is functioning properly and the terminal voltage of said battery has not depleted beyond a predetermined limit; said apparatus further comprising rate limit processing circuit means for detecting when said rate limit signal fails to occur before the end of said rate time out period, each such detection comprising a rate limit event, said rate limit processing circuit means including counter circuit means for counting such rate limit events in successive occurrence and being responsive to a first predetermined number of such rate limit events for increasing said rate time out period of said first timing circuit means.

5. The apparatus of claim 4 wherein said rate limit processing circuit means is further responsive to a second predetermined number of such rate limit events following said first predetermined number of such events for causing said generator means to generate stimulating signals at a fixed rate, and wherein said second timing source derives said timing signals for said generator means and defines the duration of said stimulating signal.

6. The apparatus of claim 5 wherein said rate limit processing circuit means is responsive to a predetermined number of such events occurring in sequence prior to increase in said rate time out period.

7. The apparatus of claim 4 wherein said rate limit processing circuit means is further responsive to said predetermined number of rate limit events for increasing the duration of a stimulating signal when such predetermined number of rate limit events is detected.

8. The apparatus of claim 4 further comprising circuit means responsive to the application of an external magnet for substituting said second timing circuit means for said first timing circuit means to define said rate time out period and for shortening said period thereby increasing the rate of the system in an attempt to artificially stimulate the heart.

9. The apparatus of claim 8 wherein said circuit means responsive to the application of an external magnet further defines the duration of a stimulating pulse during such application using said first timing circuit means.

10. The apparatus of claim 8 further comprising memory means for storing data words representative of predetermined times in a cardiac cycle, including times for the beginning and end of said rate time out period; comparison circuit means for comparing timing signals derived from said first timing means representative of lapsed time in a given cardiac cycle with data words from said storage means; and state controller circuit means for coupling data words from said memory means to said comparison means, said rate limit processing circuit means being responsive to the application of an external magnet for overriding said state controller circuit means for coupling a predetermined data word from said signal storage means to said comparison means to define the end of said rate time out period during the application of said external magnet.

11. The apparatus of claim 10 wherein said predetermined word selected by said rate limit processing circuit determines the time out period for said second timing circuit means, said rate limit processing circuit means using said second timing circuit means to determine the rate time out period.

12. The apparatus of claim 11 wherein said word from said memory means selected by the application of said external magnet is of a duration to interrupt tachycardia, said rate limit processing circuitry further including counter circuit means for counting the number of pulses from said pulse generator means at said tachycardia rate and for limiting the number of pulses applied thereby to a predetermined number.

13. In cardiac pacing apparatus, the combination comprising:
    first oscillator circuit means for generating a periodic signal at a first repetition rate;
    first divider circuit means responsive to the output signal of said first oscillator circuit means for generating a digital signal representative of lapsed time;
    first memory circuit means having a plurality of selectively addressable storage locations for storing digital words representative of sequentially occurring predetermined time marks relative to a commencement time;
    first address means for addressing the storage locations of said first memory circuit means to enable selective readout of the time mark words stored therein;
    first digital comparator circuit means responsive to one of said time mark words read out from said first memory means selected by said first address means representative of a predetermined time in a cardiac cycle for comparing the same with the contents of said first divider circuit means representative of lapsed time in a cardiac cycle;
    said first digital comparator circuit means generating an output signal when said lapsed time signal contents of said first divider circuit means is equal to a time mark word read out from said first memory circuit means;
    said output signal being representative of the occurrence of a predetermined time in said cardiac cycle as represented by said digital time mark word read out from said first memory circuit means.

14. The apparatus of claim 13 wherein said time mark words stored in said first memory means represent predetermined lapsed times relative to a reset signal and include digital words representative respectively of the end of a ventricular refractory period following detection of a natural R wave or stimulated cardiac signal, the end of a PVC time period, and the end of a Ventricular Rate Time Out period.

15. The apparatus of claim 13 wherein one of said time mark words stored in said first memory circuit means represents the end of a Ventricular Rate Time Out period during which a natural heart-beat is expected to occur; and further comprising:
    second oscillator circuit means operating independently of said first oscillator circuit means for generating a second periodic signal
    second divider circuit means responsive to the output signal of said second oscillator circuit means for generating digital signal representative of lapsed time;
    second memory circuit means having a plurality of selectively addressable storage locations, at least one of said storage locations storing a digital time word representative of a lapsed time defining a predetermined ventricular rate;
    second address means for selectively addressing the storage locations of said second memory circuit means;
    second digital comparator circuit means responsive to a digital time word read out of said second memory circuit means and to the contents of said second divider circuit means for generating a rate limit signal when the contents of said divider circuit means represenative of lapsed time equal the digital time word read out from said second memory circuit means;
    pulse generator means for generating a stimulating pulse and coupling the same to the heart of a patient when actuated;
    controller circuit means responsive to the output of said first comparator circuit means representative of the end of said Ventricular Rate Time Out period for actuating said pulse generator means; and
    enable circuit means for inhibiting the actuation of said pulse generator means until said rate limit signal is generated by said second comparator circuit means,
    whereby said first oscillator circuit means defines a cardiac cycle rate during normal operation, and said second oscillator circuit means prevents run away of said first oscillator circuit means.

16. The apparatus of claim 15 further comprising means responsive to the occurrence of said signal repesentative of the end of a Ventricular Rate Time Out period prior to the occurance of said rate limit signal a predetermined number of times for disabling said first oscillator circuit means and for enabling said second oscillator circuit means to provide timing signals for said pacing apparatus.

17. The apparatus of claim 16 wherein said first oscillator circuit means is a crystal oscillator for deriving primary timing signals and said second oscillator circuit means is a voltage controlled oscillator for deriving secondary timing signals.

18. The apparatus of claim 17 wherein said occurrence of said end of a Ventricular Rate Time Out period prior to a rate limit signal defines a rate limit event and wherein said apparatus includes rate limit counter circuit means for counting successive occurrences of rate limit events, said apparatus being responsive to a first predetermined count in said rate limit counter circuit means for lengthening said Ventricular Rate Time Out Period by a predetermined amount.

19. The apparatus of claim 18 wherein said controller circuit means extends the end of said Ventricular Rate Time Out period by approximately twelve percent in response to the detection of rate limit events of said first count.

20. The apparartus to claim 19 further comprising circuit means for generating an elective replacement time signal when said controller circuit means detects said first predetermined number of rate limit events to signal battery depletion.

21. The apparatus to claim 18 wherein said controller circuit means is responsive to a second predetermined number of said rate limit events in said counter circuit means occurring in succession with said first predetermined count, said second predetermined count being greater than said second predetermined count, for disabling said first oscillator circuit means and for enabling said second oscillator circuit means to provide timing signals to said apparatus.

22. The apparatus of claim 15 further comprising rate limit synchronizer circuit means for sychronizing the output signals of said first and second comparator circuit means.

23. In cardiac pacing apparatus, including electrode means for stimulating the heart and for sensing a cardiac signal; detector circuit means responsive to the signal on said electrode means for detecting a predetermined component of a cardiac signal in response thereto; timing circuit means responsive to the output of said detection circuit means for generating signals representative of a predetermined ventricular rate time out period during which a natural R wave is expected to occur in a normal cardiac cycle;

pulse generator circuit means responsive to said timing circuit means for generating a stimulating signal and for coupled the same to said electrode means to stimulate the heart in the absence of a detected R wave during said ventricular rate time out period;

the improvement comprising:
a plurality of function circuit means each performing a predetermined cardiac function in said apparatus;
status control memory means for storing a plurality of status control data words, each word representative of a desired status condition for an associated function circuit means; and
state controller means responsive to the contents of said status control memory means for selectively enabling or disabling the operation and functioning of each of said function circuit means in response to an associated status data word in said status control memory means.

24. The apparatus of claim 23 wherein one of said function circuit comprises capture verification circuit means including sensing means for determining whether the ventricle has contracted in response to a stimulating signal and for generating a verification signal in response thereto; said status control memory circuit means storing a digital signal representative of whether said capture verification circuit means is to be enabled or disabled; said state controller means selectively enabling or disabling said capture verification circuit means in response to the contents of said status control memory circuit means.

25. The apparatus of claim 23 wherein one of said function circuit means comprises automatic tachycardia overdrive circuit means responsive to said timing circuit means for detecting whether a patient is in a state of tachycardia and for generating predetermined signals to stimulate said heart in an attempt to overcome said state of tachycardia; said status control memory means storing digital signals representative of whether said automatic tachycardia overdrive circuit means is to be enabled or disabled; said state controller means selectively enabling or disabling said overdrive circuit means in response to the contents of said status control memory circuit means.

26. The apparatus of claim 23 wherein said pacing apparatus is adapted for total implantation in a patient and wherein one of said function circuit means includes means responsive to the application of an external signal for permitting an external source to control the generation of a stimulating signal of predetermined repetition rate for application to said electrode means; and means responsive to said external signal for permitting said external source of stimulating pulses to override said timing circuit means and said pulse generator means implanted in said patient, said status control memory means storing data for controlling said pacing apparatus to be responsive to said external signal or nonresponsive thereto.

27. The apparatus of claim 23 wherein said apparatus is adapted for implantation in a patient, and said timing circuit means generates signals for defining a ventricular rate time out period during which a natural R wave is expected to occur; and wherein one of said function circuit means includes means responsive to the occurrence of a P wave in said patient during said ventricular rate time out period prior to an R wave for establishing a predetermined P-R interval after the detection of such P wave at the end of which interval said ventricular rate time out period terminates irrespective of the time remaining in said ventricular rate time out period when said P wave was detected, said status control memory means storing digital signals representative of whether said function circuit means is operative.

28. The apparatus of claim 23 wherein said apparatus is adapted for implantation in a patient; said apparatus further comprising switch means in said implanted apparatus responsive to the application of an external signal for communicating said implanted apparatus with an external source of signals;

first circuit means in said implanted apparatus responsive to the state of said switch means for generating a signal representative thereof;
inverter circuit means responsive to the output signal of said first circuit means for inverting the sense thereof;
said status control memory means storing signals representative of the operativeness of said inverter circuit means; and
state control circuit means being responsive to the signals stored in said status control memory means for selectively including or overriding said inverter circuit means whereby the signals stored in status control memory means determine whether the state of said switch means is true or inverted.

29. The apparatus of claim 23 wherein said apparatus is adapted to be implanted in a patient, and further comprising: switch means responsive to the application of an external signal for generating an internal control signal representative of whether said external signal is present or not; and one of said function circuit means is responsive to said internal control signal for forcing said pulse generator means to generate a stimulating signal at a predetermined fixed rate when said internal control signal is present; said status control memory means storing signals representative of a state of enablement or disablement for said function circuit means, said state controller circuit means being responsive to said signals stored in said status control memory for selectively enabling or disabling said one of function circuit means.

30. The apparatus of claim 23 wherein said timing circuit means includes first oscillator circuit means; and further comprising:
   counter circuit responsive to the output of said fist oscillator circuit means for generating a signal representative of lapsed time;
   time mark memory means for storing data words representative of predetermined ventricular rate time out periods in a cardiac cycle;
   comparator circuit means responsive to the contents of said counter circuit means and a ventricular rate time out data word from said time mark memory means for generating an output signal when the same are equal;
   state controller circuit means responsive to the output signal of said comparator circuit means representative of a selected ventricular rate time out time for causing said pulse generator circuit means to generate a stimulating signal if said detector circuit means had not detected an R wave prior thereto;
   means responsive to the application of an external signal for generating an internal signal in said apparatus;
   said state controller means being responsive to said internal signal for selecting a predetermined rate time out data word from said time mark memory means representative of a safe pacing condition.

31. The apparatus of claim 23 wherein said timing circuit means comprises a primary oscillator for generating clock signals for said apparatus and wherein said status control memory means stores a standby data word having a first and a second state, said apparatus being responsive to said first state for inhibiting the transmission of said clock signals for the remainder of said apparatus and being responsive to said second state for permitting said clock signals to be transmitted to the remaining circuitry of said apparatus, whereby when said stored signal is in said first state, power is fed to said oscillator but the remaining circuitry is not clocked, thereby conserving battery power in a standby mode; said apparatus being responsive to an externally applied signal to change the state of said standby word from said first state to said second state.

* * * * *

UNITED STATES PATENT AND TRADEMARK OFFICE
CERTIFICATE OF CORRECTION

PATENT NO. : 4,388,927
DATED : June 21, 1983
INVENTOR(S) : Robert C. Schober

It is certified that error appears in the above—identified patent and that said Letters Patent is hereby corrected as shown below:

Column 50, line 45, change "occurance" to ---occurence---;

Column 51, line 1, delete "to" and insert ---of---;

Column 51, line 6, delete "to" and insert ---of---;

Column 51, line 11, delete "second" and insert ---first---;

Column 51, line 31, change "coupled" to ---coupling---;

Column 52, line 21, change "implantion" to ---implantation---;

and

Column 53, line 6, change "fist" to ---first---.

Signed and Sealed this

Thirty-first Day of January 1984

[SEAL]

Attest:

GERALD J. MOSSINGHOFF

Attesting Officer

Commissioner of Patents and Trademarks